US012569456B2

(12) United States Patent
Stanton, Jr. et al.

(10) Patent No.: US 12,569,456 B2

(45) Date of Patent: Mar. 10, 2026

(54) METHODS FOR THE TREATMENT OF CYSTEAMINE SENSITIVE DISORDERS

(71) Applicant: Thiogenesis Therapeutics, Inc., San Diego, CA (US)

(72) Inventors: Vincent P. Stanton, Jr., Belmont, MA (US); Patrice P. Rioux, San Diego, CA (US); Piotr Barski, Sopot (PL); Dariusz Witt, Gdansk (PL)

(73) Assignee: Thiogenesis Therapeutics, Inc., San Diego, CA (US)

( * ) Notice: Subject to any disclaimer, the term of this patent is extended or adjusted under 35 U.S.C. 154(b) by 0 days.

(21) Appl. No.: 18/165,413

(22) Filed: Oct. 13, 2023

(65) Prior Publication Data

US 2023/0190683 A1 Jun. 22, 2023

Related U.S. Application Data

(63) Continuation of application No. 16/648,725, filed as application No. PCT/US2018/052080 on Sep. 20, 2018, now Pat. No. 11,612,576.

(60) Provisional application No. 62/561,101, filed on Sep. 20, 2017.

(51) Int. Cl.

*A61K 31/16* (2006.01)
*A61K 9/00* (2006.01)
*A61K 31/145* (2006.01)
*A61K 45/06* (2006.01)
*C07C 319/18* (2006.01)

(52) U.S. Cl.

CPC .............. *A61K 31/16* (2013.01); *A61K 9/009* (2013.01); *A61K 31/145* (2013.01); *A61K 45/06* (2013.01); *C07C 319/18* (2013.01)

(58) Field of Classification Search

CPC .... A61K 31/145; A61K 31/16; A61K 31/164; A61K 31/355; A61K 31/375; A61P 25/00; C07C 319/18; C07C 323/25

See application file for complete search history.

(56) References Cited

U.S. PATENT DOCUMENTS

| | | | | |
|---|---|---|---|---|
| 5,338,545 | A | 8/1994 | Clark et al. | |
| 10,537,528 | B2 | 1/2020 | Dohil et al. | |
| 11,173,135 | B2 | 11/2021 | Stanton, Jr. et al. | |
| 11,612,576 | B2 | 3/2023 | Stanton, Jr. et al. | |
| 2003/0176359 | A1 | 9/2003 | Neuwelt et al. | |
| 2004/0009613 | A1 | 1/2004 | Zhou et al. | |
| 2004/0116496 | A1 | 6/2004 | Kirkpatrick et al. | |
| 2005/0101565 | A1 | 5/2005 | Dasseux | |
| 2005/0245433 | A1 | 11/2005 | Chan et al. | |
| 2009/0076166 | A1 | 3/2009 | Dohil et al. | |
| 2011/0182988 | A1 | 7/2011 | Pillay et al. | |
| 2012/0277305 | A1 | 11/2012 | Milne et al. | |
| 2014/0275279 | A1 | 9/2014 | Eddy et al. | |
| 2014/0288117 | A1* | 9/2014 | Chan | A61K 31/145 514/567 |
| 2018/0338928 | A1 | 11/2018 | Dohil et al. | |

FOREIGN PATENT DOCUMENTS

| | | | | |
|---|---|---|---|---|
| CN | 101653426 | A | 2/2010 | |
| CN | 101932238 | A | 12/2010 | |
| CN | 102947287 | A | 2/2013 | |
| CN | 104825430 | A | 8/2015 | |
| CN | 105400855 | A | 3/2016 | |
| CN | 107106875 | A | 8/2017 | |
| EP | 1744737 | A2 | 1/2007 | |
| JP | 2012-504551 | A | 2/2012 | |
| JP | 2019-512510 | A | 5/2019 | |
| KR | 20140125644 | A | 10/2014 | |
| WO | WO-2007/089670 | A2 | 8/2007 | |
| WO | WO-2007088421 | A2 * | 8/2007 | A23D 9/00 |
| WO | WO-2014/068463 | A2 | 5/2014 | |
| WO | WO-2014/087307 | A2 | 6/2014 | |
| WO | WO-2014/106804 | A2 | 7/2014 | |
| WO | WO-2017/161318 | A1 | 9/2017 | |

OTHER PUBLICATIONS

"Compound Summary for CID 74539418," PubChem, <https://pubchem.ncbi.nlm.nih.gov/compound/74539418>, dated Jun. 16, 2014 (12 pages).

Abbott et al., "Modulation of γ-Glutamyl Transpeptidase Activity by Bile Acids," J Biol Chem. 258(10):6193-97 (1983) (6 pages).

Amoruso et al., "Therapeutic effects of cystamine in a murine model of liver fibrosis," Digestive and Liver Disease. 40S:S46, Abstract OC3.04.3 (2008) (Abstract only).

Antoniow et al., "A Novel and Efficient Synthesis of Unsymmetrical Disulfides," Synthesis. 3:363-6 (2007).

Bhaskar et al., "Measuring Glutathione Redox Potential of HIV-1-infected Macrophages," J Biol Chem. 290(2):1020-38 (2015) (20 pages).

Chung et al., "Glutathione mixed disulfide inhibitors of the human placental NADP-linked 15-hydroxyprostaglandin dehydrogenase," Prostaglandins. 33(3):383-90 (1987).

Communication pursuant to Article 94(3) EPC for European Application No. 17767662.4, mailed Aug. 13, 2020 (6 pages).

Dahm et al., "Rat Jejunum Controls Luminal Thiol-Disulfide Redox," J Nutr. 130(11):2739-45 (2000).

(Continued)

*Primary Examiner* — Sarah Pihonak

(74) *Attorney, Agent, or Firm* — Clark & Elbing LLP

(57) ABSTRACT

The invention features methods for the treatment of cystinosis and other cysteamine sensitive disorders in a subject including administration of a disulfide convertible to cysteamine in vivo. The methods can include the separate administration of a reducing agent to the subject to increase the bioavailability and extend the plasma pharmacokinetic profile of the cysteamine produced following administration of the disulfide. The methods permit sustained cysteamine plasma concentrations in a subject.

20 Claims, 43 Drawing Sheets

(56) References Cited

OTHER PUBLICATIONS

Dahm et al., "Secretion of cysteine and glutathione from mucosa to lumen in rat small intestine," Am J Physiol. 267(2 Pt 1):G292-300 (1994).
Dohil et al., "Enteric-coated cysteamine for the treatment of paediatric non-alcoholic fatty liver disease" Aliment Pharmacol Ther. 33(9):1036-44 (2011).
Dohil et al., "Pharmacokinetic Studies of Cysteamine Bitartrate Delayed-Release," Clin Pharmacol Drug Dev. 2(2):178-85 (2013).
Dohil et al., "The Effect of Food on Cysteamine Bitartrate Absorption in Healthy Participants," Clin Pharmacol Drug Dev. 1(4):170-4 (2012).
Dohil et al., "Understanding intestinal cysteamine bitartrate absorption," J Pediatr. 148(6):764-9 (2006).
Eberle et al., "Rapid Oxidation in Vitro of Endogenous and Exogenous Glutathione in Bile of Rats," J Biol Chem. 256(5):2115-7 (1981).
EPAR—Product Information, Annexes I-IIIA for PROCYSBI (cysteamine in the form of mercaptamine bitartrate), manufactured by Chiesi Farmaceutici S.p.A. Italy (2013) (33 pages).
Evans et al., "Pantethine, a derivative of vitamin B5, favorably alters total, LDL and non-HDL cholesterol in low to moderate cardiovascular risk subjects eligible for statin therapy: a triple-blinded placebo and diet-controlled investigation," Vasc Health Risk Manag. 10:89-100 (2014).
Examination Report for Indian Patent Application No. 201847035780, mailed Jul. 21, 2020 (6 pages).
Extended European Search Report for European Application No. 18858763.8, dated May 18, 2021 (10 pages).
Fujisawa et al., "Cysteamine Suppresses Invasion, Metastasis and Prolongs Survival by Inhibiting Matrix Metalloproteinases in a Mouse Model of Human Pancreatic Cancer," PLoS One. 7(4):e34437 (2012) (10 pages).
Gahl et al., "In vivo alteration of a mutant human protein using the free thiol cysteamine," Am J Med Genet. 20(2):409-17 (1985).
Giustarini et al., "Is ascorbate able to reduce disulfide bridges? A cautionary note," Nitric Oxide. 19(3):252-8 (2008).
Görmer et al., "Efficient Microwave-Assisted Synthesis of Unsymmetrical Disulfides," J Org Chem. 75(5):1811-3 (2010).
Hagen et al., "Bioavailability of dietary glutathione: effect on plasma concentration," Am J Physiol. 259(4 Pt 1):G524-9 (1990).
Harrison et al., "Vitamin E and vitamin C treatment improves fibrosis in patients with nonalcoholic steatohepatitis," Am J Gastroenterol. 98(11):2485-90 (2003).
Herzenberg et al., "Glutathione deficiency is associated with impaired survival in HIV disease," Proc Natl Acad Sci U S A. 94(5):1967-72 (1997).
Hou et al., "Gastric retentive dosage forms: a review," Crit Rev Ther Drug Carrier Syst. 20(6):461-97 (2003).
International Preliminary Report on Patentability for International Application No. PCT/US2018/052080, dated Mar. 24, 2020 (7 pages).
International Search Report and Written Opinion for International Application No. PCT/US2018/52080, mailed Jan. 28, 2019 (17 pages).
Jeitner et al., "Mechanism for the inhibition of transglutaminase 2 by cystamine," Biochem Pharmacol. 69(6):961-70 (2005).
Kowalczyk et al., "Versatile and Efficient Synthesis of omega-Functionalized Asymmetric Disulfides via Sulfenyl Bromide Adducts," Langmuir. 23(5):2318-21 (2007).
Langman et al., "A Randomized Controlled Crossover Trial with Delayed-Release Cysteamine Bitartrate in Nephropathic Cystinosis: Effectiveness on White Blood Cell Cystine Levels and Comparison of Safety," Clin J Am Soc Nephrol. 7(7):1112-20 (2012).
Levtchenko et al., "Strict cysteamine dose regimen is required to prevent nocturnal cystine accumulation in cystinosis," Pediatr Nephrol. 21(1):110-3 (2006).
Mandel et al., "Modular Synthesis of Pantetheine and Phosphopantetheine," Org Lett. 6(26):4801-3 (2004).
McCaughan et al., "A potential new prodrug for the treatment of cystinosis: design, synthesis and in-vitro evaluation," Bioorg Med Chem Lett. 18(5):1716-9 (2008).
Min-Oo et al., "Cysteamine, the natural metabolite of pantetheinase, shows specific activity against Plasmodium," available in PMC Apr. 11 2016, published in final edited form as: Exp Parasitol. 125(4):315-24 (2010) (21 pages).
Musiejuk et al., "DDQ-mediated synthesis of functionalized unsymmetrical disulfanes," RSC Adv. 5:31347-51 (2015).
Musiejuk et al., "Recent Developments in the Synthesis of Unsymmetrical Disulfanes (Disulfides). A Review," Org Prep Proced Int. 47(2):95-131 (2015) (38 pages).
Nalini et al., "Studies on acid soluble thiols in the human gastric juice," Biochem Mol Biol Int. 32(3):449-54 (1994) (2 pages) (Abstract only).
Naquet et al., "Role of the Vnn1 pantetheinase in tissue tolerance to stress," Biochem Soc Trans. 42(4):1094-100 (2014).
Nayak et al., "Gastroretentive drug delivery technologies: Current approaches and future potential," J Pharm Educ Res. 1(2):1-12 (2010).
Office Action for Chinese Patent Application No. 201780025812.3, mailed Jun. 29, 2020 (37 pages).
Oiry et al., "NAC/MEA conjugate: a new potent antioxidant which increases the GSH level in various cell lines," Bioorg Med Chem Lett. 11(9):1189-91 (2001).
Okamura et al., "Cysteamine Modulates Oxidative Stress and Blocks Myofibroblast Activity in CKD," J Am Soc Nephrol. 25(1):43-54 (2014).
Omran et al., "Synthesis and in vitro evaluation of novel pro-drugs for the treatment of nephropathic cystinosis," Bioorg Med Chem. 19(11):3492-6 (2011).
Registry(STN), CAS Registry No. 1609174-63-1, dated May 29, 2014, retrieved Aug. 25, 2022.
Sato et al., "Hepatic gene expression in hepatocyte-specific Pten deficient mice showing steatohepatitis without ethanol challenge," Hepatol Res. 34(4):256-65 (2006) (1 page) (Abstract).
Shibata et al., "Hydrolysis and Absorption of Pantothenate and Its Coenzymes in the Rat Small Instestine," J Nutr. 113(10):2107-15 (1983).
Singh et al., "Thiol-disulfide interchange," *The chemistry of sulphur-containing functional groups*. Patai and Rappoport, 633-58 (1993).
Srinivasan et al., "Extracellular 4'-phosphopantetheine is a source for intracellular coenzyme A synthesis," Nat Chem Biol. 11(10):784-92 (2015) (12 pages).
Szymelfejnik et al., "Functionalization of Cysteine Derivatives by Unsymmetrical Disulfide Bond Formation," Synthesis. 22:3528-34 (2007).
Van Rensburg et al., "Reactions of unsymmetrical disulfides, I. Sulfitolysis of sulfur derivatives of cysteamine and cysteine," Arch Biochem Biophys. 118(3):531-5 (1967).
Van Wyk et al., "One-pot preparation of coenzyme A analogues via an improved chemo-enzymatic synthesis of pre-CoA thioester synthons," Chem Commun (Camb). 4:398-400 (2007).
Vu et al., "Fatty Acid Cysteamine Conjugates as Novel and Potent Autophagy Activators That Enhance the Correction of Misfolded F508del-Cystic Fibrosis Transmembrane Conductance Regulator (CFTR)," J Med Chem. 60(1):458-473 (Jan. 12, 2017).
Wang et al., "Disulfide linkage: a potent strategy in tumor-targeting drug discovery," Curr Med Chem. 19(18):2976-83 (2012).
Wittwer et al., "Metabolism of Pantethine in Cystinosis," J Clin Invest. 76(4):1665-72 (1985).

* cited by examiner 1. cysteamine
1x. pantothenic acid
2. pantetheine
3. 4-phosphopantotheine
4. dephospho-coenzyme A
5. coenzyme A FIG. 2
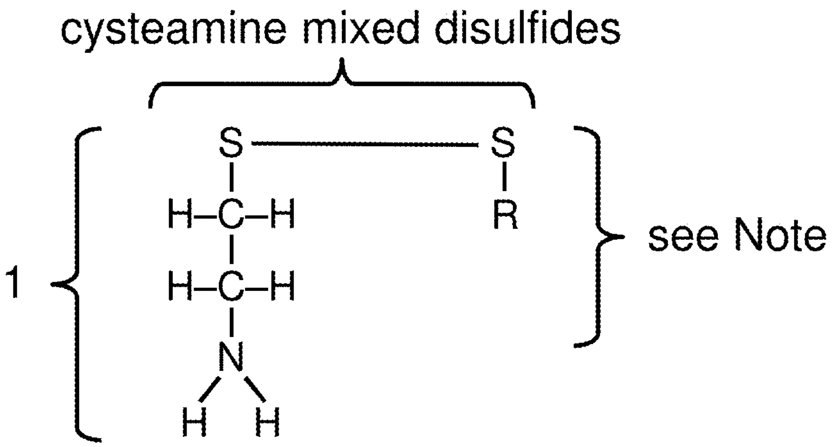
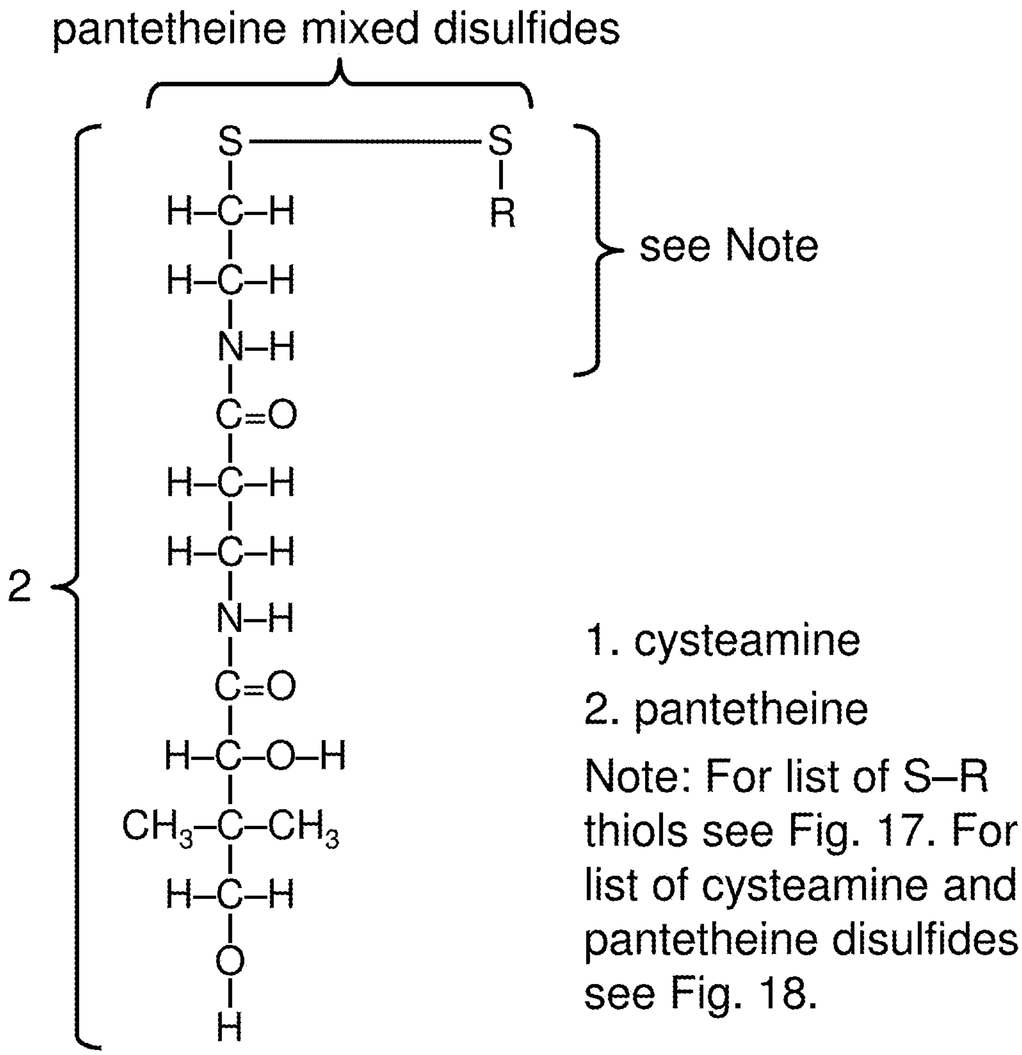
1. cysteamine
2. pantetheine
Note: For list of S–R thiols see Fig. 17. For list of cysteamine and pantetheine disulfides see Fig. 18.

FIG. 3
1 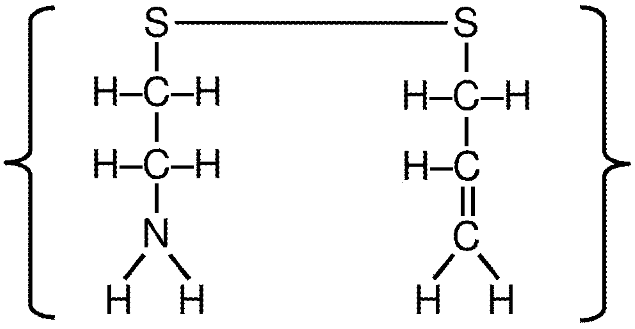 7
1. cysteamine
7. allyl mercaptan
12. L-cysteine
13. L-cysteine ethyl ester • HCl
15. N-acetyl-L-cysteine
1 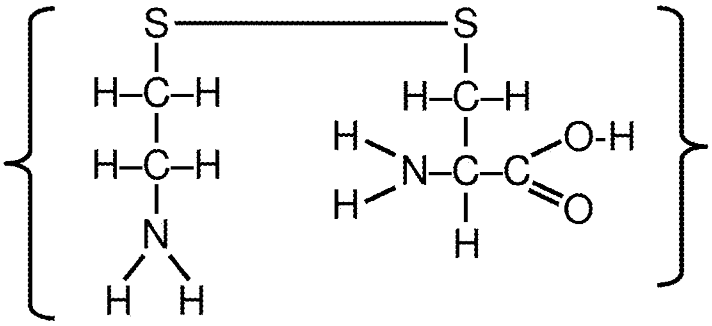 12
1 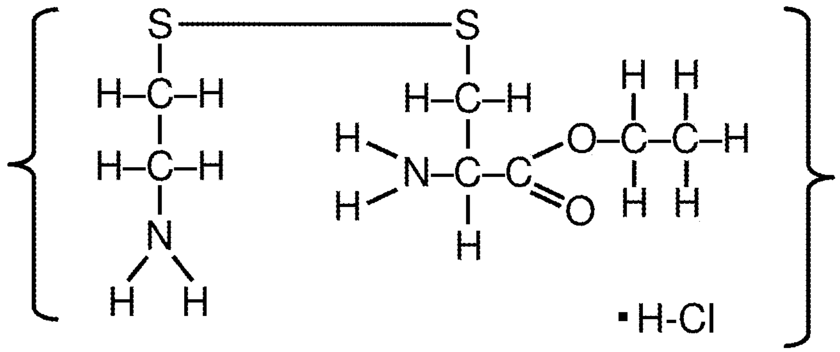 13
1 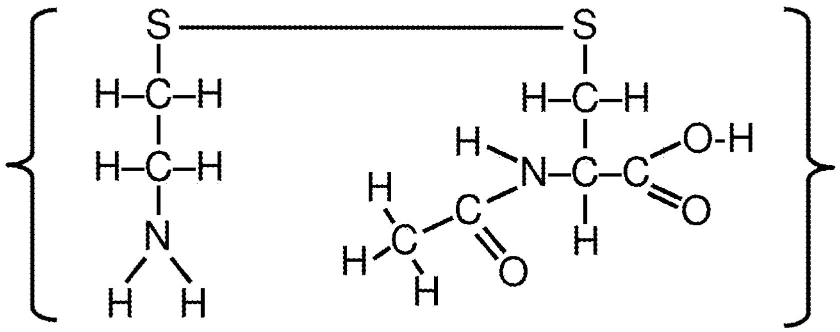 15

FIG. 4
1
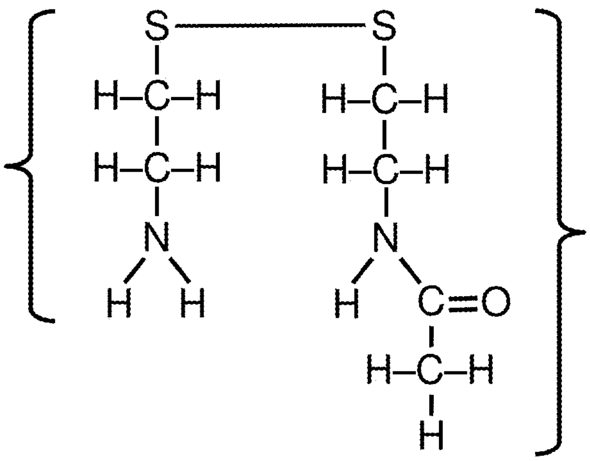
6
1. cysteamine
6. N-acetylcysteamine
17. N-acetylcysteine amide
1
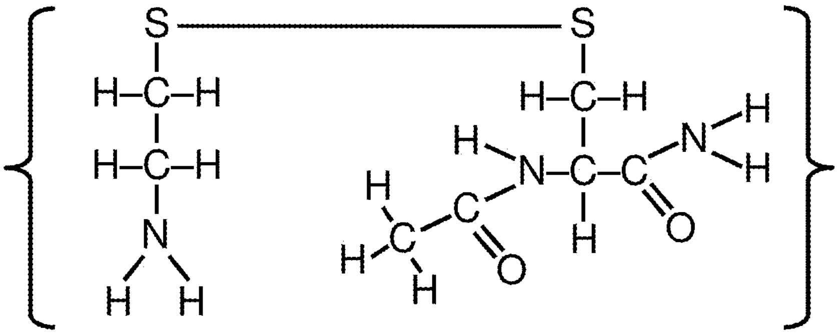
17
6
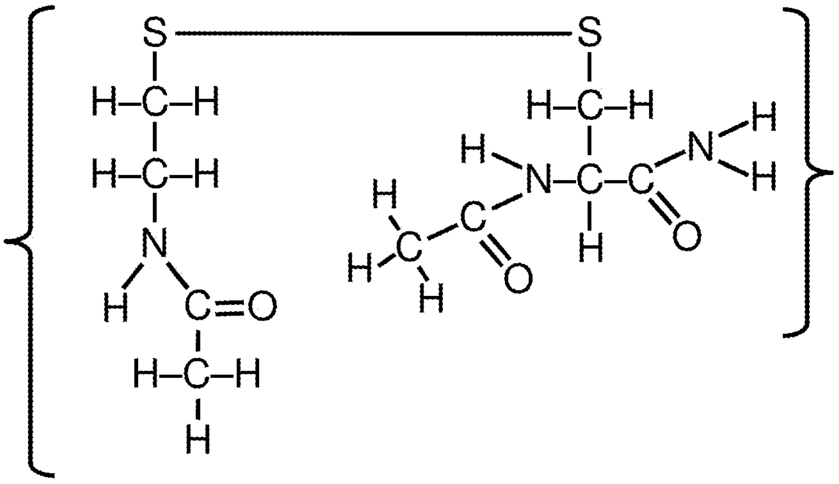
17

FIG. 5
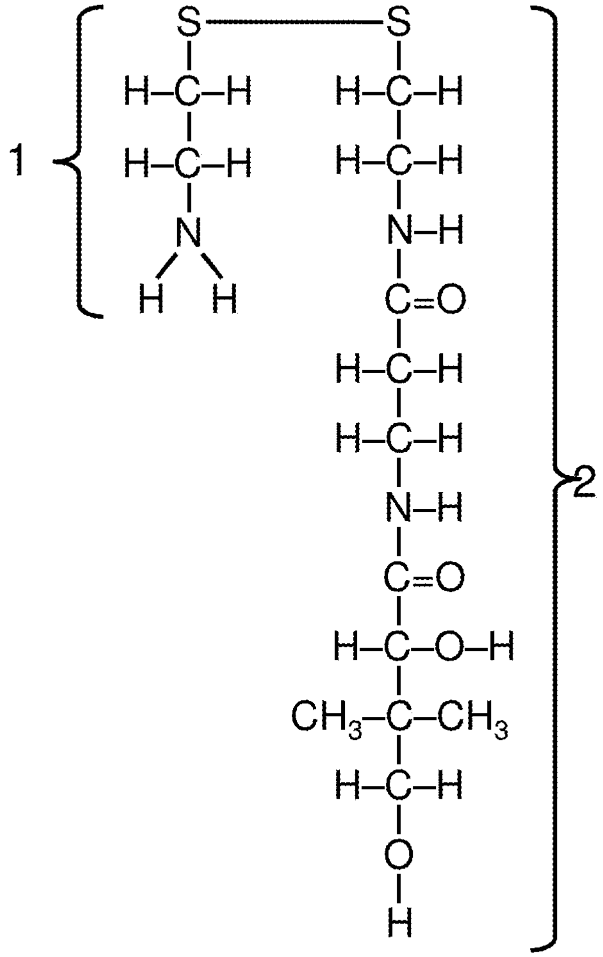
1. cysteamine
2. pantetheine
22. glutathione
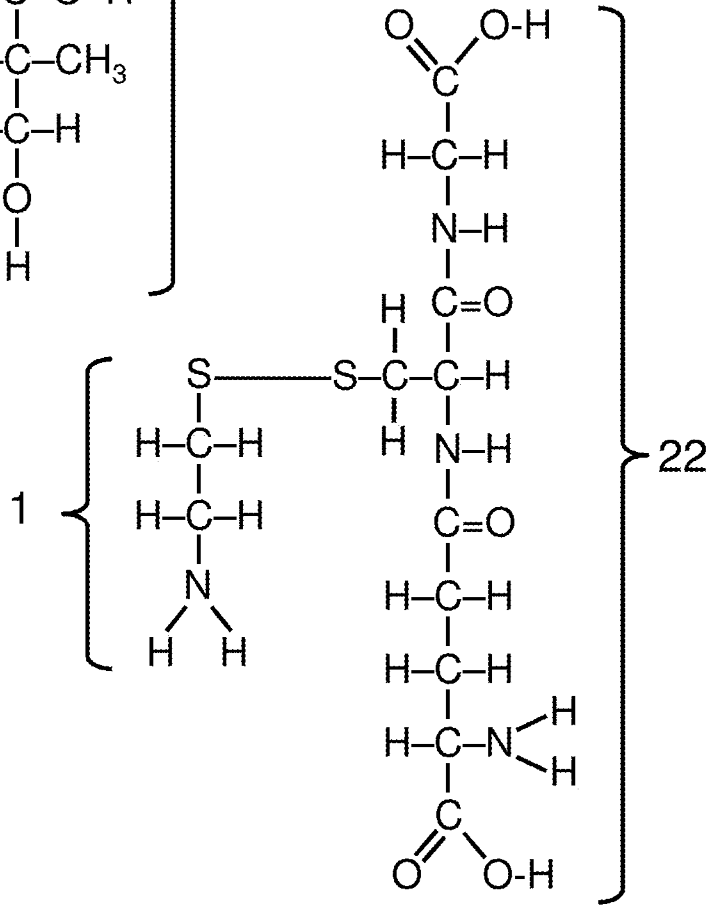

1

5

1. cysteamine 5. coenzyme A

FIG. 7
2
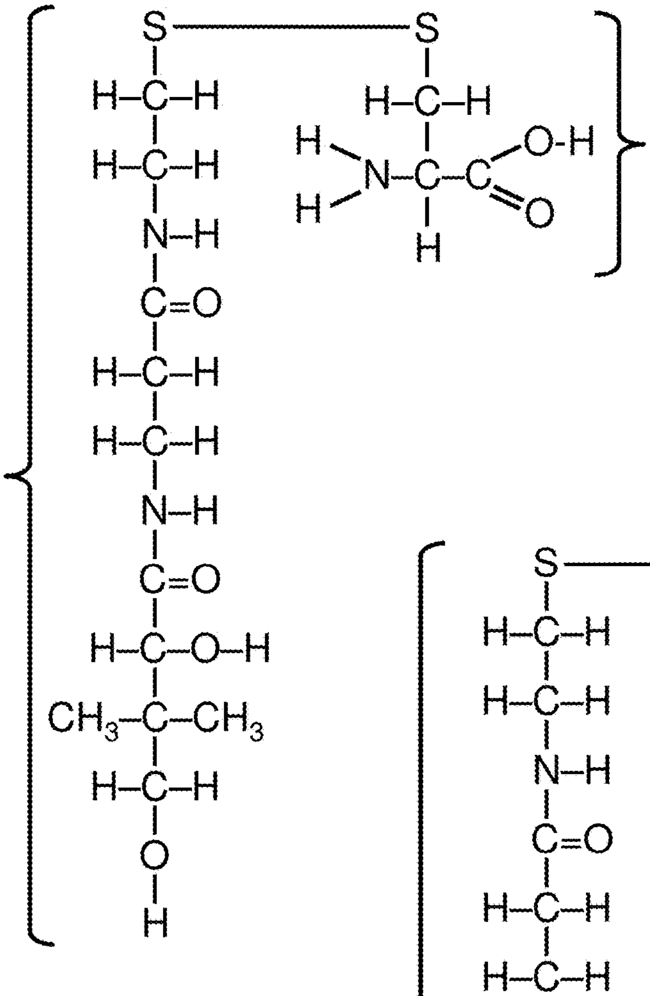
12
2. pantetheine
6. N-acetylcysteamine
12. L-cysteine
2
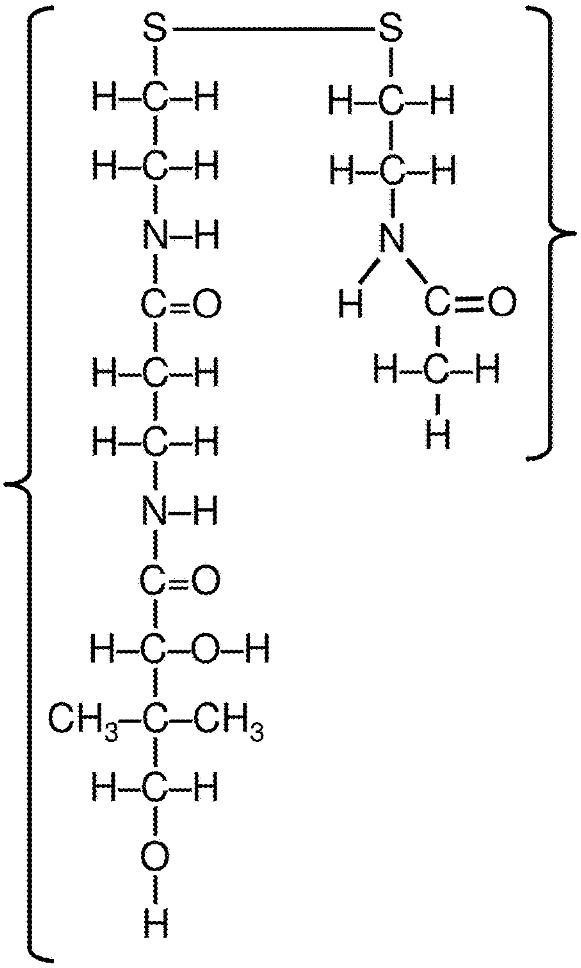
6

FIG. 8
2
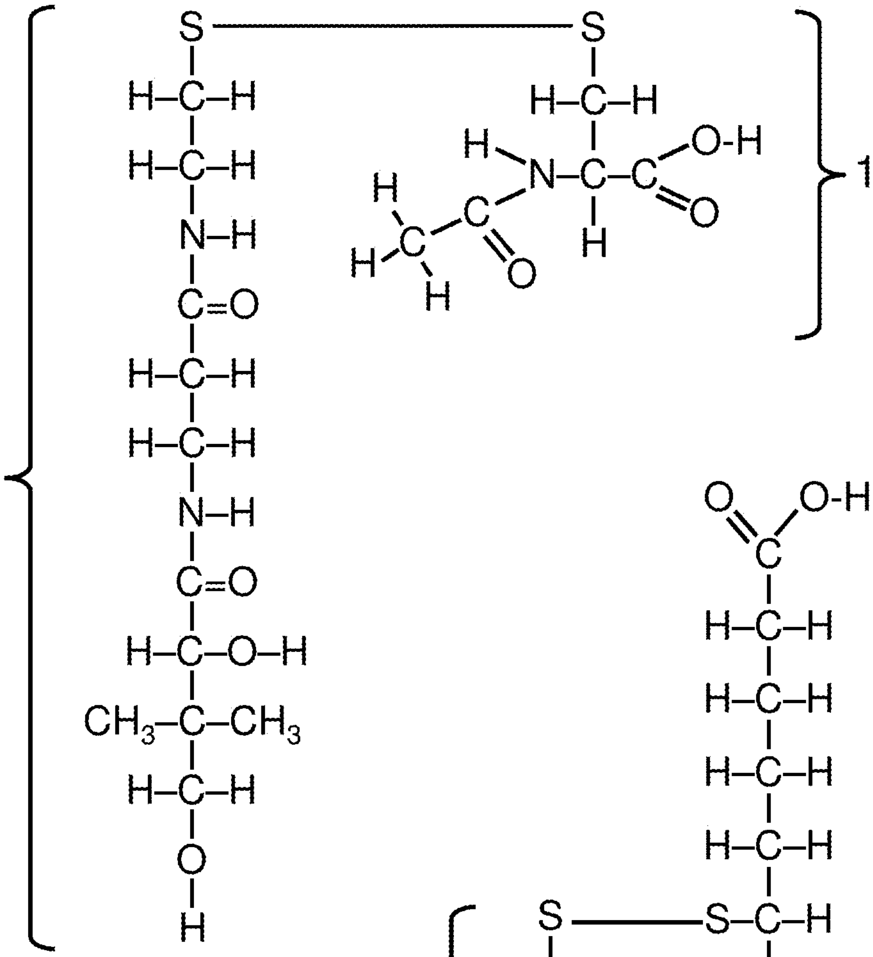
15
30
1
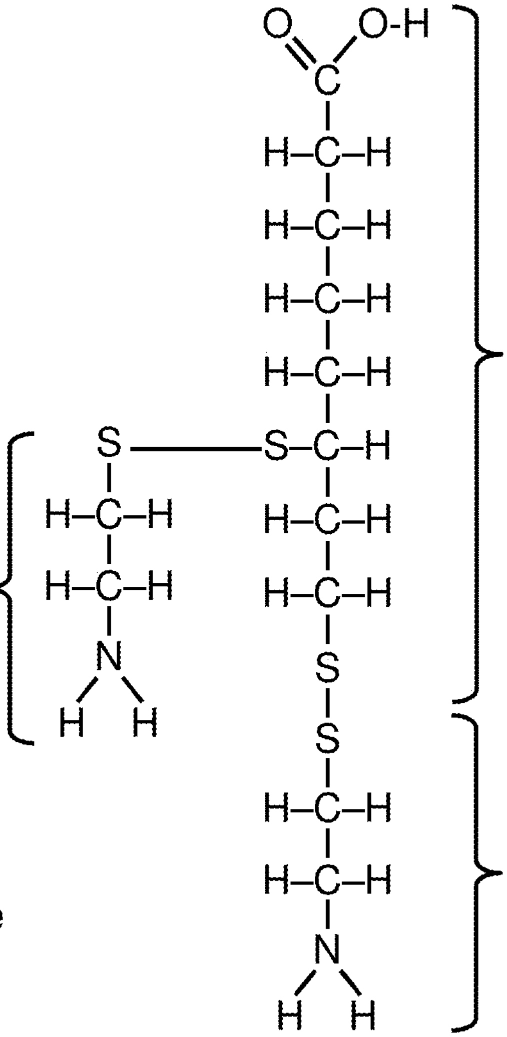
1
1. cysteamine
2. pantetheine
15. N-acetyl-L-cysteine
30. dihydrolipoic acid

22

2

2. pantetheine 22. glutathione

3

5

3. 4-phosphopantetheine 5. coenzyme A

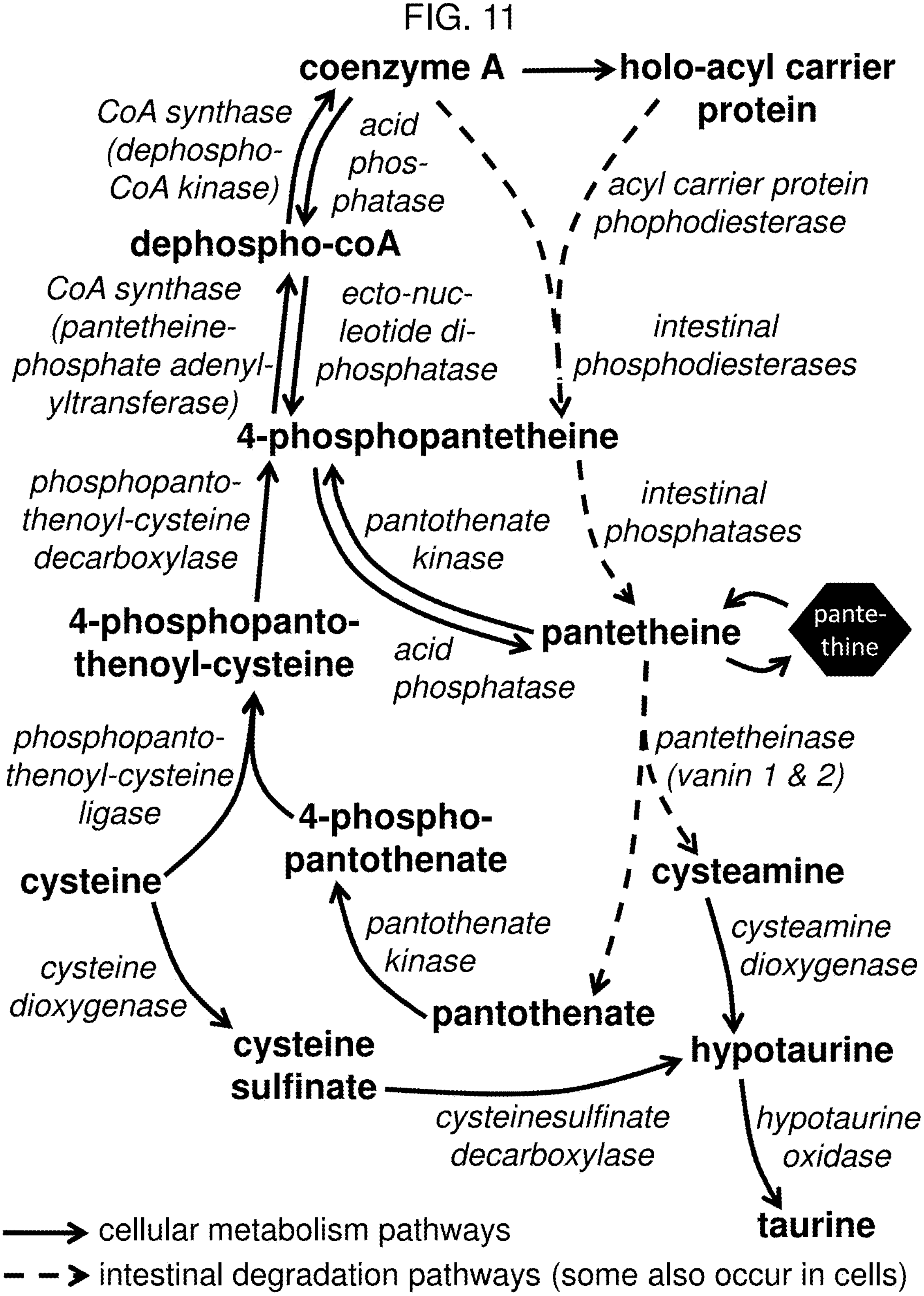

FIG. 11 coenzyme A ⟶ holo-acyl carrier protein

*CoA synthase (dephospho-CoA kinase)*

*acid phos-phatase*

*acyl carrier protein phophodiesterase* dephospho-coA

*CoA synthase (pantetheine-phosphate adenyl-yltransferase)*

*ecto-nuc-leotide di-phosphatase*

*intestinal phosphodiesterases*

4-phosphopantetheine

*phosphopanto-thenoyl-cysteine decarboxylase*

*pantothenate kinase*

*intestinal phosphatases*

4-phosphopanto-thenoyl-cysteine

*acid phosphatase* pantetheine pante-thine

*phosphopanto-thenoyl-cysteine ligase*

*pantetheinase (vanin 1 & 2)* cysteine

4-phospho-pantothenate cysteamine

*pantothenate kinase*

*cysteamine dioxygenase*

*cysteine dioxygenase* cysteine sulfinate pantothenate hypotaurine

*cysteinesulfinate decarboxylase*

*hypotaurine oxidase* taurine

⟶ cellular metabolism pathways

- - ⟶ intestinal degradation pathways (some also occur in cells)

FIG. 12

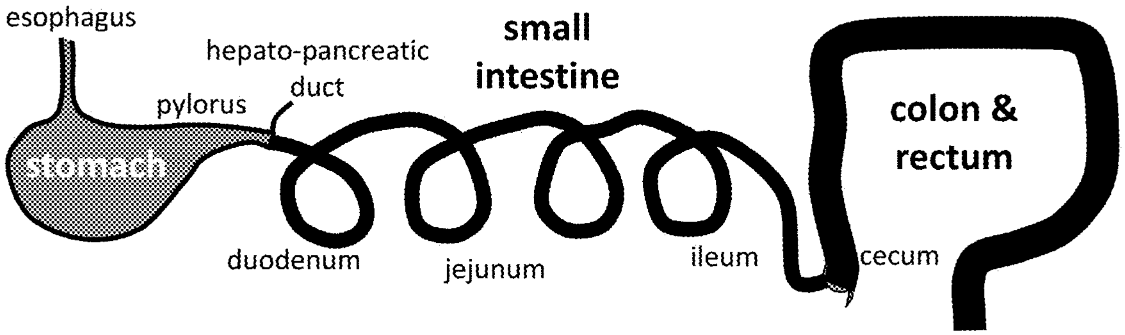

| | | stomach | small intestine | colon & rectum |
|---|---|---|---|---|
| anatomy | **length:** | 0.25 – 0.3 meters | 3.5 – 8.8 m | 1.5 m |
| anatomy | **diameter:** | 1 - 1.3 cm (pylorus) | 2 - 3 cm | 8 cm |
| anatomy | **surface area:** | <1 sq. meters | 30 sq. m. | 2 sq. m. |
| anatomy | **venous drainage:** | liver (portal circulation) | liver (portal circulation) | liver, except ⅔ rectum which drains to heart |
| physiology | **pH:** | 1 – 2 (4 - 5 after a meal) | 5.5 - 6.5 (duodenum) 6.5 - 7.4 (jejun.,ileum) | 5.7 – 7.2 |
| physiology | **GSH levels:** | very low | high (3-4 mM in bile) | intermediate |
| physiology | **food transit time:** | 1 - 40 mins fasted 3 - 5 hrs after meal | 3 – 4 hours | 15 – 40 hours |
| physiology | **enteric bacteria:** | sparse (100 – 10,000 per ml) | sparse (100–10,000 per ml) until ileum | dense (~100 billion per ml) |

| cysteamine formation & uptake | | | stomach RNA | stomach protein | small intestine RNA | small intestine protein | colon & rectum RNA | colon & rectum protein |
|---|---|---|---|---|---|---|---|---|
| | pantetheinases | **VNN1:** | 2 | low | 91-153 | 0 - medium | 13 | 0 - low |
| | pantetheinases | **VNN2:** | 10 | low | 3 | medium | 3 - 29 | 0 – low |
| | pantetheinases | **VNN3:** | 1 | high | 0 | high | 0 - 5 | medium-high |
| | transporters | **OCT1:** | 0 | medium | 0 | medium | 0 – 1 | medium |
| | transporters | **OCT2:** | 0 | 0 | 0 | 0 | 0 | 0 |
| | transporters | **OCT3:** | 4 | medium | 2 – 3 | medium | 2 – 4 | medium-high |

Abbreviations: 4PP = 4- phosphopantetheine; dp-coA = dephospho-coA; coA = coenzyme A; RA = reducing agent; PI = pantetheinase inducer

FIG. 13

| Classification of cysteamine precursors | | | Steps to generate cysteamine | | | | |
|---|---|---|---|---|---|---|---|
| category | components | # | disulfide reduction | catabolism to pantetheine | pantetheinase cleavage | enhancers | pharmacological properties |
| cysteamine mixed disulfides | cysteamine + pantetheine | 2 | required | not required | required for ½ reduced thiols | RA PI | rapid & slower cysteamine gneration, redox |
| | cysteamine + 4PP, dp-coA or coA | 2 | required | required for ½ reduced thiols | required for ½ reduced thiols | RA PI | |
| | cysteamine + other thiol or dithiol | 1<br>2 | required | not required | not required | RA | rapid cysteamine generation, redox |
| pantetheine disulfides | pantetheine + pantetheine | 2 | required | not required | required for all reduced thiols | RA PI | slower cysteamine generation depending on redox level, pantetheinase, other enzymes |
| | pantetheine + 4PP, dp-coA or coA | 2 | required | required for ½ reduced thiols | required for all reduced thiols | RA PI | |
| | pantetheine + other thiol or dithiol | 1<br>2 | required | not required | required for ½ reduced thiols | RA PI | |
| other disulfides | 4PP, dp-coA or coA + 4PP, dp-coA or coA | 2 | required | required for all reduced thiols | required for all reduced thiols | RA PI | slow cysteamine generation, depends on redox, several enzymes |
| | 4PP, dp-coA or coA + other thiol or dithiol | 1<br>2 | required | required for ½ reduced thiols | required for ½ reduced thiols | RA PI | |

GR: gastroretentive, IR: immediate release, SR: sustained release, EC: enteric coated, CT: colon targeted, 4PP: 4-phosphopantetheine, de-coA: dephospho-coenzyme A; RA: reducing agent, PI: pantetheinase inducer, sto: stomach, SI: small intestine, LI: large intestine, CP: cysteamine precursor, C: cysteamine.

See Fig. 13 for abbreviations. AE: absorption enhancer. Doses are in milligrams.

See Figs. 13 & 14 for abbreviations. Doses are in milligrams.

FIG. 17

| # | thiols (common name) | CAS# | formula | MW |
|---|---|---|---|---|
| 1 | cysteamine | 60-23-1 | C2 H7 N S | 77.15 |
| 2 | pantetheine | 496-65-1 | C11 H22 N2 O4 S | 278.37 |
| 3 | 4-phosphopantetheine | 2226-71-3 | C11 H23 N2 O7 P S | 358.35 |
| 4 | dephospho-coenzyme A | 3633-59-8 | C21 H35 N7 O13 P2 S | 687.55 |
| 5 | coenzyme A | 85-61-0 | C21 H36 N7 O16 P3 S | 1075.99 |
| 6 | N-acetylcysteamine | 1190-73-4 | C4 H9 N O S | 119.185 |
| 7 | allyl mercaptan | 870-23-5 | C3 H6 S | 74.145 |
| 8 | furfuryl mercaptan | 98-02-2 | C5 H6 O S | 114.165 |
| 9 | benzyl mercaptan | 100-53-8 | C7 H8 S | 124.203 |
| 10 | thioterpineol | 71159-90-5 | C10 H18 S | 170.31 |
| 11 | 3-mercaptopyruvate | 2464-23-5 | C3 H4 O3 S | 119.12 |
| 12 | L-cysteine | 52-90-4 | C3 H7 N O2 S | 121.15 |
| 13 | L-cysteine ethyl ester HCl | 868-59-7 | C5 H11 N O2 S * HCl | 185.672 |
| 14 | L-cysteine methyl ester HCl | 18598-63-5 | C4 H9 N O2 S * HCl | 171.646 |
| 15 | N-acetyl-L-cysteine | 7218-04-4 | C5 H9 N O3 S | 163.195 |
| 16 | N-acetylcysteine ethyl ester | 59587-09-6 | C7 H13 N O3 S | 191.25 |
| 17 | N-acetylcysteine amide | 38520-57-9 | C5 H10 N2 O2 S | 162.21 |
| 18 | L-homocysteine | 6027-13-0 | C4 H9 N O2 S | 135.185 |
| 19 | cysteinylglycine | 19246-18-5 | C5 H10 N2 O3 S | 178.21 |
| 20 | γ-glutamylcysteine | 686-58-8 | C8 H14 N2 O5 S | 250.272 |
| 21 | γ-glutamylcysteine ethyl ester | 114627-30-4 | C10 H18 N2 O5 S | 278.325 |
| 22 | glutathione | 70-18-8 | C10 H17 N3 O6 S | 307.32 |
| 23 | glutathione monoethyl ester | 118421-50-4 | C12 H21 N3 O6 S | 335.377 |
| 24 | glutathione diethyl ester | 97451-40-6 | C14 H25 N3 O6 S | 363.43 |
| 25 | mercaptoethylgluconamide | 3786-84-3 | C8 H17 N O6 S | 255.289 |
| 26 | thiosalicylic acid | 147-93-3 | C7 H6 O2 S | 154.186 |
| 27 | thiocysteine | 5652-32-4 | C3 H7 N O2 S2 | 153.223 |
| 28 | tiopronin | 1953-02-2 | C5 H9 N O3 S | 163.195 |
| 29 | diethyldithiocarbamic acid | 147-84-2 | C5 H11 N S2 | 149.277 |
| | **dithiols (common name)** | **CAS#** | **formula** | **MW** |
| 30 | dihydrolipoic acid | 462-20-4 | C8 H16 O2 S2 | 208.341 |
| 31 | meso-2,3-dimercaptosuccinic acid | 304-55-2 | C4 H6 O4 S2 | 182.218 |
| 32 | 2,3-dimercaptopropanesulfonic acid | 74-61-3 | C3 H8 O3 S3 | 188.289 |
| 33 | 2,3-dimercapto-1-propanol | 59-52-9 | C3 H8 S2 O | 124.225 |
| 34 | bucillamine | 65002-17-7 R | C7 H13 N O3 S2 | 223.313 |

FIG. 18

Disulfide Table 1A
cysteamine disulfides

| thiols | MW (Daltons) | cysteamine yield | | |
|---|---|---|---|---|
| | | # | percent | steps |
| 1 + 2 | 353.52 | 2 | 43.6% | 1/2 |
| 1 + 3 | 433.50 | 2 | 35.6% | 1/3 |
| 1 + 4 | 762.70 | 2 | 20.2% | 1/4 |
| 1 + 5 | 1151.14 | 2 | 13.4% | 1/4+ |
| 1 + 6 | 194.34 | 2 | 79.4% | 1/2 |
| 1 + 7 | 149.30 | 1 | 51.7% | 1 |
| 1 + 8 | 189.32 | 1 | 40.8% | 1 |
| 1 + 11 | 194.27 | 1 | 39.7% | 1 |
| 1 + 12 | 196.30 | 1 | 39.3% | 1 |
| 1 + 9 | 199.35 | 1 | 38.7% | 1 |
| 1 + 33 | 199.38 | 1 | 38.7% | 1 |
| 1 + 18 | 210.34 | 1 | 36.7% | 1 |
| 1 + 29 | 224.43 | 1 | 34.4% | 1 |
| 1 + 27 | 228.37 | 1 | 33.8% | 1 |
| 1 + 26 | 229.34 | 1 | 33.6% | 1 |
| 1 + 17 | 237.36 | 1 | 32.5% | 1 |
| 1 + 28 | 238.35 | 1 | 32.4% | 1 |
| 1 + 15 | 238.35 | 1 | 32.4% | 1 |
| 1 + 10 | 245.46 | 1 | 31.4% | 1 |
| 1 + 14 | 246.80 | 1 | 31.3% | 1 |
| 1 + 19 | 253.36 | 1 | 30.5% | 1 |
| 1 + 31 | 257.37 | 1 | 30.0% | 1 |
| 1 + 13 | 260.82 | 1 | 29.6% | 1 |
| 1 + 32 | 263.44 | 1 | 29.3% | 1 |
| 1 + 16 | 266.40 | 1 | 29.0% | 1 |
| 1 + 30 | 283.49 | 1 | 27.2% | 1 |
| 1 + 34 | 298.46 | 1 | 25.8% | 1 |
| 1 + 20 | 325.42 | 1 | 23.7% | 1 |
| 1 + 25 | 330.44 | 1 | 23.3% | 1 |
| 1 + 21 | 353.48 | 1 | 21.8% | 1 |
| 1 + 35 | 359.54 | 1 | 21.5% | 1 |
| 1 + 22 | 382.47 | 1 | 20.2% | 1 |
| 1 + 23 | 410.53 | 1 | 18.8% | 1 |
| 1 + 24 | 438.58 | 1 | 17.6% | 1 |

Disulfide Table 1B
pantetheine disulfides

| thiols | MW (Daltons) | cysteamine yield | | |
|---|---|---|---|---|
| | | # | percent | steps |
| 2 + 2 | 554.74 | 2 | 27.8% | 2/2 |
| 2 + 3 | 634.72 | 2 | 24.3% | 2/3 |
| 2 + 4 | 963.92 | 2 | 16.0% | 2/4 |
| 2 + 5 | 1352.36 | 2 | 11.4% | 2/4+ |
| 2 + 6 | 395.56 | 2 | 39.0% | 2/2 |
| 2 + 7 | 350.52 | 1 | 22.0% | 2 |
| 2 + 8 | 390.54 | 1 | 19.8% | 2 |
| 2 + 11 | 395.49 | 1 | 19.5% | 2 |
| 2 + 12 | 397.52 | 1 | 19.4% | 2 |
| 2 + 9 | 400.57 | 1 | 19.3% | 2 |
| 2 + 33 | 400.60 | 1 | 19.3% | 2 |
| 2 + 18 | 411.56 | 1 | 18.7% | 2 |
| 2 + 29 | 425.65 | 1 | 18.1% | 2 |
| 2 + 27 | 429.59 | 1 | 18.0% | 2 |
| 2 + 26 | 430.56 | 1 | 17.9% | 2 |
| 2 + 17 | 438.58 | 1 | 17.6% | 2 |
| 2 + 28 | 439.57 | 1 | 17.6% | 2 |
| 2 + 15 | 439.57 | 1 | 17.6% | 2 |
| 2 + 10 | 446.68 | 1 | 17.3% | 2 |
| 2 + 14 | 448.02 | 1 | 17.2% | 2 |
| 2 + 19 | 454.58 | 1 | 17.0% | 2 |
| 2 + 31 | 458.59 | 1 | 16.8% | 2 |
| 2 + 13 | 462.04 | 1 | 16.7% | 2 |
| 2 + 32 | 464.66 | 1 | 16.6% | 2 |
| 2 + 16 | 467.62 | 1 | 16.5% | 2 |
| 2 + 30 | 484.71 | 1 | 15.9% | 2 |
| 2 + 34 | 499.68 | 1 | 15.4% | 2 |
| 2 + 20 | 526.64 | 1 | 14.6% | 2 |
| 2 + 25 | 531.66 | 1 | 14.5% | 2 |
| 2 + 21 | 554.70 | 1 | 13.9% | 2 |
| 2 + 35 | 560.76 | 1 | 13.8% | 2 |
| 2 + 22 | 583.69 | 1 | 13.2% | 2 |
| 2 + 23 | 611.75 | 1 | 12.6% | 2 |
| 2 + 24 | 639.80 | 1 | 12.1% | 2 |

FIG. 19

Disulfide Table 1C

4-phosphopantetheine disulfides

| thiols | MW (Daltons) | cysteamine yield | | |
|---|---|---|---|---|
| | | # | percent | steps |
| 3 + 3 | 714.70 | 2 | 21.6% | 3/3 |
| 3 + 4 | 1043.90 | 2 | 14.8% | 3/4 |
| 3 + 5 | 1432.34 | 2 | 10.8% | 3/4+ |
| 3 + 6 | 475.54 | 2 | 32.4% | 3/2 |
| 3 + 7 | 430.50 | 1 | 17.9% | 3 |
| 3 + 8 | 470.52 | 1 | 16.4% | 3 |
| 3 + 11 | 475.47 | 1 | 16.2% | 3 |
| 3 + 12 | 477.50 | 1 | 16.2% | 3 |
| 3 + 9 | 480.55 | 1 | 16.1% | 3 |
| 3 + 33 | 480.58 | 1 | 16.1% | 3 |
| 3 + 18 | 491.54 | 1 | 15.7% | 3 |
| 3 + 29 | 505.63 | 1 | 15.3% | 3 |
| 3 + 27 | 509.57 | 1 | 15.1% | 3 |
| 3 + 26 | 510.54 | 1 | 15.1% | 3 |
| 3 + 17 | 518.56 | 1 | 14.9% | 3 |
| 3 + 28 | 519.55 | 1 | 14.8% | 3 |
| 3 + 15 | 519.55 | 1 | 14.8% | 3 |
| 3 + 10 | 526.66 | 1 | 14.6% | 3 |
| 3 + 14 | 528.00 | 1 | 14.6% | 3 |
| 3 + 19 | 534.56 | 1 | 14.4% | 3 |
| 3 + 31 | 538.57 | 1 | 14.3% | 3 |
| 3 + 13 | 542.02 | 1 | 14.2% | 3 |
| 3 + 32 | 544.64 | 1 | 14.2% | 3 |
| 3 + 16 | 547.60 | 1 | 14.1% | 3 |
| 3 + 30 | 564.69 | 1 | 13.7% | 3 |
| 3 + 34 | 579.66 | 1 | 13.3% | 3 |
| 3 + 20 | 606.62 | 1 | 12.7% | 3 |
| 3 + 25 | 611.64 | 1 | 12.6% | 3 |
| 3 + 21 | 634.68 | 1 | 12.2% | 3 |
| 3 + 35 | 640.74 | 1 | 12.0% | 3 |
| 3 + 22 | 663.67 | 1 | 11.6% | 3 |
| 3 + 23 | 691.73 | 1 | 11.2% | 3 |
| 3 + 24 | 719.78 | 1 | 10.7% | 3 |

Disulfide Table 1D dephospho-coenzyme A disulfides

| thiols | MW (Daltons) | cysteamine yield | | |
|---|---|---|---|---|
| | | # | percent | steps |
| 4 + 4 | 1373.10 | 2 | 11.2% | 4/4 |
| 4 + 5 | 1761.54 | 2 | 8.8% | 4/4+ |
| 4 + 6 | 804.74 | 2 | 19.2% | 4/2 |
| 4 + 7 | 759.70 | 1 | 10.2% | 4 |
| 4 + 8 | 799.72 | 1 | 9.6% | 4 |
| 4 + 11 | 804.67 | 1 | 9.6% | 4 |
| 4 + 12 | 806.70 | 1 | 9.6% | 4 |
| 4 + 9 | 809.75 | 1 | 9.5% | 4 |
| 4 + 33 | 809.78 | 1 | 9.5% | 4 |
| 4 + 18 | 820.74 | 1 | 9.4% | 4 |
| 4 + 29 | 834.83 | 1 | 9.2% | 4 |
| 4 + 27 | 838.77 | 1 | 9.2% | 4 |
| 4 + 26 | 839.74 | 1 | 9.2% | 4 |
| 4 + 17 | 847.76 | 1 | 9.1% | 4 |
| 4 + 28 | 848.75 | 1 | 9.1% | 4 |
| 4 + 15 | 848.75 | 1 | 9.1% | 4 |
| 4 + 10 | 855.86 | 1 | 9.0% | 4 |
| 4 + 14 | 857.20 | 1 | 9.0% | 4 |
| 4 + 19 | 863.76 | 1 | 8.9% | 4 |
| 4 + 31 | 867.77 | 1 | 8.9% | 4 |
| 4 + 13 | 871.22 | 1 | 8.9% | 4 |
| 4 + 32 | 873.84 | 1 | 8.8% | 4 |
| 4 + 16 | 876.80 | 1 | 8.8% | 4 |
| 4 + 30 | 893.89 | 1 | 8.6% | 4 |
| 4 + 34 | 908.86 | 1 | 8.5% | 4 |
| 4 + 20 | 935.82 | 1 | 8.2% | 4 |
| 4 + 25 | 940.84 | 1 | 8.2% | 4 |
| 4 + 21 | 963.88 | 1 | 8.0% | 4 |
| 4 + 35 | 969.94 | 1 | 8.0% | 4 |
| 4 + 22 | 992.87 | 1 | 7.8% | 4 |
| 4 + 23 | 1020.93 | 1 | 7.6% | 4 |
| 4 + 24 | 1048.98 | 1 | 7.4% | 4 |

FIG. 20

Disulfide Table 1E

Coenzyme A disulfides

| thiols | MW (Daltons) | cysteamine yield | | |
|---|---|---|---|---|
| | | # | percent | steps |
| 5 + 5 | 2149.98 | 2 | 7.2% | 4+/4+ |
| 5 + 6 | 1193.18 | 2 | 12.9% | 4+/2 |
| 5 + 7 | 1148.14 | 1 | 6.7% | 4+ |
| 5 + 8 | 1188.16 | 1 | 6.5% | 4+ |
| 5 + 11 | 1193.11 | 1 | 6.5% | 4+ |
| 5 + 12 | 1195.14 | 1 | 6.5% | 4+ |
| 5 + 9 | 1198.19 | 1 | 6.4% | 4+ |
| 5 + 33 | 1198.22 | 1 | 6.4% | 4+ |
| 5 + 18 | 1209.18 | 1 | 6.4% | 4+ |
| 5 + 29 | 1223.27 | 1 | 6.3% | 4+ |
| 5 + 27 | 1227.21 | 1 | 6.3% | 4+ |
| 5 + 26 | 1228.18 | 1 | 6.3% | 4+ |
| 5 + 17 | 1236.20 | 1 | 6.2% | 4+ |
| 5 + 28 | 1237.19 | 1 | 6.2% | 4+ |
| 5 + 15 | 1237.19 | 1 | 6.2% | 4+ |
| 5 + 10 | 1244.30 | 1 | 6.2% | 4+ |
| 5 + 14 | 1245.64 | 1 | 6.2% | 4+ |
| 5 + 19 | 1252.20 | 1 | 6.2% | 4+ |
| 5 + 31 | 1256.21 | 1 | 6.1% | 4+ |
| 5 + 13 | 1259.66 | 1 | 6.1% | 4+ |
| 5 + 32 | 1262.28 | 1 | 6.1% | 4+ |
| 5 + 16 | 1265.24 | 1 | 6.1% | 4+ |
| 5 + 30 | 1282.33 | 1 | 6.0% | 4+ |
| 5 + 34 | 1297.30 | 1 | 5.9% | 4+ |
| 5 + 20 | 1324.26 | 1 | 5.8% | 4+ |
| 5 + 25 | 1329.28 | 1 | 5.8% | 4+ |
| 5 + 21 | 1352.32 | 1 | 5.7% | 4+ |
| 5 + 35 | 1358.38 | 1 | 5.7% | 4+ |
| 5 + 22 | 1381.31 | 1 | 5.6% | 4+ |
| 5 + 23 | 1409.37 | 1 | 5.5% | 4+ |
| 5 + 24 | 1437.42 | 1 | 5.4% | 4+ |

Disulfide Table 1F

N-acetylcysteamine disulfides

| thiols | MW (Daltons) | cysteamine yield | | |
|---|---|---|---|---|
| | | # | percent | steps |
| 6 + 6 | 236.37 | 2 | 65.3% | 2/2 |
| 6 + 7 | 191.33 | 1 | 40.3% | 2 |
| 6 + 8 | 231.35 | 1 | 33.3% | 2 |
| 6 + 11 | 236.31 | 1 | 32.6% | 2 |
| 6 + 12 | 238.34 | 1 | 32.4% | 2 |
| 6 + 9 | 241.39 | 1 | 32.0% | 2 |
| 6 + 33 | 241.41 | 1 | 32.0% | 2 |
| 6 + 18 | 252.37 | 1 | 30.6% | 2 |
| 6 + 29 | 266.46 | 1 | 29.0% | 2 |
| 6 + 27 | 270.41 | 1 | 28.5% | 2 |
| 6 + 26 | 271.37 | 1 | 28.4% | 2 |
| 6 + 17 | 279.40 | 1 | 27.6% | 2 |
| 6 + 28 | 280.38 | 1 | 27.5% | 2 |
| 6 + 15 | 280.38 | 1 | 27.5% | 2 |
| 6 + 10 | 287.50 | 1 | 26.8% | 2 |
| 6 + 14 | 288.83 | 1 | 26.7% | 2 |
| 6 + 19 | 295.39 | 1 | 26.1% | 2 |
| 6 + 31 | 299.40 | 1 | 25.8% | 2 |
| 6 + 13 | 302.86 | 1 | 25.5% | 2 |
| 6 + 32 | 305.47 | 1 | 25.3% | 2 |
| 6 + 16 | 308.44 | 1 | 25.0% | 2 |
| 6 + 30 | 325.53 | 1 | 23.7% | 2 |
| 6 + 34 | 340.50 | 1 | 22.7% | 2 |
| 6 + 20 | 367.46 | 1 | 21.0% | 2 |
| 6 + 25 | 372.47 | 1 | 20.7% | 2 |
| 6 + 21 | 395.51 | 1 | 19.5% | 2 |
| 6 + 35 | 401.58 | 1 | 19.2% | 2 |
| 6 + 22 | 424.51 | 1 | 18.2% | 2 |
| 6 + 23 | 452.56 | 1 | 17.0% | 2 |
| 6 + 24 | 480.61 | 1 | 16.1% | 2 |

FIG. 21

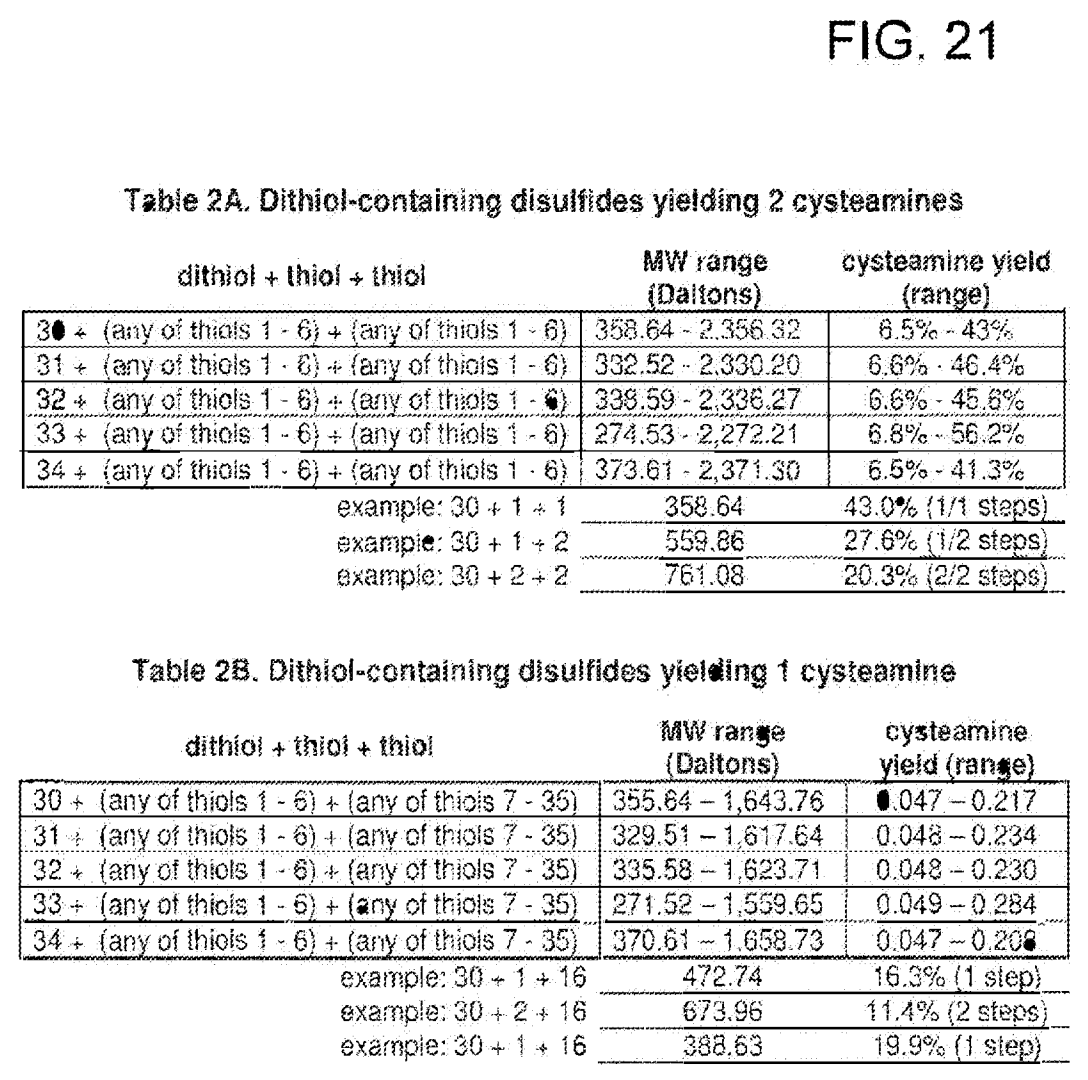

Table 2A. Dithiol-containing disulfides yielding 2 cysteamines

| dithiol + thiol + thiol | MW range (Daltons) | cysteamine yield (range) |
|---|---|---|
| 30 + (any of thiols 1 - 6) + (any of thiols 1 - 6) | 358.64 - 2,356.32 | 6.5% - 43% |
| 31 + (any of thiols 1 - 6) + (any of thiols 1 - 6) | 332.52 - 2,330.20 | 6.6% - 46.4% |
| 32 + (any of thiols 1 - 6) + (any of thiols 1 - 6) | 338.59 - 2,336.27 | 6.6% - 45.6% |
| 33 + (any of thiols 1 - 6) + (any of thiols 1 - 6) | 274.53 - 2,272.21 | 6.8% - 56.2% |
| 34 + (any of thiols 1 - 6) + (any of thiols 1 - 6) | 373.61 - 2,371.30 | 6.5% - 41.3% |
| example: 30 + 1 + 1 | 358.64 | 43.0% (1/1 steps) |
| example: 30 + 1 + 2 | 559.86 | 27.6% (1/2 steps) |
| example: 30 + 2 + 2 | 761.08 | 20.3% (2/2 steps) |

Table 2B. Dithiol-containing disulfides yielding 1 cysteamine

| dithiol + thiol + thiol | MW range (Daltons) | cysteamine yield (range) |
|---|---|---|
| 30 + (any of thiols 1 - 6) + (any of thiols 7 - 35) | 355.64 – 1,643.76 | 0.047 – 0.217 |
| 31 + (any of thiols 1 - 6) + (any of thiols 7 - 35) | 329.51 – 1,617.64 | 0.048 – 0.234 |
| 32 + (any of thiols 1 - 6) + (any of thiols 7 - 35) | 335.58 – 1,623.71 | 0.048 – 0.230 |
| 33 + (any of thiols 1 - 6) + (any of thiols 7 - 35) | 271.52 – 1,559.65 | 0.049 – 0.284 |
| 34 + (any of thiols 1 - 6) + (any of thiols 7 - 35) | 370.61 – 1,658.73 | 0.047 – 0.208 |
| example: 30 + 1 + 16 | 472.74 | 16.3% (1 step) |
| example: 30 + 2 + 16 | 673.96 | 11.4% (2 steps) |
| example: 30 + 1 + 16 | 388.63 | 19.9% (1 step) |

FIG. 22
Step 1: activate thiols
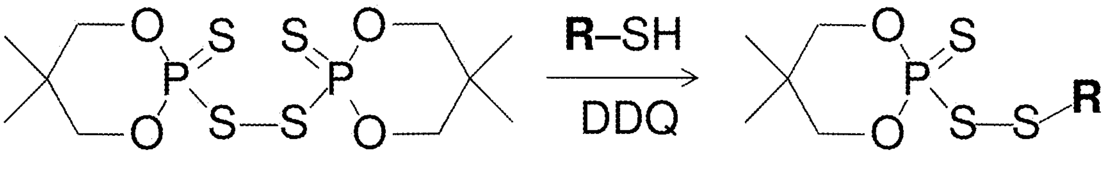
1
2
R–SH =
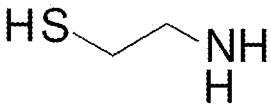
3
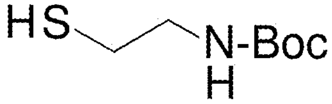
4
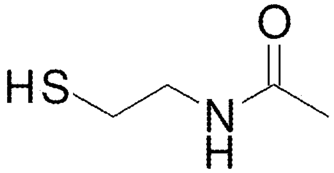
5
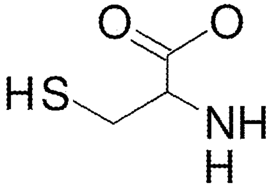
6
7
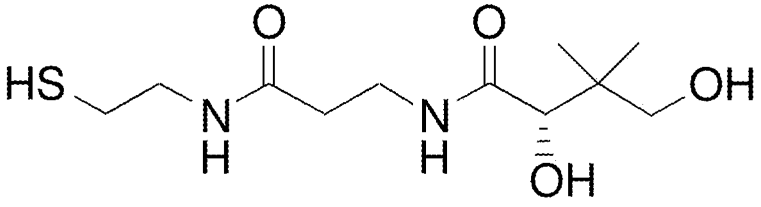

Step 1: protect amine group of cysteamine with Boc

Step 2: add PDTA to cysteamine-Boc

Step 3: remove Boc group with acid

Step 4: react PDTA-cysteamine with (R)-pantetheine (R)     compound 1

Step 1: add PDTA to (R)-pantetheine (R) compound 1

FIG. 25
Step 1: add PDTA to N-acetylcysteamine
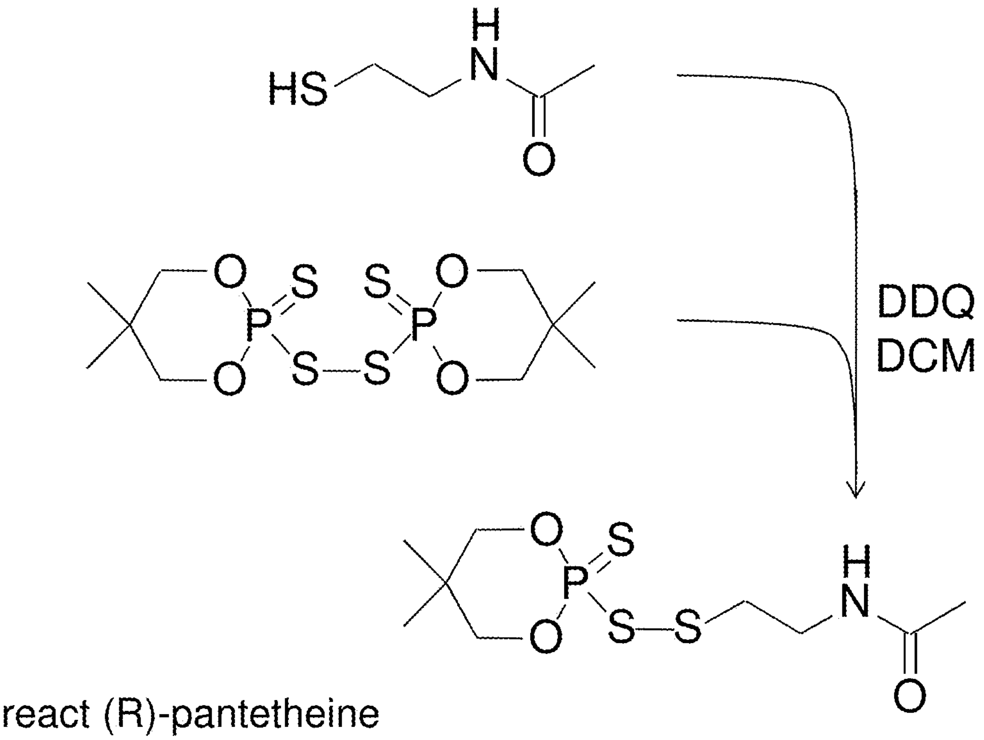
Step 2: react (R)-pantetheine
with N-acetylcysteamine-PDTA
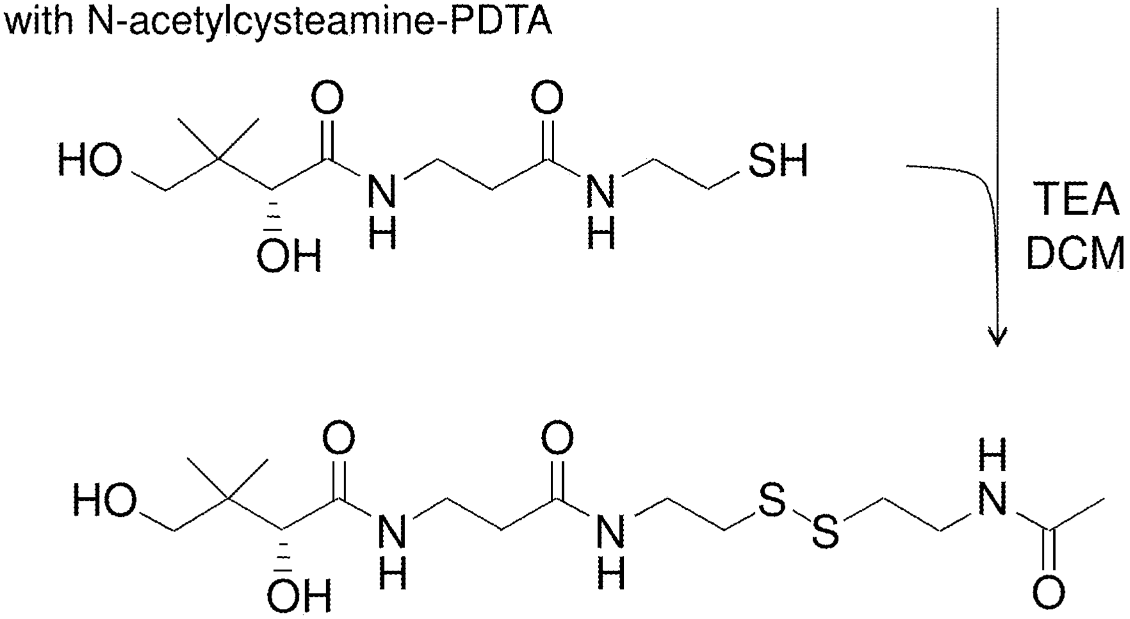
(R) compound 2

Step 1: add PDTA to N-acetylcysteine

Step 2: react (R)-pantetheine with N-acetylcysteine-PDTA cysteamine – (R)-pantetheine disulfide (compound 1)

| INDEX | FREQUENCY | PPM | HEIGHT |
|---|---|---|---|
| 1 | 2327.9 | 4.658 | 590.6 |
| 2 | 1909.7 | 3.821 | 34.4 |
| 3 | 1687.4 | 3.376 | 10.4 |
| 4 | 1680.8 | 3.363 | 23.8 |
| 5 | 1677.7 | 3.357 | 25.5 |
| 6 | 1675.1 | 3.351 | 19.0 |
| 7 | 1670.7 | 3.343 | 14.2 |
| 8 | 1666.7 | 3.335 | 22.8 |
| 9 | 1617.1 | 3.235 | 21.4 |
| 10 | 1613.6 | 3.228 | 11.8 |
| 11 | 1607.0 | 3.215 | 27.9 |
| 12 | 1600.8 | 3.203 | 12.4 |
| 13 | 1594.7 | 3.191 | 103.5 |
| 14 | 1417.6 | 2.836 | 11.1 |
| 15 | 1411.5 | 2.824 | 21.3 |
| 16 | 1404.9 | 2.811 | 10.2 |
| 17 | 1349.1 | 2.699 | 9.3 |
| 18 | 1343.0 | 2.687 | 19.8 |
| 19 | 1336.8 | 2.675 | 15.9 |
| 20 | 1178.7 | | |
| 21 | 1172.5 | | |
| 22 | 1165.9 | | |
| 23 | 389.7 | | |
| 24 | 377.8 | | |
| 25 | 359.8 | | |

N-acetylcysteamine – (R)-pantetheine disulfide
(compound 2)

N-acetyl-L-cysteine – (R)-pantetheine disulfide

FIG. 34B

| | Cysteamine HCl | TTI-01 30 mg/kg | TTI-01 60 mg/kg | TTI-01 100 mg/kg |
|---|---|---|---|---|
| $C_{max}$ (μM) | 55.3 ± 29.8 | 29.4 ± 4.3 | 34.4 ± 5.1 | 34.4 ± 7.6 |
| $C_{max}$ (μg/L) | 4.3 ± 2.3 | 2.3 ± 0.3 | 2.6 ± 0.4 | 2.6 ± 0.6 |
| $T_{max}$ (min) | 17 ± 11 | 45 ± 15 | 45 | 75 ± 21 |
| $AUC_{last}$ (min*μg/L) | 365 ± 57 | 175 ± 3 | 252 ± 51 | 499 ± 1.5 |
| Absorption $t_{1/2}$ (min) | 1 | 26 | 48 | 86 |
| $MRT_{last}$ (min) | 78 ± 20 | 73 ± 4 | 88 ± 11 | 142 ± 15 |

Chemical Formula: $C_{15}H_{31}N_3O_6S_2$
Molecular Weight: 413,55

FIG. 37
CCPANTAc_1H_02102017
Solvent: d2o
Ambient temperature
INOVA-500
Oct 2 2017
Total time 15 min
| INDEX | FREQUENCY | PPM | HEIGHT |
| --- | --- | --- | --- |
| 1 | 2368.2 | 4.738 | 2.3 |
| 2 | 2328.2 | 4.658 | 486.7 |
| 3 | 1908.4 | 3.818 | 30.6 |
| 4 | 1702.5 | 3.406 | 1.8 |
| 5 | 1696.1 | 3.394 | 3.4 |
| 6 | 1691.2 | 3.384 | 7.9 |
| 7 | 1688.8 | 3.379 | 7.2 |
| 8 | 1685.4 | 3.372 | 16.6 |
| 9 | 1682.0 | 3.365 | 11.5 |
| 10 | 1677.1 | 3.355 | 21.1 |
| 11 | 1670.7 | 3.343 | 9.5 |
| 12 | 1665.8 | 3.333 | 18.9 |
| 13 | 1656.6 | 3.314 | 2.9 |
| 14 | 1629.7 | 3.261 | 1.8 |
| 15 | 1617.0 | 3.235 | 19.0 |
| 16 | 1615.1 | 3.231 | 13.3 |
| 17 | 1608.7 | 3.219 | 24.9 |
| 18 | 1605.8 | 3.213 | 14.4 |
| 19 | 1602.4 | 3.206 | 12.5 |
| 20 | 1592.6 | 3.187 | 16.2 |
| 21 | 1431.3 | 2.864 | 13.4 |
| 22 | 1415.0 | 2.831 | 24.2 |
| 23 | 1408.1 | 2.817 | 12.4 |
| 24 | 1356.4 | 2.714 | 12.1 |
| 25 | 1350.1 | 2.701 | 24.3 |
| 26 | 1343.7 | 2.688 | 11.0 |
| 27 | 1179.2 | 2.359 | 10.6 |
| 28 | 1172.4 | 2.346 | 21.6 |
| 29 | 1166.0 | 2.333 | 10.1 |
| 30 | 1009.9 | 2.021 | 2.6 |
| 31 | 945.9 | 1.893 | 513.9 |
| 32 | 880.5 | 1.762 | 2.8 |
| 33 | 377.8 | 0.756 | 68.3 |
| 34 | 359.7 | 0.720 | 69.9 |
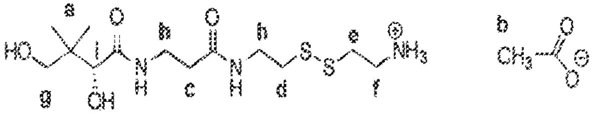
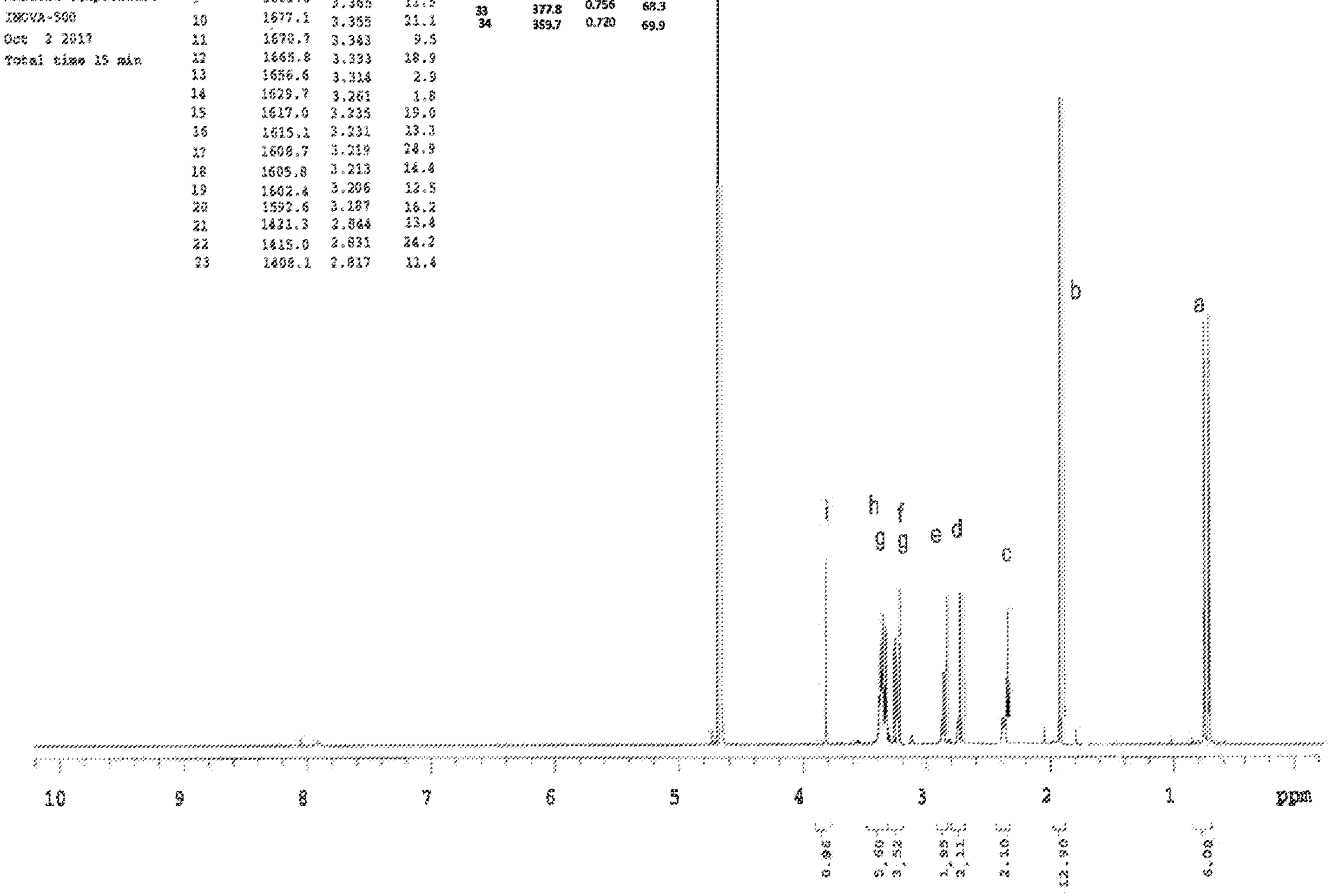

Pantetheine-cysteamine disulfide acetate

| peak | predicted | observed |
| --- | --- | --- |
| a | 6 | 6.00 |
| b | 3 | 12.90 |
| c | 2 | 2.10 |
| d | 2 | 2.11 |
| e | 2 | 1.95 |
| f + ½g | 3 | 3.52 |
| ½g + h | 5 | 5.60 |
| I | 1 | 0.96 |

METHODS FOR THE TREATMENT OF CYSTEAMINE SENSITIVE DISORDERS

FIELD OF THE INVENTION

The invention features compositions and methods for treating cysteamine sensitive symptoms, syndromes and diseases.

BACKGROUND OF THE INVENTION

Cysteamine is a naturally occurring aminothiol, generated in vivo via catabolism of pantetheine. Preclinical and early stage clinical studies suggest that cysteamine may be therapeutically active in a variety of diseases, but broad clinical development has been hampered by a lack of a convenient dosing regimen and poor toxicology.

Cysteamine has several mechanisms of action, most of them relating to the reducing capacity of its thiol moiety. Cysteamine was first studied clinically in the 1950s as radioprotectant for cancer patients undergoing radiation therapy and as a treatment for radiation poisoning. The thiol group of cysteamine can reduce free radicals and other oxidized compounds that may be detrimental to cells, thereby contributing to redox homeostasis. Cysteamine can also indirectly neutralize harmful oxidants by increasing levels of other antioxidant thiols such as glutathione and cysteine. For example cysteamine can participate in thiol-disulfide exchange with cystine, the dimeric oxidized form of cysteine to form a cysteamine-cysteine disulfide and a free cysteine. Cysteamine can also form disulfides with cysteine residues of proteins, thereby affecting protein structure and function. Cysteamine can inhibit enzymes including transglutaminases, caspases, matrix metalloproteinases and glutaminyl cyclase. Cysteamine is a chelating agent, with particular affinity for copper. Cysteamine also blocks secretion of certain peptide hormones including somatostatin.

Diseases for which there is preclinical or clinical evidence for cysteamine therapeutic benefit include neurodegenerative diseases, including Alzheimer's disease, Huntington's disease and Parkinson's disease; inflammatory and fibrotic diseases of the kidney, liver and lung; metabolic diseases including diabetes, metabolic syndrome and the spectrum of fatty liver diseases; infectious diseases, including viral, bacterial and parasitic infections; hypercholesterolemia; ischemic disease including ischemic heart disease or stroke; sickle cell anemia; inherited mitochondrial disorders; hereditary diseases caused by mutation of arginine to cysteine; and cancer.

Unfortunately cysteamine has very unpleasant sensory properties (foul odor and bitter taste) and can produce body odor and halitosis when ingested in therapeutically effective amounts (over one gram per day in adolescents and adults). Most patients also experience gastrointestinal side effects including anorexia, nausea, vomiting, and/or stomach pain. The halitosis, body odor and gastrointestinal side effects have all been associated with high peak cysteamine blood levels (frequently over 50-fold higher than endogenous cysteamine levels in healthy subjects). Furthermore, the elimination half-life of cysteamine is only about 25 minutes, which necessitates frequent dosing. In summary there are problems with the organoleptic properties (bitter taste, bad smell), pharmacology (sub-therapeutic blood levels for much of the inter-dose interval), toxicology (gastrointestinal and other side effects) and stability (short shelf life due to oxidation) of the existing oral formulations of cysteamine. Many of these problems are intrinsic to the drug, a volatile thiol compound. As a consequence many cystinosis patients are not fully compliant with cysteamine therapy and as a result suffer from disease progression.

Clinical development has been hindered by the inability of the cysteamine formulations to deliver therapeutic levels of drug over sustained time periods with acceptable toxicology. Accordingly, there is a need for improved treatment regimens, including improved cysteamine producing compounds, improved formulations and improved dosing regimens, that can produce sustained elevated blood levels of cysteamine while reducing peak concentrations and raising trough concentrations so as to provide improved efficacy while minimizing side effects. Further, in view of the known inter-patient variation in cysteamine pharmacokinetics, compositions that enable individualization of dosing regimens are needed to improve efficacy and reduce toxicity.

SUMMARY OF THE INVENTION

In a first aspect, the invention features a method for treating a cysteamine sensitive disorder in a subject including administering to the subject a dose of from 50 to 150 milligrams per kilogram of body weight (mg/kg) (e.g., 60±10, 70±10, 80±10, 90±10, 100±25, 110±20, 120±10, 130±10, or 140±10 mg/kg) of compound 1:

(1)

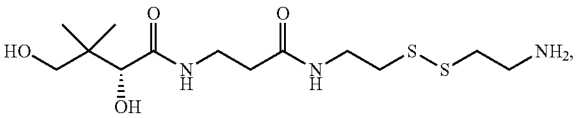

or a pharmaceutically acceptable salt thereof, one or more times daily (e.g., one, two, or three times daily). In particular embodiments, within 2 hours (e.g., within 30 minutes, 1 hour, 90 minutes, or 2 hours) of the administering of the dose no reducing agent is administered to the subject. In particular embodiments, between 2 hours and 8 hours after the administering of the dose a reducing agent is administered to the subject. In particular embodiments, the reducing agent is administered 3±1 hours, 4±1 hours, 5±1 hours, 6±1 hours, 7±1 hours, or 4±2 hours, after the administering of the dose of compound 1 or a pharmaceutically acceptable salt. In one embodiment, the reducing agent is selected from glutathione, glutathione diethyl ester, gamma glutamylcysteine, dihydrolipoic acid, N-acetylcysteine, homocysteine, pantetheine, 4-phosphopantetheine, dephospho-coenzyme A, coenzyme A, vitamin E, and ascorbic acid. In particular embodiments, wherein the compound 1, or a pharmaceutically acceptable salt thereof, is formulated for immediate release. In particular embodiments the compound 1, or a pharmaceutically acceptable salt thereof, is formulated as a powder and the dosage form is a sachet. In particular embodiments, a pantetheinase inducing agent selected from the group including PPAR alpha agonists, PPAR gamma agonists, or Nrf2 inducing agents is administered to the subject. In one embodiment, the pantetheinase inducing agent is an isothiocyanate present in cruciferous vegetables, a sulforaphane, S-allyl cysteine, diallyl trisulfide, oxidized fat, omega-3 fatty acids, or oleylethanolamide. In particular embodiments, within 30 minutes (e.g., 5 minutes, 10 minutes, 15 minutes, 20 minutes, 25 minutes, or 30 minutes) of administering the compound 1, or a pharmaceutically acceptable salt thereof, from 10 to 50 mg/kg (e.g., 15±5, 20±5, 25±5, 30±5, 35±5, 40±5, or 45±5 mg/kg) of cystamine, or a pharmaceutically acceptable salt thereof, is administered to the subject. In one embodiment, the cystamine, or a pharmaceutically acceptable salt thereof, is formulated for immediate release. In particular embodiments, the cystamine, or a pharmaceutically acceptable salt thereof, is administered simultaneously with the administration of compound 1, or a pharmaceutically acceptable salt thereof.

In particular embodiments, within 30 minutes (e.g., 5 minutes, 10 minutes, 15 minutes, 20 minutes, 20 minutes, or 25 minutes) of administering the compound 1, or a pharmaceutically acceptable salt thereof, administering to the subject a dose from 10 to 50 mg/kg (e.g., 15±5, 20±5, 25±5, 30±5, 35±5, 40±5, or 45±5 mg/kg) of compound 3:

(3)

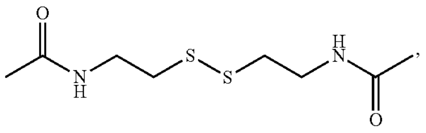

or a pharmaceutically acceptable salt thereof, is administered to the subject. Optionally, compound 3, or a pharmaceutically acceptable salt thereof, is formulated for immediate release. In particular embodiments, compound 3, or a pharmaceutically acceptable salt thereof, is administered simultaneously with the administration of compound 1, or a pharmaceutically acceptable salt thereof.

In any of the above methods, the cysteamine sensitive disorder can be selected from cystinosis; neurodegenerative disease; neurodevelopmental disease; neuropsychiatric disease; mitochondrial disease; fibrotic diseases of the kidney, of the liver, or of the lung; parasitic infection; sickle cell anemia; cancer; ischemic disease including ischemic heart disease or stroke; chronic obstructive pulmonary disease (COPD); cystic fibrosis (CF); bacterial infection; viral infection; non-alcoholic steatohepatitis (NASH); alcoholic steatohepatitis; and non-alcoholic fatty liver disease (NAFLD), or any other cysteamine sensitive disorder described herein.

In a related aspect, the invention features a kit including: (i) a first pharmaceutical composition including compound 1, or a pharmaceutically acceptable salt thereof; (ii) a second pharmaceutical composition including a reducing agent; and (iii) instructions for administering the second pharmaceutical composition at least two hours after the first pharmaceutical composition is administered to a subject for the treatment of a cysteamine sensitive disorder.

In another aspect, the invention features a kit including: (i) a first pharmaceutical composition including compound 1, or a pharmaceutically acceptable salt thereof; (ii) a second pharmaceutical composition including a pantetheinase inducing agent; and (iii) instructions for administering the first pharmaceutical composition and the second pharmaceutical composition to a subject for the treatment of a cysteamine sensitive disorder.

In another related aspect, the invention features a kit including: (i) a first pharmaceutical composition including compound 1, or a pharmaceutically acceptable salt thereof; (ii) a second pharmaceutical composition including cystamine, or a pharmaceutically acceptable salt thereof; and (iii) instructions for administering the second pharmaceutical composition within 30 minutes of administration of the first pharmaceutical composition to a subject for the treatment of a cysteamine sensitive disorder.

In another aspect, the invention features a kit including: (i) a first pharmaceutical composition including compound 1, or a pharmaceutically acceptable salt thereof; (ii) a second pharmaceutical composition including compound 3, or a pharmaceutically acceptable salt thereof; and (iii) instructions for administering the second pharmaceutical composition within 30 minutes of administration of the first pharmaceutical composition to a subject for the treatment of a cysteamine sensitive disorder.

In any of the above kits, the instructions can include instructions for performing the method of administering compound 1 described above.

In another aspect, the invention features a method for treating a cysteamine sensitive disorder in a subject including administering to the subject a dose of from 50 to 150 milligrams per kilogram of body weight (mg/kg) (e.g., 60±10, 70±10, 80±10, 90±10, 100±25, 110±20, 120±10, 130±10, or 140±10 mg/kg) of compound 2:

(2)

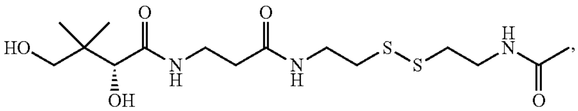

or a pharmaceutically acceptable salt thereof, one or more times daily (e.g., one, two, or three times daily). In particular embodiments, within 2 hours (e.g., within 30 minutes, 1 hour, 90 minutes, or 2 hours) of the administering of the dose no reducing agent is administered to the subject. In particular embodiments, between 2 hours and 8 hours after the administering of the dose a reducing agent is administered to the subject. In particular embodiments, the reducing agent is administered 3±1 hours, 4±1 hours, 5±1 hours, 6±1 hours, 7±1 hours, or 4±2 hours, after the administering of the dose of compound 2 or a pharmaceutically acceptable salt. In one embodiment, the reducing agent is selected from glutathione, glutathione diethyl ester, gamma glutamylcysteine, dihydrolipoic acid, N-acetylcysteine, homocysteine, pantetheine, 4-phosphopantetheine, dephospho-coenzyme A, coenzyme A, vitamin E, and ascorbic acid. In particular embodiments, wherein the compound 2, or a pharmaceutically acceptable salt thereof, is formulated for immediate release. In particular embodiments the compound 2, or a pharmaceutically acceptable salt thereof, is formulated as a powder and the dosage form is a sachet. In particular embodiments, a pantetheinase inducing agent selected from the group including PPAR alpha agonists, PPAR gamma agonists, or Nrf2 inducing agents is administered to the subject. In one embodiment, the pantetheinase inducing agent is an isothiocyanate present in cruciferous vegetables, a sulforaphane, S-allyl cysteine, diallyl trisulfide, oxidized fat, omega-3 fatty acids, or oleylethanolamide. In particular embodiments, within 30 minutes (e.g., 5 minutes, 10 minutes, 15 minutes, 20 minutes, 25 minutes, or 30 minutes) of administering the compound 2, or a pharmaceutically acceptable salt thereof, from 10 to 50 mg/kg (e.g., 15±5, 20±5, 25±5, 30±5, 35±5, 40±5, or 45±5 mg/kg) of cystamine, or a pharmaceutically acceptable salt thereof, is administered to the subject. In one embodiment, the cystamine, or a pharmaceutically acceptable salt thereof, is formulated for immediate release. In particular embodiments, the cystamine, or a pharmaceutically acceptable salt thereof, is administered simultaneously with the administration of compound 2, or a pharmaceutically acceptable salt thereof.

In particular embodiments, within 30 minutes (e.g., 5 minutes, 10 minutes, 15 minutes, 20 minutes, 20 minutes, or 25 minutes) of administering the compound 2, or a pharmaceutically acceptable salt thereof, administering to the subject a dose of from 10 to 50 mg/kg (e.g., 15±5, 20±5, 25±5, 30±5, 35±5, 40±5, or 45±5 mg/kg) of compound 3:

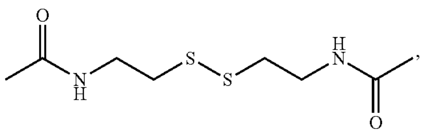

(3)

or a pharmaceutically acceptable salt thereof. Optionally, compound 3, or a pharmaceutically acceptable salt thereof, is formulated for immediate release. In particular embodiments, compound 3, or a pharmaceutically acceptable salt thereof, is administered simultaneously with the administration of compound 2, or a pharmaceutically acceptable salt thereof.

In any of the above methods, the cysteamine sensitive disorder can be selected from cystinosis; neurodegenerative disease; neurodevelopmental disease; neuropsychiatric disease; mitochondrial disease; fibrotic diseases of the kidney, of the liver, or of the lung; parasitic infection; sickle cell anemia; cancer; ischemic disease including ischemic heart disease or stroke; chronic obstructive pulmonary disease (COPD); cystic fibrosis (CF); bacterial infection; viral infection; non-alcoholic steatohepatitis (NASH); alcoholic steatohepatitis; and non-alcoholic fatty liver disease (NAFLD), or any other cysteamine sensitive disorder described herein.

In a related aspect, the invention features a kit including: (i) a first pharmaceutical composition including compound 2, or a pharmaceutically acceptable salt thereof; (ii) a second pharmaceutical composition including a reducing agent; and (iii) instructions for administering the second pharmaceutical composition at least two hours after the first pharmaceutical composition is administered to a subject for the treatment of a cysteamine sensitive disorder.

In another aspect, the invention features a kit including: (i) a first pharmaceutical composition including compound 2, or a pharmaceutically acceptable salt thereof; (ii) a second pharmaceutical composition including a pantetheinase inducing agent; and (iii) instructions for administering the first pharmaceutical composition and the second pharmaceutical composition to a subject for the treatment of a cysteamine sensitive disorder.

In yet another aspect, the invention features a kit including: (i) a first pharmaceutical composition including compound 2, or a pharmaceutically acceptable salt thereof; (ii) a second pharmaceutical composition including cystamine, or a pharmaceutically acceptable salt thereof; and (iii) instructions for administering the second pharmaceutical composition within 30 minutes of administration of the first pharmaceutical composition to a subject for the treatment of a cysteamine sensitive disorder.

In still another aspect, the invention features a kit including: (i) a first pharmaceutical composition including compound 2, or a pharmaceutically acceptable salt thereof; (ii) a second pharmaceutical composition including compound 3, or a pharmaceutically acceptable salt thereof; and (iii) instructions for administering the second pharmaceutical composition within 30 minutes of administration of the first pharmaceutical composition to a subject for the treatment of a cysteamine sensitive disorder.

In any of the above kits, the instructions can include instructions for performing the method of administering compound 2 described above.

The invention features a pharmaceutical composition including compound 3:

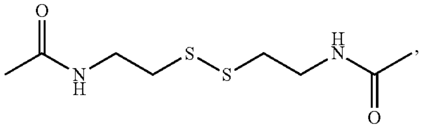

(3)

or a pharmaceutically acceptable salt thereof. The pharmaceutical composition can include compound 3, or a pharmaceutically acceptable salt thereof, formulated for immediate release, formulated for delayed release, or formulated for sustained release. In particular embodiments, the pharmaceutical composition further includes a second active including a cysteamine precursor or a pharmaceutically acceptable salt thereof. Optionally, the second active is formulated for immediate release. In a particular embodiment, the second active is formulated for delayed release or formulated for sustained release. In one particular embodiment, compound 3, or a pharmaceutically acceptable salt thereof, is formulated for immediate release and the second active is formulated for delayed release.

In a related aspect, the invention features a method for treating a cysteamine sensitive disorder in a subject including administering to the subject a therapeutically-effective amount of the pharmaceutical composition including compound 3 or a pharmaceutically acceptable salt thereof. The cysteamine sensitive disorder can be selected from cystinosis; neurodegenerative disease; neurodevelopmental disease; neuropsychiatric disease; mitochondrial disease; fibrotic diseases of the kidney, of the liver, or of the lung; parasitic infection; sickle cell anemia; cancer; ischemic disease including ischemic heart disease or stroke; chronic obstructive pulmonary disease (COPD); cystic fibrosis (CF); bacterial infection; viral infection; non-alcoholic steatohepatitis (NASH); alcoholic steatohepatitis; and non-alcoholic fatty liver disease (NAFLD), or any other cysteamine sensitive disorder described herein.

In another aspect, the invention features a method for treating a cysteamine sensitive disorder in a subject including administering to the subject a dose of from 50 to 150 milligrams per kilogram of body weight (mg/kg) (e.g., 60±10, 70±10, 80±10, 90±10, 100±25, 110±20, 120±10, 130±10, or 140±10 mg/kg) of compound 3:

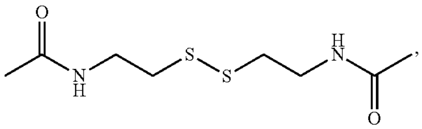

(3)

or a pharmaceutically acceptable salt thereof, one or more times daily (e.g., one, two, or three times daily). In particular embodiments, within 2 hours (e.g., within 30 minutes, 1 hour, 90 minutes, or 2 hours) of the administering of the dose no reducing agent is administered to the subject. In particular embodiments, between 2 hours and 8 hours after the administering of the dose a reducing agent is administered to the subject. In particular embodiments, the reducing agent is administered 3±1 hours, 4±1 hours, 5±1 hours, 6±1 hours, 7±1 hours, or 4±2 hours, after the administering of the dose of compound 3 or a pharmaceutically acceptable salt. In one embodiment, the reducing agent is selected from glutathione, glutathione diethyl ester, gamma glutamylcysteine, dihydrolipoic acid, N-acetylcysteine, homocysteine, pantetheine, 4-phosphopantetheine, dephospho-coenzyme A, coenzyme A, vitamin E, and ascorbic acid. In particular embodiments, wherein the compound 3, or a pharmaceutically acceptable salt thereof, is formulated for immediate release. In particular embodiments the compound 3, or a pharmaceutically acceptable salt thereof, is formulated as a powder and the dosage form is a sachet. In particular embodiments, a pantetheinase inducing agent selected from the group including PPAR alpha agonists, PPAR gamma agonists, or Nrf2 inducing agents is administered to the subject. In one embodiment, the pantetheinase inducing agent is an isothiocyanate present in cruciferous vegetables, a sulforaphane, S-allyl cysteine, diallyl trisulfide, oxidized fat, omega-3 fatty acids, or oleoylethanolamide. In particular embodiments, within 30 minutes (e.g., 5 minutes, 10 minutes, 15 minutes, 20 minutes, 25 minutes, or 30 minutes) of administering the compound 3, or a pharmaceutically acceptable salt thereof, from 10 to 50 mg/kg (e.g., 15±5, 20±5, 25±5, 30±5, 35±5, 40±5, or 45±5 mg/kg) of cystamine, or a pharmaceutically acceptable salt thereof, is administered to the subject. In one embodiment, the cystamine, or a pharmaceutically acceptable salt thereof, is formulated for immediate release. In particular embodiments, the cystamine, or a pharmaceutically acceptable salt thereof, is administered simultaneously with the administration of compound 3, or a pharmaceutically acceptable salt thereof.

In any of the above methods, the cysteamine sensitive disorder can be selected from cystinosis; neurodegenerative disease; neurodevelopmental disease; neuropsychiatric disease; mitochondrial disease; fibrotic diseases of the kidney, of the liver, or of the lung; parasitic infection; sickle cell anemia; cancer; ischemic disease including ischemic heart disease or stroke; chronic obstructive pulmonary disease (COPD); cystic fibrosis (CF); bacterial infection; viral infection; non-alcoholic steatohepatitis (NASH); alcoholic steatohepatitis; and non-alcoholic fatty liver disease (NAFLD), or any other cysteamine sensitive disorder described herein.

In a related aspect, the invention features a kit including: (i) a first pharmaceutical composition including compound 3, or a pharmaceutically acceptable salt thereof; (ii) a second pharmaceutical composition including a reducing agent; and (iii) instructions for administering the second pharmaceutical composition at least two hours after the first pharmaceutical composition is administered to a subject for the treatment of a cysteamine sensitive disorder.

In another aspect, the invention features a kit including: (i) a first pharmaceutical composition including compound 3, or a pharmaceutically acceptable salt thereof; (ii) a second pharmaceutical composition including a pantetheinase inducing agent; and (iii) instructions for administering the first pharmaceutical composition and the second pharmaceutical composition to a subject for the treatment of a cysteamine sensitive disorder.

In yet another aspect, the invention features a kit including: (i) a first pharmaceutical composition including compound 3, or a pharmaceutically acceptable salt thereof; (ii) a second pharmaceutical composition including cystamine, or a pharmaceutically acceptable salt thereof; and (iii) instructions for administering the second pharmaceutical composition within 30 minutes of administration of the first pharmaceutical composition to a subject for the treatment of a cysteamine sensitive disorder.

In any of the above kits, the instructions can include instructions for performing the method of administering compound 3 described above.

In another aspect, the invention features an acid addition salt of compound 1, where the acid is hydrochloric acid, acetic acid, trifluoroacetic acid, or tartaric acid. In particular embodiments, the acid is acetic acid or tartaric acid. In particular embodiments, the acid is acetic acid.

In one embodiment, the acid addition salt has the formula:

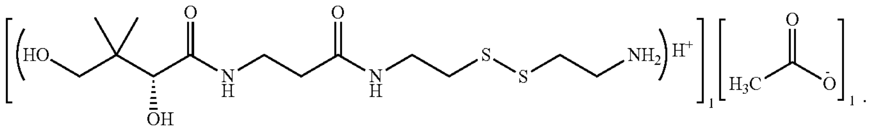

In some embodiments, the acid addition salt has the formula:

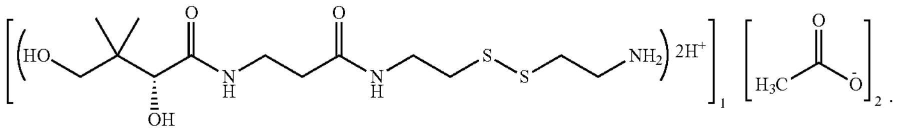

In particular embodiments, the acid is tartaric acid.

In one embodiment the acid addition salt has the formula:

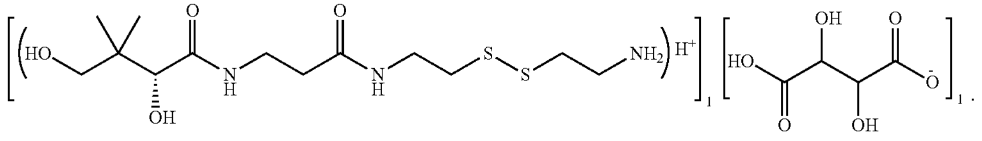

In one embodiment, the acid addition salt has the formula:

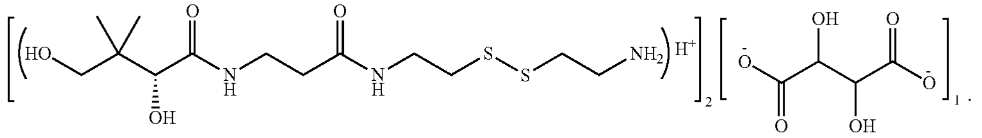

In one embodiment, the acid addition salt has the formula:

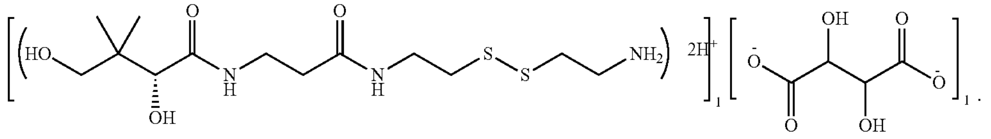

In another aspect, the invention features a method for treating a cysteamine sensitive disorder in a subject comprising administering to the subject an effective amount of any of the foregoing acid addition salts.

In particular embodiments, within 2 hours (e.g., within 30 minutes, 1 hour, 90 minutes, or 2 hours) of the administering of the dose no reducing agent is administered to the subject. In particular embodiments, between 2 hours and 8 hours after the administering of the dose a reducing agent is administered to the subject. In particular embodiments, the reducing agent is administered 3±1 hours, 4±1 hours, 5±1 hours, 6±1 hours, 7±1 hours, or 4±2 hours, after the administering of the dose of compound 1 or a pharmaceutically acceptable salt. In one embodiment, the reducing agent is selected from glutathione, glutathione diethyl ester, gamma glutamylcysteine, dihydrolipoic acid, N-acetylcysteine, homocysteine, pantetheine, 4-phosphopantetheine, dephospho-coenzyme A, coenzyme A, vitamin E, and ascorbic acid.

In particular embodiments, wherein any of the foregoing acid addition salts is formulated for immediate release. In particular embodiments, any of the foregoing acid addition salts is formulated as a powder and the dosage form is a sachet, or formulated in a bottle for resuspension in an aqueous solution suitable for drinking. In particular embodiments, a pantetheinase inducing agent selected from the group including PPAR alpha agonists, PPAR gamma agonists, or Nrf2 inducing agents is administered to the subject. In one embodiment, the pantetheinase inducing agent is an isothiocyanate present in cruciferous vegetables, a sulforaphane, S-allyl cysteine, diallyl trisulfide, oxidized fat, omega-3 fatty acids, or oleylethanolamide. In particular embodiments, within 30 minutes (e.g., 5 minutes, 10 minutes, 15 minutes, 20 minutes, 25 minutes, or 30 minutes) of administering any of the foregoing acid addition salts from 10 to 50 mg/kg (e.g., 15±5, 20±5, 25±5, 30±5, 35±5, 40±5, or 45±5 mg/kg) of cystamine, or a pharmaceutically acceptable salt thereof, is administered to the subject. In one embodiment, the cystamine, or a pharmaceutically acceptable salt thereof, is formulated for immediate release. In particular embodiments, the cystamine, or a pharmaceutically acceptable salt thereof, is administered simultaneously with the administration of any of the foregoing acid addition salts.

In particular embodiments, within 30 minutes (e.g., 5 minutes, 10 minutes, 15 minutes, 20 minutes, 20 minutes, or 25 minutes) of administering the compound 1, or a pharmaceutically acceptable salt thereof, administering to the subject a dose from 10 to 50 mg/kg (e.g., 15±5, 20±5, 25±5, 30±5, 35±5, 40±5, or 45±5 mg/kg) of compound 3:

(3)

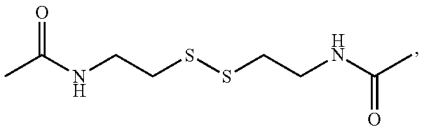

or a pharmaceutically acceptable salt thereof, is administered to the subject. Optionally, compound 3, or a pharmaceutically acceptable salt thereof, is formulated for immediate release. In particular embodiments, compound 3, or a pharmaceutically acceptable salt thereof, is administered simultaneously with the administration of compound 1, or a pharmaceutically acceptable salt thereof.

In any of the above methods, the cysteamine sensitive disorder can be selected from cystinosis; neurodegenerative disease; neurodevelopmental disease; neuropsychiatric disease; mitochondrial disease; fibrotic diseases of the kidney, of the liver, or of the lung; parasitic infection; sickle cell anemia; cancer; ischemic disease including ischemic heart disease or stroke; chronic obstructive pulmonary disease (COPD); cystic fibrosis (CF); bacterial infection; viral infection; non-alcoholic steatohepatitis (NASH); alcoholic steatohepatitis; and non-alcoholic fatty liver disease (NAFLD), or any other cysteamine sensitive disorder described herein.

In yet another aspect, the disclosure features a method of synthesizing an asymmetric disulfide, said method comprising combining: (a) 1 molar equivalent of an organic carboxylic acid, or a salt thereof; (b) from 2 to 4 molar equivalents (e.g., 2, 2.5, 3, 3.5, or 4 molar equivalents) of cystamine, or a salt thereof; and (c) an amide coupling reagent, to form a mixture comprising greater than 90% (e.g., 91%, 92%, 93%, 94%, 95%, 96%, 97%, 98%, 99%, or 99.5%) of the organic carboxylic acid, or a salt thereof, is converted to the asymmetric disulfide of formula (A) and less than 10% (e.g., 9%, 8%, 7%, 6%, 5%, 4%, 3%, 2%, 1%, or 0.5%) organic carboxylic acid remains unreacted or is converted into the symmetric disulfide of formula (B):

(A)

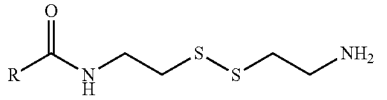

(B)

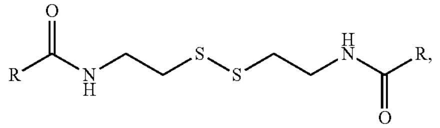

where R is an organic radical. In particular embodiments, the group R—C(O)— is a moiety of less than 1,000 Daltons, 700 Daltons, 400 Daltons, or 200 Daltons. In some embodiments, R—C(O)— is a natural or synthetic amino acid, or an ester or amide thereof.

In some embodiments, the organic carboxylic acid, or a salt thereof is selected from pantothenic acid, 4-phosphopantothenic acid, acetic acid, or salts thereof. In particular embodiments, the organic carboxylic acid, or a salt thereof is pantothenic acid or a salt thereof. In some embodiments, the amide coupling reagent is hydroxybenzotriazole. In some embodiments, the amide coupling reagent is N,N'-dicyclohexylcarbodiimide. In some embodiments, the combining is in one or more solvents selected from dichloromethane, tetrahydrofuran, acetonitrile dimethylformamide, water, and combinations thereof.

In another aspect, the disclosure features a method of synthesizing an asymmetric disulfide, said method comprising combining in an organic solvent:

(a) from 2 to 4 molar equivalents (e.g., from 2 to 2.3, from 2.2 to 3, from 2.7 to 3.3, or from 3.1 to 4 molar equivalents) of a thiol selected from cysteamine, N-acetylcysteamine, cysteine, N-acetylcysteine, N-acetylcysteine amide, or salts thereof; and (b) 1 molar equivalent of a disulfide selected from cystamine, pantethine, or salts thereof.

In some embodiments, the molar ratio of the thiol to the disulfide is about 2:1 to about 4:1 (e.g., about 2:1 to about 2.5:1, about 2.5:1 to 3.5:1, about 2.7:1 to about 3.3:1, about 2.5:1 to about 3:1, about 3:1 to about 3.5, or about 3:1 to about 3.5, to about 4:1, about 3.5:1 to about 4:1). In particular embodiments, the molar ratio of the thiol to the disulfide is about 2.5:1 to about 3.5:1 (e.g., about 2.5:1 to 2.7:1, about 2.7:1 to about 3.3:1, or about 3.3:1 to about 3.5:1). In other embodiments, the molar ratio of the thiol to the disulfide is about 2.7:1 to about 3.3:1 (e.g., about 2.7:1 to about 3.1:1 or about 3.1 to about 3.3).

In some embodiments, the thiol is N-acetylcysteamine, or a salt thereof.

In some embodiments, the disulfide is cystamine, or a salt thereof.

In some embodiments, the organic solvent is methanol or ethanol. In particular embodiments, the organic solvent is methanol.

Definitions

By "immediate release" is meant a mode of releasing the active agent (e.g. a cysteamine precursor, or a pharmaceutically acceptable salt thereof) formulated in a unit dosage form that has a dissolution release profile in a simulated gastric medium in which at least 55%, 65%, 75%, 85%, or 95% of the agent is released within the first two hours of testing using a USP compatible instrument.

By "controlled release" is meant a mode of releasing the active agent (e.g. a cysteamine precursor, or a pharmaceutically acceptable salt thereof) from the formulation thereof in a manner that permits control over either the anatomical site of release or the rate of release, or both. In general, the purpose of a controlled release formulation is to prolong the period of time during which therapeutic drug levels are present in the body (e.g. relative to an immediate release formulation), and/or to optimize delivery of drug to sites of cysteamine absorption, thereby reducing the number of doses which must be administered in a 24 hour period. Gastroretentive, delayed release, sustained release and colon-targeted formulations are all examples of controlled release formulations. A controlled release formulation may also allow a reduction in the peak concentration of drug (Cmax) relative to that observed for an immediate release formulation administered at the same dose level (i.e. a reduced cysteamine Cmax in the case of a cysteamine precursor of the invention). A controlled release formulation of an active agent may be accomplished, for example, by embedding the active agent in a matrix substance that the body is slow to dissolve or erode, such that the active ingredient slowly and regularly leeches from the coating, either by diffusion out of the matrix or by erosion of the surface of the matrix, or both, or by formation of a gel with a semipenetrable surface, wherein the drug slowly exits the semipermeable layer.

By "delayed release" is meant a pharmaceutical preparation, e.g. an orally administered formulation, which passes through the acidic environment of the stomach substantially intact and dissolves in the more basic environment of the small intestine such that the active agent (e.g., a cysteamine precursor or a pharmaceutically acceptable salt thereof) formulated in a unit dosage form has a dissolution release profile in a simulated gastric medium in which less than 25%, 20%, 15%, 10%, or 5% of the agent is released within the first hour of testing, and additionally a dissolution release profile in a simulated intestinal fluid at pH 6.0 or 6.3 or 6.5 in which at least 55%, 65%, 75%, 85%, or 95% of the agent is released within the first two hours of testing. In some embodiments, delayed release of the active agent (e.g. a cysteamine precursor, or a pharmaceutically acceptable salt thereof) results from the use of a pH-sensitive enteric coating of an oral dosage form). An enteric coating can be combined with, for example, either a rapid or a slow (sustained) release formulation, or a combination of the two, so as to extend the period of time over which drug is released.

The term "sustained release" (also referred to as "extended release" in the literature) refers to a drug formulation that provides for gradual release of a drug over an extended period of time, e.g., 6-12 hours or more, compared to an immediate release formulation of the same drug, such that the active agent (e.g., a cysteamine precursor, or a pharmaceutically acceptable salt thereof) formulated in a unit dosage form has a dissolution release profile in a simulated gastric or intestinal fluid in which at least 10-45% (i.e., 15-45%, 20-45%, 25-45%, 25-45%, 35-45%, 30-45%, or 40-45%) of the agent is released within the first three hours of testing and not less than 65%, 75%, 85%, 90%, 93%, 95%, or 97% of the agent is released within 8 hours, when in a simulated small intestinal fluid. Preferably, although not necessarily, sustained release results in substantially constant blood levels of a drug over an extended time period that are within the therapeutic range for the disease being treated. Preferably a sustained release formulation of a cysteamine precursor yields plasma cysteamine levels that fall within a concentration range that is between, for example, 5-50 μM, 5-40 μM, 5-35 μM, 5-30 μM, 5-25 μM, 5-20 μM, or 10-50 μM, 10-45 μM, 10-40 μM, 10-35 μM, 10-30 μM, 10-25 μM, or 10-20 μM.

The term "colon-targeted" refers to a formulation, or a composition, that provides for drug release in the colon (which has a much higher density of enteric flora than the small intestine), and optionally also in the distal ileum (which tends to be the most alkaline region of the gastrointestinal tract). One method for targeting drug release to the distal ileum and colon is to use a pH sensitive coating that dissolves around pH 7 (e.g. pH 6.8, pH 6.9, pH 7.0), a typical pH in the ileum. A formulation designed for pH-dependent drug release in the ileum is very likely to also release drug in the colon (especially if the drug is embedded in a sustained release matrix), and/or some of the cysteamine precursor released in the ileum may pass into the colon still in precursor form (i.e. not yet converted to cysteamine). Another type of colon-targeted formulation relies on enzymes made by enteric bacteria to degrade drug-enclosing polymers that cannot be degraded by salivary, gastric or pancreatic enzymes, thereby effecting drug delivery in the colon. The density of intestinal flora is also high in the distal ileum, so enteric flora may start digesting the polymer, and hence releasing drug, in the distal ileum. Ileum- and colon targeted formulations are collectively referred to herein as colon-targeted formulations.

The term "unit dosage form" refers to physically discrete units suitable as unitary dosages, such as a pill, tablet, caplet, hard capsule or soft capsule, each unit containing a predetermined quantity of a cysteamine precursor, or a pharmaceutically acceptable salt thereof. By "hard capsule" is meant a capsule that includes a membrane that forms a two-part, capsule-shaped, container capable of carrying a solid or liquid payload of drug and excipients. By "soft capsule" is meant a capsule molded into a single container carrying a liquid or semisolid or solid payload of drug and excipients. Granules, powders and liquids can also be provided in "unit dosage form" by using appropriate packaging. For example granules or powders can be administered in a sachet and liquids in an ampoule, vial, or plastic container.

The term "microparticles", as used herein, refers to microbeads, microspheres, micropellets, nanoparticles, nanobeads, nanospheres or other fine particles used in drug formulations wherein each microparticle is between 0.05-999 micrometers in average diameter. Tens, hundreds or thousands of such microparticles may be used in a single unit dosage form, for example they may be packed inside a capsule or formulated as a powder or suspended in a liquid.

The term an "effective amount" of an agent, as used herein, is that amount sufficient to effect beneficial or desired results in a patient, such as disease remission, and, as such, an "effective amount" depends upon the context in which it is being applied, including the age and weight of the patient, the nature of the disease, including the disease-affected organ(s), the disease status or level of activity, the sensitivity of the patient to cysteamine and other factors.

As used herein "pantetheine", "4-phosphopantetheine", "dephospho-coenzyme A" and "coenzyme A," as well as any analog or derivative convertible to one of those compounds in the gastrointestinal tract, all refer to the D enantiomer (also occasionally referred to as the R enantiomer using more recent nomenclature). Each of these compounds contains a chiral carbon in the pantothenoyl moiety which can exist in either the D (dextro) or L (levo) form, also referred to as the (R) or (S) forms, respectively. Only the D-pantetheine enantiomer is a substrate for pantetheinase, and it therefore is the only pantetheine enantiomer that is a cysteamine precursor. Similarly, only the D-enantiomers of compounds that are convertible into pantetheine, such as 4-phosphopantetheine, dephospho-coenzyme A and coenzyme A, are useful in the compositions and methods of the invention.

As used herein, "disulfide compounds" are compounds containing a sulfur atom chemically bonded to a second sulfur atom in the form: R1-S—S—R2, where R1 and R2 are organic compounds. R1 and R2 can be identical or different. Disulfide compounds are generally formed by oxidation of two thiols (i.e. R1-S—H plus R2-S—H yields R1-S—S—R2 plus $2H^+$) and can be reversibly converted back to two thiols by reduction (i.e. R1-S—S—R2 plus $2H^+$ yields R1-S—H+R2-S—H). Disulfide compounds can also be formed by reacting one or two thiols with a dithiol (e.g. R1-S—H plus R2-S—H plus H—S—R3-S—H yields R1-S—S—R3-S—S—R2 plus $4H^+$, where R1, R2 and R3 are organic compounds and $H^+$ is hydrogen ion). Disulfide compounds of the present invention are biologically active sulfur-containing compounds that encompass: 1) cysteamine mixed disulfide compounds of the formula: $C_2H_6NS$—S—R1, where R1 is an organic moiety, 2) pantetheine disulfide compounds of the formula: $C_{11}H_{21}N_2O_4S$—S—R1, where R1 is an organic moiety, 3) 4-phosphopantetheine disulfide compounds of the formula: $C_{11}H_{22}N_2O_7PS$—S—R1, where R1 is an organic moiety, 4) dephospho-coenzyme A disulfide compounds of the formula: $C_{21}H_{34}N_7O_{13}P_2S$—S—R1, where R1 is an organic moiety, 5) coenzyme A disulfide compounds of the formula: $C_{21}H_{35}N_7O_{16}P_3S$—S—R1, where R1 is an organic moiety, or 6) N-acetylcysteamine compounds of the formula: $C_4H_8NOS$—S—R1, where R1 is an organic moiety. Additional disulfides can be formed using dithiols, compounds which can form two disulfide bonds. At least one, and optionally both, disulfide bonds are with cysteamine or compounds that are degradable to cysteamine in the gastrointestinal tract. Alternatively, a dithiol is disulfide bonded to only one such compound, the second thiol of the dithiol remaining in thiol form, or the second thiol can be disulfide bonded to any thiol, including, for example any thiol listed in FIG. 17. Compounds that are degradable to cysteamine in the gastrointestinal tract include, in addition to pantetheine, 4-phosphopantetheine, dephospho-coenzyme A, coenzyme A or N-acetylcysteamine, or any analog or derivative convertible to one of those five compounds in the gastrointestinal tract (e.g. by chemical or enzymatic processes). Any such analog or derivative, herein referred to as a "suitable analog or derivative," is a thiol of the invention and may substitute for one of those five compounds. A "mixed disulfide" is a disulfide formed from two different thiols. By "cysteamine mixed disulfide" is meant a disulfide that connects cysteamine with another (non-cysteamine) thiol; by "pantetheine mixed disulfide" is meant a disulfide that connects pantetheine with another (non-pantetheine) thiol; and so forth. In general, mixed disulfides are classified by the simpler of the two constituent thiols (e.g. cysteamine-pantetheine is referred to as a cysteamine mixed disulfide). Thiols useful for forming disulfide cysteamine precursors include, e.g., L-cysteine, N-acetylcysteine, glutathione, any thiol listed in FIG. 17 and other thiols as described herein. Several exemplary mixed disulfides are illustrated in FIGS. 2 through 10. The tables in FIGS. 18-21 show how the thiols in FIG. 17 can be usefully combined to form disulfides. For brevity and clarity, the names of the two thiols that are connected via a disulfide bond are used herein to name the disulfide, rather than the formal chemical name (e.g. using IUPAC nomenclature). Thus cysteamine-pantetheine refers to a disulfide formed from those two compounds. Three important exceptions to that rule: the disulfide formed by reacting two pantetheines is commonly called pantethine, the disulfide formed by reacting two cysteines is commonly called cystine, and the disulfide formed by reacting two cysteamines is commonly called cystamine.

As used herein the terms "disulfides formed by reacting . . . " or "compound formed by reacting . . . " refer specifically to the disulfide formed between the two named thiols. For example, the disulfide formed by reacting cysteamine with pantetheine, referred to as cysteamine-pantetheine, means the heterodimer formed between a cysteamine molecule and a pantetheine molecule. This definition does not reflect what may actually occur when the two named thiols are reacted. That is, when cysteamine is reacted with pantetheine under oxidizing conditions three disulfides may be formed in varying proportions, depending on the chemical conditions: cysteamine-cysteamine (i.e. cystamine), cysteamine-pantetheine (also pantetheine-cysteamine, which is identical for the purposes of the invention) and pantetheine-pantetheine (i.e. pantethine). When the actual reaction products are meant (i.e. a mixture of three disulfides) the text clearly states that.

By "cysteamine precursor" is meant a compound that can be converted under physiological conditions into at least one cysteamine. The means of conversion include reduction in the case of cysteamine containing disulfides (i.e. cysteamine mixed disulfides), enzymatic hydrolysis in the case of pantetheinase substrates (pantetheine as well as compounds that are metabolically convertible into pantetheine in the gastrointestinal tract, such as 4-phosphopantetheine, dephospho-coenzyme A and coenzyme A and suitable analogs or derivatives thereof, or both reduction and enzymatic cleavage.

Examples of precursors include, but are not limited to, cysteamine mixed disulfides, pantetheine disulfides, 4-phosphopantetheine disulfides, dephospho-coenzyme A disulfides, coenzyme A disulfides and N-acetylcysteamine disulfides, as well as pantetheine, 4-phosphopantetheine, dephospho-coenzyme A, coenzyme A, and N-acetylcysteamine. The chemical relationship between cysteamine, pantetheine, 4-phosphopantetheine, dephospho-coenzyme A and coenzyme A (the four latter compounds being cysteamine precursors) is illustrated as follows. A homodimer of two pantetheine molecules (i.e. pantethine), or of two 4-phosphopantetheine molecules, or of two dephospho-coenzyme A molecules or of two coenzyme A molecules or of two N-acetylcysteamine molecules are also each disulfide cysteamine precursor compounds, as the constituent thiols are all cysteamine precursors.

By "suitable analogs or derivatives," in reference to the cysteamine precursors pantetheine, 4-phosphopantetheine, dephospho-coenzyme A, coenzyme A or N-acetylcysteamine, or disulfides containing any of them, is meant compounds that are convertible to pantetheine, 4-phosphopantetheine, dephospho-coenzyme A, coenzyme A or N-acetylcysteamine in the gastrointestinal tract, whether by chemical or enzymatic processes.

By "compounds convertible into pantetheine" is meant compounds such as 4-phosphopantetheine, dephospho-coenzyme A and coenzyme A which can be degraded in the gastrointestinal tract to pantetheine, and analogs or derivatives of those compounds which can be converted to the parent compound in the gastrointestinal tract.

By "constituent thiols," used in reference to a disulfide, is meant the thiol (and optionally dithiol) compounds reacted to form the disulfide.

By "cysteamine content" is meant the fraction, by weight, of a cysteamine precursor convertible to cysteamine in vivo upon chemical and/or enzymatic degradation.

The term "pharmaceutically acceptable salt," as used herein, represents those salts which are, within the scope of sound medical judgment, suitable for use in contact with the tissues of humans and animals without undue toxicity, irritation, allergic response and the like, and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds of the invention or separately by reacting the free base group with a suitable organic or inorganic acid. Representative acid addition salts include acetate, adipate, alginate, ascorbate, aspartate, benzenesulfonate, benzoate, bisulfate, bitartrate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

By "gastroretentive", "gastric-retentive" and the like is meant pharmaceutical compositions capable of residence in the stomach of a mammal, preferably a human, for prolonged periods of time, preferably as long as that of food, more preferably longer than that of food. "Gastric retention" is therefore the maintenance of a drug composition in the stomach, for a time period longer than the time it would have been retained in the stomach when delivered in a free form, e.g. within an oral delivery vehicle which is not considered gastroretentive. Gastroretentive formulations may be characterized by retention in the stomach for a period that is longer than the normal emptying time from the stomach, i.e. longer than about 2 hours, particularly longer than about 3 hours and usually more than about 4, 6, 8 or 10 hours. Gastroretentive formulations are typically retained in the stomach for about 3, 4, 6, 8, 10 or at times 18 hours or longer following ingestion with a meal. It is however noted that in accordance with the invention, retention of the controlled-release gastroretentive drug delivery system is not observed after more than 48 hours after administration to non-fasting stomach, and preferably not after 24 hours. Gastroretentive formulations include floating or buoyant formulations, swelling or expandable formulations, bioadhesive or mucoadhesive formulations, unfolding formulations and magnetic formulations, or any combination thereof. Combinations of two or more types of gastroretentive formulation are common as it has proven difficult to maintain residence in the stomach with only one gastroretentive mechanism. Gastroretentive formulations are preferably administered with a meal.

By "floating", "flotation" and "buoyant," used interchangeably, is meant a type of formulation with the ability to position the composition of the invention onto or in the proximity of the surface of the gastric contents, which is chyme in the fed state (gastric fluid in the fasting state or the post-gastric emptying state). By floating on the gastric contents the formulation has a smaller chance of being propelled through the pylorus into the duodenum during contractions of the stomach muscles, the pylorus being located at the bottom of the stomach when in a sitting or standing position. Floating formulations may consist of small (e.g. micron scale), medium (e.g. millimeter scale) or large (e.g. centimeter scale) particles. Large compositions may simultaneously work via a swellable/expandable mechanism, as explained herein. Any size formulation may simultaneously work via a mucoadhesive mechanism.

By "swelling" and "expandable", used interchangeably, is meant the ability of a composition to increase its dimensions upon contact with a fluid-containing medium such as gastric juice or chyme. Preferably, "swelling" is characterised by increasing the dimensions of the initial tablet to the size that would not readily be cleared from the stomach. Clearance from the stomach involves passage through the pylorus. The average resting diameter of the pylorus in humans varies in the fed and fasting state. In the fed state it is about 1 centimeter or less, in the fasted state about 1.28 centimeters, plus or minus 7 millimeters. Preferably the "swelling" entails increasing the dimensions of the composition to over 14 mm, over 16 mm, over 18 mm, over 20 mm or over 22 mm in at least two dimensions, but alternatively in one dimension, with second and third dimensions both being greater than 12 mm, 14 mm or 16 mm.

By "mucoadhesion", is meant the ability of a composition to adhere to the layer of mucous that lines the gastrointestinal tract. In the case of a gastroretentive formulation, mucoadhesion" refers to adhesion to the mucous layer that lines the stomach. Mucoadhesion is one of several technologies for prolonging gastric residence time, however the mucous layer of the stomach turns over continuously, albeit slowly, limiting the duration of mucoadhesion. Therefore mucoadhesion is usually combined with other gastroretentive methods to effect prolonged gastric residence time. By "bioadhesion" is meant the ability of a composition to adhere to other molecules lining the gastrointestinal tract, including molecules on the surface of enterocytes.

By "unfolding" or "shape-changing," used interchangeably, is meant the ability of a composition to unfold, uncoil, unwind, decompress or otherwise open in the stomach to transform into a composition of a size and/or geometry that does not easily pass through the pylorus, and hence is retained in the stomach for a prolonged period. Unfolding" or shape-changing formulations may be formulated inside a capsule. Ideally, but not necessarily, the dimensions of the unfolding formulation in the unfolded or unwrapped state are greater than 16 mm, 18 mm, 20 mm or 22 mm in at least two dimensions, but alternatively only in one dimension, with second and third dimensions being over 12 mm, 14 mm or 16 mm.

By "magnetic formulation" is meant a composition that contains a magnet or a disseminated magnetized material capable of interacting with an externally applied magnetic field created by a magnet or magnets located outside the body so as to effect retention of the composition in the stomach or small intestine for a prolonged period. A stomach-targeted composition is preferably retained at least as long as food is retained in the stomach, more preferably longer than food is retained. A small intestine-targeted composition is preferably retained until substantially complete drug dissolution, or until loss of adequate magnetic strength to hold the composition in place, whichever comes first. The magnet or magnetic material used must be safe for human ingestion. External magnets can also be used to position a magnet-containing pharmaceutical composition in other regions of the gastrointestinal tract, such as the colon, however in most cases a magnetic formulation is a type of gastroretentive or small intestine-targeted formulation.

As used herein, a "therapeutically-effective amount" refers to that amount that must be administered to a patient (a human or non-human mammal) in order to ameliorate a disease or modulate a biomarker that serves as a surrogate for disease activity. Clinical endpoints for different diseases, including neurodegenerative, metabolic, fibrotic, ischemic, infectious, neoplastic and hereditary diseases vary widely but are generally well known in the art. Specific biomarkers may include, for example, (i) white blood cell (WBC) cystine levels, which serve as a surrogate for disease control in patients with cystinosis; (ii) indices of cognitive, motor or emotional status may be used to measure treatment response in patients with neurodegenerative diseases, including instruments such as the Clinical Global Impressions (CGI) score, the Clinician Interview-Based Assessment of Change Plus Caregiver Input (CIBIC-Plus) the global score, the Alzheimer's Disease Cooperative Study Clinician's Global Impression of Change (ADCS-CCGIC) score, the Alzheimer's Disease Assessment Scale—Cognitive Subscale (ADAS-Cog) score, the Alzheimer's Disease Cooperative Study Activities of Daily Living Inventory modified for severe dementia (ADCS-ADLsev) score, the Mini-Mental State Examination (MMSE), the Neuropsychiatric Inventory (NPI) score, the Unified Huntington's Disease Rating Scale (UDHRS), the MATTIS test, the Hopkins Trail Making Test, categorical fluency, the Unified Parkinson's Disease Rating Scale (UPDRS) score, or the Parkinson's Disease Sleep Scale (PDSS-2) total score; (iii) biochemical measures of neurodegenerative disease activity include AD biomarkers (e.g. plasma beta-amyloid proteins) or brain-derived neurotrophic factor (BDNF) levels; (iv) indices of metabolic and fibrotic liver diseases include anatomical tests such as or liver biopsy-based measurements of hepatic fibrosis including the (NAFLD) Activity Score (NAS) and the liver fibrosis score; (v) biochemical indices of liver health including liver and adipose tissue insulin sensitivity as measured by HOMA-IR and adipo-IR indices, respectively, the serum aminotransferase and gamma-glutamyl transpeptidase (GGT) levels, the CK-18 derived fragments in blood for NAFLD, NASH, ASH or hereditary liver diseases; (vi) indices of disease status for mitochondrial diseases include the Newcastle Pediatric Mitochondrial Disease Scale (NPMDS) score as a clinical endpoint, as well as (vii) biomarkers including levels of glutathione, total serum thiols, acetoacetate, beta-hydroxybutyrate, lactate or malondialdehyde (a marker of oxidative stress). Other surrogate disease markers include modulation of an immune response, modulation of gene or protein expression or modulation of a validated radiological disease measure (e.g. assessed by X-ray, CT scan, MRI scan or PET scan). Methods of determining therapeutically effective amounts of cysteamine precursors are highly disease specific and are well known to clinicians who specialize in each of the above diseases.

As used herein, a "pharmaceutically acceptable excipient" is a natural or synthetic substance included (together with the active ingredient) in the formulation of a composition that is suitable for use in humans and/or non-human mammals without undue adverse side effects (such as toxicity, irritation or allergic response). Excipients may include, for example: anti-adherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives (including anti-oxidants), printing inks, sorbents, suspending or dispersing agents, solvents, colloid stabilizers, sweeteners, and water. The US FDA maintains a database of "inactive ingredients" which contains information on thousands of substances commonly used in formulating drugs. The database can be searched for excipients commonly used in controlled, delayed, sustained or extended release formulations. Excipients include, but are not limited to: butylated hydroxytoluene (BHT), calcium carbonate, calcium phosphate (dibasic), calcium stearate, carbomer, croscarmellose, crosslinked polyvinyl pyrrolidone, citric acid, crospovidone, cellulose derivatives including ethylcellulose, hydroxypropyl cellulose, hydroxypropyl methylcellulose or hypromellose, docusate sodium, gelatin, gelucire 43/01, lactose, magnesium stearate, maltitol, mannitol, methylcellulose, methyl paraben, microcrystalline cellulose, polyethylene glycol, poly(ethylene oxide), polyvinyl pyrrolidone, povidone, pregelatinized starch, propyl paraben, shellac, silicon dioxide, sodium carboxymethyl cellulose, sodium starch glycolate, sorbitol, starch (corn), stearic acid, sucrose, talc, titanium dioxide, vegetable oils, wax, including white, yellow or bees wax, and xylitol. Excipients may also include diluents (e.g., saline and aqueous buffer solutions), aqueous carriers, and nonaqueous carriers, for example, water, ethanol, polyols (such as glycerol, propylene glycol, polyethylene glycol, and the like), and suitable mixtures thereof, vegetable oils, such as olive oil, and injectable organic esters, such as ethyl oleate. Excipients useful for formulating compositions with particular properties are described more particularly in the Detailed Description.

By "enteric coating" is meant an agent or compound added to the formulations described herein that protects the active ingredient(s) described herein (e.g., cysteamine precursors and enhancers of cysteamine precursor degradation and absorption) as they pass through the stomach. Enteric coatings also protect the stomach from irritating pharmaceutical ingredients (e.g. cysteamine). Examples of commercial enteric coating technologies include but are not limited to: AcryIEZE, Opadry, Nutrateric and Sureteric products (Colorcon, West Point PA), Advantia Performance Specialty Coatings (International Specialty Products, Wayne NJ), Kollicoat product line (BASF Corporation, Ludwigshafen Germany), Aquacoat products (FMC BioPolymer), Eastman C-A-P (Eastman Chemical Co. Kingsman TN), Eudragit product line (Evonik Industries), and AQOAT, HP-50 and HP-55 product lines (Shin Etsu Pharma). Ashland Specialty Ingredients, Encap Drug Delivery, and Sanyo Chemical Industries, Ltd. also sell enteric coating systems. Examples of pH sensitive film forming polymers commonly used in enteric coated formulations include: (i) cellulose-based polymers such as cellulose acetate phthalate (e.g. Aquacoat CPD, FMC; C-A-P, Eastman Chemical Co.), cellulose acetate succinate, cellulose acetate trimellitate, hydroxypropylmethylcellulose phthalate, hydroxypropylmethylcellulose acetate succinate (e.g. AquaSolve, Ashland Specialty Ingredients, Wilmington DE); (ii) polymethacrylates such as poly(methacrylic acid-ethyl acrylate) (e.g. Eudragit L30D-55 and Eudragit L100-55, Evonik Industries; AcryIEZE, Colorcon; Kollicoat MAE 30 DP and Kollicoat MAE 100 P, BASF Pharma Ingredients and Services; Polyquid PA-30, Sanyo Chemical Industries) and poly(methacrylic acid-methyl methacrylate) in 1:1 and 1:2 ratios; (iii) polyvinyl derivatives such as poly(vinyl acetate) phthalate (e.g. Sureteric, Colorcon); and (iv) other copolymers such as half esters of the copolymer of styrene and maleic acid, half esters of the copolymer of vinyl ether and maleic acid, and copolymers of vinyl acetate and crotonic acid. Enteric coatings are also made using shellac (e.g. PROTECT, Sensient Pharmaceutical Coating Systems) or sodium alginate and zein (Encap Drug Delivery). Hydroxypropylmethylcellulose is also referred to as hypromellose or HPMC. Examples of other excipients commonly used in enteric coated formulations include: wet microcrystalline cellulose, wet powdered cellulose, gellan gum, and stearic acid. Enteric coatings can be applied to a variety of formulations, including tablets, capsules and microparticles.

As used herein, "combination therapy" means that the patient (or non-human mammal) in need of treatment according to the present invention, is given medication not herein fully described, or in some cases not contemplated, in addition to that herein disclosed. Combination therapy can be sequential (before or after) or simultaneous with the cysteamine precursor therapies of the invention.

By "treating" is meant subjecting a patient to a management regimen for the purpose of treating a disease or disorder and obtaining beneficial or desired results, such as amelioration of disease signs or symptoms or improvement in biochemical, radiological, behavioral or physical markers of disease activity or disease status. Examples of beneficial or desired results can include, but are not limited to resolution of inflammation, resolution of biochemical imbalances, improvement in quality of life, improvement in cognitive and behavioral status, improvement in motor function, improvement in emotional and mood status, sleep improvement, or more generally alleviation or amelioration of one or more symptoms or conditions; diminishment of extent of disease; stabilization of a state of disease; prevention of spread of disease; delay or slowing the progress of the disease; amelioration or palliation of a disease, disorder, or condition; and partial or complete remission of a significant disease manifestation.

The term "mammals" is intended to mean both human and non-human mammals.

By "delivering" is meant providing and/or administering the active ingredient(s) described herein by oral administration of tablets, capsules, liquids, powders, granules, microparticles, sachets, suppositories, etc. (collectively referred to as "pharmaceutical compositions," or just "compositions") which contain the active ingredient(s) and (optionally) one or more carriers and/or diluents and/or adjuvants or other excipients. The compositions may be provided with instructions for delivery including explanation of any color coding or alphanumeric text on the surface or packaging of the compositions, as well as instructions regarding whether the compositions should be ingested at certain times of day, or with food (e.g. specific types or amounts of food), liquids, a meal (including details about the type of meal) or other medications, and whether the patient should remain upright or sitting for some period of time after drug administration.

Several disease acronyms, gene names and other medical terms are represented by abbreviations. Disease acronyms include MELAS (Mitochondrial Encephalomyopathy, Lactic Acidosis, and Stroke-like episodes) and MERFF (Myoclonic Epilepsy with Ragged Red Fibers). Gene names include POLG, which encodes the catalytic subunit of DNA polymerase gamma, a mitochondrial DNA polymerase; OCT1, OCT2 and OCT3, which code for organic cation transporters 1, 2 and 3 (also known as SLC22A1, SLC22A2 and SLC22A3, respectively); PANK2, which encodes pantothenate kinase 2; VNN1 which encodes vanin 1, also known as pantetheinase; VNN2 which encodes vanin 2, also known as GPI-80 and also a pantetheinase.

As used herein "cysteamine sensitive disease" means a disease for which there is evidence that cysteamine can be an effective treatment. The evidence may be derived from either clinical or preclinical studies of disease in mammals (e.g. humans, dogs, mice, rats, monkeys, rabbits), or from in vitro studies of disease mechanisms. Cysteamine sensitive diseases constitute a broad, heterogeneous group of diseases with widely varying manifestations and pathogenesis. Diseases and disorders for which there is evidence of cysteamine efficacy may be classified according to pathogenesis, with the important caveat that the mechanism of cysteamine efficacy is not always clear and there may be unknown mechanisms of action. Important categories of cysteamine sensitive diseases include (i) disorders of cystine transport, among which cystinosis is the best known; (ii) disorders associated with oxidative damage, including neurodegenerative and liver diseases; (iii) disorders associated with pathological enzyme activity, including neurodegenerative diseases, hereditary mitochondrial diseases, diseases associated with mutant MECP2 and POLG; (iv) fibrotic disorders, including fibrosis of the kidney, liver or lung; (v) metabolic disorders, including metabolic syndrome X, diabetes and the spectrum of non-alcoholic fatty liver disease, culminating in non-alcoholic steatohepatitis (NASH); (vi) infectious diseases, including certain viral infections (e.g. influenza), bacterial infections (e.g. *Pseudomonas aeruginosa*) and parasite infections (e.g. malaria; (vii) ischemic diseases, including ischemis-reperfusion injury of the heart and other organs; (viii) diseases associated with abnormal adiponectin metabolism; and (ix) cancer as well as amelioration of the deleterious effects of cancer therapy.

As used herein, the term "about" means ±20% of the recited value.

BRIEF DESCRIPTION OF THE DRAWINGS

FIG. 2 depicts two chemical structures of disulfides of the invention. The chemical structure at the top depicts a mixed cysteamine disulfide molecule, with cysteamine on the left and a second thiol (depicted R—S—) on the right. The chemical structure at the bottom depicts a pantetheine disulfide, with pantetheine on the left and a second thiol (depicted R—S—) on the right. FIGS. 3, 4 and 5 show exemplary mixed cysteamine disulfides. Other mixed cysteamine disulfides can be formed with the thiols listed in FIG. 17, as shown schematically in FIGS. 18 and 21.

FIG. 3 depicts four chemical structures of exemplary cysteamine mixed disulfides. Specifically, mixed cysteamine disulfides are shown with the partner thiols allyl mercaptan, L-cysteine, L-cysteine ethyl ester and N-acetylcysteine, as indicated in the labels.

FIG. 4 depicts two chemical structures of exemplary cysteamine mixed disulfides and one chemical structure of an exemplary N-acetylcysteamine mixed disulfide. The two cysteamine mixed disulfides are formed between cysteamine and N-acetylcysteamine and cysteamine and N-acetylcysteine amide. Also shown is a mixed disulfide formed between N-acetylcysteamine and N-acetylcysteine amide (as indicated in labels).

FIG. 5 depicts two chemical structures of exemplary cysteamine mixed disulfides formed between cysteamine and pantetheine and between cysteamine and glutathione, as indicated in labels.

FIG. 7 depicts two chemical structures. At the top is an exemplary pantetheine mixed disulfide formed between pantetheine and cysteine. At the bottom is an exemplary N-acetylcysteamine mixed disulfide formed with pantetheine.

FIG. 8 depicts the chemical structures of two exemplary mixed disulfides, one formed between pantetheine and N-acetylcysteine, the other formed between the dithiol dihydrolipoic acid and two cysteamines (one disulfide bonded to each of the two thiols of dihydrolipoic acid), as indicated in the labels.

FIG. 11 is a schematic representation of part of the coenzyme A, pantetheine and cysteamine metabolic pathways, including both intracellular metabolism (solid lines) and catabolic reactions that occur in the gastrointestinal tract (dotted lines). Some reactions occur in both locations (e.g. phosphatases are present in the cytoplasm and the gastrointestinal lumen). Compounds are named in regular type, enzymes in italic type. Both the compounds and enzymes have a variety of alternative names to those shown in the Figure. This Figure is not a complete rendering of coenzyme A, pantetheine and cysteamine metabolism, but intended merely to convey that coenzyme A, dephospho-coenzyme A, 4-phosphopantetheine and pantetheine can be catabolized to cysteamine (and pantothenate) in the gut.

FIG. 12 depicts the anatomy of the gastrointestinal (GI) tract in schematic form (top). Below that is a table that summarizes, for each segment of the GI tract, certain anatomical and physiological parameters relevant to the in vivo generation and uptake of cysteamine from the cysteamine precursors of the invention. In particular, the table indicates the anatomical sites where cysteamine formation and uptake occur and the levels of physiological variables that affect the rates of in vivo generation of cysteamine from cysteamine precursors (e.g. via disulfide bond reduction and pantetheinase cleavage), and the rate of cysteamine absorption along the GI tract (e.g. by organic cation transporters 1, 2 and 3). For example, pH influences disulfide exchange reactions. The level of glutathione (GSH) is a proxy for the redox environment, which influences the equilibrium between oxidized and reduced forms of disulfides and thiols, including the reduction of disulfide cysteamine precursors. The absorptive surface area and transit time, together with the levels of pantetheine digesting enzymes and cysteamine transporters influence the rates of cysteamine production from pantetheine and subsequent cysteamine absorption. Other physiological variables in the figure influence the performance of certain types of formulations. For example some types of gastroretentive formulations swell to a size that prevents passage through the pylorus; some pH sensitive pharmaceutical coatings dissolve around pH 5.5, pH 6 or pH 6.5 in the duodenum, while other coatings dissolve around pH 7, which is more typical of the ileum; some types of colon-targeted formulations are composed, in part, of polymers which are refractory to digestion by human (or mammalian) enzymes but can be degraded by enzymes produced by enteric bacteria, thereby effecting release of cysteamine precursors co-formulated with said polymers. The values or ranges provided in the table are from literature sources, but may not encompass the full range of normal human variation. Nonetheless, the degree of variation indicated may, in part, account for the extensive inter-individual variation in cysteamine uptake and metabolism observed clinically.

FIG. 13 is a table showing a classification of cysteamine precursors and some of their salient pharmacological properties. The cysteamine precursors are classified on the left (bottom) side of the table according to whether (i) they are thiols or disulfides, (ii) if disulfides, whether they are cysteamine-containing mixed disulfides (including cysteamine-pantetheine), pantetheine-containing disulfides (except cysteamine-pantetheine), or contain other thiols degradable to pantetheine in the gastrointestinal tract, and (iii) how many cysteamines are generated upon chemical reduction and/or enzymatic degradation (under the #symbol). By "other thiol or dithiol" is meant any dithiol, as well as any thiol that is not cysteamine, pantetheine, 4-phosphopantetheine, dephospho-coenzyme A, coenzyme A or N-acetylcysteamine. (See FIG. 17 for exemplary thiols and dithiols). The number of cysteamines generated from degradation of disulfide cysteamine precursors containing "other thiols" is one, however disulfide cysteamine precursors containing dithiols can yield one or two cysteamines upon degradation because one dithiol can bind, for example, two cysteamines (see Table 21 for a summary of how thiols and dithiols can be combined). The table further shows, under "Steps to generate cysteamine," what chemical and/or enzymatic steps are required to generate cysteamine from each class of cysteamine precursors. For example, a cysteamine mixed disulfide containing cysteamine plus another thiol (e.g. cysteine) requires only one step: disulfide bond reduction. Similarly the thiol pantetheine requires only one step: pantetheinase cleavage. Other cysteamine precursors require two steps. For example the pantetheine homodimer pantethine requires disulfide bond reduction followed by pantetheinase cleavage. Still other cysteamine precursors require three or more steps. For example a 4-phosphopantetheine homodimer requires disulfide bond reduction, phosphatase cleavage and pantetheinase cleavage. Dephospho-coenzyme A and coenzyme A containing disulfides require additional steps. In some disulfide cysteamine precursors the number of degradative steps to cysteamine differs between the two thiols produced by disulfide bond reduction, as shown in the table. The table further shows classes of compounds that can be co-formulated or co-administered with cysteamine precursors to enhance in vivo generation of cysteamine, and shows which class(es) of enhancers are useful for each class of cysteamine precursors. For example, any disulfide cysteamine precursor can be productively co-formulated or co-administered with a reducing agent (abbreviated RA in the table) to promote disulfide bond reduction. A cysteamine precursor that is, or that includes, a pantetheine, or any thiol that can be degraded to pantetheine, can be productively co-formulated or co-administered with an inducer of the enzyme pantetheinase (abbreviated PI in the table). A pantetheine disulfide can be productively co-formulated or co-administered with both a reducing agent and a pantetheinase inducer. Not shown in the table are enhancers of cysteamine absorption (e.g. inducers of cysteamine transporters such as the organic cation transporters), or inhibitors of cysteamine catabolism, because such compounds may be productively co-formulated or co-administered with all classes of cysteamine precursor. At the far right (top) the table summarizes in a few words the salient pharmacological properties of the different classes of cysteamine precursors, which may be influenced by the number of degradative steps required to generate cysteamine, the yield of cysteamines, or the presence of enhancers of in vivo cysteamine generation. The very brief descriptions provided are not complete, and should not be construed as limiting.

FIG. 17 is a list of exemplary thiols and dithiols that either are thiol-type cysteamine precursors (compounds 2-6) or that can be combined to make disulfide-type cysteamine precursors. The chemical formula, the Chemical Abstracts Service (CAS) registry number and the formula molecular weight for each thiol or dithiol is shown. In some cases the CAS number is specific to a particular enantiomer. Each thiol is numbered (in the far left column of FIG. 17) to facilitate concise reference to these thiols in FIGS. 18-21.

FIG. 18 contains two tables that show how the thiols and dithiols in FIG. 17 can be combined to make two classes of disulfide cysteamine precursors: cysteamine mixed disulfides and pantetheine disulfides. The five columns in each of the two tables lists, from the left:

Figure 1:
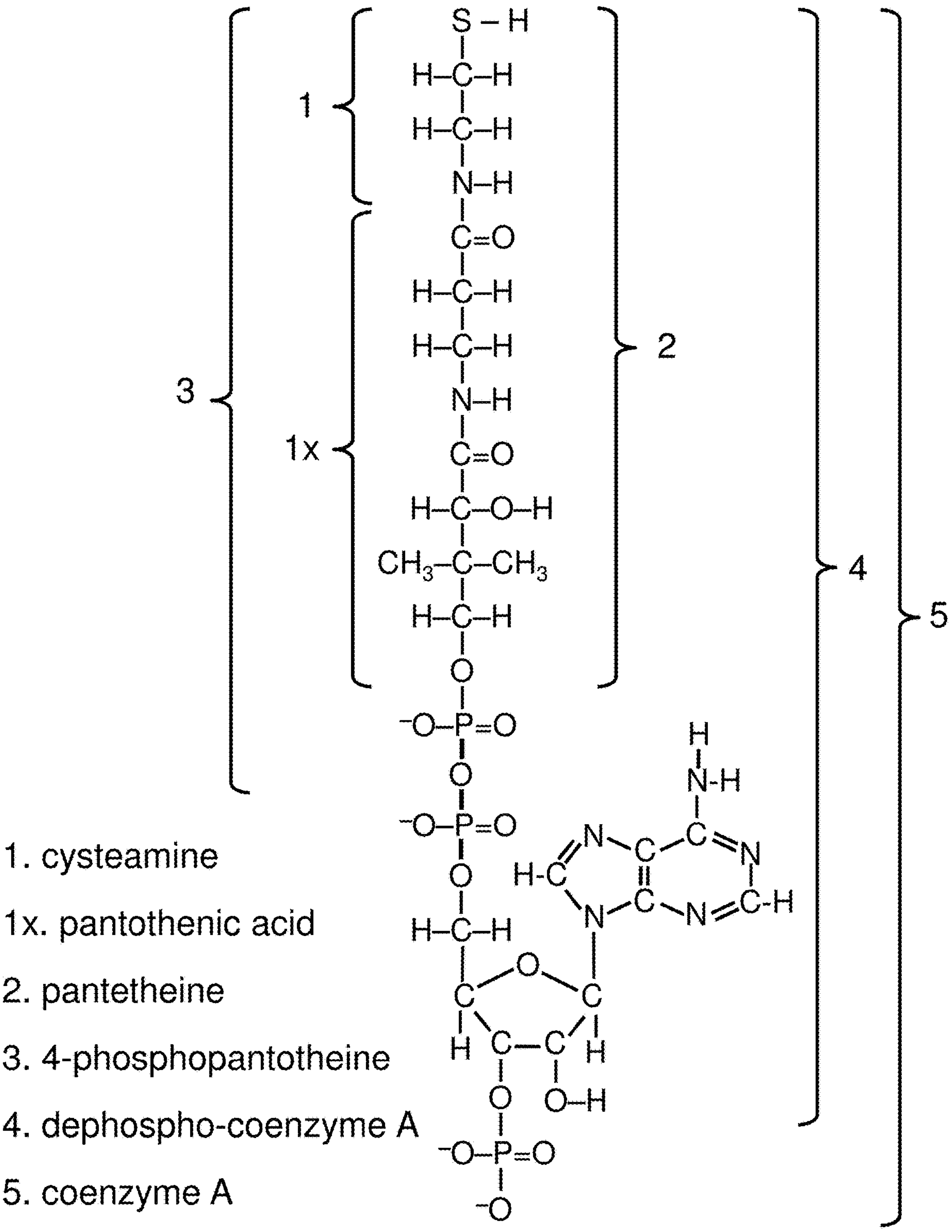
FIG. 1 depicts a chemical structure of coenzyme A, from which a dephospho-coenzyme A, molecule, 4-phosphopantetheine molecule, pantetheine molecule, pantothenic acid molecule, or a cysteamine molecule may be derived by enzyme catalyzed reactions (shown in FIG. 11).
Figure 6:
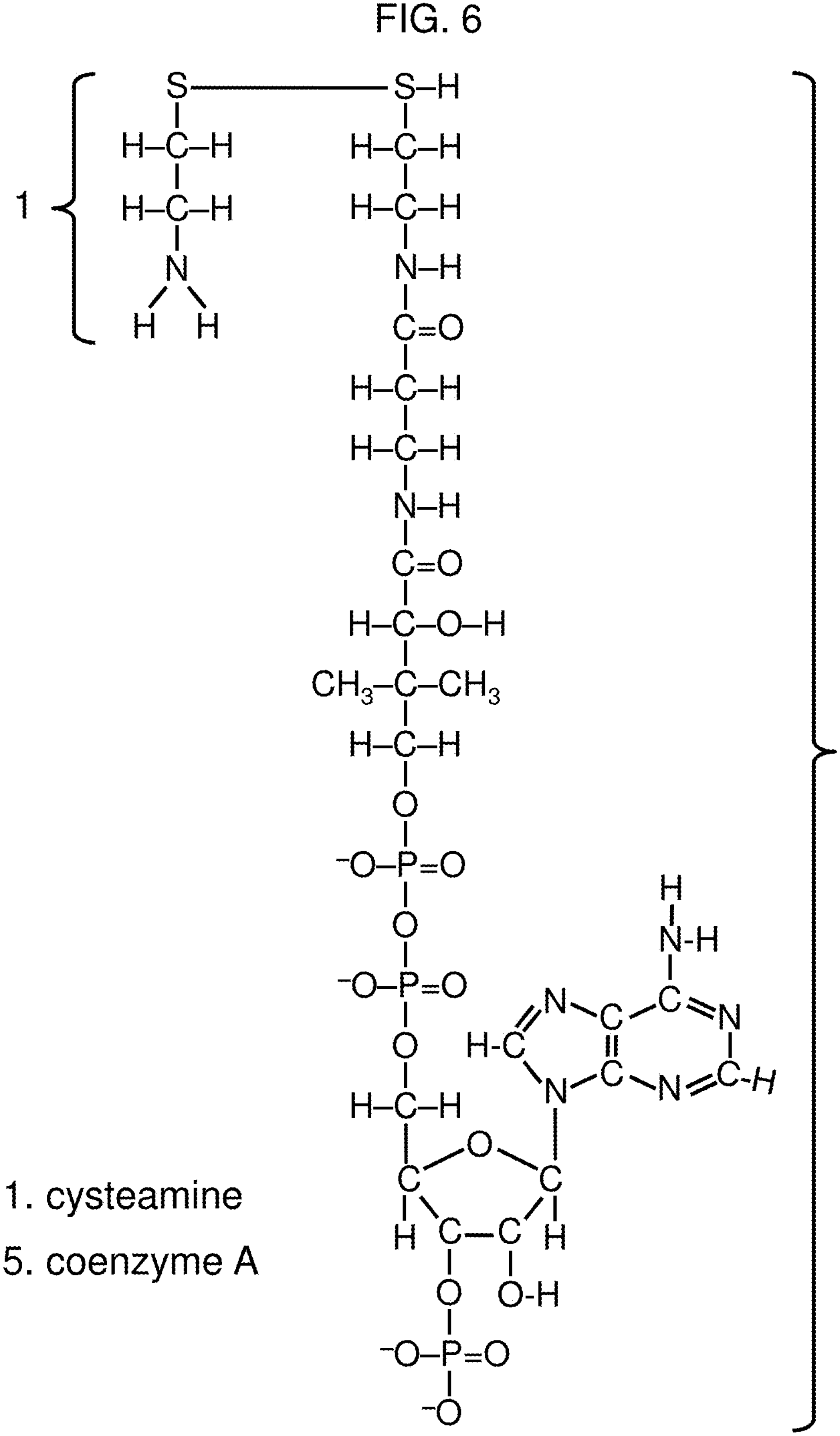
FIG. 6 depicts the chemical structure of an exemplary cysteamine mixed disulfide formed between cysteamine and coenzyme A.
Figure 9:
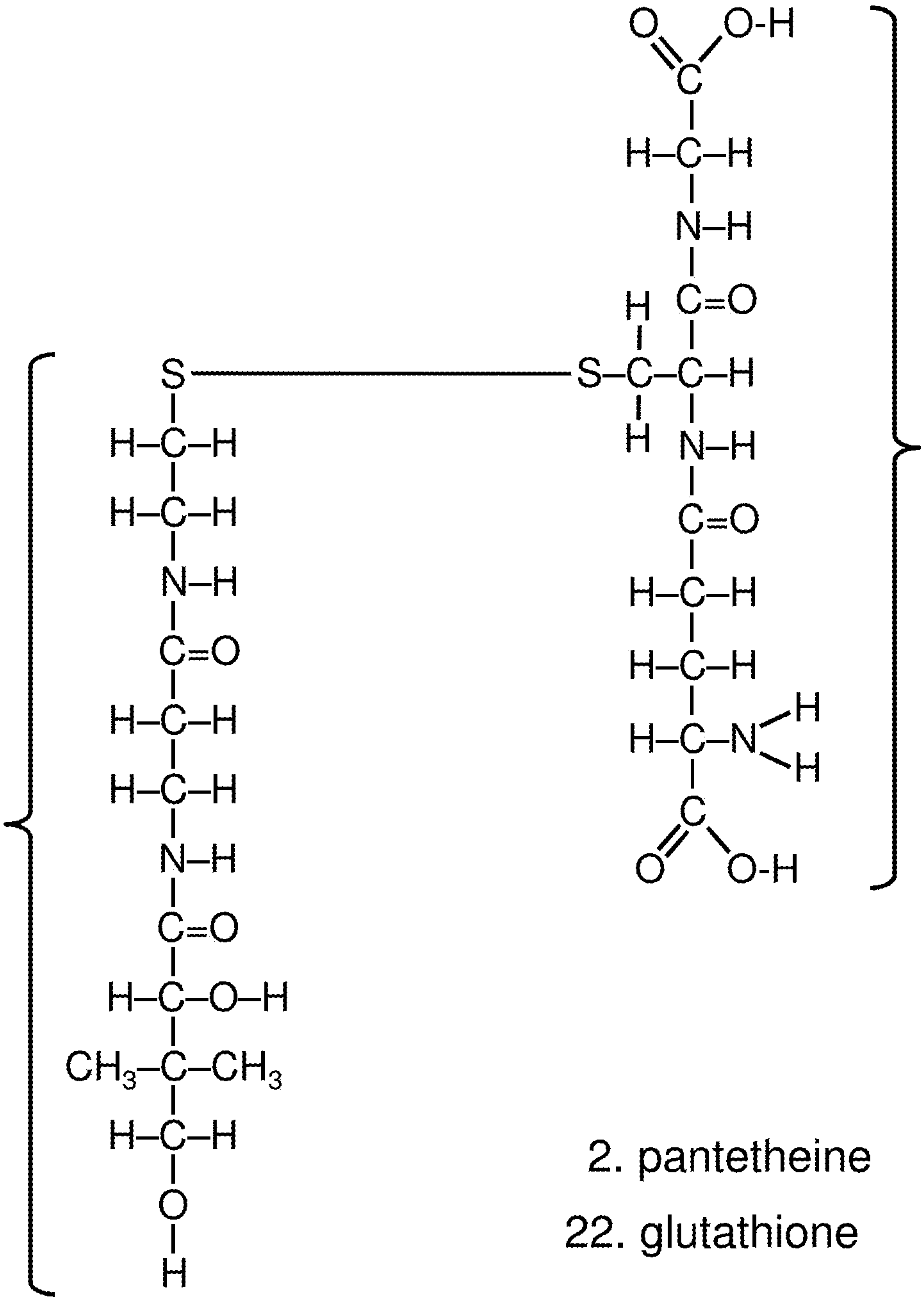
FIG. 9 depicts a chemical structure of an exemplary pantetheine mixed disulfide formed between pantetheine and glutathione.
Figure 10:
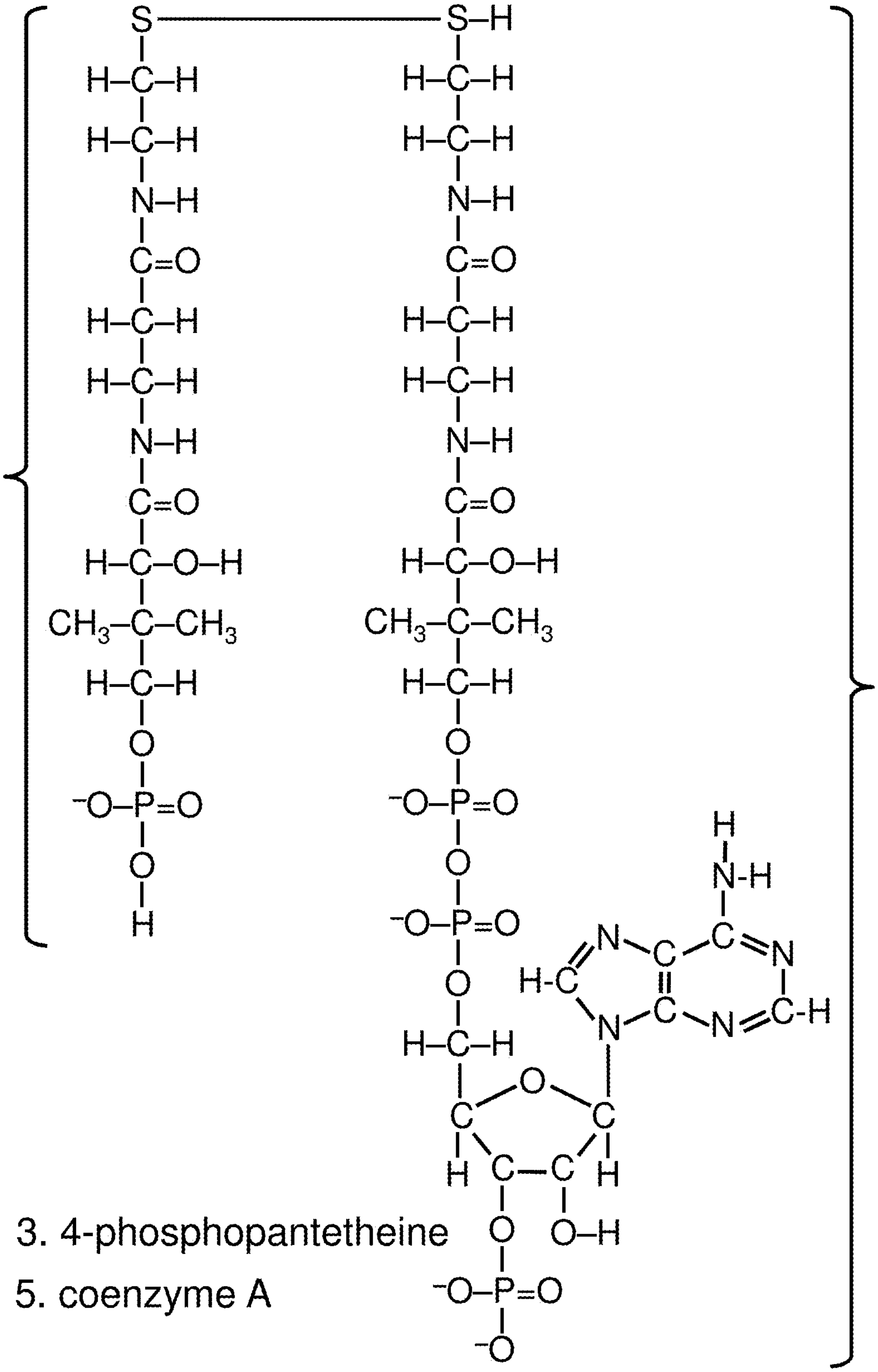
FIG. 10 depicts a chemical structure of an exemplary 4-phosphopantetheine mixed disulfide formed between 4-phosphopantetheine and coenzyme A.

(i) The two thiols reacted to form a disulfide, which are referred to by the numbers in the far left column of FIG. 17 (thiols are numbered 1-29 and dithiols 30-35). Thus, for example, the notation: "1+28" represents the disulfide formed by reacting thiol 1 (cysteamine) with thiol 28 (tiopronin). All of the disulfides in the left table comprise cysteamine (compound 1) plus a second thiol (any of compounds 2 through 35). All of the disulfides in the right table comprise pantetheine (compound 2) plus a second thiol (any of compounds 2 through 35).

(ii) The formula molecular weight (MW) of the disulfide represented in the first column; for example the MW of the disulfide 1+28 is 238.35 Daltons (the sum of the masses of the two constituent thiols minus 2 to account for the two lost protons). Note that in the case of thiols 13 and 14 (L-cysteine ethyl ester HCl and L-cysteine methyl ester HCl) the mass of the salt form is used. The actual mass of the free disulfide is 36.46 Daltons less than the mass shown.

(iii) The number of cysteamines that can be produced upon degradation of the cysteamine precursor in vivo. The disulfides are sorted, with those yielding two cysteamines listed above the bold horizontal line and those yielding one cysteamine below.

(iv) The fraction of the cysteamine precursor convertible to free cysteamine in vivo. For example, the fraction of the 238.35 Daltons of disulfide 1+28 that can be converted to cysteamine is 32.4%. The disulfides that yield one cysteamine are ranked, from high to low, by the fraction of their molecular weight convertible to cysteamine.

(v) The number of degradative steps (chemical or enzymatic) required to yield cysteamine from the disulfide cysteamine precursor. For disulfides above the horizontal bold line, in which both thiols are degradable to cysteamine (or one of the two thiols is cysteamine itself) two numbers are provided, showing the number of steps for each thiol constituent of the disulfide. The order of the two numbers corresponds to the order in which the two thiols are listed in the first column of the table. For disulfides in which only one of the thiols is degradable to cysteamine (below the horizontal bold line) only one number is shown, indicating the number of degradative steps for that thiol. For example, in Disulfide Table 1B the disulfide represented "2+5" signifies pantetheine (thiol 2) disulfide bonded to coenzyme A (thiol 5). The MW of this disulfide is 1,352.36. Upon degradation in the gut this disulfide yields two cysteamines. The two cysteamines together weigh 154.3 Daltons, which is 11.4 percent of the mass of the disulfide, as shown in column 4. The degradative pathway from the disulfide to two cysteamines comprises two steps in the case of the pantetheine moiety (step 1: disulfide bond reduction, step 2: pantetheinase cleavage) and four or more steps (indicated 4+) in the case of the coenzyme A moiety (step 1: disulfide bond reduction, step 2: ectonucleotide diphosphatase catalyzed detachment of the nucleotide (other catabolic pathways are possible), step 3: dephosphorylation to pantetheine, step 4: pantetheinase cleavage). Thus the numbers: 2/4+ in column 5 indicate the number of degradative steps from the disulfide to cysteamine for the pantetheine and coenzyme A moieties, respectively.

FIG. 19 contains two tables that show how the thiols and dithiols in FIG. 17 can be combined to make two classes of disulfide cysteamine precursors: 4-phosphopantetheine disulfides and dephospho-coenzyme A disulfides. The five columns in each of the two tables provide the same information as in FIG. 18. Again, note that in the case of thiols 13 and 14 (L-cysteine ethyl ester HCl and L-cysteine methyl ester HCl) the mass of the salt form is used. The actual mass of the free disulfide is 36.46 Daltons less than the mass shown.

FIG. 20 contains two tables that show how the thiols and dithiols in FIG. 17 can be combined to make two classes of disulfide cysteamine precursors: coenzyme A disulfides and N-acetylcysteamine disulfides. The five columns in each of the two tables provide the same information as in FIG. 18. Again, note that in the case of thiols 13 and 14 (L-cysteine ethyl ester HCl and L-cysteine methyl ester HCl) the mass of the salt form is used. The actual mass of the free disulfide is 36.46 Daltons less than the mass shown.

FIG. 21 contains two tables that show how a dithiol can be joined to two thiols to make a disulfide capable of yielding two cysteamines (top table) or one cysteamine (bottom table) upon degradation in vivo. The numbering of thiols and dithiols is as in FIG. 17. Within each table various possible dithiol-thiol-thiol combinations are grouped by dithiol moiety (compounds 30-35) for concision, and the molecular weight and cysteamine yields for each group are provided as ranges. Three exemplary dithiol-thiol-thiol combinations are shown at the bottom of each table, and include specific MW, percent of MW convertible to cysteamine and number of degradative steps to cysteamine (see explanation of FIG. 18, above). Additional details are provided in explanatory text below the two tables.

FIG. 22 illustrates the initial thiol activation step used in the chemical synthesis of mixed (asymmetric) disulfides.

Figure 23:
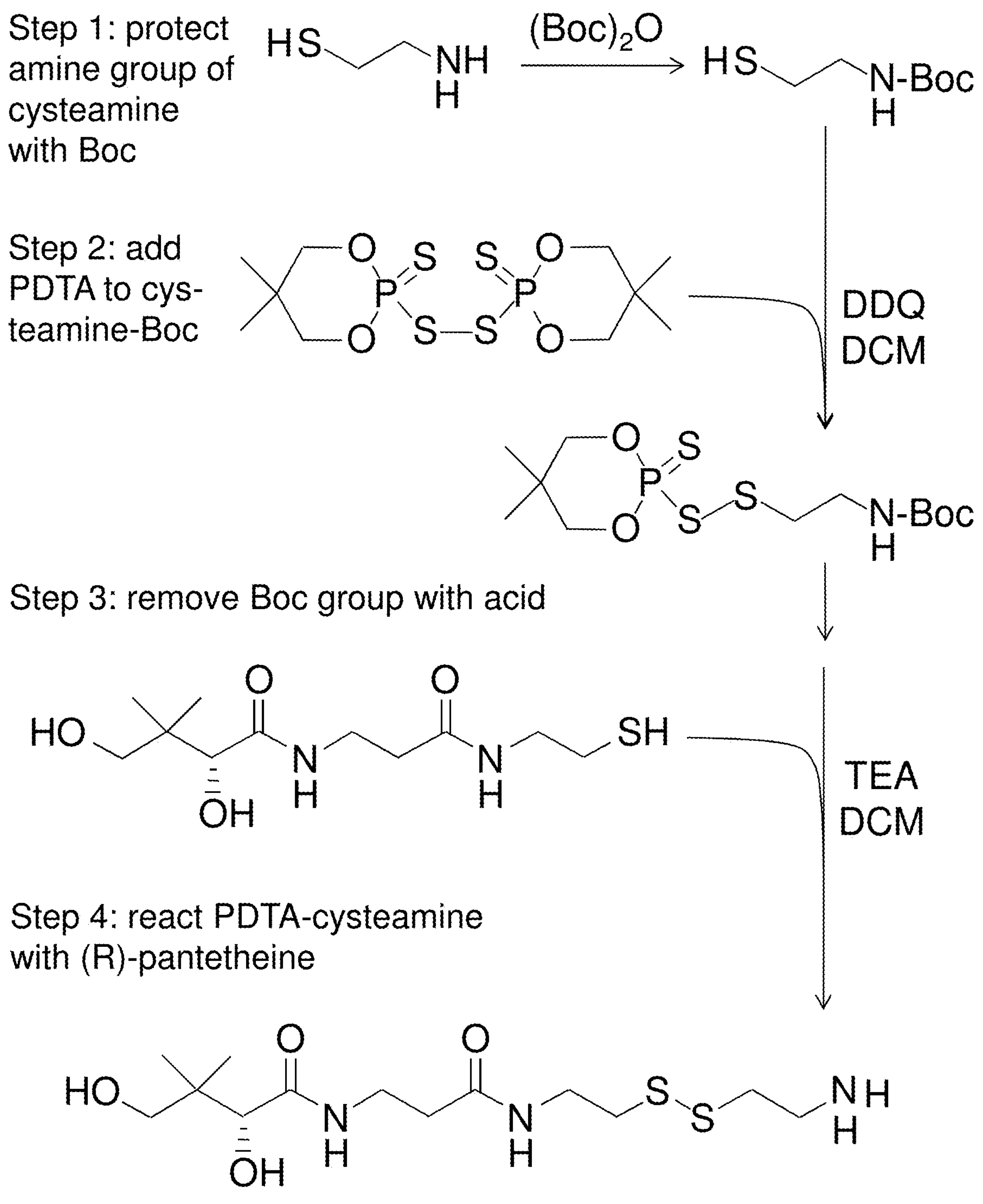

FIG. 23 illustrates one synthetic scheme used to make cysteamine-pantetheine disulfide (referred to as TTI-0102, where 01 refers to cysteamine, which is thiol 1 in FIG. 17, and 02 refers to pantetheine, which is thiol 2 in FIG. 17). The primary amine of cysteamine is first protected with tert-butyloxycarbonyl (Boc), then the —SH of cysteamine-Boc is activated with bis(5,5-dimethyl-2-thioxo-1,3,2-dioxaphosphorinan-2-yl)disulfane (referred to by the shorthand PDTA) in the presence of 2,3-dichloro-5,6-dicyanobenzoquinone (DDQ), in dichloromethane (DCM). Then the Boc group is removed with acid and the activated cysteamine is reacted with (R)-pantetheine.

Figure 24:
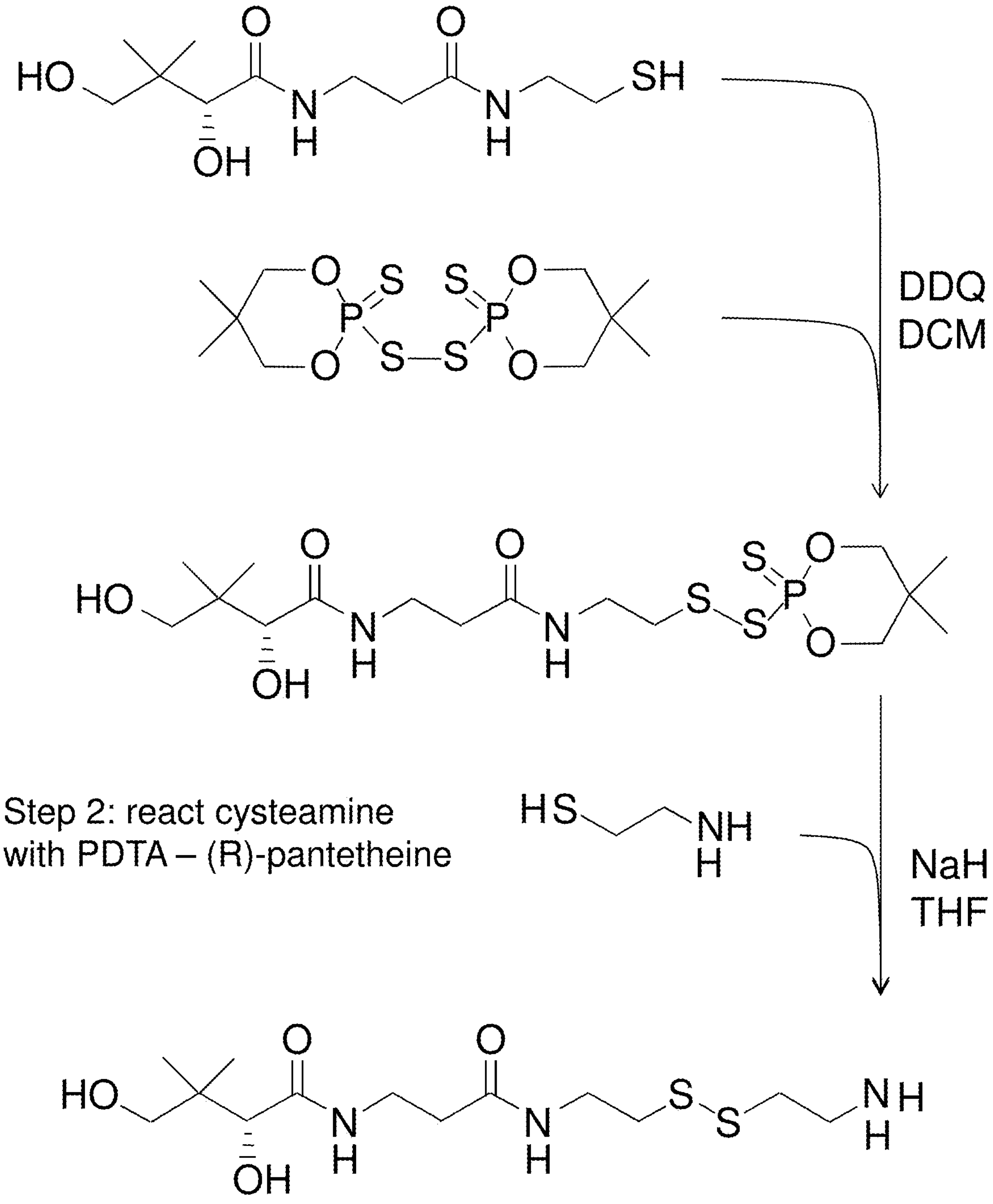

FIG. 24 illustrates a second synthetic scheme used to make cysteamine-pantetheine disulfide (TTI-0102). (R)-pantetheine is activated with bis(5,5-dimethyl-2-thioxo-1,3,2-dioxaphosphorinan-2-yl)disulfane (referred to by the shorthand PDTA) in the presence of 2,3-dichloro-5,6-dicyanobenzoquinone (DDQ), in dichloromethane (DCM). Then the activated (R)-pantetheine is reacted with cysteamine in sodium hydride (NaH) and tetrahydrofuran (THF).

FIG. 25 illustrates the synthetic scheme used to make N-acetylcysteamine-pantetheine disulfide (referred to as TTI-0602, where the numbers 6 and 2 refer to the two combined thiols, as numbered in FIG. 17). N-acetylcysteamine is activated with bis(5,5-dimethyl-2-thioxo-1,3,2-dioxaphosphorinan-2-yl)disulfane (PDTA) in the presence of 2,3-dichloro-5,6-dicyanobenzoquinone (DDQ), in dichloromethane (DCM). Then the activated N-acetylcysteamine is reacted with (R)-pantetheine in triethanolamine (TEA) in DCM.

Figure 26:
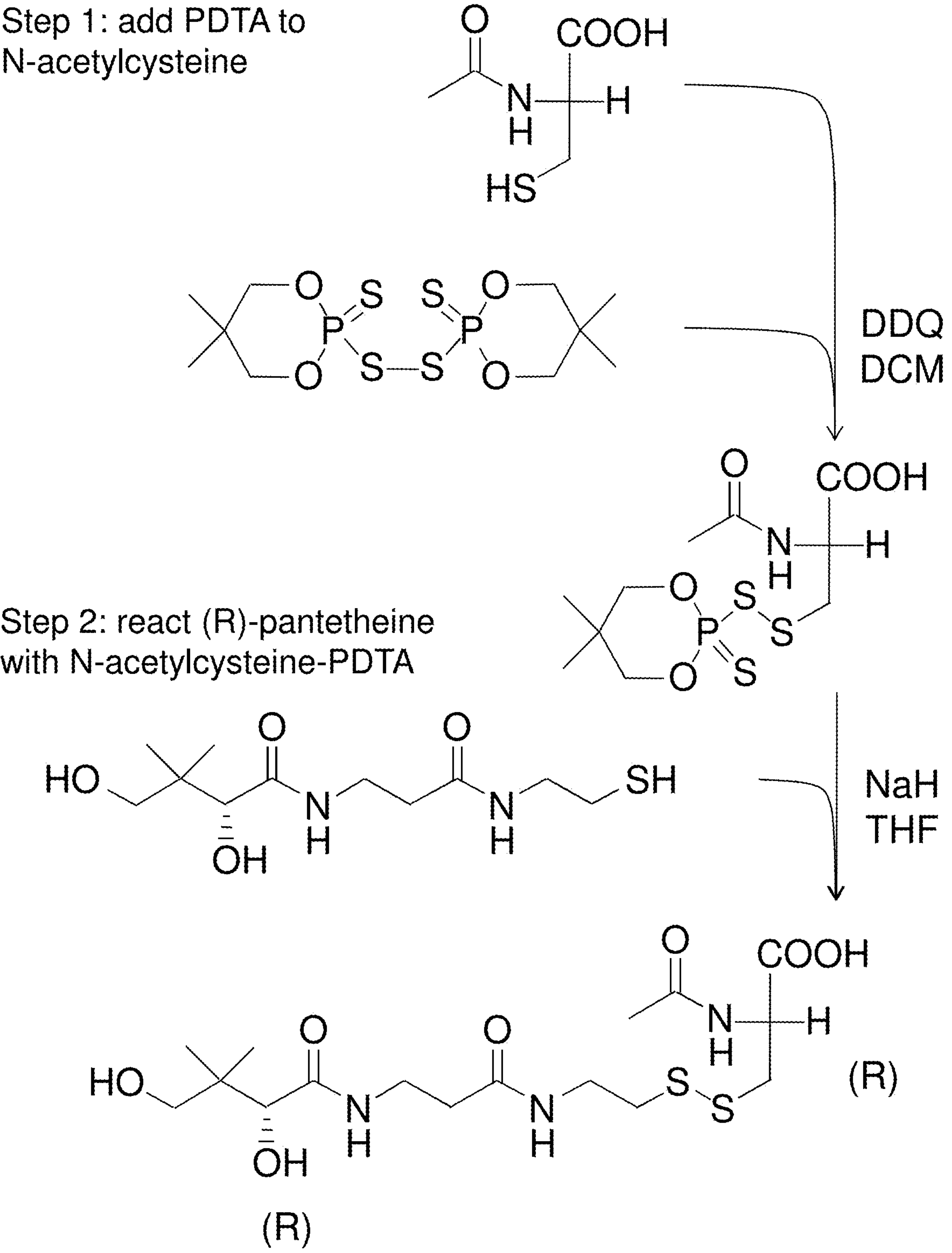

FIG. 26 illustrates the synthetic scheme used to make N-acetylcysteine-pantetheine disulfide (referred to as TTI-1502, where the numbers 15 and 2 refer to the two combined thiols, as numbered in FIG. 17). N-acetylcysteine is activated with bis(5,5-dimethyl-2-thioxo-1,3,2-dioxaphosphorinan-2-yl)disulfane (PDTA) in the presence of 2,3-dichloro-5,6-dicyanobenzoquinone (DDQ), in dichloromethane (DCM). Then the activated N-acetylcysteine is reacted with (R)-pantetheine in sodium hydride (NaH) and tetrahydrofuran (THF).

Figure 27:
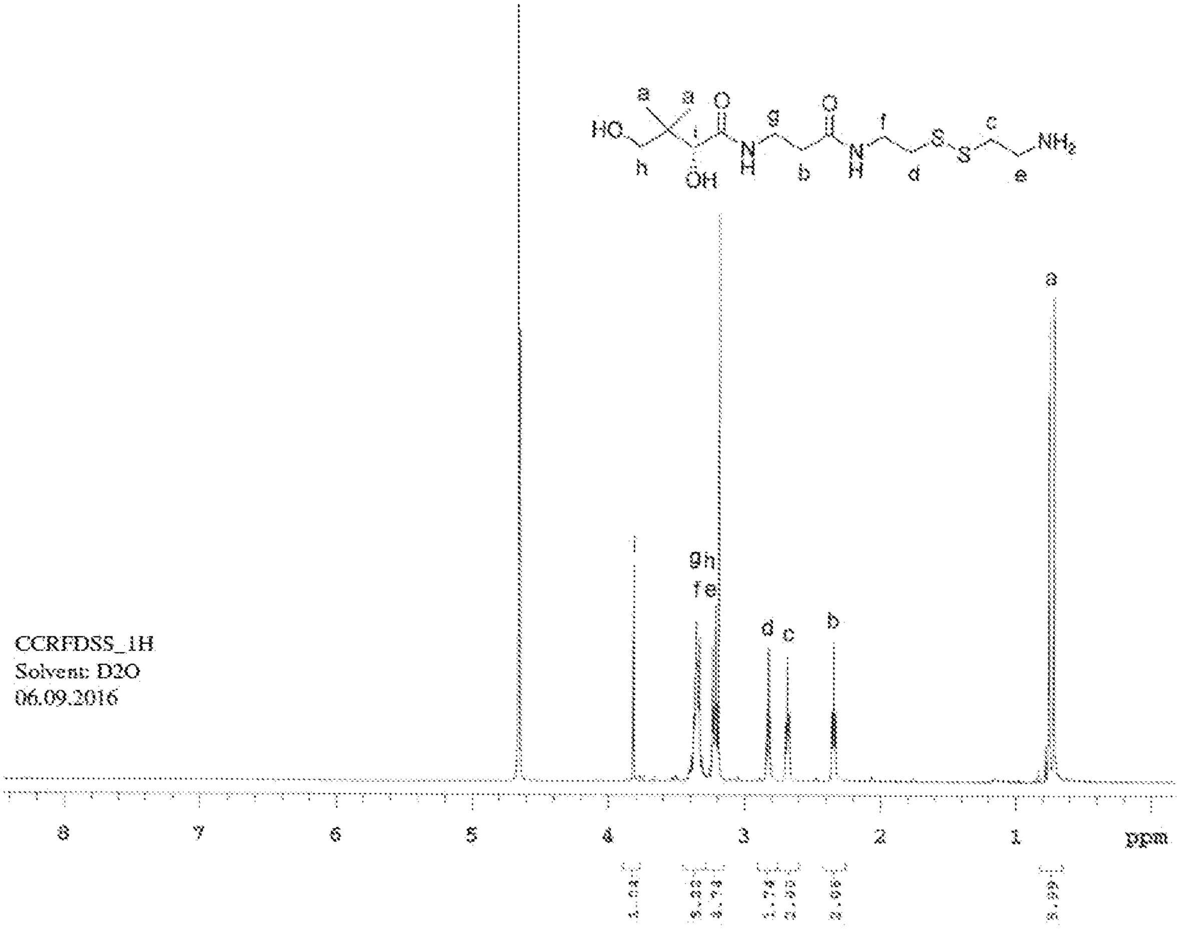

FIG. 27 contains the nuclear magnetic resonance (NMR) spectrum of TTI-0102, obtained on a Varian INOVA 500. The inset structure of TTI-0102 is annotated with letters a through i to indicate specific bonds, which are also highlighted on the NMR spectrum.

Figure 28:
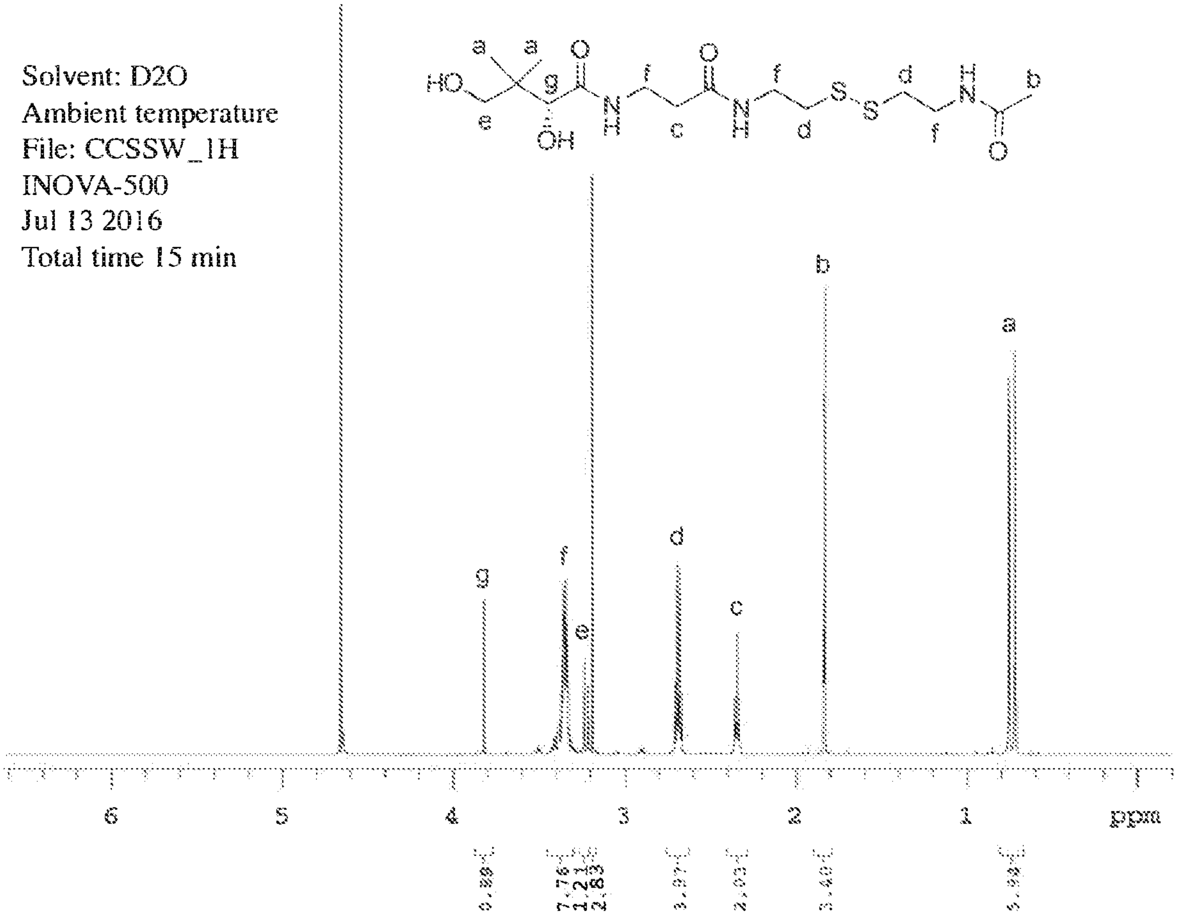

FIG. 28 contains the nuclear magnetic resonance (NMR) spectrum of TTI-0602, obtained on a Varian INOVA 500. The inset structure of TTI-0602 is annotated with letters a through g to indicate specific bonds, which are also highlighted on the NMR spectrum.

Figure 29:
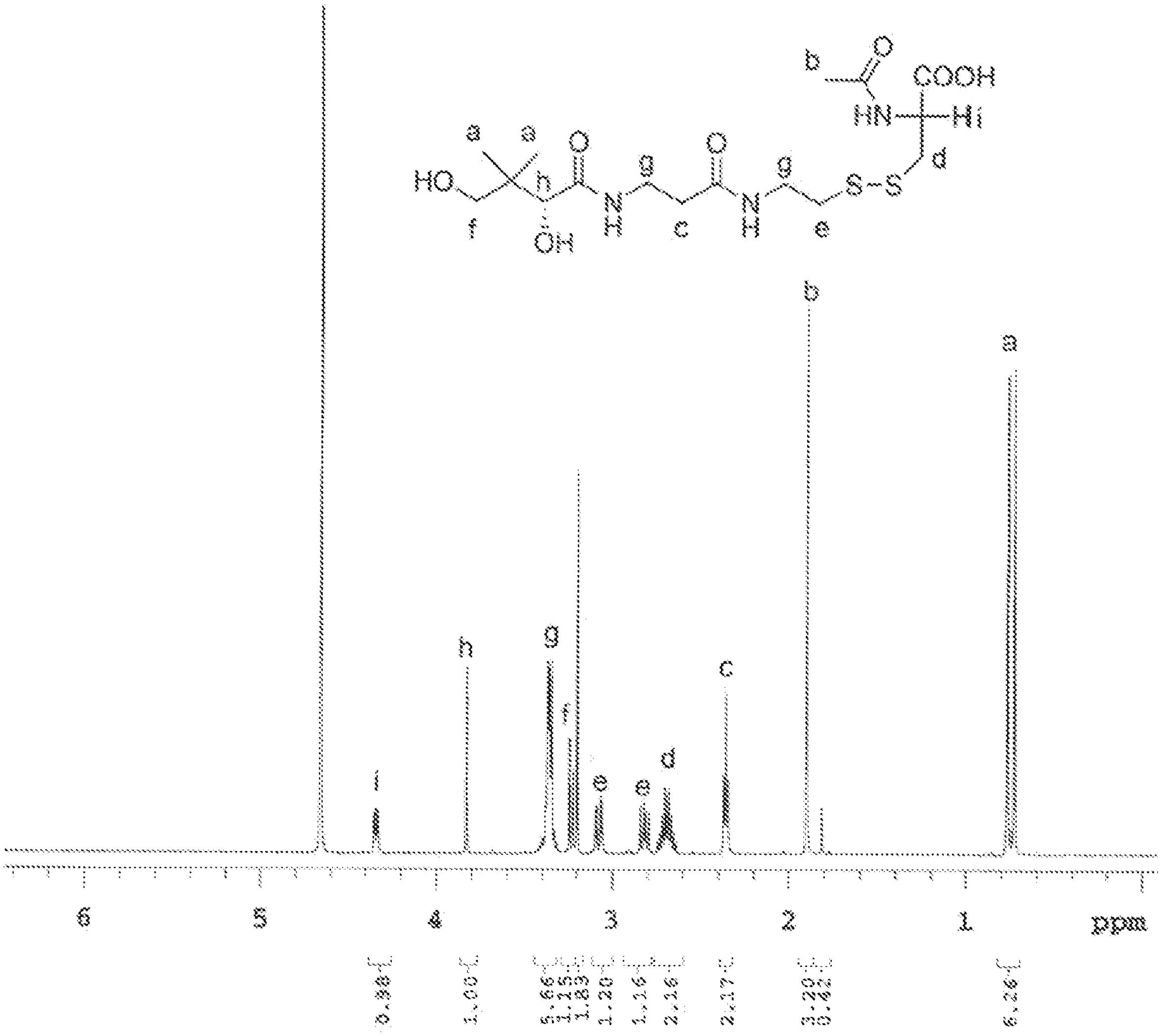

FIG. 29 contains the nuclear magnetic resonance (NMR) spectrum of TTI-1502, obtained on a Varian INOVA 500. The inset structure of TTI-1502 is annotated with letters a through i to indicate specific bonds, which are also highlighted on the NMR spectrum.

Figure 30A:
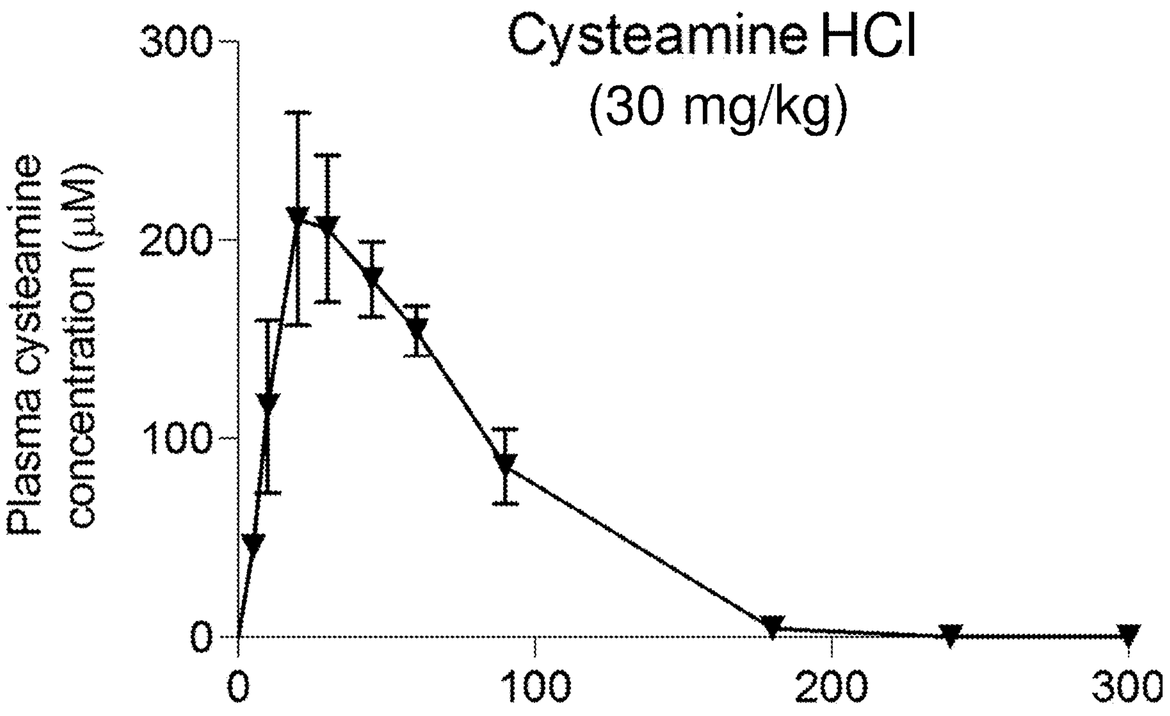
Figure 30B:
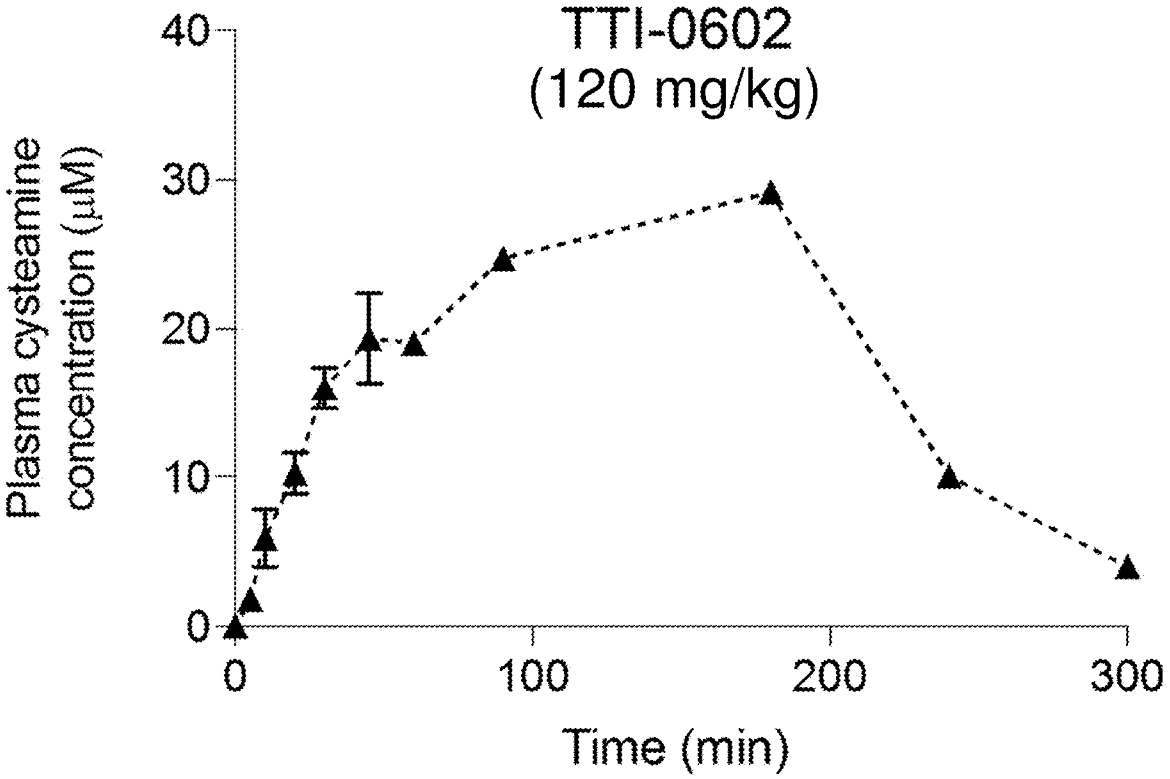

FIG. 30A and FIG. 30B. Contain the concentration-time curve of cysteamine in blood plasma after administration of cysteamine hydrochloride (30 mg/kg; FIG. 30A) or compound 2 (aka TTI-0602) (120 mg/kg; FIG. 30B) to Sprague-Dawley rats via gavage, as described in Example 10. The values in both curves are the mean of three rats. Standard deviation is indicated by the error bars.

Figure 31A:
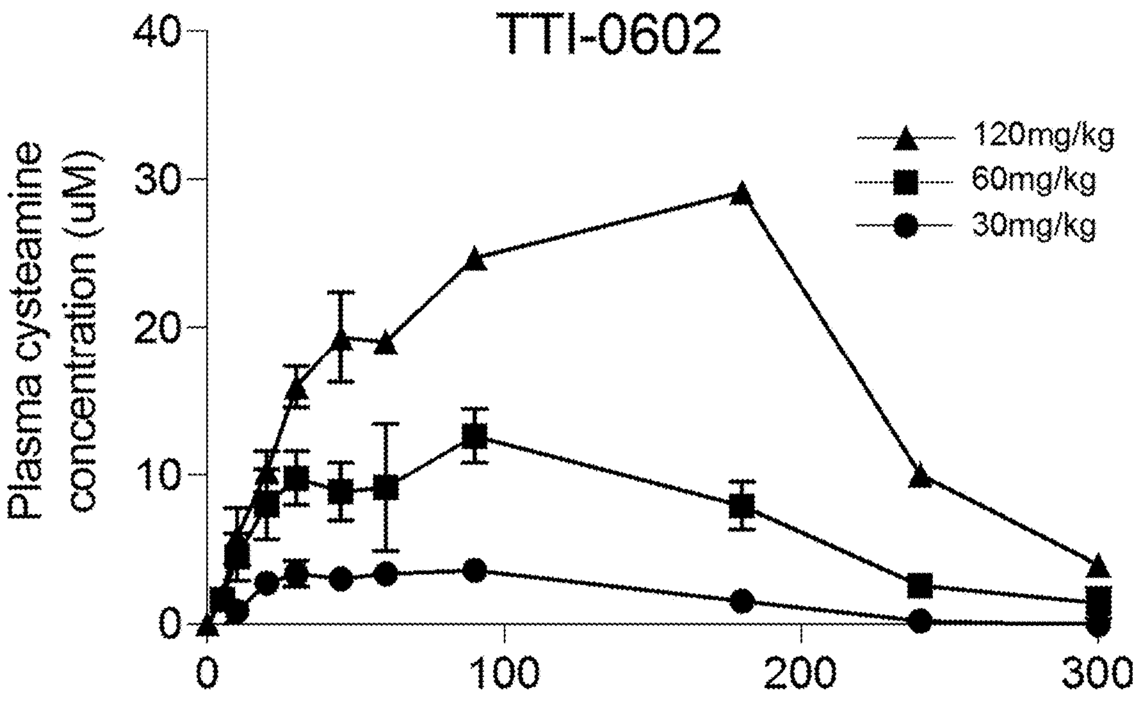
Figure 31B:
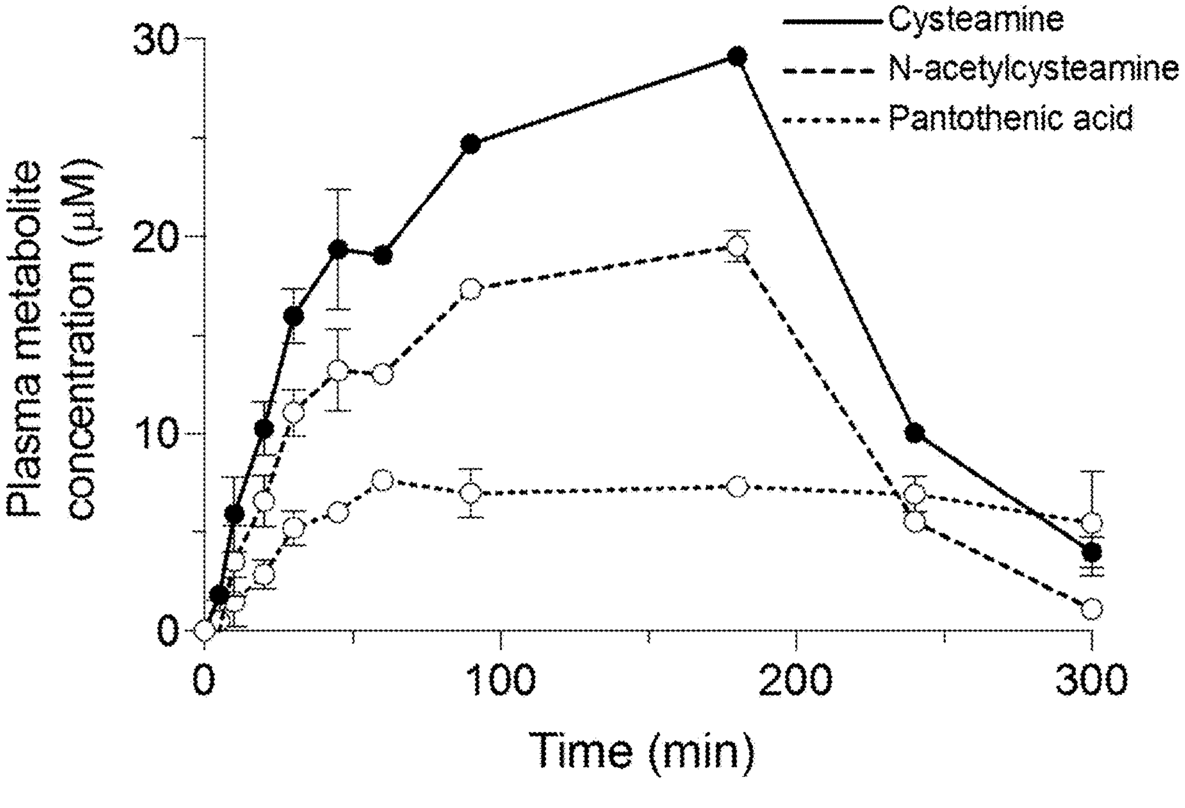

FIG. 31A and FIG. 31B. Contain the concentration-time curve of cysteamine in blood plasma following administration of compound 2 (aka TTI-0602) at doses of 30 mg/kg, 60 mg/kg or 120 mg/kg to Sprague-Dawley rats (3 rats per dose) via gavage (FIG. 31A), as described in Example 10, and the concentration time curves of cysteamine, N-acetylcysteamine and pantothenic acid in blood plasma following administration of compound 2 (aka TTI-0602) at 120 mg/kg to Sprague-Dawley rats via gavage (FIG. 31B), also described in Example 10.

Figure 32:
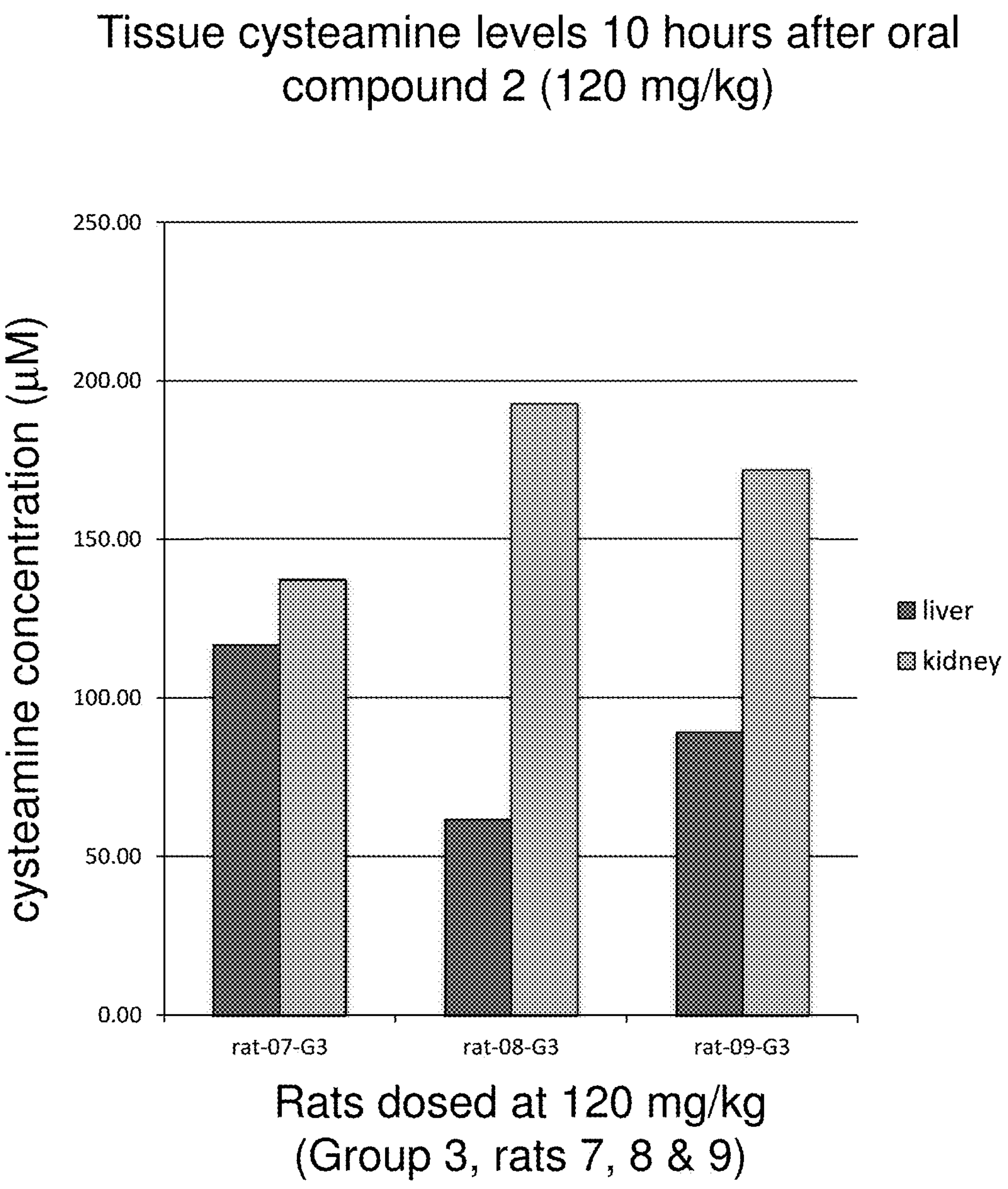

FIG. 32 contains a chart illustrating the concentration of cysteamine (micromolar) in liver and kidney 10.5 hours after administration of compound 2 (aka TTI-0602) at 120 mg/kg to Sprague-Dawley rats via gavage, as described in Example 10.

Figure 33:
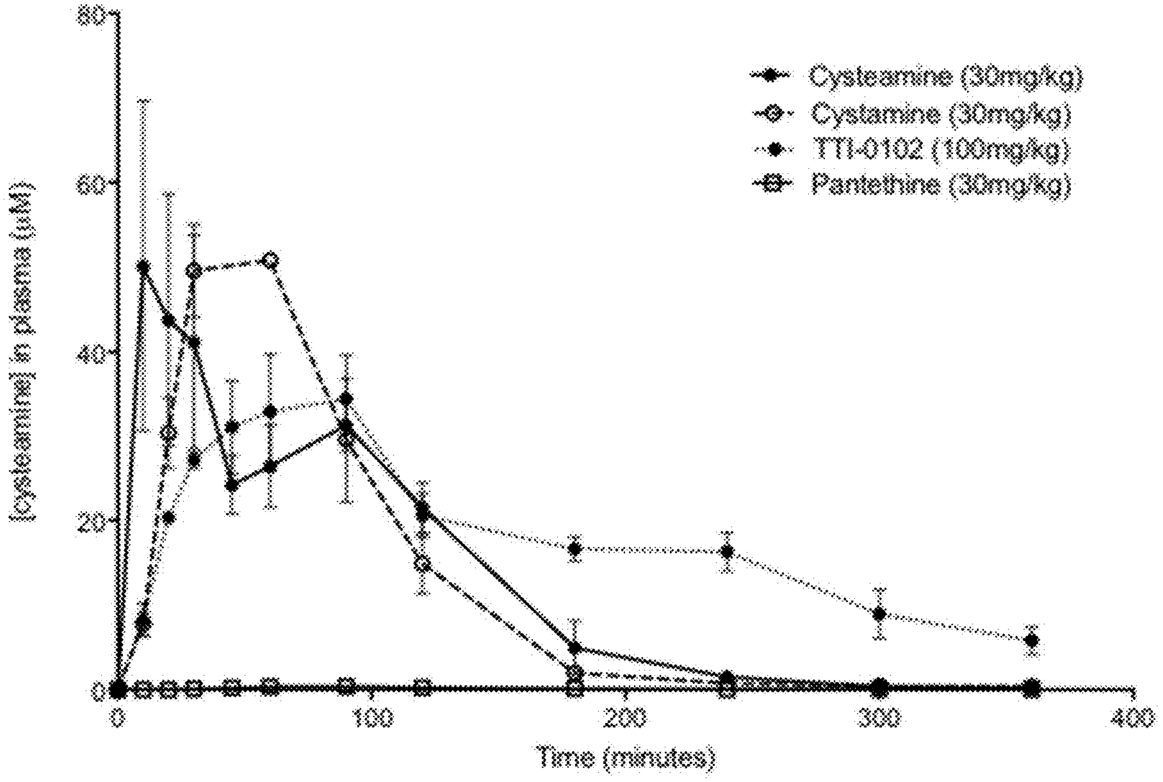

FIG. 33 depicts the concentration-time curve of cysteamine in blood plasma following administration of either: (i) cysteamine hydrochloride (30 mg/kg) or cystamine dihydrochloride (30 mg/kg) or pantethine (30 mg/kg) or compound 1 (aka TTI-0102) (100 mg/kg) to male Sprague-Dawley rats via gavage, as described in Example 1. The concentrations are the mean of three rats, and the error bars indicate standard deviations.

Figure 34A:
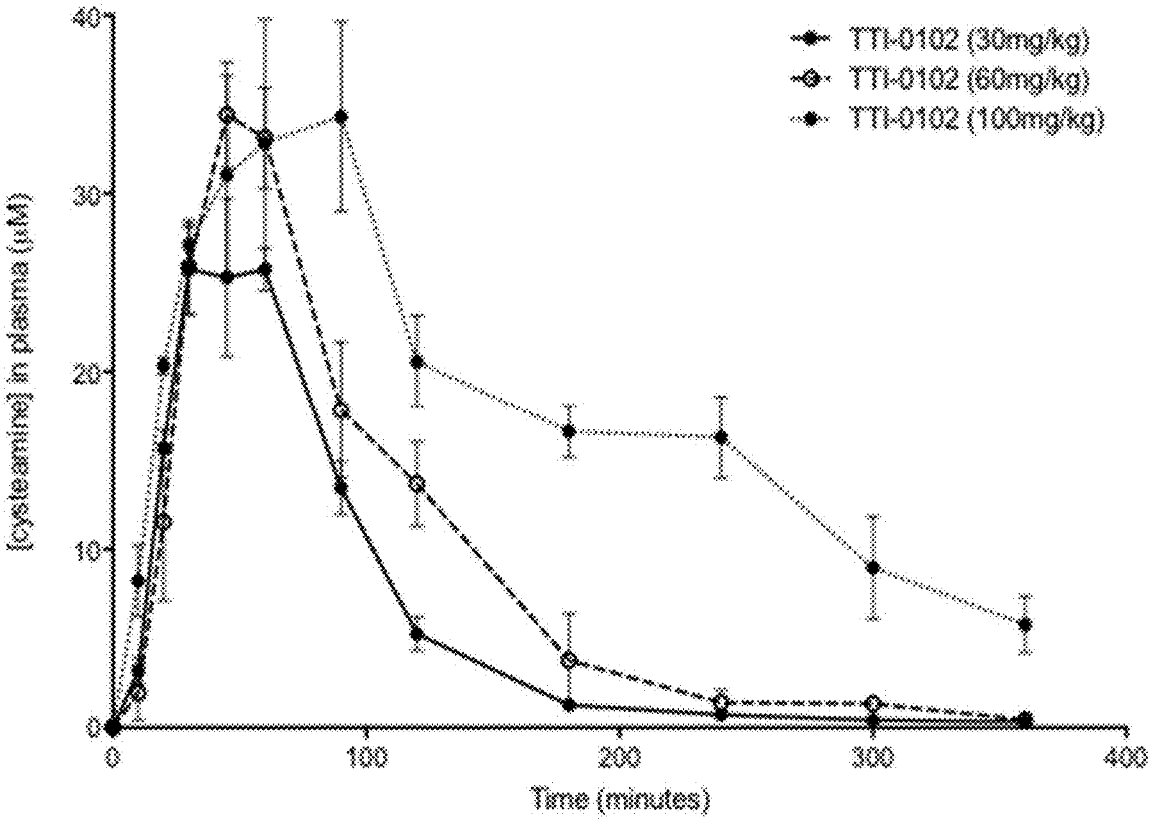

FIG. 34A and FIG. 34B. Depict the concentration-time curve of cysteamine in blood plasma following administration of compound 1 (aka TTI-0102) at doses of 30 mg/kg, 60 mg/kg or 100 mg/kg to male Sprague-Dawley rats via gavage (FIG. 34A), as described in Examples 11-13, and the pharmacokinetic parameters derived from each dose (FIG. 34B). Abbreviations: Cmax=maximum cysteamine concentration; Tmax=time at which maximum cysteamine concentration occurs; AUC last=area under the drug concentration time curve from time 0 to six hours; T½=half life of cysteamine in plasma; MRT last=mean residence time based on 6 hour data.

Figure 35A:
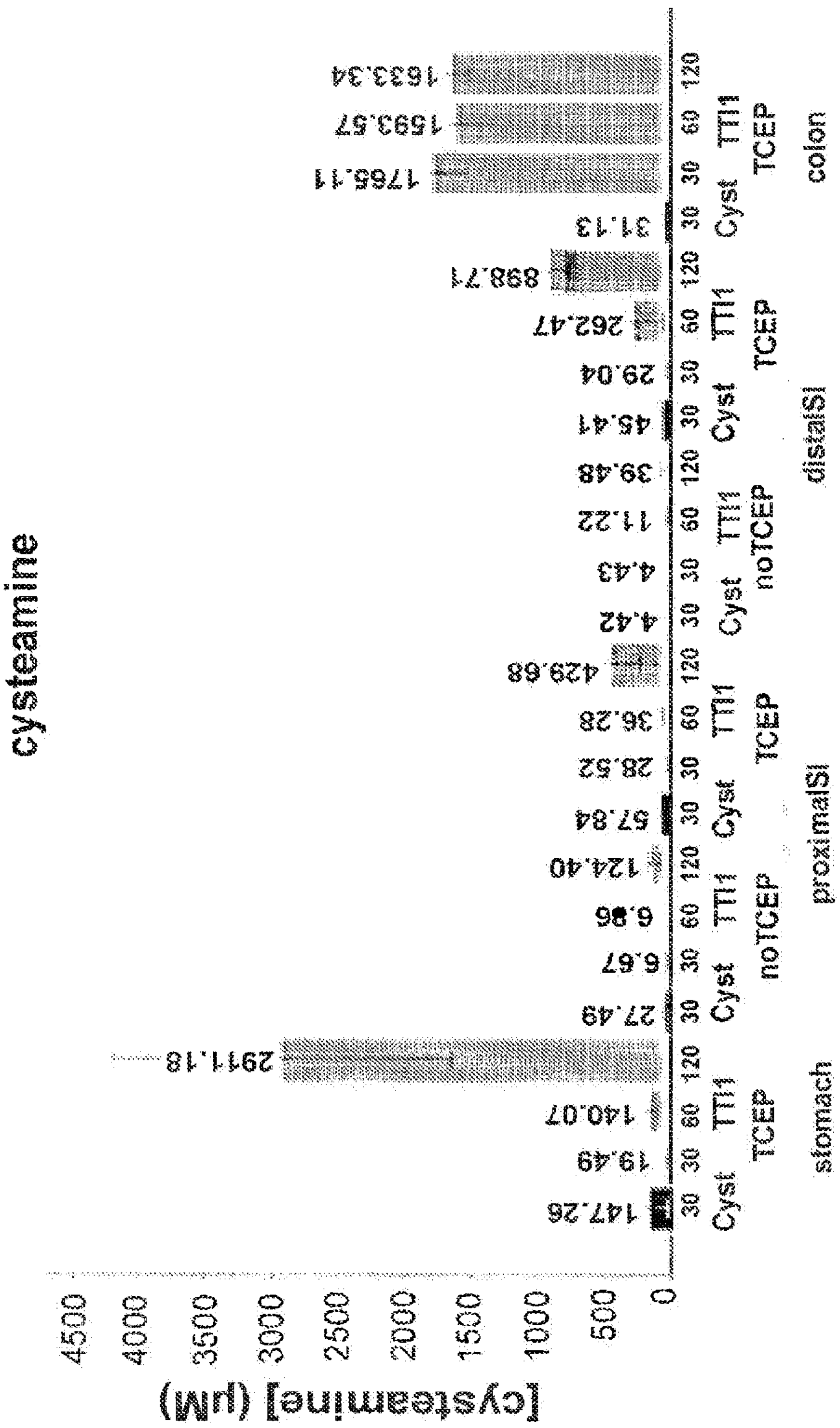
Figure 35B:
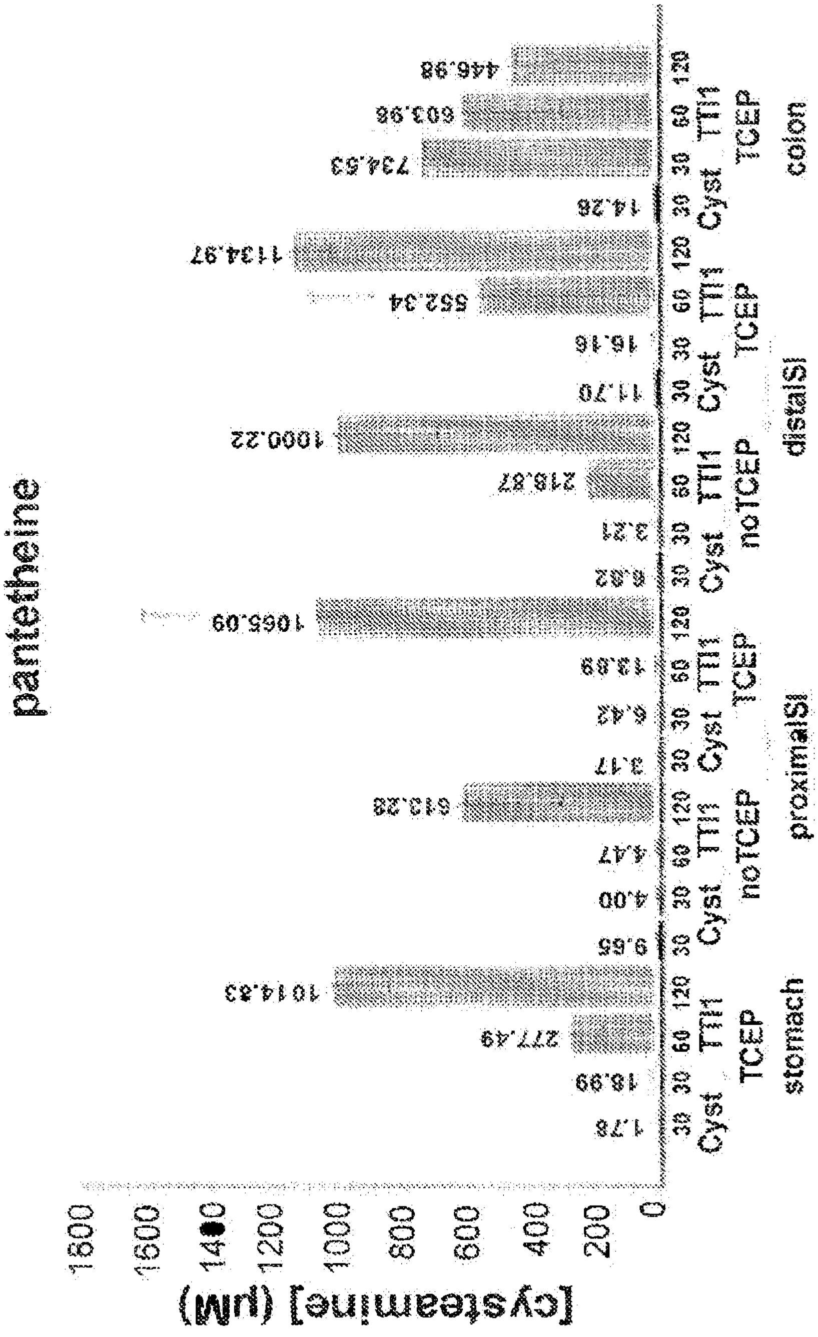

FIG. 35A and FIG. 35B. depict a bar graph showing the concentration of cysteamine (FIG. 35A) and pantetheine (FIG. 35B) in the gastrointestinal tracts of rats six hours after administration of cysteamine hydrochloride (30 mg/kg) or compound 1 (aka TTI-0102) at doses of 30 mg/kg, 60 mg/kg or 100 mg/kg to male Sprague-Dawley rats via gavage. Gastrointestinal contents obtained from the stomach, proximal small intestine, distal small intestine and cecum/colon were analyzed as described in Examples 11-13. Samples from all four gut segments were reduced with TCEP. Proximal and distal small intestinal contents were also analyzed without TCEP. The numbers above each bar indicate the value of that sample. The samples are aligned in the upper and lower panels to facilitate comparison of cysteamine and pantetheine levels in the same sample.

Figure 36A:
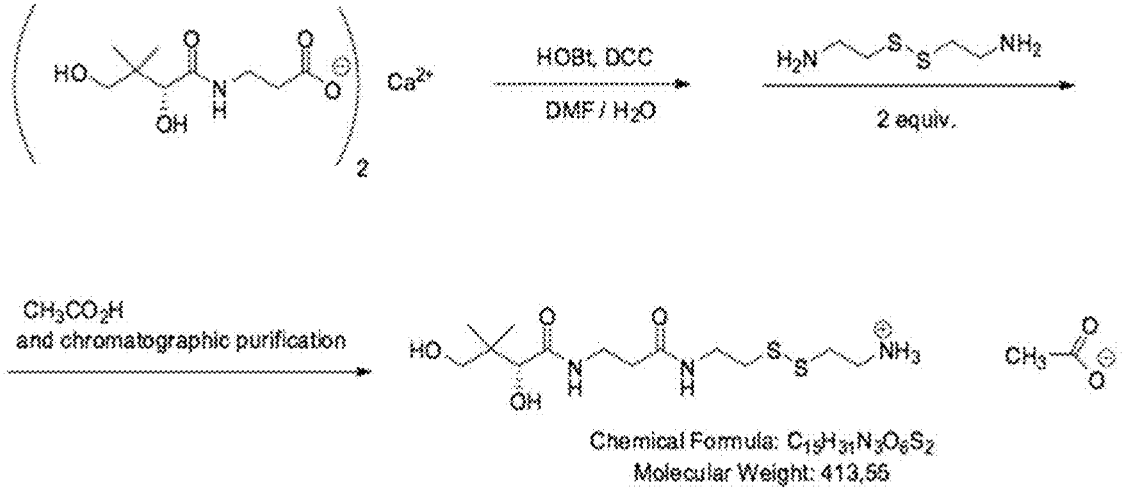

FIG. 36A. Depicts the synthetic scheme for hemi-acylation of cystamine to produce compound 1 (cysteamine-pantetheine asymmetric disulfide). DCC is an abbreviation for the coupling reagent N,N'-dicyclohexylcarbodiimide. HOBt is an abbreviation for 1-Hydroxybenzotriazole hydrate. DMF is an abbreviation for the solvent dimethylformamide.

Figure 36B:
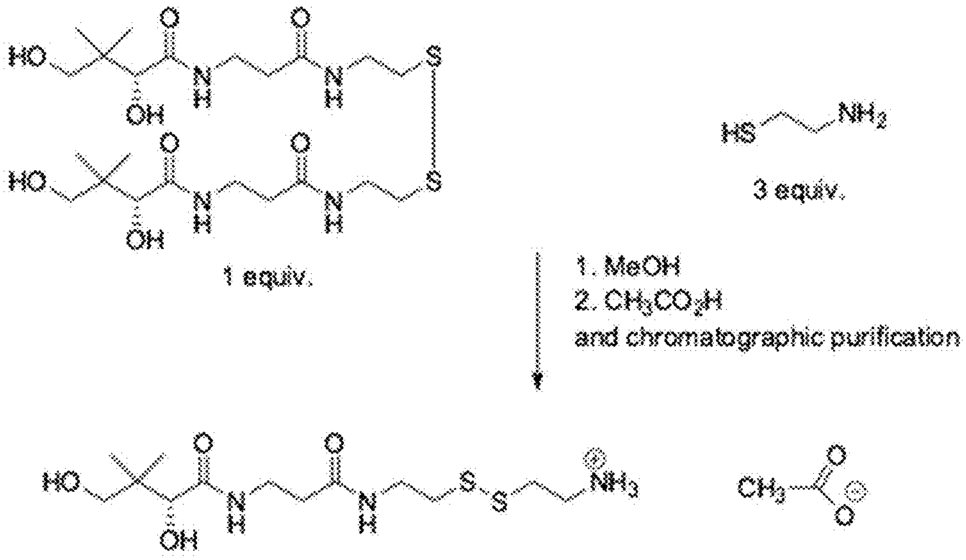

FIG. 36B. Depicts the scheme for compound 1 synthesis by thiol-disulfide exchange. The illustrated reaction, involving cysteamine (thiol) and pantetheine (disulfide), is one of two thiol-disulfide exchange reactions discussed in Example 14.

FIG. 37. Depicts the proton nuclear magnetic resonance ($^1$H NMR) spectrum of TTI-0102 made via hemi-acylation of cystamine (illustrated in FIG. 36 A). The structure of TTI-0102 is displayed, and annotated with lower case letters keyed to the peaks in the $^1$H NMR spectrum. The table displays numerical values for all the peaks with their delta value (expressed in parts per million, or ppm) and peak height.

Figure 38:
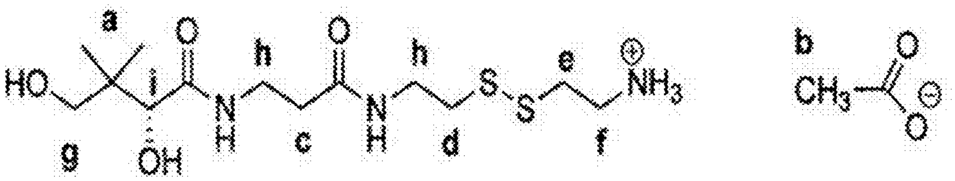

FIG. 38. Depicts in tabular form the relationship between the predicted and observed proton peak heights in the $^1$H NMR spectrum of shown in FIG. 37, with the protons labeled (a, b, c, d, e, f, g, h, i) as in FIG. 37.

DETAILED DESCRIPTION OF THE INVENTION

The invention features compositions and methods that permit in vivo production of cysteamine from precursor compounds (cysteamine precursors) in controlled amounts and at controlled locations in the gastrointestinal tract, and methods of treating cysteamine sensitive symptoms, syndromes and diseases. The methods and compositions of the invention can include any one of compounds 1-3, shown below, or a pharmaceutically acceptable salt thereof.

(1)

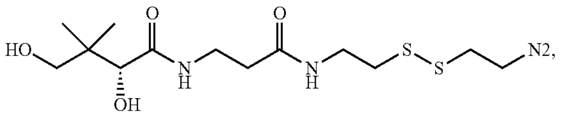

(2)

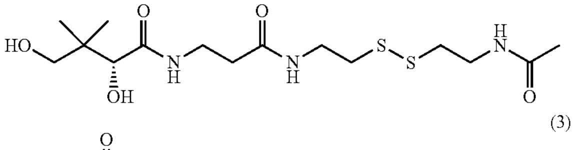

(3)

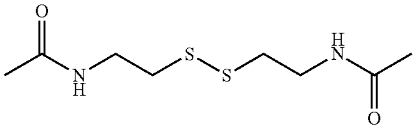

Compounds 1-3 can be administered alone, or in combination with a second active that is a cysteamine precursor, or in combination with an agent that modifies the release or uptake of cysteamine into a subject following the administration of the compound, such as a reducing agent or a pantetheinase inducing agent.

Cysteamine is a small, highly reactive thiol molecule (NH2-CH2-CH2-SH) present in all life forms from bacteria to people. The IUPAC name for cysteamine is 2-aminoethanethiol. Other common names include mercaptamine, beta-mercaptoethylamine, 2-mercaptoethylamine, decarboxycysteine and thioethanolamine. In humans cysteamine is produced by the enzyme pantetheinase, which cleaves pantetheine into cysteamine and pantothenic acid, also known as pantothenate or vitamin B5. Human pantetheinases are encoded by the Vanin 1 and Vanin 2 genes (abbreviated VNN1 and VNN2) and are widely expressed, including in the gastrointestinal tract. Thus dietary pantetheine, which is present in many foods, (e.g. in nuts and dairy products), is cleaved in the gastrointestinal lumen to generate cysteamine and pantothenic acid, which are then absorbed. In particular, cysteamine can be transported across the gastrointestinal epithelium by organic cation transporters (OCTs), a family of transporters that includes organic cation transporter 1 (OCT1), OCT2 and OCT3, which have been shown to transport cysteamine in enterocytes. Based on its ability to be converted into cysteamine in the gastrointestinal tract pantetheine is a cysteamine precursor. Cysteamine precursors represent a class of compounds which can have advantages over cysteamine salts with respect to (i) tolerability and side effects, (ii) pharmacokinetics and dosing intervals, (iii) manufacturing and (iv) product stability. More generally, administering a cysteamine precursor from which cysteamine can be generated in vivo at varying rates, and using formulation methods to deliver those precursors to selected sites in the gastrointestinal tract at selected times, can be useful in a treatment regimen by providing much better control of cysteamine pharmacokinetics, which up until the present has been a major hindrance to wide spread use of cysteamine and other thiols.

Cysteamine Precursors

Pantetheine, and its catabolic products cysteamine and pantothenate, are intermediate compounds in coenzyme A biosynthesis in plants and animals (see FIG. 11 for a diagram of relevant metabolic and catabolic pathways). Several compounds in the coenzyme A biosynthetic pathway such as 4-phosphopantetheine, dephospho-coenzyme A and coenzyme A, can be catabolized to pantetheine, and then to cysteamine and pantothenate, in the human gastrointestinal tract. Thus 4-phosphopantetheine, dephospho-coenzyme A and coenzyme A, by virtue of being convertible to cysteamine in the gut, are cysteamine precursors. N-acetylcysteamine is also a cysteamine precursor, via deacetylation either in the gut or by cellular deacetylases (e.g. the deacetylases which convert N-acetylcysteine to cysteine in vivo).

Pantethine is a dimer of two pantetheine molecules, joined by a disulfide bond. In other words pantethine is an oxidized form of pantetheine. The interconversion of pantethine into two pantetheines is not enzymatically mediated and does not require ATP. The reaction is instead controlled largely by the redox environment in the gut. In a reducing environment, which tends to prevail in vivo, particularly intracellularly, pantetheine will predominate, while in a more oxidizing environment, such as the stomach, the equilibrium will shift towards pantethine. A small clinical study by Wittwer (Wittwer et al., J. Exp. Med. 76:4 (1985)) showed that, when administered orally, a significant fraction of pantethine is chemically reduced to pantetheine in the human gastrointestinal tract, and subsequently cleaved to cysteamine and pantothenate. Thus pantethine is a cysteamine precursor. Pantetheine herein refers to the D-enantiomer.

The pantothenoyl moiety of pantetheine contains a chiral carbon. Thus there are two enantiomeric forms of pantetheine, traditionally referred to as D-pantetheine and L-pantetheine (also referred to as R-pantetheine and S-pantetheine). Only the D-enantiomer of pantetheine can be cleaved by pantetheinase, thus only the D-enantiomer qualifies as a cysteamine precursor. The two enantiomers of pantetheine can combine in four ways to form the disulfide pantethine: D-,D-; D-,L-; L-,D-; and L-,L-pantethine. Only D-,D-pantethine can be chemically reduced to two D-pantetheines and then cleaved to produce two cysteamines. Thus the D-,D-form of pantethine is strongly preferred, and the term pantethine as used herein refers to the D-,D-enantiomer. The pantetheine-related compounds 4-phosphopantetheine, dephospho-coenzyme A and coenzyme A also must be in the D-stereoisomeric configuration to yield D-pantetheine (and thence cysteamine) upon degradation in the gut. Therefore "4-phosphopantetheine", "dephospho-coenzyme A" and "coenzyme A," as well as any analogs or derivatives thereof, herein refer to the D-enantiomer. None of pantetheine, 4-phosphopantetheine, dephospho-coenzyme A or coenzyme A is absorbed by enterocytes, rather each compound must be catabolized to pantothenate and cysteamine which are absorbed (see Shibata et al., J. Nutr. 113:2107 (1983)).

Analogs or derivatives of the D-stereoisomer of pantetheine, 4-phosphopantetheine, dephospho-coenzyme A or coenzyme A that can be converted to the parent compound in the gastrointestinal tract (e.g. by natural enzymatic or chemical processes) can also be used to form either thiol or disulfide-type cysteamine precursors and are herein referred to as "suitable analogs or derivatives." For example there are many physiologic forms of coenzyme A (e.g. acetyl CoA, succinyl coA, malonyl coA, etc.) that are readily degraded to coenzyme A in the gut. Any acetylated, alkylated, phosphorylated, lipidated or other analog may be used as a cysteamine precursor. Analogs of pantetheine, 4-phosphopantetheine, dephospho-coenzyme A or coenzyme A have been described in the literature, as well as methods for producing them (van Wyk et al., Chem Commun 4:398 (2007)).

Pantetheine can form disulfides with thiols other than itself, referred to as pantetheine mixed disulfides, which constitute another class of cysteamine precursors. The thiols reacted with pantetheine are preferably naturally occurring thiols, or non-natural thiols known to be safe in man based on a history of human or animal use. For example, mixed disulfides can be formed by reacting pantetheine with 4-phosphopantetheine, dephospho-coenzyme A or coenzyme A, compounds present in the human body and in many foods. Such mixed disulfides, upon reduction and degradation in the gut yield two cysteamines. Pantetheine coupled to N-acetylcysteamine also yields two cysteamines upon reduction and degradation in the gut. In certain embodiments disulfide cysteamine precursors that can yield two cysteamines are preferred. FIGS. 18-21 show the cysteamine yield of different classes of disulfide cysteamine precursors. Analogs or derivatives of 4-phosphopantetheine, dephospho-coenzyme A or coenzyme A that can be converted to the parent compound in the gastrointestinal tract via chemical or enzymatic processes (i.e. suitable analogs or derivatives) can also be coupled to pantetheine to form pantetheine mixed disulfide cysteamine precursors, or they can be coupled to other thiols.

Pantetheine mixed disulfides can also be formed by reacting pantetheine with thiols not themselves degradable to cysteamine, such as L-cysteine, homocysteine, N-acetylcysteine, N-acetylcysteine amide, N-acetylcysteine ethyl ester, N-acetylcysteamine, L-cysteine ethyl ester hydrochoride, L-cysteine methyl ester hydrochoride, thiocysteine, allyl mercaptan, furfuryl mercaptan, benzyl mercaptan, thioterpineol, 3-mercaptopyruvate, cysteinylglycine, gamma glutamylcysteine, gamma-glutamylcysteine ethyl ester, glutathione, glutathione monoethyl ester, glutathione diethyl ester, mercaptoethylgluconamide, thiosalicylic acid, thiocysteine, tiopronin or diethyldithiocarbamic acid. See FIG. 17 for the chemical abstracts service (CAS) registration numbers, molecular formulae and molecular weight of exemplary thiol compounds that can be reacted with pantetheine to form pantetheine mixed disulfides. Disulfides formed by pantetheine and any of thiols 6-35 (see FIG. 17 for thiol numbering) yield, upon disulfide bond reduction and pantetheinase cleavage, one cysteamine. Although these second thiols are not convertible into cysteamine in the gut, they may nonetheless enhance cysteamine production by, for example, stimulating pantetheinase activity or participating in disulfide exchange with cysteamine-containing disulfides, or they may provide a therapeutic benefit complementary to that provided by cysteamine by, for example, acting as reducing agents, or by other mechanisms.

Dithiol compounds such as dihydrolipoic acid (DHLA), meso-2,3-dimercaptosuccinic acid (DMSA), 2,3-dimercaptopropanesulfonic acid (DMPS), 2,3-dimercapto-1-propanol, bucillamine or N,N'-bis(2-mercaptoethyl)isophthalamide can also be reacted with pantetheine to form either a pantetheine mixed disulfide with one free thiol group, or a tripartite compound with two disulfide bonds connecting two pantetheine molecules to the dithiol. The former category of mixed pantetheine disulfides yields one cysteamine upon disulfide bond reduction and pantetheinase cleavage, while the latter category yields two cysteamines. See FIG. 21 for tables showing how cysteamine, pantetheine, 4-phosphopantetheine, dephospho-coenzyme A, coenzyme A or N-acetylcysteamine can be combined with various dithiols to produce useful cysteamine precursors. Alternatively, two different thiols can be bonded to a dithiol to yield a cysteamine precursor, so long as one of the thiols is cysteamine, pantetheine, 4-phosphopantetheine, dephospho-coenzyme A, coenzyme A or N-acetylcysteamine, or a suitable analog or derivative thereof; that is, a compound which can ultimately be degraded to cysteamine in the gastrointestinal tract. Tables 2A and 2B in FIG. 21 show some of the salient properties of such cysteamine precursors, including the range of molecular weights and cysteamine yields (i.e. the percent of the cysteamine precursor convertible to cysteamine in vivo), and for selected examples, the number of in vivo degradative steps from the cysteamine precursor to cysteamine.

Similarly to pantetheine, any of 4-phosphopantetheine, dephospho-coenzyme A, coenzyme A or N-acetylcysteamine, or suitable analogs or derivatives, can be (i) reacted with itself to form a homodimeric disulfide, or (ii) reacted with each other in various pairs to form mixed disulfides, or (iii) reacted with other thiols (not convertible into cysteamine in vivo), to form mixed disulfides. All such disulfides are cysteamine precursors. The first two categories can yield two cysteamines upon reduction and degradation in the gut while the third category can yield only one cysteamine.

For example, any of the thiols listed in FIG. 17 can be reacted with 4-phosphopantetheine (as shown in FIG. 19), with dephospho-coenzyme A (FIG. 19), with coenzyme A (FIG. 20) or with N-acetylcysteamine (FIG. 20) to form mixed disulfide cysteamine precursors. Other naturally occurring kthiols can also be used, as can non-natural thiols known to be safe in man. FIGS. 18-21 show schematically some of the combinations of thiols and dithiols that can be reacted to form disulfide cysteamine precursors. Conversion of such compounds to cysteamine in the human gastrointestinal tract requires: (i) reduction of the disulfide bond to generate free thiols, (ii) in the case of disulfides containing 4-phosphopantetheine, dephospho-coenzyme A, coenzyme A or suitable analogs or derivatives thereof, degradation by enzymes present in the intestine (e.g. phosphatases, diphosphatases, phosphodiesterases) to generate pantetheine, (iii) cleavage of pantetheine by pantetheinase. N-acetylcysteamine containing disulfides must be reduced and deacetylated in the gut, blood or tissues.

Cysteamine itself can also be reacted with other thiols to form mixed disulfide cysteamine precursors. For example cysteamine can be reacted with pantetheine, 4-phosphopantetheine, dephospho-coenzyme A, coenzyme A or N-acetylcysteamine, with analogs or derivatives of those five thiols degradable to the parent compound in the gastrointestinal tract, or with any of the other thiols listed in FIG. 17, to form any of the disulfides in FIGS. 18-20. Two cysteamines can be joined to a dithiol via two disulfide bonds to produce another type of disulfide cysteamine precursor (FIG. 21). FIG. 8 illustrates the chemical structure of such a cysteamine precursor: a dihydrolipoate disulfide bonded to two cysteamines. Upon disulfide bond reduction two cysteamines are released, along with dihydrolipoic acid, which is a strong reducing agent and may complement the therapeutic properties of cysteamine in certain disease settings.

To summarize, cysteamine precursors can be classified in three main categories: (i) thiols degradable to cysteamine, (ii) mixed disulfides which include cysteamine, including disulfides formed with dithiols, (ii) disulfides which include pantetheine, (iii) disulfides which include 4-phosphopantetheine, dephospho-coenzyme A or coenzyme A or suitable analogs or derivatives. Each of the latter three categories can be further decomposed depending on the second thiol: (a)

pantetheine or suitable analogs or derivatives, (b) 4-phosphopantetheine, dephospho-coenzyme A, or coenzyme A or suitable analogs or derivatives, or (c) a thiol which is not itself a cysteamine precursor (e.g. L-cysteine, homocysteine, N-acetyl-cysteine, N-acetylcysteine amide, N-acetylcysteine ethyl ester, N-acetylcysteamine, L-cysteine ethyl ester hydrochoride, L-cysteine methyl ester hydrochloride, thiocysteine, allyl mercaptan, furfuryl mercaptan, benzyl mercaptan, 3-mercaptopyruvate, thioterpineol, glutathione, cysteinylglycine, gamma glutamylcysteine, gamma-glutamylcysteine ethyl ester, glutathione monoethyl ester, glutathione diethyl ester, mercaptoethylgluconamide, thiosalicylic acid, thiocysteine, tiopronin or diethyldithiocarbamic acid). Dithiol compounds such as dihydrolipoic acid, meso-2,3-dimercaptosuccinic acid (DMSA), 2,3-dimercaptopropanesulfonic acid (DMPS), 2,3-dimercapto-1-propanol, bucillamine or N,N'-bis(2-mercaptoethyl)isophthalamide can also be combined with cysteamine, pantetheine, 4-phosphopantetheine, dephospho-coenzyme A or coenzyme A or suitable analogs or derivatives to form disulfides.

Pharmacological Properties of Cysteamine Precursors

The temporal and spatial pattern of in vivo cysteamine generation from cysteamine precursors can vary widely depending on the type of cysteamine precursor. Cysteamine precursors that require multiple chemical and enzymatic reactions to generate cysteamine will, on average, generate cysteamine later than those that require only one step. This property of cysteamine precursors can be used to design a plurality of pharmaceutical compositions with varying rates and durations of in vivo cysteamine creation. Further, the pharmaceutical compositions can be administered in combinations and in ratios that bring about desirable pharmacological ends. For example, to provide elevated plasma cysteamine levels shortly after drug administration a cysteamine mixed disulfide may be administered. The only step required to produce a cysteamine from a cysteamine mixed disulfide is reduction of the disulfide bond. Depending on the identity of the second thiol a second cysteamine may be produced, following one or more degradative steps. The second cysteamine can only be generated after disulfide bond reduction and another step, so it will necessarily be produced later than the first cysteamine, thereby extending the period of time over which cysteamine is generated in the gut and absorbed into the blood. Since cysetamine free base and cysteamine salts (e.g. Cystagon® and Procysbi®) have a very short half life this prolongation of cysteamine creation in vivo from cysteamine precursors represents a significant advance over present therapeutics.

In one approach, if the second thiol is pantetheine (i.e. a cysteamine-pantetheine disulfide) then a pantetheinase cleavage step is necessary to generate a second cysteamine. Pantetheinase is generally located on the surface of enterocytes, and thus is only in contact with a fraction of gut contents at any one time, thereby extending the period of time during which cysteamine is generated. This combination of early and late cysteamine generation from one disulfide molecule has several advantages: (i) cysteamine becomes available upon disulfide bond reduction, providing early therapeutic benefit, (ii) the cleavage of pantetheine occurs over time (pantetheinases are expressed at varying levels throughout the gastrointestinal tract), extending the duration of therapeutic benefit, (iii) the extended production of cysteamine overtime and space, via both disulfide bond reduction and pantetheine cleavage, reduces the high peak cysteamine concentrations that are strongly associated with side effects, while also (iv) avoiding saturation of pantetheinase or cysteamine uptake mechanisms such as transport by OCTs. In short, the prolonged elevated blood cysteamine levels provide both a more efficacious medication and a less toxic and more convenient dosing form for patients.

Alternatively, if the second thiol is L-cysteine (i.e. a cysteamine-L-cysteine disulfide) then only one cysteamine is generated, upon reduction of the disulfide, and there is no long-duration cysteamine generation. However, as described below, the cysteamine-L-cysteine disulfide can be formulated for release in virtually any part of the gastrointestinal tract, including the ileum or colon, where a cysteamine precursor capable of rapid cysteamine release may be useful. Further, cysteine has also been shown to enhance the activity of pantetheinase, and to have beneficial effects in several disease models. Thus a cysteamine-L-cysteine disulfide may be a useful complement to another cysteamine precursor, or may be useful for treatment of diseases responsive to both cysteamine and cysteine.

Disulfides that contain a thiol requiring two or more catabolic reactions to generate cysteamine, such as 4-phosphopantetheine, dephospho-coenzyme A or coenzyme A, or suitable analogs or derivatives thereof, can be more efficiently degraded in the small intestine, where they are exposed to the digestive enzymes present in pancreatic juice, than in the stomach or large intestine. Disulfides made by reacting two such thiols with each other, or with thiols other than cysteamine, will generate cysteamine starting at a later time point and extending over a longer time period than, for example, a cysteamine-L-cysteine disulfide. On average 4-phosphopantetheine, dephospho-coenzyme A or coenzyme A, or suitable analogs will generate cysteamine later than pantetheine, and the same is true of disulfides containing those compounds.

Cysteamine precursors such as pantetheine and compounds degradable to pantetheine in the gut, as well as disulfides containing any of those compounds all yield pantothenate, along with cysteamine, upon cleavage by pantetheinase. Pantothenate, or vitamin B5, is a water soluble compound that is present in the diet and is synthesized by enteric bacteria. When pantothenate is administered in large doses the excess is excreted in urine. A review of panthothenate by the Panel on Folate, Other B Vitamins, and Choline of the US Institute of Medicine Standing Committee on the Scientific Evaluation of Dietary Reference Intakes (National Academies Press (US), 1998) found that: "No reports of adverse effects of oral pantothenic acid in humans or animals were found."

Mixtures of Cysteamine Precursors

The methods and compositions of the invention can include mixtures of cysteamine precursors to take advantage of their differing pharmacological properties. In particular, individualized improvement (or personalization for a given patient's needs) of cysteamine plasma levels can be achieved by using mixtures of cysteamine precursors. For example, the cysteamine-pantetheine mixed disulfide described above fixes the ratio of cysteamine to pantetheine at 1:1. However cysteamine is absorbed and cleared from the body rapidly (elimination half life: ~25 minutes), producing a sharp peak in blood levels, while pantetheine provides cysteamine (via pantetheinase cleavage) over several hours. Thus a dose of a cysteamine-pantetheine mixed disulfide that produces therapeutic cysteamine levels early (from the cysteamine released upon disulfide bond reduction) may produce sub-therapeutic cysteamine levels later, because cysteamine generation from pantetheine is spread over a longer period of time. Thus a 1:1 ratio of cysteamine:pantetheine may not be ideal for a specific patient or purpose. Adding more pantetheine to the dosage form would keep blood cysteamine in the therapeutic concentration range for a longer period of time. To increase the ratio of pantetheine to cysteamine, either the thiol pantetheine or the disulfide pantethine or another pantetheine-containing disulfide can, for example, be co-formulated or co-administered with the cysteamine-pantetheine mixed disulfide to achieve blood cysteamine levels in the therapeutic range for a longer period of time. The ratio of the two cysteamine precursors can be adjusted to achieve desired pharmacokinetic parameters, such as maximizing the area under the cysteamine concentration-time curve (AUC), or minimizing the peak concentration (Cmax) of cysteamine, or maximizing the trough concentration (Cmin), or maintaining cysteamine blood levels above a threshold, or any combination of such parameters.

Cysteamine precursors such as 4-phosphopantetheine, dephospho-coenzyme A or coenzyme A, and disulfides formed from those three compounds, require more catabolic steps to yield cysteamine than does pantetheine (which only requires one step). Accordingly, the rate of cysteamine production from those cysteamine precursors is, on average, slower and more prolonged than from pantetheine or certain pantetheine disulfides. Thus co-administration or co-formulation of 4-phosphopantetheine, dephospho-coenzyme A or coenzyme A, or their disulfides in combination with cysteamine-pantetheine, and optionally pantetheine or pantethine, provides another way to control cysteamine pharmacokinetics by selecting appropriate cysteamine precursors. In particular, use of such cysteamine precursors can be used to further extend the time over which cysteamine is produced in the gastrointestinal tract.

4-Phosphopantetheine, Dephospho-Coenzyme a and Coenzyme a Containing Disulfides

The canonical biosynthetic pathway for coenzyme A, shown schematically in FIG. 11, involves five steps catalyzed by four enzymes (CoA synthase catalyzes the final two steps). The initial step—phosphorylation of pantothenate by pantothenate kinase—controls flux through the pathway. Until recently it was believed that none of the intermediate compounds in the coenzyme A synthetic (or catabolic) pathways is efficiently absorbed in the gastrointestinal tract. Rather, only the catabolic products of pantetheine (pantothenate and cysteamine) are absorbed in the gut. Two important consequences of that understanding of the coenzyme A pathway for cysteamine precursor therapy are (i) cysteamine precursors must be degraded to cysteamine in the gut, then absorbed and transported to the site of therapeutic effect (e.g. liver, central nervous system), and (ii) cellular coenzyme A synthesis necessarily starts from pantothenate (since other metabolic intermediates do not cross cell membranes).

However, 4-phosphopantetheine crosses cell membranes efficiently (Srinivasan et al., Nature Chemical Biology 11:784 (2015)). This observation has implications for the design and use of the cysteamine precursors described herein to treat a variety of diseases and disorders. First, it permits treatment approaches involving in situ cysteamine creation in multiple tissues and organs (as opposed to just the gut), including diseased tissues. In a second aspect it enables cell delivery of a coenzyme A precursor (4-phosphopantetheine) downstream of the initial synthetic step catalyzed by pantothenate kinase, which can be used to treat pantothenate kinase deficient subjects. Methods for using cysteamine precursors to treat these two categories of disease are described below and illustrated with several examples.

In one approach, diseases of the kidney, liver, lung and connective tissues, as well as infectious diseases, can be effectively treated because these organs (and others) all contain pantetheinase, expressed from either the VNN1 or VNN2 gene. The method includes (i) dosing a patient with a cysteamine precursor that can be degraded in the gut to yield one or two molecules of 4-phosphopantetheine, some fraction of which will (ii) be absorbed by enterocytes and pass into the blood (where 4-phosphopantetheine is quite stable), and then, via the circulation, (iii) pass through the diseased organ, where (iv) it can be degraded by phosphatase and pantetheinase to yield cysteamine at the locus of disease.

Advantages of this treatment method can include (i) higher cysteamine concentration at the site of disease than can be achieved with cysteamine absorbed from the intestine, per equivalent dose, (ii) lower plasma cysteamine concentration (because 4-phosphopantetheine is the circulating delivery vehicle) with resulting lower toxicity, (iii) longer half life in blood than cysteamine (over 3 hours for 4-phosphopantetheine vs. about 25 minutes for cysteamine), which lengthens dosing intervals and thereby increases patient convenience, and (iv) the ability to selectively target cysteamine to disease tissues in which pantetheinase overexpression is pathogenic, including, for example, metabolic diseases such as NASH (Sato W. et al., Hepatol Res. 34:256 (2006)), and certain inflammatory diseases (Naquet P. et al., Biochem Soc Trans. 42:1094 (2014)). Inflammation is often present at sites of infection, so selective cysteamine creation at sites of infection is also possible, and useful in settings where cysteamine has anti-microbial, anti-viral or anti-parasitical effects. Thus, 4'-phosphopantetheine can be absorbed in the gut, circulated in the blood, and then degraded to cysteamine in an organ or disease tissue that expresses pantetheinase, whether constitutively, as in the kidney, or as a manifestation of active disease, as in inflammation.

4-Phosphopantetheine—Yielding Disulfides for Kidney Diseases

As noted above, pantetheinases (encoded by both the VNN1 and VNN2 genes) are expressed at high levels in kidney. Thus some circulating 4-phosphopantetheine will be degraded in the kidney, yielding cysteamine. Advantages of kidney-specific cysteamine creation include higher tissue levels than would be achievable via cysteamine absorption by the gastrointestinal tract, and fewer side affects associated with elevated blood levels of cysteamine (e.g. malodorous breath and sweat, nausea, vomiting, anorexia and stomach pain). Kidney diseases responsive to cysteamine therapy include fibrotic diseases (e.g. glomerulonephritis) as well as metabolic diseases including nephropathic cystinosis (where renal failure is a major complication that can be delayed for up to a decade by cysteamine therapy).

Cystinuria is another hereditary kidney disease, associated with recurrent kidney stones (nephrolithiasis). On average, adult patients require a surgical procedure for pain, infection or other complication associated with kidney stones every 3 years, and the average patient has undergone seven surgical procedures for nephrolithiasis by middle age. Patients with cystinuria are at increased risk of kidney loss, requiring nephrectomy. A small but significant proportion of cases (1-3 percent) develop end-stage renal disease and must be treated with dialysis or kidney transplantation.

Cystinuria is caused by mutations in one of the two genes (SLC3A1 and SLC7A9) encoding the low affinity cystine transporter, rBAT, a heterodimer. Disease transmission is autosomal recessive; individuals who inherit two defective copies of either gene develop cystinuria.

In healthy human subjects only 0.4% of cystine filtered through the glomerulus ends up in the urine; the other 99.6% is reabsorbed in the proximal tubule by rBAT (and to a lesser extent by another transporter). When rBAT is defective high concentrations of cystine remain in the urine as it collects in the renal pelvis. The cystine can precipitate as stones, which can cause ureteral obstruction and severe pain. Kidney stones also increase the risk of infection. (Not all patients with cystinuria develop stones; the spectrum of disease is quite broad.)

Initial treatment of cystinuria patients who do develop stones is dietary: drinking up to 5 liters of liquids per day, and alkalinizing the urine to around pH 7.5, which increases the solubility of cystine. Second line therapy is administration of thiol compounds that can form mixed disulfides with cysteine. The mixed disulfides are more soluble than cystine, and so remain dissolved in urine. The thiols penicillamine and tiopronin have been used in this way, however they are not well tolerated by most patients. Alpha-mercaptopropionylglycine has also been approved by the US FDA for cystinuria, but it is not tolerated by about one third of patients.

Orally administered cysteamine precursors degradable to 4-phosphopanthetheine in the gut, then absorbed, passed into the circulation, and eventually degraded to pantetheine and then to cysteamine by pantetheinase in the kidney, are a useful class of therapeutic compounds for cystinuria. Cysteamine readily forms mixed disulfides with cysteine via disulfide exchange with cystine, and the cysteamine-cysteine disulfide is more soluble than cystine in aqueous solutions (e.g. urine). Because this therapeutic approach entails formation of cysteamine in the kidney, lower doses of cysteamine precursor are required than would be necessary for cysteamine formed in, and absorbed from, the gut (only a small fraction of which reaches the kidney).

Other kidney diseases amenable to cysteamine therapy can be treated using a similar approach, including fibrotic diseases associated with oxidative damage and hereditary diseases, including diseases caused by mutations that alter an arginine codon to a cysteine codon. The blood supply of the kidney is a major fraction of cardiac output, ensuring delivery of a significant fraction of absorbed 4-phosphopantetheine to the kidney.

More generally, cysteamine precursors degradable to 4-phosphopantetheine (including 4-phosphopantetheine disulfides) are useful for providing therapeutic doses of cysteamine to all organs which express significant levels of phosphatase and pantetheinase. For example diseases of the lung associated with oxidative damage can be treated.

Useful cysteamine precursors for these treatment methods include coenzyme A, dephospho-coenzyme A and 4'-phosphopantetheine containing disulfides, each of which can be degraded to 4'-phosphopantetheine in the gastrointestinal tract, either by disulfide bond reduction (in the case of 4'-phosphopantetheine-containing disulfides), or by disulfide bond reduction followed by enzymatic degradation (in the case of coenzyme A and dephospho-coenzyme A-containing disulfides). In some embodiments cysteamine precursors which provide two molecules of 4'-phosphopantetheine are preferred over those that provide one. For example a 4'-phosphopantetheine-dephospho-coenzyme A mixed disulfide, or a homodimeric 4'-phosphopantetheine disulfide can deliver more in situ cysteamine generating capacity than a cysteine-4-phosphopanthetheine mixed disulfide. Another useful class of cysteamine precursors comprises dithiols linked to one or two thiols degradable to 4'-phosphopantetheine. For example, dihydrolipoic acid linked via disulfide bonds to one or two molecules of 4'-phosphopantetheine.

More generally, any disulfide composed of 4'-phosphopantetheine, dephospho-coenzyme A or coenzyme A and another thiol can, after disulfide bond reduction and (in the case of dephospho-coenzyme A or coenzyme A) partial degradation in the gastrointestinal tract, be a source of 4'-phosphopantetheine. After transport across the gastrointestinal epithelium, and upon reaching the circulation, 4'-phosphopantetheine may either be degraded by a serum phosphatase to pantetheine (which, however, is a slow reaction) and then by pantetheinase to cysteamine and pantothenate in the blood (a fast reaction), or 4'-phosphopantetheine may be degraded upon contacting tissues that express phosphatase and pantetheinase. Phosphatases, including, for example, acid phosphatases encoded by the ACP1, ACP2, ACP5 and ACPT genes, as well as alkaline phosphatases encoded by the ALPI, ALPL, ALPP and ALPPL2 genes, are (collectively) widely expressed. Tissues that express VNN1 encoded pantetheinase include the liver, kidney, heart and gastrointestinal tract, while VNN2 encoded pantetheinase is expressed in the kidney, bladder, pancreas, spleen, lung, hematopoietic system (e.g. bone marrow, lymph nodes, tonsil), connective tissue (smooth muscle, adipose tissue) and, to a lesser extent, in thyroid, adrenal gland, heart and reproductive organs (testis, ovary, fallopian tubes, endometrium). The VNN3 gene has been described as a pseudogene, however several reports describe differential VNN3 expression, suggesting a functional role. VNN3 is widely expressed. Data on tissue and cell line expression of the vanin family genes can be found in public databases such as the protein atlas (www.proteinatlas.org) and in several publications (e.g. Jansen, P. A. M. et al. Expression of the Vanin Gene Family in Normal and Inflamed Human Skin: Induction by Proinflammatory Cytokines. J. Investigative Dermatology 129: 2167-2174, 2009).

Pantothenate Kinase Associated Neurodegeneration (PKAN)

A second treatment method in which disulfide cysteamine precursors that deliver 4-phosphopantetheine can be used therapeutically is illustrated by a disease known as pantothenate kinase associated neurodegeneration (PKAN). There is preclinical and clinical evidence that cysteamine is therapeutically effective in several neurodegenerative diseases, including Parkinson's disease, Huntington's disease and neurodegeneration with brain iron accumulation (NBIA). NBIA refers to a group of rare, clinically heterogeneous diseases variably associated with progressive extrapyramidal signs, delayed motor development and cognitive decline, among other symptoms. The age of onset ranges from infancy to late adulthood. Presenting symptoms vary widely, as do rates of progression. Consequently, the diagnosis is usually suggested by observation of abnormal iron accumulation in the basal ganglia on MRI scan of the brain. Cerebellar atrophy may also be present. NBIA is associated with mutations in any of ten genes: PANK2, PLA2G6, C19orf12, FA2H, ATP13A2, WDR45, COASY, FTL, CP and DCAF17. Except for mutations in the WDR45 gene, located on the X chromosome, NBIA is transmitted as an autosomal recessive disease.

The most common type of NBIA (30-50% of all cases) is pantothenate kinase associated neurodegeneration (PKAN), which is caused by mutation in the gene encoding pantothenate kinase 2 (PANK2). Pantothenate kinase 2, which is localized to mitochondria, phosphorylates pantothenic acid to generate 4-phosphopantothenic acid, which is converted into 4-phosphopantothenoyl-cysteine, which is subsequently decarboxylated to 4-phosphopantetheine (see FIG. 11). Providing a source of 4'-phosphopantetheine, a metabolite downstream of the PANK2 catalyzed step, overcomes the requirement for functional PANK2 enzyme. Coenzyme A and dephospho-coenzyme A can both be degraded to 4'-phosphopantetheine in the gastrointestinal tract. Thus any disulfide consisting of 4'-phosphopantetheine, dephospho-coenzyme A or coenzyme A and another thiol can complement deficiency of PANK2.

In certain embodiments 4'-phosphopantetheine, dephospho-coenzyme A or coenzyme A containing disulfides can be administered to patients suffering from a PANK2 deficiency to ameliorate disease symptoms. Specifically, disulfides shown in FIG. 19 (Tables 1C and 1D), FIG. 20 (Table 1E) and FIG. 21 (the subset of compounds comprising at least one 4'-phosphopantetheine, one dephospho-coenzyme A, or one coenzyme A; thiols 3, 4 and 5, respectively, in the nomenclature of the Figures).

Disulfide cysteamine precursors of the instant application are particularly suited to implement the treatment methods outlined above. Disulfides provide an effective way to deliver 4'-phosphopantetheine (and ultimately cysteamine) because (i) disulfides are stable in air (i.e. stable to oxygen), and therefore easier to formulate and store than thiols, and stable for longer periods, (ii) the thiol group is protected until the disulfide is reduced in the small intestine, close to the site of absorption, (iii) a second thiol, with additive or complementary therapeutic properties, can be delivered simultaneously. For example, in some embodiments cysteamine-4-phosphopantetheine mixed disulfide, cysteamine-dephosphocoenzyme A mixed disulfide, and cysteamine-coenzyme A mixed disulfide are useful therapeutic compounds.

N-Acetylcysteamine Disulfide (Compound 3)

In certain embodiments the cysteamine precursor is compound 3 or a pharmaceutically acceptable salt thereof. The homodimer of two N-acetylcysteamines is an efficient delivery vehicle for cysteamine which can be used in two ways: it can be administered as a single agent, or in combination with one or more other cysteamine precursors. In both cases the goal is to provide sustained blood N-acetylcysteamine and cysteamine levels in the therapeutic range (e.g. greater than 5 micromolar but less than 75 micromolar, or greater than 10 micromolar but less than 65 micromolar in blood plasma) for the longest possible time.

In those embodiments in which compound 3 is administered as a single agent it is preferably formulated in a way that provides at least two release profiles: an early release profile and a later release profile. The early release formulation (aka instant release) starts to release compound 3 within ten minutes after oral administration. The later release formulation starts to release substantial amounts of compound 3 between about two to four hours later. The two formulations are admixed so they can be ingested together in a single dosage form. The ratio of the dose of compound 3 formulated for early release to that formulated for later release is at least 1:2, and may range up to 1:8 (e.g. 1:2, 1:3, 1:4, 1:5, 1:6, 1:7, 1:8). In one embodiment the early and late release dose components are both formulated as microbeads. Microbeads with the two release profiles can be manufactured separately then mixed together in the desired ratio to produce the dosage form (e.g., in a sachet). That approach facilitates manufacturing doses with different ratios of early to late release microbeads. Different ratios of the two types of microbeads can be used to individualize therapy for patients.

In some embodiments compound 3 is formulated in three release profiles: early, intermediate and late. The early release component starts to release compound 3 within ten minutes after oral administration, the intermediate release component starts to release substantial amounts of Compound 3 between about two to four hours after dose ingestion, and the late formulation about 3 to 6 hours after ingestion. The three release components are admixed so they can be ingested together in a single dosage form. The ratio of compound 3 in the three dose components (early:intermediate:late) is at least 1:2:2. The compound 3 in the intermediate and late components may vary independently between 2-8 times the amount in the early component, however the late release component is at least equal to the intermediate release component (e.g. 1:2:8, 1:4:6, 1:4:4, 1:5:5, 1:6:8 and so forth). In one embodiment the early, intermediate and late release dose components are all formulated as microbeads, which can be manufactured separately then mixed together in the desired ratio (e.g. a ratio customized to the gastrointestinal and liver physiology of an to produce the dosage form (e.g. in a sachet).

In certain embodiments the late dose component, or both the intermediate and late dose components are formulated for prolonged retention in the stomach (gastroretentive formulation). In other embodiments the late, or both the intermediate and late dose components are formulated for sustained release. In certain embodiments the two- or three-component dosage form is ingested with a meal, preferably a meal containing at least 500 calories, more preferably at least 700 calories. Preferably the meal is nutritionally complex (e.g. contains whole foods of several types) and at least 25% of the caloric content is derived from fat.

In those embodiments in which compound 3 is co-administered with at least one additional cysteamine precursor it is formulated to provide a release profile that complements the release profile of the at least one other cysteamine precursor, so that together the cysteamine precursors provide plasma cysteamine concentrations in the therapeutic range for the greatest length of time possible. In preferred embodiments compound 3 provides cysteamine in the first 1 to 3 hours after dosing and the at least one additional cysteamine precursor provides cysteamine for hours 3-6, 3-8, 4-10 or 3-12 of, for example, a 12 hour interval between doses. In such an embodiment the compound 3 may be formulated for instant release. In certain embodiments the at least one additional cysteamine precursor co-administered with compound 3 is compound 1 or a pharmaceutically acceptable salt thereof.

Enhancers of Cysteamine Production from Cysteamine Precursors

The methods and compositions of the invention can utilize enhancers of cysteamine production. Additional flexibility in controlling cysteamine blood levels can be achieved by combining cysteamine precursors with enhancers of the steps required to chemically and enzymatically break down cysteamine precursors to cysteamine in the gut, to absorb cysteamine into blood, and to prevent cysteamine from being rapidly catabolized in the gut, the blood or in tissues. Specific enhancers exist for each of these several steps. Thus any of the cysteamine precursors described herein may optionally be co-formulated or co-administered or administered in sequence with an agent that enhances cysteamine generation or intestinal uptake or slows cysteamine breakdown.

The first step in converting disulfide cysteamine precursors to cysteamine is reduction of the disulfide to produce two thiols. The redox environment in the gastrointestinal tract may not contain sufficient reducing equivalents to quantitatively reduce cysteamine precursors to their respective thiols, thereby limiting cysteamine generation. For example, the concentration of the reducing agents glutathione and cysteine in gastric juice is very low or undetectable (see Nalini et al., Biol Int. 32:449 (1994)). Further, in a small clinical study of high dose pantethine much of the pantethine was excreted unchanged in the stool, apparently reflecting incomplete disulfide bond reduction (see Wittwer et al., J. Exp. Med. 76:4 (1985)). To address this potential constraint, reducing agents may be co-administered or co-formulated with disulfide cysteamine precursors, or administered before or after cysteamine precursors so they are available at the time and in the place where needed. Reducing agents may promote disulfide bond reduction, freeing two thiols, or they may promote thiol-disulfide exchange reactions, in which a thiol (A) and a disulfide (B-C) react to produce a new disulfide (A-B or A-C) and a thiol (B or C), thereby releasing one of the thiols in the original disulfide (e.g. cysteamine, pantetheine or a compound degradable to cysteamine).

A variety of reducing agents may be used to promote reduction of disulfides, or thiol-disulfide exchange, in the gastrointestinal tract. Reducing agents may either directly reduce disulfide cysteamine precursors or they may reduce other disulfides, such as glutathione disulfide, that in turn reduce disulfide cysteamine precursors or participate in thiol-disulfide exchanges. In some embodiments physiological compounds (i.e. substances normally found in the body) or food-derived compounds with reducing capacity may be used to promote reduction of disulfide cysteamine precursors, or to promote thiol-disulfide exchange reactions. Physiologic reducing agents such as the thiols glutathione or cysteine (both present in the small intestine as a result of bile and enterocyte secretion) may be used, as may other compounds normally present in the body and in food such as ascorbic acid (vitamin C), tocopherols (vitamin E) or the dithiol dihydrolipoic acid, a potent reducing agent. Other widely available reducing agents including thiols such as N-acetylcysteine and non-thiols such as nicotinamide adenine dinucleotide (NADH), may also be used, as may any thiol listed in FIG. 17. Preferred reducing agents include those known to be safe in the doses required to bring about a change in the local gastrointestinal redox environment. Up to several grams of reducing agent may be required per dosing period, for example 0.5-5 grams. Disulfide cysteamine precursors that may benefit from co-administration of reducing agents are shown in FIG. 13. In particular, the compounds 1-3 can benefit from the co-administration or appropriately times subsequent administration of one or more reducings agents, as described herein. Two or more reducing agents may be combined. Preferably reducing agents have a molecular mass less than 300 Daltons.

Adult humans produce between 400 to over 1,000 milliliters (ml) of bile daily; 750 ml has been estimated as an average volume (Boyer, Compr. Physiol. 3:32 (2013)). Bile is produced in the liver throughout the day. Some is stored in the gall bladder, while the remainder provides a steady slow flow of bile, even in the fasted state (bile serves an excretory function as well as aiding in digestion and fat absorption). A meal stimulates duodenal secretion of the peptide hormones secretin and cholecystokinin, and they stimulate bile production and gall bladder contraction, respectively. The concentration of thiols in bile is approximately 4 mM, consisting mostly glutathione but also including gamma-glutamylcysteine, cysteinylglycine and cysteine (Eberle et al., J Biol. Chem. 256:2115 (1981); Abbott & Meister, J. Biol. Chem 258:6193 (1984))

Cysteine and, to a lesser extent, glutathione are also secreted into the lumen of the gastrointestinal tract by enterocytes to regulate the luminal redox potential. The thiol concentration in intestinal fluid from the jejunum of rats has been measured directly, independent of contributions from bile. It ranges from 60-200 μM in fasted rats and from 120-300 μM in fed animals (Hagen et al., Am. J. Physiol. 259:G524 (1990); Dahm and Jones, Am. J. Physiol. 267: G292 (1994)). Furthermore, unlike bile secretion, the maintenance of luminal thiol levels is a dynamic process, so that increases in intestinal levels of oxidized molecules (such as disulfide cysteamine precursors) may be countered, at least to some extent, by increased cysteine production by enterocytes (Dahm and Jones, J. Nutr. 130:2739 (2000)). The human small intestine secretes about 1.8 liters of fluid per day, and the colon about 0.2 liters, for a total of about 2 liters. The concentration of thiols (mainly cysteine) in the secreted fluid varies according to the region of the gastrointestinal tract, luminal redox potential and diet.

The total concentration of gastrointestinal thiols (both bile and enterocyte-derived) will affect the rate and extent of disulfide bond reduction and/or thiol-disulfide exchange necessary to convert cysteamine precursors to thiols, which is the necessary first step in their degradation to cysteamine. The amount of reducing equivalents available in the upper gastrointestinal tract following a meal can be estimated by making a few assumptions. For example, if we assume (i) 200 ml of bile is secreted in the hour following a large meal, and a further 100 ml in the following 2-3 hours, and (ii) the thiol concentration in bile is 4 mM, then the milliequivalents of thiol reducing power in bile amount to 0.3 L×0.004 moles/L=0.0012 moles of thiol (1.2 millimoles). Further assume that small intestinal enterocytes secrete an additional 400 milliliters during the four hours following a meal, with a thiol concentration of 200 uM, providing an additional 0.4 liters×0.0002 moles/liter=80 micromoles of luminal thiols. Combined with bile thiols a total of ~1.28 millimoles are available to reduce dietary disulfides and maintain intestinal redox potential. This is not an estimate of the upper limit of thiol secretion, which may be considerably greater, but of the normal levels of thiols in the small intestine in the hours after a meal.

A 0.5 gram dose of cysteamine-(R)-pantetheine disulfide (MW: 353.52 g/L) contains ~1.41 millimoles of disulfide bonds, and could therefore, in principal, be converted to thiols (either via disulfide bond reduction or thiol-disulfide exchange) by endogenous levels of thiols (ignoring the need for luminal thiols for other physiological purposes).

More generally, cysteamine precursor doses in excess of 1.25 millimoles may benefit from co-administration of an exogenous reducing agent. Many natural products, normally present in the diet, can provide reducing power to facilitate cysteamine precursor reduction or thiol-disulfide exchange, including the principal endogenous intestinal thiols cysteine or glutathione. Cysteine or glutathione analogs may also be used, such as N-acetylcysteine, N-acetylcysteine ethyl ester or N-acetylcysteine amide. Ascorbic acid is another agent that can reduce disulfide bonds (Giustarini et al. Nitric Oxide 19:252 (2008)). The dose of ascorbic acid required to provide reducing power equivalent to, for example, 1 gram of the disulfide cysteamine precursor cysteamine-(R)-pantetheine disulfide can be calculated as follows:

The molecular weight of ascorbic acid (176.12 g/mol) is roughly half that of cysteamine-(R)-pantetheine disulfide, also known as compound 1 (353.52 g/mol). Thus 1 gram of ascorbic acid has equimolar reducing equivalents to the number of disulfide bonds in a 2 gram dose of compound 1. Although the daily intake of vitamin C recommended by the U.S. Food and Nutrition Board is only 75 milligrams for women and 90 milligrams for men, many people take much higher doses, including doses of 1 gram per day or more, with apparently few or no adverse effects.

Similar reasoning provides the amounts of other reducing agents needed to match a compound 1 dose in molar terms. For example cysteine (molecular weight: 121.15 Daltons) is about 34% of the mass of compound 1; N-acetylcysteine (molecular weight: 163.195 Daltons) is about 46% of the mass of compound 1; alpha lipoic acid (molecular weight: 208.34 Daltons) is about 59% of the mass of compound 1, and so forth. Alpha lipoic acid and N-acetylcysteine are widely available in vitamin stores and on the internet in 600 and 1,000 mg capsules and tablets, respectively, including sustained release formulations, indicating their non-regulated status. Similar calculations can be made for other disulfide cysteamine precursors based on their molecular weight.

Because bile is the main source of thiols, and bile is successively diluted along the length of the small and large intestines, extra reducing power for cysteamine precursor reduction may be more useful in the jejunum, ileum or colon than in the duodenum. Hence formulations designed to release reducing agents in the distal small intestine and/or large intestine may be particularly useful supplements to disulfide cysteamine precursors. Sustained release formulations of ascorbic acid and other reducing agents are commercially available. Alternatively ascorbic acid could be co-formulated with a cysteamine precursor to ensure co-delivery of both agents.

The electrochemical potentials (reducing strength) associated with different biological reducing agents are known, and provide a guide to their use, however the capacity of such agents to reduce different disulfide cysteamine precursors is best determined empirically.

The kinetics of thiol-disulfide exchange reactions are strongly influenced by pH (i.e. retarded by low pH). Such exchange reactions are an alternative mechanism to disulfide bond reduction for freeing cysteamine from a cysteamine mixed disulfide, or pantetheine from a pantetheine disulfide, and so forth. To enhance the kinetics of thiol-disulfide exchange reactions basic compounds may be co-administered or co-formulated with disulfide cysteamine precursors, so they are available at the time and place where needed. Physiological compounds such as bicarbonate, present at high concentrations in pancreatic juice, may be used to modulate local gastrointestinal pH.

An essential step in converting many cysteamine precursors to cysteamine is the enzyme pantetheinase, encoded by the VNN1 and VNN2 genes in man. Pantetheine and pantetheine disulfides, including pantethine, require this enzyme to yield cysteamine. Pantetheinase is also ultimately required for cysteamine generation from compounds convertible into pantetheine in the gastrointestinal tract, such as 4-phosphopantetheine, dephospho-coenzyme A, coenzyme A and suitable analogs and derivatives. Normal levels of pantetheinase in the gastrointestinal tract may not be adequate to quantitatively cleave all the pantetheine molecules provided by pharmacological doses. To address this constraint, compounds that induce pantetheinase expression can be co-administered or co-formulated with cysteamine precursors that contain pantetheine, or compounds convertible into pantetheine, to increase the amount of pantetheinase in the gastrointestinal tract at the time and place where needed (i.e. when and where pantetheine is present). Agents that induce expression of pantetheinases include both physiological substances, including certain food components, and pharmacological agents, including FDA approved drugs. Physiological inducers of VNN1 include a variety of substances that act via the transcription factors NF-E2-related factor-2 (more commonly referred to by the acronym Nrf2), peroxisome proliferator activated receptor alpha (PPAR alpha) and peroxisome proliferator activated receptor gamma (PPAR gamma).

Factors that induce Nrf2 activation (via translocation to the nucleus) include both natural products and certain drugs. For example, sulforaphane, an isothiocyanate present in cruciferous vegetables, such as broccoli, Brussels sprouts, cabbage and cauliflower, induces VNN1 expression via Nrf2. Foods rich in sulforaphane (e.g. broccoli sprouts) may be used to induce pantetheinase expression, or sulforaphane can be administered as a pure substance in a pharmaceutical composition. Certain food-derived thiols, including S-allyl cysteine and diallyl trisulfide (both present in onions, garlic and garlic extract) also induce Nfr2, and can be included in meals administered with cysteamine precursors. Alternatively either compound may be obtained in pure form and administered in a pharmaceutical composition. Lipids present in certain foods, including some polyunsaturated fatty acids, oxidized fat, omega-3 fatty acids and the naturally occurring lipid oleylethanolamide (OEA) also induce Nrf2 and/or PPAR alpha. Foods rich in oxidized fat include French fries and other deep fried foods, which can be coadministered with cysteamine precursors that require pantetheinase cleavage to generate cysteamine. Omega-3 fatty acids are present in fish and available in fish oil extracts and in pure form for use in pharmaceutical compositions.

Naturally occurring PPAR alpha ligands include endogenous compounds such as arachidonic acid and arachidonic acid metabolites including leukotriene B4, 8-hydroxyeicosatetraenoic acid and certain members of the family. Pharmacological PPAR alpha ligands include the fibrates (e.g. benzafibrate, ciprofibrate, clinofibrate, clofibrate, fenofibrate, gemfibrozil), pirinixic acid (Wy14643) and di(2-ethylhexyl) phthalate (DEHP). Any natural or synthetic PPAR alpha ligand may be co-formulated or co-administered with a cysteamine precursor which requires pantetheinase cleavage to produce cysteamine. For a review of PPAR ligands see Grygiel-Gorniak, B. Nutrition Journal 13:17 (2014).

Natural and synthetic PPARG agonists may also be used to stimulate Nrf2-mediated transcription of the pantetheinase genes VNN1 and/or VNN2. Natural product PPARG agonists include arachidonic acid and metabolites including 15-hydroxyeicosatetraenoic acid (15(S)-HETE, 15(R)-HETE, and 15(S)-HpETE), 9-hydroxyoctadecadienoic acid, 13-hydroxyoctadecadienoic acid, 15-deoxy-(delta)12,14-prostaglandin J2 and prostaglandin PGJ2, as well as honokiol, amorfrutin 1, amorfrutin B and amorphastilbol. Other natural products activate both PPARG and PPARA, including genistein, biochanin A, sargaquinoic acid, sargahydroquinoic acid, resveratrol and amorphastilbol. Natural product PPARG agonists are described and reviewed in Wang et al., Biochemical Pharmacology 92:73 (2014)). Pharmacological PPAR gamma agonists include thiazolidinediones (also called glitazones, e.g. pioglitazone, rosiglitazone, lobeglitazone). Heme, derived from red meat, also induces VNN1 expression. PPARA or PPARG agonists that stimulate pantetheinase expression may be co-administered or co-formulated with cysteamine precursors containing pantetheine or a compound degradable to pantetheine in the gut. Two or more inducers of pantetheinase expression may be combined to enhance expression or to reduce the dose of any single agent.

Another important step in making cysteamine bioavailable throughout the body is absorption across the intestinal epithelium. Cysteamine uptake from the intestinal lumen is mediated by transporters, natural levels of which may not be sufficiently high to transport all cysteamine in the intestinal lumen. Accordingly, compounds that induce expression of cysteamine transporters can be co-administered or co-formulated with cysteamine precursors to enhance cysteamine absorption. Cysteamine is transported across the intestinal epithelium by organic cation transporters 1, 2 and 3 (encoded by the OCT1, OCT2 and OCT3 genes, also referred to as the SLC22A1, SLC22A2 and SLC22A3 genes) and possibly by other transporter proteins. Inducers of organic cation transporter expression include the transcription factors PPAR alpha and PPAR gamma, the pregnane X receptor (PXR), retinoic acid receptor (RAR) and (in the case of OCT1) the RXR receptor, as well as by the glucocorticoid receptor. Accordingly, either natural or synthetic ligands of these receptors can be used to increase OCT expression and consequently enhance cysteamine uptake by intestinal epithelial cells. Agents that stimulate expression of cysteamine transporter(s) may be co-administered or co-formulated with cysteamine precursors of any type.

The elimination half life of cysteamine in the human body (time from Cmax to half Cmax after an intravenous bolus) is about 25 minutes. Some of the cysteamine dose is transformed into a variety of disulfides, including mixed disulfides with free cysteine, with cysteinyl residues of proteins and with glutathione. No pharmacological intervention can prevent that mode of elimination, and in any event that pool of cysteamine remains available for further disulfide exchanges. There is a cysteamine catabolic pathway, however, that irreversibly transforms cysteamine, effectively removing it from the body. The enzyme cysteamine dioxygenase, which oxidizes cysteamine to hypotaurine, is a significant factor in cysteamine elimination. Hypotaurine is subsequently further oxidized to taurine. Co-administration of a cysteamine precursor with one or both of these catabolic products may slow cysteamine catabolism by end-product inhibition. Thus in certain embodiments a cysteamine precursor is co-formulated, co-administered or administered in optimal temporal sequence with hypotaurine and/or with taurine.

FIG. 13 shows a classification of cysteamine precursors based on their thiol constituents, the number of cysteamine molecules that can be generated, the metabolic steps required to generate cysteamine, potentially useful enhancers of in vivo cysteamine generation, and cysteamine release profiles. Compounds that induce higher expression of cysteamine transporter(s) (not shown in FIG. 13) are useful for all types of cysteamine precursors. Compounds that alkalinize the intestinal contents and thereby promote thiol-disulfide exchange and/or disulfide bond reduction (not shown in FIG. 13) are useful for disulfide cysteamine precursors.

In summary, flexibility in controlling cysteamine blood levels can be achieved by co-formulation or co-administration of (i) one or more cysteamine precursors with selected properties, (ii) one or more enhancers of in vivo cysteamine precursor breakdown and/or cysteamine absorption (iii) one or more inhibitors of cysteamine catabolism, using (iv) one or more types of formulation (e.g. immediate, delayed, sustained, gastroretentive or colon-targeted or a combination) and (v) a dosing schedule that enables optimal co-delivery of cysteamine precursor(s) and enhancer(s) to targeted segments of the gastrointestinal tract in amounts that can be effectively degraded and absorbed. The consequence of individualized application of these tools is sustained cysteamine blood levels in the therapeutic range for a prolonged period, resulting in a superior pharmacological effect on disease compared to existing compounds and formulations.

Pharmaceutical Compositions

The present invention provides compositions formulated to achieve a therapeutically effective plasma concentration of cysteamine over an extended period of time in order to: (i) reduce the side effects associated with high peak concentrations of cysteamine, (ii) reduce undertreatment caused by sub-therapeutic trough concentrations of cysteamine and (iii) improve patient convenience and hence compliance with therapy by reducing the number of doses per day. The compounds and formulations of the invention are also designed to (i) provide improved organoleptic properties compared to existing cysteamine formulations, (ii) reduce contact of free cysteamine with the gastric epithelium, a known source of gastrointestinal side effects, (ii) minimize the dose of cysteamine precursor required to achieve therapeutic cysteamine blood levels by matching the dose and delivery site(s) with the relevant digestive and absorptive processes in the gastrointestinal tract, which purpose may be achieved by (iii) optimizing cysteamine precursor breakdown and absorption by co-formulation or co-administration with enhancers of those processes.

For the compositions of the invention, a pharmaceutical excipient is included in all formulations to prevent exposure of a cysteamine precursor, or a salt thereof, in the mouth. Formulation methods for masking bitter or other unpleasant tastes include coatings, which may be applied in several layers. Flavorants and dyes may also be used. Methods for producing pharmaceutical compositions with acceptable mouth feel and/or taste are known in the art (e.g. see textbooks on pharmaceutical formulation, cited elsewhere; the patent literature also provides methods for producing organoleptically acceptable pharmaceutical compositions (see, e.g., U.S. Patent Publication No. 20100062988).

Gastroretentive Compositions

A first composition provides a cysteamine precursor, or a salt thereof, in a gastroretentive formulation. A variety of gastroretentive technologies are known in the art, several of which have been successfully used in marketed products. For reviews see, e.g., Pahwa et al., Recent Patents in Drug Delivery and Formulation, 6:278 (2012); and Hou et al., Gastric retentive dosage forms: a review. Critical Reviews in Therapeutic Drug Carrier Systems 20:459 (2003).

A gastroretentive formulation provides sustained release of a cysteamine precursor in the stomach. Depending on the type of cysteamine precursor subsequent in vivo cysteamine generation may start in the stomach, or in the small intestine, which is the tissue from which cysteamine is most efficiently absorbed. Some cysteamine precursors may continue to be converted into cysteamine in the large intestine, even if release from a pharmaceutical composition in the stomach or small intestine. For example, disulfide cysteamine precursors released in the stomach may remain predominately in the oxidized state in the acidic, oxidizing environment of the stomach, then start to release cysteamine after encountering reducing agents (e.g. biliary glutathione) in the small intestine. The gastroretentive composition will yield elevated blood cysteamine levels during hours 1-4 after ingestion, preferably hours 1-6, more preferably hours 1-8, hours 1-10, or longer.

Contrary to what is recommended for cysteamine bitartrate (see, for example, Procysbi® FDA Full Prescribing Information) gastroretentive formulations of cysteamine precursors should be administered with food, preferably with a meal containing sufficient caloric content and nutrient density to slow gastric emptying. A nutrient dense meal triggers osmoreceptors and chemoreceptors in the small intestine (and to a lesser extent in the stomach) which has the effect of stimulating neural and hormonal signals which diminish gastric motility, thereby delaying emptying. Delaying gastric emptying is a mechanism for prolonging the effect of a gastroretentive composition. However, filling the stomach with a large volume of food or liquid tends to promote gastric motility and speed up emptying, thus nutrient density is a more important property of a meal than volume. Solid food, which must be ground into small particles in the antrum and pylorus before emptying into the duodenum, prolongs gastric residence compared to liquid or semi-liquid food. Among liquid foods high viscosity liquids may slow gastric emptying relative to low viscosity liquids. Food with high osmotic content triggers duodenal osmoreceptors to transmit signals that slow gastric emptyping. The release of cysteamine precursors in the stomach (e.g. from a gastroretentive formulation) may increase the osmolarity of the gastric contents, and hence the duodenal contents.

In certain embodiments disulfide cysteamine precursors are preferred for gastroretentive formulations because the acidic, oxidizing environment of the stomach tends to maintain disulfides in their oxidized form, thereby limiting exposure of the gastric epithelium to cysteamine, which is believed to be one cause of cysteamine toxicity. Upon entering the duodenum and mixing with bile, which contains a high (millimolar) concentration of glutathione, cysteine and other reducing agents, the disulfide will be reduced, thereby producing free thiols in a location where they are exposed to pantetheinases and where cysteamine transporters are expressed on enterocytes.

The presence of fat in the small intestine is the most potent known inhibitor of gastric emptying, and leads to relaxation of the proximal stomach and diminished contractions in the pyloric region. Once the fat has been absorbed in the small intestine and is no longer triggering inhibitory signals to the stomach, gastric motility resumes its normal pattern. Gastroretentive formulations may therefore ideally be administered with meals containing fatty foods. Protein-rich meals also slow gastric emptying but to a lesser extent, and carbohydrate rich meals still less.

Gastroretentive compositions may also be administered with compounds that slow gastric emptying, including certain lipids, for example fatty acids with at least 12 carbon atoms stimulate cholecystokinin release from enteroendocrine cells, reducing gastric motility, while fatty acids with shorter carbon cells are not as effective. In some embodiments food or a meal may be supplemented with fatty acids or triglycerides containing fatty acids with carbon chains of 12 or longer (e.g. oleic acid, myristic acid, triethanolamine myristate, a fatty acid salt).

Fat and protein, when they reach the duodenum, stimulate secretion of several gut hormones, including ghrelin, cholecystokinin (CCK) and glucagon-like peptide 1 (GLP1). CCK slows gastric emptying by binding the CCK1 receptor (abbreviated CCK1R, formerly called the CCK-A receptor). In some embodiments orally active CCK agonists or mimics, positive allosteric modulators of CCK1R, or agents that promote release of endogenous CCK, or that inhibit CCK degradation, or that otherwise prolong CCK action through some combination of those or other mechanisms, are administered with gastroretentive compositions to slow gastric emptying and prolong gastric residence of the gastroretentive composition. CCK is a peptide that exists in several forms ranging from 8 amino acids up to 53 amino acids (e.g. CCK-8, CCK-53). Oral administration of the peptides is not effective because they are digested in the gastrointestinal tract. Small molecule CCK agonists have been developed and tested by several research groups. For example SR-146,131 and related compounds were developed by scientists at Sanofi (U.S. Pat. Nos. 5,731,340 and 6,380,230, herein incorporated by reference).

Certain protease inhibitors induce CCK production or release, or prolong its half life, or otherwise potentiate its effect, including both food-derived mixtures and pure compounds. For example ingestion of a protease inhibitor concentrate derived from potato is associated with elevated levels of CCK, as is ingestion of soybean peptone and soybean beta-conglycinin peptone. Camostate is a synthetic protease inhibitor with pleiotropic effects, including stimulation of endogenous CCK release, and consequent slowing of gastric emptying. Camostat mesilate is a pharmaceutical salt that has been used extensively in man. FOY-251 is an active metabolite of camostat. In some embodiments an agent that stimulates CCK production or release, or prolongs CCK half life, or otherwise potentiate CCK effect is co-formulated or co-administered with a gastroretentive composition in an amount that slows gastric emptying. In some embodiments, camostat, FOY-251, or a prodrug, derivative or active metabolite of camostat, or a pharmaceutically acceptable salt thereof, is co-formulated or co-administered with a gastroretentive composition in an amount ranging between 50-300 mg/kg, or between 100-250 mg/kg.

Gastric emptying is also slowed by acidification of the chyme. For example citric and acetic acids have been shown to delay gastric emptying. In some embodiments food or a meal includes a natural source of citric acid (e.g. fruit or juice from an orange, lemon, lime, grapefruit or other citrus rich fruit) or acetic acid (e.g. vinegar, pickles or other pickled vegetables) or lactic acid (e.g. sauerkraut or kimchi). In some embodiments an amount of acidic food or liquid sufficient to lower the pH of gastric chyme below pH 4 or below pH 3.5 is administered with a gastroretentive composition.

Glucagon-like peptide-1 (GLP1) is another gut hormone that is released by cells in the duodenum in response to food, particularly ingested fat, and that influences gastric emptying. Orally administered GLP1 receptor agonists have been discovered by several research groups (e.g. Sloop et al., Diabetes 59:3099 (2010)). Positive allosteric modulators of the GLP1 receptor, which are not agonists themselves but which potentiate endogenous GLP1, are another category of GLP1R stimulating agents (e.g. Wootten et al., J. Pharmacol. Exp. Ther. 336:540 (2011); Eng et al., Drug Metabolism and Disposition 41:1470 (2013); also see U.S. Patent Publication Nos. 20060287242, 20070021346, 20070099835, 20130225488 and 20130178420, each of which is incorporated herein by reference). Among the compounds that positively modulates GLP-1 receptor signaling in the presence of endogenous GLP1 is quercetin, which acts by binding an allosteric site on the GLP-1 receptor and positively influencing receptor signaling upon binding of endogenous ligands (GLP-1, a peptide, is present in several forms.) Some quercetin analogs are also positive modulators of endogenous GLP1. Quercetin is a flavonol present in many fruits, vegetables, leaves and grains. It is used as an ingredient in health supplements, beverages and foods. In some embodiments a GLP-1 receptor agonist or positive allosteric modulator of GLP-1 is co-formulated or co-administered with a gastroretentive composition in an amount sufficient to delay gastric emptying. In some embodiments the GLP-1 receptor agonist or positive allosteric modulator is quercetin or an analog, derivative or active metabolite of quercetin. Certain small molecule drugs are also able to slow gastric emptying time, and may be co-administered or co-formulated with gastroretentive compositions.

Gastric emptying is also slowed by acidification of the chyme. For example citric and acetic acids have been shown to delay gastric emptying. In some embodiments, food or a meal includes a natural source of citric acid (e.g. orange, grapefruit or other citrus rich fruits) or acetic acid (e.g. vinegar, pickles or other pickled vegetables) or lactic acid (e.g. sauerkraut or kimchi). In some embodiments the pH of the chyme is reduced below 4 or below 3.5 by administration of acidic food or liquid with a gastroretentive composition.

U.S. Pat. No. 8,741,885 describes a method for prolonging gastric retention of a gastroretentive pharmaceutical composition (e.g. a floating, swelling or mucoadhesive composition) by combining an active pharmaceutical ingredient with an opioid. The purpose of the co-formulated opioid is to slow gastric emptying. Gastroparesis, or severely depressed gastrointestinal motility, is a well known and potentially serious complication of opioid therapy.

Sustained Release Compositions

A second composition provides a cysteamine precursor, or a salt thereof, in a non-gastroretentive sustained release formulation. Sustained release formulations are well known in the art: Wen, H. and Park, K. (editors) Oral Controlled Release Formulation Design and Drug Delivery: Theory to Practice. Wiley, 2010; Augsburger, and L. L. and Hoag, S. W. (editors) Pharmaceutical Dosage Forms—Tablets, volume 3: Manufacture and Process Control. CRC Press, 2008. The sustained release component may be a tablet, a powder, or a capsule filled with microparticles. Optionally the particles may vary in size, in composition (e.g the type or concentration of a sustained release polymer), or in the type or thickness of a coating agent, or in the number and composition of layers if coated with multiple layers of coating agents, such that drug is released at different rates, or at different starting times, from individual particles, thereby providing, in aggregate, drug release over an extended period of time compared to a formulation in which all particles are substantially identical. The sustained release formulation may optionally be coated with a pH sensitive material that prevents dissolution in the stomach (referred to as an enteric coating). The microparticles in a single composition may vary in the type or thickness of one or more coating agents. For example, the pH at which the coating dissolves may very. The two or microparticles used in such mixed compositions may be manufactured separately to tight specifications and then blended in a ratio to achieved prolonged drug release in vivo.

A sustained release composition may provide prolonged release of the cysteamine precursor in the stomach and/or the small intestine (not the former if enteric coated) and consequently sustained in vivo cysteamine generation. A sustained release formulation may be designed to release drug for a period of time roughly equal to the sum of the average gastric and small intestinal transit times, e.g. 3-5 hours if administered in the fasting state or 5-8 hours if administered with food or with a meal. Alternatively the sustained release formulation may be designed to release drug for longer than the sum of the average stomach and small intestinal transit times, so as to continue to release cysteamine precursors in the large intestine. In some embodiments such a sustained release composition may release a cysteamine precursor for between 4-8 hours when administered in the fasted state or between 6-10 hours, or longer, when administered with a meal.

The sustained release formulation may yield elevated blood cysteamine levels during hours 1-4 after ingestion, preferably hours 1-6, more preferably hours 1-8, still more preferably hours 1-10 or longer. Sustained release formulations of cysteamine precursors may be administered with food or between meals, and optionally with enhancers of cysteamine precursor degradation or cysteamine absorption. Food tends to inhibit absorption of free cysteamine, particularly fatty foods, and it is generally recommended to ingest cysteamine salts on an empty stomach, though small amounts of applesauce or similar foods are permitted.

Mixed Formulations

Some compositions necessarily have elements of two types of formulation, one mainly directed at controlling the rate of drug release and the other mainly directed at controlling the anatomical site of drug release. For example gastroretentive formulations always contain drug in a sustained release formulation, otherwise there would be no point in prolonged gastric residence. However, there are ways to combine immediate and sustained release components in a single gastroretentive formulation. For example, the immediate release component may form an outer layer that is rapidly dissolved or that rapidly disintegrates in the stomach, leaving a core sustained release component that remains in the stomach by one or more of the gastroretentive mechanisms described herein. However, not all types of formulation can be productively combined. For example an enteric coated gastroretentive formulation would be counterproductive because gastroretentive formulations are designed to release drug in the stomach—and gastric release would be blocked by a coating resistant to dissolution in acidic medium.

Compositions with different temporal or anatomical drug release profiles can, when combined with suitable cysteamine precursors, and optionally with enhancers of cysteamine generation or absorption, provide blood cysteamine levels in the therapeutic range for 0.5-6 hours, more preferably 0.5-8 hours, and most preferably 0.5-12, 0.5-15 hours or longer. Examples of productive combinations of formulations follow, including mixed formulations with up to two drug release components, and separately formulated compositions that can be combined in various amounts and ratios to tailor the amount and timing of in vivo cysteamine generation and absorption to the needs of an individual patient.

A third composition provides a mixed formulation of a first enteric coated component formulated for delayed release of a cysteamine precursor, or a salt thereof, in the small intestine; and a second component of enteric coated microparticles formulated for sustained release of a cysteamine precursor, or a salt thereof throughout the small intestine and the proximal part of the large intestine. The mixed formulation provides a first component to initially achieve elevated levels of cysteamine in the blood, while the second component sustains cysteamine levels in the blood over time.

A fourth composition provides a mixed formulation that includes (i) a sustained release gastroretentive formulation of a cysteamine precursor, or a salt thereof, (ii) an immediate release formulation of a cysteamine precursor, or a salt thereof designed to release drug in the stomach. The second component of the mixed formulation is on the exterior surface of the composition and starts to dissolve immediately on contact with the stomach contents. It is the first to generate cysteamine, albeit not necessarily in the stomach. The first (gastroretentive) component provides prolonged cysteamine precursor release in the stomach, and ensuing in vivo cysteamine generation throughout the small intestine and, depending on the characteristics of the cysteamine precursor, into the large intestine. The combined in vivo generation and absorption of cysteamine from the two components starts within 1 hour after administration of the mixed composition and continues for at least 5 hours, preferably remaining within the therapeutic concentration range for 8, 10, 12 or more hours.

In a fifth composition, a first component is formulated for immediate release in the stomach and includes a cysteamine precursor, preferably a cysteamine mixed disulfide or a pantetheine disulfide, or a salt thereof and a second component is formulated for sustained release of a cysteamine precursor, or a salt thereof. The first component is on the exterior surface of the composition, so that the second component remains intact after dissolution or disintegration of the first component. The mixed formulation of this fifth composition may produce an initial elevation of plasma cysteamine concentration from the immediated release component and maintain elevated levels of cysteamine from the second (sustained release) component, with continued in vivo cysteamine production for 6 hours, 8 hours, 10 hours of longer. The release of a cysteamine precursor (or several different cysteamine precursors) along the gastrointestinal tract, from the stomach to the large intestine allows the amount of cysteamine precursor to be matched to the levels of panthetheinase and cysteamine transporters in all segments of the gut, thereby maximizing cysteamine generation and absorption. Continuous intestinal generation and absorption of cysteamine avoids reliance on a high Cmax for lengthening exposure, thereby lessening cysteamine side-effects associated with high peak levels. Thus, mixed formulations of cysteamine precursors allow for administration of cysteamine to numerous disorders that are sensitive to the effects of cysteamine.

In a sixth composition, a first component is formulated for immediate release in the stomach and includes a cysteamine precursor, preferably a cysteamine mixed disulfide or a pantetheine disulfide, or a salt thereof; a second component is formulated for release of a cysteamine precursor, or a salt thereof in the ileum and/or colon. The mixed formulation of this sixth composition may produce an initial elevation of plasma cysteamine levels from the immediated release component and a second elevation of plasma cysteamine levels from the ilium and colon-targeted component around the time the first peak is rapidly decreasing. The second component may start to release cysteamine precursor four to eight hours after administration, depending on whether it was administered with or without food. The controlled release of a cysteamine precursor (or different cysteamine precursors) along the gastrointestinal tract, from the stomach to the large intestine allows the amount of cysteamine precursor to be matched to the levels of panthetheinase and cysteamine transporters in all segments of the gut to maximize cysteamine generation and absorption.

Compounds

The pharmaceutically acceptable compositions of the invention include one or more cysteamine precursors, or pharmaceutically acceptable salt(s) thereof. Salts of the invention may include, without limitation, salts of alkali metals, e.g., sodium, potassium; salts of alkaline earth metals, e.g., calcium, magnesium, and barium; and salts of organic bases, e.g., amine bases and inorganic bases. Exemplary salts are found in Remington's Pharmaceutical Sciences, 17th ed., Mack Publishing Company, Easton, Pa., 1985, p. 1418, Berge et al., J. Pharmaceutical Sciences 66:1 (1977), and Pharmaceutical Salts: Properties, Selection, and Use, (Eds. P. H. Stahl and C. G. Wermuth), Wiley-VCH, 2008, each of which is incorporated herein by reference in its entirety.

The compositions of the invention may include a cysteamine precursor, or a salt thereof, in a component of a gastroretentive or mixed formulation to achieve plasma concentrations of cysteamine in the therapeutic range within the first 4 hours following administration, preferably within the first 2 hours following administration, and most preferably within the first hour. The cysteamine plasma concentration preferably remains in the therapeutic range for at least 5 hours, preferably 6 hours, more preferably 8 hours, 10 hours or longer. The formulation may include a thiol cysteamine precursor which can be enzymatically degraded to produce cysteamine, such as pantetheine, or a compound which can be degraded to pantetheine (and thence cysteamine) in the gastrointestinal tract, such as 4-phosphopantetheine, dephospho-coenzyme A or coenzyme A, or derivatives or prodrugs thereof that can be degraded to pantetheine in the gastrointestinal tract (and then to cysteamine). Alternatively, the cysteamine precursor may be formed by reacting cysteamine, or a compound which can be degraded to produce cysteamine, with another thiol-containing organosulfur compound to form a disulfide compound. A disulfide cysteamine precursor, or a salt thereof, may be formed by reacting cysteamine with a thiol cysteamine precursor such as pantetheine, 4-phosphopantetheine, dephospho-coenzyme A, coenzyme A or N-acetylcysteamine, or by reacting cysteamine with other thiols including N-acetylcysteine (NAC), N-acetylcysteine amide, N-acetylcysteine ethyl ester, homocysteine, glutathione (GSH), allyl mercaptan, furfuryl mercaptan, benzyl mercaptan, thioterpineol (grapefruit mercaptan), 3-mercaptopyruvate, L-cysteine, L-cysteine ethyl ester, L-cysteine methyl ester, thiocysteine, cysteinylglycine, gamma-glutamylcysteine, gamma-glutamylcysteine ethyl ester, glutathione monoethyl ester, glutathione diethyl ester, mercaptoethylgluconamide, thiosalicylic acid, tiopronin or diethyldithiocarbamic acid. Thiol cysteamine precursors, or cysteamine, may also be reacted with dithiols such as dihydrolipoic acid, meso-2,3-dimercaptosuccinic acid (DMSA), 2,3-dimercaptopropanesulfonic acid (DMPS), 2,3-dimercapto-1-propanol (dimercaprol), bucillamine or N,N'-bis(2-mercaptoethyl) isophthalamide ($BDTH_2$) to form disulfide cysteamine precursors. See FIG. 17 for a list of thiols that can be used to form disulfide cysteamine precursors, and FIGS. 18-21 for tables summarizing pairs of thiols than can be joined to form disulfide cysteamine precursors. Other thiols suitable for forming cysteamine precursors are known in the art. For example PCT Patent Publication No. WO 1993006832, incorporated herein by reference in its entirety, discloses additional useful thiols not included in FIG. 17, including N,N-dimethylcysteamine, thiocholine, aminopropanethiol, aminobutanethiol and aminopentanethiol, among others The disulfides formed may delay the release of cysteamine in the stomach and/or facilitate its in vivo generation and absorption in the small intestine, depending on the properties of the cysteamine precursor used (e.g. the number of degradative steps required to form cysteamine). FIG. 13 shows a classification of cysteamine precursors and summarizes selected pharmacologically relevant properties. FIGS. 18-21 provide information on the cysteamine yield of many disulfide cysteamine precursors. The stomach is generally a more oxidizing and more acidic environment than the small intestine. When the gastric contents pass into the duodenum they mix with pancreatic juice, which contains bicarbonate that neutralizes stomach acid, and with bile, which contains the physiologic reducing agent glutathione at millimolar concentrations, as well as related thiols including cysteine. Consequently, disulfides tend to remain oxidized in the stomach and are more likely to be reduced, or to participate in disulfide exchange reactions with thiols, in the small intestine. Disulfide exchange reactions are generally catalyzed by the thiolate ion, which is much more nucleophilic than the thiol form; thiolate ion formation is not favored in the acidic environment of the stomach.

For instance pantetheine, a thiol cysteamine precursor, may form a homodimeric disulfide where two pantetheines are covalently linked to form a pantethine (a disulfide cysteamine precursor). In some preferred embodiments, the cysteamine precursor provides more than one cysteamine, as provided by, for example, the mixed cysteamine disulfides formed by joining cysteamine with either pantetheine, 4-phosphopantetheine, dephospho-coenzyme A or coenzyme A, or by the corresponding mixed pantetheine disulfides formed by oxidizing pantetheine with either 4-phosphopantetheine, dephospho-coenzyme A or coenzyme A, or a suitable prodrug or analog convertible to the parent compound in the gastrointestinal tract. Also, 4-phosphopantetheine can be disulfide bonded to dephospho-coenzyme A or coenzyme A, or dephospho-coenzyme A can be disulfide bonded to coenzyme A to make cysteamine precursors capable of yielding two cysteamines in vivo. FIG. 13 shows the number of cysteamines that can be generated in vivo from different classes of cysteamine precursors. FIGS. 18-21 show specific disulfide cysteamine precursors; those that yield two cysteamines in vivo are listed at the top of the tables and the fractional yield of cysteamine (in percent) for each disulfide Is also shown, as are the number of degradative steps required to yield cysteamine. In some embodiments, the reactive thiol group of cysteamine or an organosulfur may be modified to include a substituent such as an acetyl group, ester group, glutamyl, succinyl, phenylalanyl, polyethylene glycol (PEG), and/or a folate.

In preferred embodiments, the composition of the invention may include a pantetheine, a disulfide containing pantetheine, or a salt thereof, in a component of the gastroretentive formulation and/or a component of a mixed formulation to sustain elevated blood levels of cysteamine for 5-10 hours after administration or longer. The composition may be a cysteamine precursor that requires chemical reduction or enzymatic conversion of the parent compound into at least one cysteamine, thereby delaying the release of cysteamine. The formulation may include pantetheine, or a compound which can be degraded to pantetheine in the gastrointestinal tract (e.g. 4-phosphopantetheine, dephospho-coenzyme A or coenzyme A; collectively pantetheine precursors), in which the thiol group of pantetheine, or a pantetheine precursor, is reacted with a thiol group of another organosulfur compound to form a disulfide compound. Since pantetheinase is expressed at higher levels in the intestine than in the stomach, and the lumen of the small intestine is a more reducing environment than the stomach, the pantetheine component of a disulfide cysteamine precursor may be converted to cysteamine, and subsequently absorbed, in the small intestine. For instance, pantetheine may form a homodimeric disulfide in which two pantetheines are covalently linked to form a pantethine. Pantetheine-containing cysteamine precursors may also include pantetheine mixed disulfides, where the pantetheine thiol reacts with a thiol group to form a disulfide. In preferred embodiments, the pantetheine precursor provides more than one cysteamine, as provided, for example, by the mixed disulfide formed from cysteamine and pantetheine, which when reduced and subsequently cleaved by pantetheinase yields 2 cysteamines and one pantothenic acid; or by the mixed disulfide pantetheine-coenzyme A, which when reduced and subsequently degraded and then cleaved by pantetheinase yields 2 cysteamines, 2 pantothenic acids, and ADP. Other disulfide cysteamine precursors that yield two cysteamines upon degradation in the gut are shown in FIGS. 18-21. In some embodiments, the reactive thiol group of pantetheine or an organosulfur compound may be modified to include a substituent such as an acetyl group, methyl ester, ethyl ester, glutamyl, succinyl, phenylalanyl, polyethylene glycol (PEG), and/or a folate.

The distinction between cysteamine precursors requiring pantetheinase cleavage to generate cysteamine vs. cysteamine precursors requiring only chemical reduction to generate cysteamine (cysteamine mixed disulfides) is significant because the kinetics of conversion of the precursor compound to cysteamine are generally more rapid with the second category, provided an adequately reducing environment exists (or can be created pharmacologically) in the intestine. A further distinction can be made between cysteamine precursors requiring reduction followed by pantetheinase cleavage (e.g. pantethine) vs. cysteamine precursors requiring first reduction then degradation to pantetheine then pantetheinase cleavage (e.g. 4-phosphopantetheine, dephospho-coenzyme A or co-enzyme A containing disulfides). The additional degradation step(s) required by the latter class of disulfide cysteamine precursors slows and extends the period of cysteamine production over a longer time period.

The compounds of the present invention can be prepared in a variety of ways known to one of ordinary skill in the art of chemical synthesis. Methods for preparing thiols, including cysteamine, pantetheine, 4-phosphopantetheine, dephospho-coenzyme A or coenzyme A and other thiols (see FIG. 17) are well known in the art. Coenzyme A, pantethine, N-acetylcysteamine and glutathione are available commercially as dietary supplements. Most of the other thiols in FIG. 17 are readily available from chemical firms.

Synthesis of Cysteamine Precursors

The present compounds, including both thiol and disulfide cysteamine precursors can be prepared from readily available starting materials using methods and procedures known in the art, such as those described by Mandel et al., Organic Letters, 6:4801 (2004). Methods for manufacturing pantethine are described in U.S. Pat. Nos. 3,300,508 and 4,060,551, each of which is incorporated herein by reference. Methods for converting liquid pantetheine to a solid form are disclosed in Japanese Patents Publication Nos. JP-A-S50-88215 and JP-A-S55-38344. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one of ordinary skill in the art by routine optimization procedures.

In preferred embodiments the composition of the invention includes one or more disulfide cysteamine precursors. Disulfides, being oxidized forms of thiols, are readily formed from constituent thiols without expensive reagents or equipment. Further, disulfides are not subject to the oxidation that can limit the long term stability of thiol compounds exposed to air. Thus with respect to manufacturing, cost, storage cost, shipping and patient convenience (i.e. long shelf life), disulfide forms of cysteamine precursors are preferable to thiol forms.

In some embodiments, mixed disulfide cysteamine precursors are synthesized by joining two different thiols, forming three reaction products: thiols A and B can join to form disulfides A-A, A-B and B-B. For example, disulfides formed by reacting cysteamine with pantetheine include: cysteamine-cysteamine (referred to as cystamine), cysteamine-pantetheine and pantetheine-pantetheine (referred to as pantethine). All three compounds are useful in providing cysteamine, and in fact the dissimilar steps involved in converting each compound to cysteamine can be pharmacologically beneficial by expanding the period of time over which cysteamine is generated in vivo by disulfide bond reduction or by a combination of reduction and enzymatic degradation steps. Thus the co-formulation of all three oxidation products without purification (except to remove unreacted thiols and/or unwanted impurities such as solvent) may be pharmacologically useful. This is particularly so when the two reacted thiols are each convertible into cysteamine (e.g. pantetheine, 4-phosphopantetheine, dephospho-coenzyme A, coenzyme A, N-acetylcysteine or suitable analogs and prodrugs), or when cysteamine itself is reacted with a thiol convertible into cysteamine. Consequently, in certain embodiments all three disulfides formed by reacting two different thiols, each convertible to cysteamine (or one of which is cysteamine), are co-formulated in a single composition. This method of synthesis and formulation does not require the more complex synthetic steps, or the post-synthesis purification steps required to separate a mixed disulfide from the two homodimeric disulfides which are created simultaneously in the oxidation reaction. (Unreacted thiols and other impurities must of course be removed before formulating a pharmaceutical composition.)

The advantages of manufacturing and co-formulating a mixture of three disulfides are not as fully realized in the case of disulfide cysteamine precursors made by reacting a thiol convertible to cysteamine with a second thiol not convertible to cysteamine. For example the three disulfides formed by reacting pantetheine with N-acetylcysteine (NAC) are: pantetheine-pantetheine (pantethine), pantetheine-NAC and NAC-NAC. The first two compounds are cysteamine precursors, the third (NAC-NAC) is not. However, NAC-NAC may nevertheless have beneficial pharmacological properties with respect to modulating the intestinal redox environment, or beneficial medical properties as a consequence of providing, upon chemical reduction, two NAC molecules. Thus in certain embodiments all three disulfide products formed by reacting cysteamine or a thiol convertible into cysteamine in vivo with a second thiol not convertible into cysteamine in vivo are co-formulated in a single composition.

The expected ratio of reaction products when two different thiols are oxidized depends on the molar ratio of the two thiols, the absolute concentration of the two thiols, pH, and/or the chemical environment around the sulfhydryl group of each thiol. If the ratio of thiol A to thiol B is 1:1 the expected molar ratio of the reaction products A-A, B-B, A-B is about: 1:1:2. (Deviations from the expected ratio may occur as a result of differences in the chemical bonds adjacent to the thiol that may affect, for example, the kinetics of disulfide bond formation, which may be influenced by the electronegativity of the atom bound to the sulfhydryl. Any deviation can be predicted or measured using methods known in the art.) The ratio of reaction products can be altered by changing the molar ratio of the two thiols. For example to increase the proportion of A-A and A-B relative to B-B the molar concentration of thiol A may be increased relative to that of thiol B. When reacting two thiols, one of which is cysteamine or a compound degradable to cysteamine (thiol A) and the other a thiol not degradable to cysteamine (thiol B), the molar concentration of the first thiol may be increased relative to that of the second thiol so as to increase the proportion of cysteamine precursors produced. For example reacting thiols A and B in a molar ratio of 2:1 increases the proportion of A-A and A-B (both cysteamine precursors) relative to B-B (not a cysteamine precursor).

In certain embodiments the oxidation of two unlike thiols can be promoted, and/or the mix of reaction products altered, by inclusion of a catalyst (reviewed in Musiejuk and Witt (2015)). For example an oxidant like hydrogen peroxide or dimethyl sulfoxide (DMSO) can be added, or a metal such as copper, manganese or telluride, or iodine, diethylazodicarboxylate (or related compounds), or dichlorodicyanoquinone (DDQ). Optimal performance of the catalyst can be achieved by empirically determining the best solvent system, catalyst concentration and reaction conditions.

In other embodiments an asymmetric disulfide can be produced via a thiol-disulfided exchange reaction between a thiol and a symmetrical disulfide. This type of reaction, like the oxidation of two dissimilar thiols, provides a mixture of all possible products (symmetrical and unsymmetrical disulfides). However, by providing a molar excess of the symmetrical disulfide over the thiol, formation of the unsymmetrical disulfide is favored, and may even be the major reaction product under optimized conditions. Example 15 and 16 describes synthesis of pantetheine-cysteamine disulfide via thio-disulfide exchange. The method works with cysteamine as the thiol and pantethine as the disulfide, and with pantetheine as the thiol and cystamine as the disulfide. In preferred embodiments of the thiol:disulfide exchange reaction the molar ratio of thiol to disulfide (e.g. cysteamine:pantethine) is between 2:1 and 4:1, between 2.5:1 and 3.5:1, between 2.7:1 and 3.3:1. In certain embodiments the solvent is methanol and the reaction time is between 1-20 hours, or between 1-12 hours, or between 1-6 hours. In certain embodiments the product of the thiol:disulfide exchange reaction (e.g. TTI-0102) is subsequently precipitated (e.g. as described in Example 17).

Alternatively, in another embodiment the ratio of cysteamine precursors used in a pharmaceutical composition may be adjusted by combining the three reaction products of a mixed disulfide oxidation reaction with a pure disulfide. For example, if the thiols cysteamine (C) and pantetheine (P), are oxidized in a 1:1 molar ratio they will combine to form 3 products: C-C, P-P and C-P in a ratio of approximately 1:1:2. Pure pantethine (P-P) can be added to the mixture in any desired amount to prolong the in vivo cysteamine-generating properties of the mixture. Doubling the starting amount of pantethine would yield a ratio of 1:2:2. Adding four times the starting amount of pantethine would yield a ratio of 1:2:5.

Two independently generated mixed disulfide reaction products may also be combined to achieve novel ratios of cysteamine precursors. For example, if the cysteamine-pantetheine reaction products (C-C, P-P and C-P) are combined with an equimolar quantity of reaction products from an N-acetylcysteine (NAC)-cysteamine (C) oxidation reaction (C-C, NAC-NAC and C-NAC in a ratio of 1:1:2), the mixture will contain five compounds, one of which, NAC-NAC, can not be converted to cysteamine. The other four disulfides, P-P, C-C, C-P, C-NAC are present in a molar ratio of approximately 1:2:2:2. Optionally, pantetheine may be added to make the ratio, for example, 2:2:2:2 (more simply expressed as 1:1:1:1) or added in greater quantity to make the ratio 1:1:1:5. Thus the molar ratio of disulfides in a pharmaceutical composition can be controlled by a variety of methods. In another example, the cysteamine-pantetheine reaction products (C-C, P-P and C-P) may be combined with an equimolar quantity of reaction products from a 4-phosphopantetheine (4P)-cysteamine (C) oxidation reaction (namely C-C, 4P-4P and C-4P in a ratio of 1:1:2), to produce a mixture of five disulfides in a ratio 1:1:1:2:2.

In summary, when oxidizing one thiol to make a cysteamine precursor disulfide there is only one product (e.g. pantetheine+pantetheine=pantethine). When oxidizing two thiols there are three products, either two or three of which are cysteamine precursors, depending on whether one or both of the thiols is degradable to cysteamine, or is cysteamine. Mixtures of cysteamine precursors are most easily made by combining the products of these two types of reactions. Mixtures may include various molar ratios of pure disulfide or three-component disulfide mixtures. However, heterodimeric cysteamine precursors may also be used in pure form, after purification, or combined with other homo- or heterodimeric cysteamine precursors.

Alternatively, by using more sophisticated chemical methods specific mixed disulfides (also called unsymmetrical disulfides) may be selectively synthesized (e.g. cysteamine and pantetheine can be combined to form substantially only the disulfide cysteamine-pantetheine). These methods employ a wide range of sulfur-protecting groups and strategies for their removal. The most widely used approach entails substitution of a sulfenyl derivative with a thiol or its derivative. Commonly utilized sulfenyl derivatives include: sulfenyl chlorides, S-alkyl thiosulfates and S-aryl thiosulfates (Bunte salts), S-(alkylsulfanyl)isothioureas, benzothiazol-2-yl disulfides, benzotriazolyl sulfides, dithioperoxyesters, (alkylsulfanyl)dialkylsulfonium salts, 2-pyridyl disulfides and derivatives, N-alkyltetrazolyl disulfides, sulfenamides, sulfenyldimesylamines, sulfenyl thiocyanates, 4-nitroarenesulfenanilides, thiolsulfinates and thiolsulfonates, sulfanylsulfinamidines, thionitrites, sulfenyl thiocarbonates, thioimides, thiophosphonium salts and 5,5-dimethyl-2-thioxo-1,3,2-dioxaphosphorinan-2-yl disulfides. Still other procedures involve: reaction of a thiol with a sulfinylbenzimidazole, rhodium-catalyzed disulfide exchange, electrochemical methods, and the use of diethyl azodicarboxylate. These and other methods are reviewed by Musiejuk, M. and D. Witt. Organic Preparations and Procedures International 47:95 (2015). Thus with only modest effort a specific mixed (unsymmetrical) disulfide of interest can be made. Examples 1 and 2 provide synthetic procedures for mixed disulfides of the invention.

In still other embodiments a mixed disulfide can be synthesized from a symmetric disulfide by preferentially coupling a substituent (e.g. an acyl group) to one end of the symmetric disulfide (i.e. hemi-acylation). For example, since cysteamine and pantetheine differ by a pantothenate moiety, the disulfide cystamine can be hemi-acylated by pantothenate to produce cysteamine-pantetheine disulfide. When the concentration of reactants is optimized, and coupling agents added to facilitate the acylation, this procedure can produce yields of greater than 95 percent. Cystamine is an attractive starting point for creating assymetric disulfides because it contains reactive amino groups at both ends. Example 14 describes efficient synthesis of pantetheine-cysteamine disulfide via hemi-acylation of cystamine by the substituent pantothenic acid via a reactive intermediate. In certain embodiments the molar ratio of the acyl group to the disulfide is between 1:2 and 1:4. In certain embodiments the acylation reaction is facilitated by addition of N,N'-dicyclohexylcarbodiimide (DCC) at a molar ratio of DCC:acyl group between 3:1 and 5:1. In certain embodiments the acylation reaction is facilitated by addition of 1-Hydroxybenzotriazole (HOBt) at a molar ratio of HOBt:acyl group between 1:1 and 1:3.

Stereochemistry

Some of the compounds of the invention exist in more than one enantiomeric form. In particular pantetheine, 4-phosphopantetheine, dephospho-coenzyme A and coenzyme A contain a chiral carbon in the pantothenoyl moiety. Thus each of these compounds can exist as the D- or L-enantiomer, or as a racemic mixture of the two with respect to the pantothenoyl group. However, human pantetheinases (encoded by the VNN1 and VNN2 genes) are specific for D-pantetheine. (Bellussi et al., Physiological Chemistry and Physics 6:505 (1974)). Thus only D-pantetheine (and not L-pantetheine) is a cysteamine precursor, and accordingly the present invention concerns only D-pantetheine, and only the D-enantiomers of 4-phosphopantetheine, dephospho-coenzyme A and coenzyme A and any analogs or prodrugs convertible to those compounds in the gastrointestinal tract. Likewise, all disulfides that contain a pantetheine, 4-phosphopantetheine, dephospho-coenzyme A and coenzyme A, or any suitable analog or prodrug, only employ the D-enantiomer.

The L-enantiomer of amino acids and amino acid derivatives is preferred. Thus "cysteine" herein refers to L-cysteine, homocysteine to L-homocysteine, and cysteine derivatives such as N-acetylcysteine, N-acetylcysteine amide, N-acetylcysteine ethyl ester, cysteine methyl ester, cysteine ethyl ester, cysteinylglycine and gamma glutamyl cysteine are all formed using the L-enantiomer of cysteine.

For dihydrolipoic acid the R enantiomer is preferred, as that is the enantiomer made in the human body. In general, for compounds that are normally present in the human body or that are present in foods the naturally occurring enantiomer is preferred.

Salt Forms and Crystallization

The pharmaceutical properties of any compound, including the cysteamine precursors of the invention, may be improved by association with a counterion, or salt. Specific properties that may be improved include stability (e.g. less hygroscopic, less susceptible to oxidation, more resistant to heat, humidity and pH extremes), better tendency to form crystals, ease of formulation (e.g. relating to the properties of solid forms of the compound such as powders).

The potential for a salt form to improve the crystallization properties of a compound are particularly important, since crystallization is a less expensive, faster and more scalable purification method than, for example, column chromatography. Methods for inducing precipitation of small molecules are known in the art (e.g. see reviews by Chen et al. and others in Crystal Growth and Design, 11(4), 2011). Crystallization can be induced by cooling a saturated solution of a target compound, or by addition of an anti-solvent (a liquid in which the target compound is poorly soluble) to a solution of compound (Mostafa et al. Chemical Engineering Science 63: 5457-5467, 2008), or by introducing a surface which promotes crystal formation (e.g. scratched glass), or by addition of crystal seeds, or by addition of a compound that will co-crystallize with the target compound (Korotkova and Karatchvil, Procedia Chemistry 10:473-476, 2014), including polymers (Edueng et al. Journal of Controlled Release 256:193-202, 2017). Industrial crystallization processes can be conducted in batch format or, increasingly, via continuous processes (Zhang et al. Engineering 3: 354-364, 2017).

Crystallization can be used in one of two ways: the disulfide compound of interest can be selectively crystallized in the presence of impurities, which remain in solution and thus can be easily removed after crystallization, or one or more impurities can be crystallized while the compound of interest remains in solution. The two approaches can be combined sequentially (one after the other).

Because cysteamine precursors will often be administered in relatively large doses (over 1 gram per day, and possibly up to ten grams in adults) any salt needs to be safe. Therefore salts that are natural products, present at significant levels in the diet, and with pleasant organoleptic properties are preferred. Examples of such salts include, without limitation, acetate, citrate and tartrate. The salt forms of cysteamine precursors that induce crystal formation may not overlap with the pharmaceutically preferred salt forms, in which case a salt form can be produced specifically to aid crystallization, then redissolved in solvent and the salt switched to a preferred pharmaceutical salt. Large salts that tend to promote crystal formation include benzoate and naphthoate (napthoic acid).

Separation Methods

Most of the synthetic routes outlined above are not capable of producing mixed disulfide of greater than 99 percent purity (i.e. in the range required by drug regulatory bodies). Crystallization may also not be sufficiently selective to reduce drug impurities to an acceptable level. Therefore robust separation methods may also be required. Thus in certain embodiments any synthetic method can be coupled with an efficient scheme for separation of the desired product (i.e. a mixed disulfide cystamine precursor) from other compounds produced in the synthesis (including other disulfides). Useful separation methods other than crystallization include a variety of chromatographic procedures, including resins that separate small molecules based on size, charge, hydrophobicity, affinity or other characteristics.

Formulations

When employed as pharmaceuticals, cysteamine precursors, or a pharmaceutically acceptable salt, solvate, or prodrug thereof can be administered in the form of pharmaceutical compositions. These compositions can be prepared in a variety of ways well known in the pharmaceutical art, and can be made so as to release drug in specific segments of the gastrointestinal tract at controlled times by a variety of excipients and formulation technologies. For example, formulations may be tailored to address a specific disease, to achieve blood levels of cysteamine required to achieve therapeutic efficacy, to enable a desired duration of drug effect, and to provide a set of compositions with varying drug release characteristics that can be administered in different combinations to account for inter-patient variation in cysteamine metabolism. Administration is primarily by the oral route and may be supplemented by suppositories. Cysteamine precursors may also be co-formulated with agents that enhance in vivo cysteamine generation or absorption, including, for example, reducing agents, buffers, pantetheinase inducers or inducers of cysteamine uptake by intestinal epithelial cells.

The pharmaceutical composition can contain one or more pharmaceutically acceptable carriers. In making a pharmaceutical composition for use in a method of the invention, the cysteamine precursor, pharmaceutically acceptable salt, solvate, or prodrug thereof is typically mixed with an excipient, diluted by an excipient or enclosed within such a carrier in the form of, for example, a capsule, tablet, sachet, paper, vial or other container. The active component of the invention can be administered alone, or in a mixture, in the presence of a pharmaceutically acceptable excipient or carrier. The excipient or carrier is selected on the basis of the mode and route of administration, the region of the gastrointestinal tract targeted for drug release, and the intended time profile of drug release. When the excipient serves as a diluent, it can be a solid, semisolid, or liquid material (e.g., normal saline), which acts as a vehicle, carrier, matrix or other medium for the active ingredient. Thus, the compositions can be in the form of tablets, powders, granules, lozenges, sachets, cachets, elixirs, suspensions, emulsions, solutions, syrups, and soft and hard gelatin capsules. As is known in the art, the type and amount of excipients vary depending upon the intended drug release characteristics. The resulting compositions can include additional agents, such as preservatives or coatings.

Suitable pharmaceutical carriers, as well as pharmaceutical necessities for use in pharmaceutical formulations, are described in Remington: The Science and Practice of Pharmacy, 21st Ed., Gennaro, Ed., Lippencott Williams & Wilkins (2005), a well-known reference text in this field, and in the USP/NF (United States Pharmacopeia and the National Formulary) or corresponding European or Japanese reference documents. Examples of suitable excipients are lactose, dextrose, sucrose, sorbitol, mannitol, starches, gum acacia, calcium carbonate, calcium phosphate, alginates, tragacanth, gelatin, calcium silicate, microcrystalline cellulose, cellulose derivatives, polyvinylpyrrolidone, poly(lactic-co-glycolic acid) (PLGA), cellulose, water, syrup, methyl cellulose, vegetable oils, polyethylene glycol, hydrophobic inert matrix, carbomer, hypromellose, gelucire 43/01, docusate sodium, and white wax. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. Other exemplary excipients and details of their use are described in Handbook of Pharmaceutical Excipients, 6th Edition, Rowe et al., Eds., Pharmaceutical Press (2009).

The pharmaceutical composition can include cysteamine precursor salts, optionally co-formulated or co-administered with other agents that enhance the in vivo degradation of cysteamine precursors to cysteamine or enhance the intestinal absorption of cysteamine. The pharmaceutical composition may also include other therapeutic agents that complement the pharmacological effects of cysteamine in targeted diseases. Exemplary enhancers of in vivo cysteamine production or absorption, and exemplary therapeutic agents that may be included in the compositions described herein are provided herein.

The compositions of the invention may contain a single active component (i.e. a single cysteamine precursor), or a combination of a first and a second active component in a single unit dosage form, or a combination of a first, second, third and, optionally, a fourth active and optionally a fifth component in a single unit dosage form. In compositions with two active components both components may be cysteamine precursors or one component may be an enhancer of in vivo cysteamine production (e.g. a reducing agent that promotes reduction of disulfide cysteamine precursors, or an agent that induces increased intestinal expression of pantetheinase) or an enhancer of intestinal absorption of cysteamine (e.g. an agent that induces increased expression of one or more organic cation transporters, such as OCT1, OCT2 or OCT3). In compositions with three or four active components all components may be cysteamine precursors or one or two components may be enhancers of in vivo cysteamine production and/or intestinal absorption. In compositions with two or more cysteamine precursors the types of cysteamine precursors are selected to achieve in vivo cysteamine production over a sustained time period. For example a mixed disulfide cysteamine precursor, which only requires disulfide bond reduction to generate one cysteamine, and will therefore start generating cysteamine shortly after reaching a region of the gastrointestinal tract with a redox environment conducive to disulfide bond reduction, can be mixed with pantetheine, or with a pantetheine disulfide, which requires both disulfide bond reduction and pantetheinase cleavage to yield cysteamine, and optionally also combined with a compound degradable to pantetheine in the gut, or a disulfide containing such a compound, which requires additional steps to generate pantetheine and thence cysteamine. Compounds degradable to pantetheine in the gut include 4-phosphopantetheine, dephospho-coenzyme A, coenzyme A and suitable analogs and derivatives. The time course of in vivo cysteamine production will vary according to the number of degradative steps between the cysteamine precursor and cysteamine. In some embodiments compositions containing multiple cysteamine precursors are formulated as a powder, as granules or as a liquid—i.e. formulation types that can accommodate large quantities of drug substance.

The pharmaceutical composition may also include one or more agents that enhance the performance of the formulation. For example a gastroretentive composition may include a compound that slows gastric emptying in order to prolong the residence of the composition in the stomach.

In compositions with two cysteamine precursor components the first and second components may be present at a ratio of, for example, about 1:1.5 to about 1:4. In compositions with three cysteamine precursor components the first, second and third components may be present at a ratio of, for example, between about 1:1:2 to about 1:4:4. In compositions with four active components the first through fourth active components may be present at a ratio of, for example, about 1:1:1:2 to about 1:2:5:5. In compositions with five active components the first through fifth active components may be present at a ratio of, for example, about 1:1:2:2:2 to about 1:1:2:5:5:8.

In some embodiments compositions that contain two or more cysteamine precursors include one precursor selected for rapid in vivo cysteamine production (e.g. simply requiring disulfide bond reduction) and a second precursor selected for intermediate or slower in vivo conversion to cysteamine e.g. requiring chemical reduction and at least one enzymatic degradative step). In some embodiments a pharmaceutical composition containing two or more cysteamine precursors at least one precursor is a cysteamine mixed disulfide, which can yield cysteamine upon disulfide bond reduction. In additional related embodiments at least one additional component is a disulfide containing pantetheine or a compound degradable to pantetheine in the gastrointestinal tract.

The compositions can be formulated in a solid unit dosage form (e.g. a tablet or capsule), each dosage containing, e.g., 50-800 mg of the active ingredient of the first component. For example, the dosages can contain from about 50 mg to about 800 mg, from about 50 mg to about 700 mg, from about 50 mg to about 600 mg, from about 50 mg to about 500 mg; from about 75 mg to about 800 mg, from about 75 mg to about 700 mg, from about 75 mg to about 600 mg, from about 75 mg to about 500 mg; from about 100 mg to about 800 mg, from about 100 mg to about 700 mg, from about 100 mg to about 600 mg, from about 100 mg to about 500 mg; from about 250 mg to about 800 mg, from about 250 mg to about 700 mg, from about 250 mg to about 600 mg, from about 250 mg to about 500 mg; from about 400 mg to about 800 mg, from about 400 mg to about 700 mg, from about 400 mg to about 600 mg; from about 450 mg to about 700 mg, from about 450 mg to about 600 mg of the active ingredient of a first component.

In alternative embodiments compositions can be formulated in a liquid or powdered unit dosage form, each dosage unit containing from about 250 mg to about 10,000 mg of cysteamine precursor. For example, the dosages can contain from about 250 mg to about 10,000 mg, from about 250 mg to about 8,000 mg, from about 250 mg to about 6,000 mg, from about 250 mg to about 5,000 mg; from about 500 mg to about 10,000 mg, from about 500 mg to about 8,000 mg, from about 500 mg to about 6,000 mg, from about 500 mg to about 5,000 mg; from about 750 mg to about 10,000 mg, from about 750 mg to about 8,000 mg, from about 750 mg to about 6,000 mg, from about 750 mg to about 5,000 mg; from about 1,250 mg to about 10,000 mg, from about 1,250 mg to about 8,000 mg, from about 1,250 mg to about 6,000 mg, from about 1,250 mg to about 5,000 mg; from about 2,000 mg to about 10,000 mg, from about 2,000 mg to about 8,000 mg, from about 2,000 mg to about 6,000 mg; from about 2,000 mg to about 5,000 mg, from about 3,000 mg to about 6,000 mg of the active ingredient of a first component.

In compositions with a first and second cystamine precursor component the amount of the second active component in a solid unit dosage form can vary, e.g., from 50-700 mg. For example, the dosage can contain from about 50 mg to about 700 mg, from about 50 mg to about 600 mg, from about 50 mg to about 500 mg, from about 50 mg to about 450 mg; from about 75 mg to about 700 mg, from about 75 mg to about 600 mg; from about 100 mg to about 700 mg; from about 100 mg to about 600 mg, from about 100 mg to about 500 mg, from about 100 mg to about 400 mg; from about 250 mg to about 700 mg, from about 250 mg to about 600 mg, from about 250 mg to about 500 mg, from about 250 mg from to about 400 mg; from about 400 mg to about 700 mg, from about 400 mg to about 600 mg, from about 400 mg to about 500 mg, from about 450 mg to about 700 mg; from about 450 mg to about 600 mg, from about 450 mg to about 500 mg. In a composition with a cysteamine precursor as the first active component and an enhancer of in vivo cysteamine generation as the second active component the amount of the second active component in a unit dosage form can vary, e.g. from 0.1 mg-400 mg.

In alternative embodiments including a first and second cystamine precursor component the amount of the second active component in a liquid or powdered unit dosage form can vary, e.g., from about 250 mg to about 6,000 mg. For example, the dosage can contain from about 250 mg to about 6,000 mg per dose, from about 250 mg to about 5,000 mg, from about 250 mg to about 4,000 mg, from about 250 mg to about 3,000 mg, from about 250 mg to about 2,000 mg; from about 500 mg to about 6,000 mg, from about 500 mg to about 5,000 mg, from about 500 mg to about 4,000 mg, from about 500 mg to about 3,000 mg; from about 750 mg to about 6,000 mg, from about 750 mg to about 5,000 mg, from about 750 mg to about 4,000 mg, from about 750 mg to about 3,000 mg; from about 1,250 mg to about 6,000 mg, from about 1,250 mg to about 5,000 mg, from about 1,250 mg to about 4,000 mg, from about 1,250 mg to about 3,000 mg; from about 2,000 mg to about 6,000 mg, from about 2,000 mg to about 5,000 mg, from about 2,000 mg to about 4,000 mg; from about 2,000 mg to about 3,000 mg, from about 2,500 mg to about 5,000 mg of the active ingredient of a second component.

In solid compositions with a third, or third and fourth cysteamine precursor component the unit dosages can contain from about 50 mg to about 400 mg of each of the third and, if present, fourth active components. For example, the dosages can contain from about 50 mg to about 400 mg, from about 50 mg to about 350 mg, from about 50 mg to about 300 mg, from about 50 mg to about 250 mg; from about 75 mg to about 400 mg, from about 75 mg to about 350 mg, from about 75 mg to about 300 mg, from about 75 mg to about 250 mg; from about 100 mg to about 400 mg, from about 100 mg to about 350 mg, from about 100 mg to about 300 mg, from about 100 mg to about 250 mg; from about 250 mg to about 400 mg, from about 250 mg to about 350 mg or from about 250 mg to about 300 mg. In compositions with five active components the unit dosages of the five components can range from about 50 mg to about 300 mg. In a composition with an enhancer of in vivo cysteamine generation as the fourth, and optionally also the third active component the amount of the fourth, and optionally the third active components in a unit dosage form can vary, e.g. from 0.1 mg-400 mg.

In alternative embodiments including a third, or a third and fourth cysteamine precursor component in a liquid or powdered unit dosage form the unit dosages of the third and optionally fourth active component can vary, e.g., from about 250 mg to about 4,000 mg. For example, the dosage can contain from about 250 mg to about 4,000 mg per dose, from about 250 mg to about 3,000 mg, from about 250 mg to about 2,000 mg, from about 250 mg to about 1,000 mg, from about 500 mg to about 4,000 mg, from about 500 mg to about 3,000 mg, from about 500 mg to about 2,000 mg, from about 500 mg to about 1,000 mg; from about 750 mg to about 4,000 mg, from about 750 mg to about 3,000 mg, from about 750 mg to about 2,000 mg, from about 750 mg to about 1,000 mg; from about 1,000 mg to about 4,000 mg, from about 1,000 mg to about 3,000 mg, from about 1,000 mg to about 2,000 mg, from about 1,000 mg to about 1,500 mg; from about 1,500 mg to about 4,000 mg, from about 1,500 mg to about 3,000 mg, from about 1,500 mg to about 2,000 mg; from about 2,000 mg to about 4,000 mg, from about 2,000 mg to about 3,000 mg of the active ingredient of a third and optionally fourth active component.

The pharmaceutical compositions can be formulated so as to provide immediate, delayed, gastroretentive, sustained or colonic release (collectively referred to as controlled release) of the active component after administration to the patient by employing procedures known in the art.

For preparing solid compositions such as tablets, the active ingredient or ingredients (e.g. several cysteamine precursors) may be mixed with one or more pharmaceutical excipients to form a solid bulk formulation composition containing a homogeneous mixture of a compound of the present invention. When referring to these bulk formulation compositions as homogeneous, the active ingredient is typically dispersed evenly throughout the composition so that the composition can be readily subdivided into equally effective unit dosage forms such as tablets, capsules or microparticles. This solid bulk formulation is then subdivided into unit dosage forms of the type described above.

Alternatively two homogeneous batches of active ingredient(s) mixed with one or more pharmaceutical excipients may be prepared, each using a different concentration of active ingredient(s). The first mixture may then be used to form a core and the second mixture a shell around the core to form a composition with variable drug release characteristics. If the high concentration batch is located in the core and the lower concentration batch in the shell an initial moderate rate of drug release will be followed by a greater rate of drug release once the shell has substantially dissolved or eroded. In some embodiments a pharmaceutical composition contains a higher concentration of active ingredient(s) in the core than in the shell. The ratio of cysteamine precursor concentrations in the core:shell may, for example, range between about 1.5:1 to 4:1. The excipients may also differ in type or in concentration between the two batches, so as to influence the rate of drug release. In some embodiments the polymer(s) or other matrix-forming ingredients in the core release the active ingredient(s) more slowly than from the shell. In such embodiments a higher concentration of cysteamine precursor(s) in the core is partially or completely balanced by a slower rate of drug release, to extend the duration of cysteamine precursor release, and hence the duration of in vivo cysteamine generation, intestinal absorption and elevated blood levels. One or more coatings may be applied to the core before the shell layer is applied, and additional coatings may be applied to the shell to enable an efficient manufacturing process and/or to help provide desired pharmacological properties, including the timing and location of drug release in the gastrointestinal tract.

The pharmaceutical compositions of the invention include those formulated to release a mixture of cysteamine precursors which differ in the mechanism(s) or number of degradative steps leading to cysteamine production. Specifically, a mixture of two, three, four or five cysteamine precursors, each of which is one, two, three or more chemical and/or enzymatic degradative steps away from releasing cysteamine. For example the one step may be disulfide bond reduction (in the case of a cysteamine mixed disulfide) or pantetheinase cleavage (in the case of pantetheine). The two steps may be disulfide bond reduction followed by pantetheinase cleavage (in the case of a pantetheine disulfide) or phosphatase cleavage followed by pantetheinase cleavage (in the case of 4-phosphopantetheine). The three steps may be disulfide bond reduction preceded or followed by degradation to pantetheine (e.g. by a phosphatase), followed by pantetheinase cleavage (e.g. in the case of a 4-phosphopantetheine disulfide). The four steps may be disulfide bond reduction followed by two degradative steps to pantetheine (e.g. removal of the adenine nucleotide moiety by ectonucleotide diphosphatase followed by removal of the 4' phosphate by a phosphatase), followed by pantetheinase cleavage (e.g. in the case of a coenzyme A or dephosphocoenzyme A disulfide). The purpose of combining cysteamine precursors that have different chemical and/or enzymatic degradative pathways to cysteamine is to extend the time during which cysteamine is produced in and absorbed from the gut, and consequently prolong the duration of therapeutically effective cysteamine blood levels. In some embodiments a pharmaceutical composition of the invention contains at least two cysteamine precursors, in further embodiments a pharmaceutical composition contains three cysteamine precursors.

The pharmaceutical compositions of the invention may be formulated for mixed release, meaning that one composition contains two drug release profiles. For example an immediate release formulation may be combined with a sustained release formulation. (See composition F in FIG. 14, for example.) In such a composition, the first active component may be formulated for immediate release starting between about 5 minutes and about 30 minutes following ingestion.

For example, the first active component may be released starting 5 minutes, 10 minutes, 15 minutes, 20 minutes, 25 minutes, 30 minutes, or 45 minutes after ingestion of the composition. The first active component is formulated such that cysteamine plasma concentrations in the therapeutic range are achieved between about 15 minutes and 3 hours following ingestion, preferably between 30 minutes and 2 hours. For example, therapeutic plasma cysteamine concentrations may be reached 0.5 hours, 1 hour, 2 hours, or 3 hours following ingestion of the composition. The type of cysteamine precursor used (e.g. thiol, cysteamine mixed disulfide, pantetheine disulfide, coenzyme A disulfide, N-acetylcysteamine disulfide, etc.) will influence the length of time to reach therapeutic blood concentrations of cysteamine, and the duration of time over which therapeutic blood concentrations are maintained.

In a composition with two, three, and optionally four or five active components (e.g. multiple cysteamine precursors and/or enhancers of in vivo cysteamine generation and absorption) each of the second, third, and/or fourth and/or fifth active components is formulated for controlled release from the composition starting between about 1 hour and about 8 hours following ingestion. A controlled release composition may include a delayed release and/or a sustained release formulation. For example, the second, third, and/or fourth active component may be released starting 1 hour, 1.5 hours, 2 hours, 3 hours, 4 hours, 5 hours, 6 hours, 7 hours, or 8 hours after ingestion of the composition. The second, third, and/or fourth active component is formulated such that the plasma concentration of cysteamine (which reflects the contributions of all active components) is maintained in the therapeutic range starting between about 30 minutes and 2 hours following ingestion and extending for between about 6 and 10 hours, more preferably extending for between 8 and 12 hours following ingestion, or for longer periods. For example, the plasma cysteamine concentration may be sustained in the therapeutic range for 6 hours, 8 hours, 10 hours, 12 hours, 15 hours, 20 hours, or 24 hours following ingestion of the active components of the composition. Depending on the age and size of the patient, the disease being treated, and the cysteamine metabolizing rate of the patient, two or more compositions may be needed to deliver enough cysteamine precursor to achieve therapeutic blood levels over multiple hours.

As an alternative or complement to pharmaceutical compositions comprising mixed formulations, in some embodiments compositions consisting of a single type of formulation may be produced. That is, time-based formulations such as immediate release or sustained release formulations, and anatomically-targeted formulations such as gastroretentive, delayed release and colon-directed formulations, may be prepared for administration as separate compositions. Formulating a collection of pharmaceutical compositions with different drug release properties (whether time-based or anatomically/physiologically-based) has certain advantages. For example, such compositions can be administered in different combinations and ratios to different patients to bring about blood cysteamine levels in the therapeutic range for an extended period of time. That is, a therapeutic regimen consisting of one, two, three or more compositions administered on a specific schedule can be tailored to the cysteamine generating, absorbing and metabolizing capacity of an individual patient. Since these capacities are known to vary among patients, the formulation of multiple homogeneous compositions containing different cysteamine precursors and different drug release properties, which can be combined in different ratios for different patients, addresses a known limitation of existing cysteamine formulations.

Preferably a combination of two or more pharmaceutical compositions can maintain cysteamine blood levels in the therapeutic range for at least hours 2-8 after ingestion, more preferably from hours 1-8 following ingestion, still more preferably from hours 2-10 and most preferably from hours 1-10, hours 1-12, hours 1-14, or longer. Separately formulated pharmaceutical compositions containing different cysteamine precursors with different drug release profiles provide the dosing flexibility needed to individualize dosing regimens to attain therapeutically effective cysteamine blood concentrations for prolonged periods.

It is well documented that gastric emptying time and large intestinal transit time vary considerably among healthy individuals (up to two-fold or more). The gut redox environment and levels of pantetheinase activity are also known to vary among individuals. These and other factors likely account for the wide inter-individual variation in plasma cysteamine levels observed following a cysteamine dose. For example in a study of immediate release cysteamine bitartrate pharmacokinetics in healthy volunteers the peak cysteamine blood level (Cmax) following a 600 mg oral dose, administered with a meal, varied over 8-fold, from 7 micromolar to 57.3 micromolar. (Dohil R. and P. Rioux, Clinical Pharmacology in Drug Development 2:178 (2013)). In the same study the Cmax following 600 mg of delayed release cysteamine bitartrate administered with a meal varied 12-fold, from 2.1 uM to 25.4 uM. Inter-patient variation in cysteamine plasma levels was less extreme when cysteamine was administered to fasting patients, but still up to four fold. (When cysteamine is dosed every six hours, as with Cystagon®, or even every 12 hours, as with Procysbi®, it is difficult to completely avoid meal times.)

Current methods of cysteamine formulation and administration provide only one tool to address inter-subject variability: raise or lower the dose. The cysteamine precursors, enhancers of in vivo cysteamine generation and absorption, drug formulation methods and drug administration methods of the invention provide multiple tools to achieve therapeutic blood cysteamine levels by tailoring compounds, dosage forms and dosing regimens to individual patients without incurring the unacceptable toxicity often associated with high Cmax or the inadequate therapeutic effect associated with prolonged blood levels below the therapeutic threshold.

Another advantage for separately formulated compositions is that they can be administered at different times with respect to meals. This is a useful option because different classes of cysteamine precursors and different types of formulations interact differently with meals. For example, a gastroretentive formulation should be administered with or shortly after a meal, preferably a nutrient rich meal to maximize the duration of gastric retention. Conversely, an immediate release formulation that contains a cysteamine mixed disulfide that can be rapidly converted to cysteamine by disulfide bond reduction should preferably not be administered with a large meal. Large meals interfere with absorption of cysteamine in some individuals, however meals are compatible with certain cysteamine precursors that produce little if any cysteamine in the stomach, e.g. pantetheine disulfides, which tend to be converted to cysteamine in the small intestine.

The individualized dosing regimens possible with the compounds and formulations of the invention are particularly useful because while extensive inter-individual variation in cysteamine intestinal absorption is well documented, it is equally well documented that intra-individual variation is moderate in comparison. That is, a given subject will absorb and metabolize a dose of cysteamine substantially similarly when administered on multiple occasions under similar circumstances. Thus a dosing regimen, once individualized to produce blood cysteamine levels in the therapeutic range for a specific patient, should be relatively stable and produce predictable results over time.

Sustained release formulations can be designed to release drugs over widely varying periods of time using methods known in the art. (Wen, H. and Park, K., editors: Oral Controlled Release Formulation Design and Drug Delivery: Theory to Practice, Wiley, 2010; Wells, J. I. and Rubinstein, M. H., editors: Pharmaceutical Technology: Controlled Drug Release, volumes I and II, Ellis and Horwood, 1991, and Gibson, M., editor: Pharmaceutical Preformulation and Formulation: A Practical Guide from Candidate Drug Selection to Commercial Dosage Form, $2^{nd}$ edition, Informa, 2009.)

Figure 14:
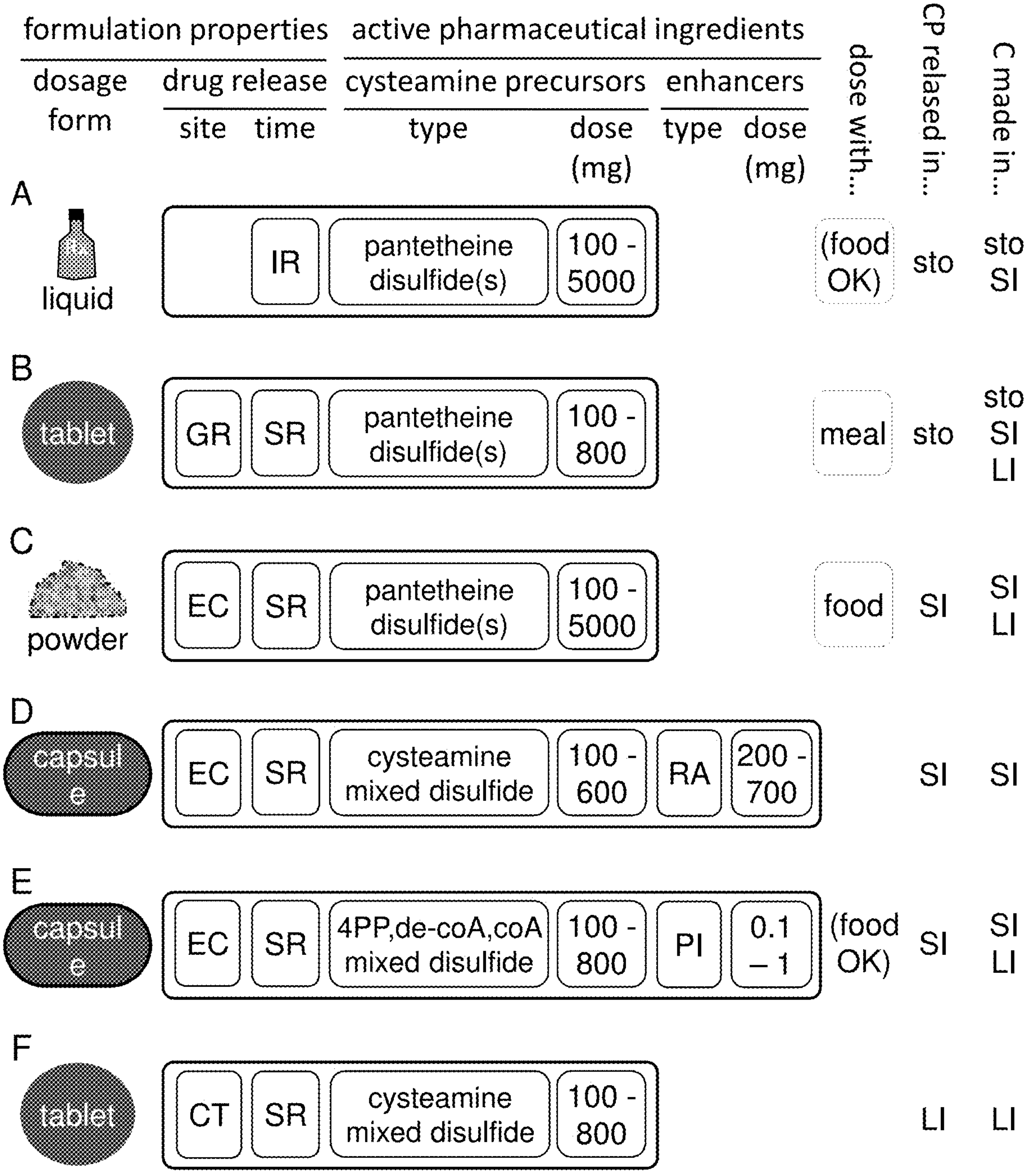
FIG. 14 is an illustration of exemplary pharmaceutical compositions. Salient properties of the exemplary compositions are shown, including: (i) the type of dosage form (e.g. tablet, capsule, powder, liquid), (ii) the properties of the formulation with respect to anatomical localization of drug release (e.g. gastroretentive formulations are retained in the stomach; enteric coated formulations may be designed to release drug in the small intestine; colon-targeted formulations are designed to release drug in the ileum or colon) as well as (iii) duration of drug release (immediate release: IR, or sustained release: SR), (iv) the type of cysteamine precursor(s), (v) the dose (provided as a range), (vi) the type of co-formulated enhancer(s) of in vivo cysteamine generation, if any, (vii) the dose of enhancer compound (provided as a range), (viii) recommendations for administering the composition with food (e.g. applesauce or yogurt) or a meal (e.g. supper), or whether food is optional ("food OK"), (ix) the site(s) of cysteamine precursor release in the gastrointestinal tract, and (vii) the sites at which cysteamine is generated in vivo (e.g. by disulfide bond reduction or pantetheinase cleavage). The compositions in FIG. 13 are each limited to a single type of formulation with respect to site and time of drug release. Such compositions (including many variants not shown in the figure) can be administered in various combinations, providing flexibility to individualize dosing. Other exemplary compositions with more active components and/or more complex formulations are shown in FIGS. 14 and 15.
Figure 15:
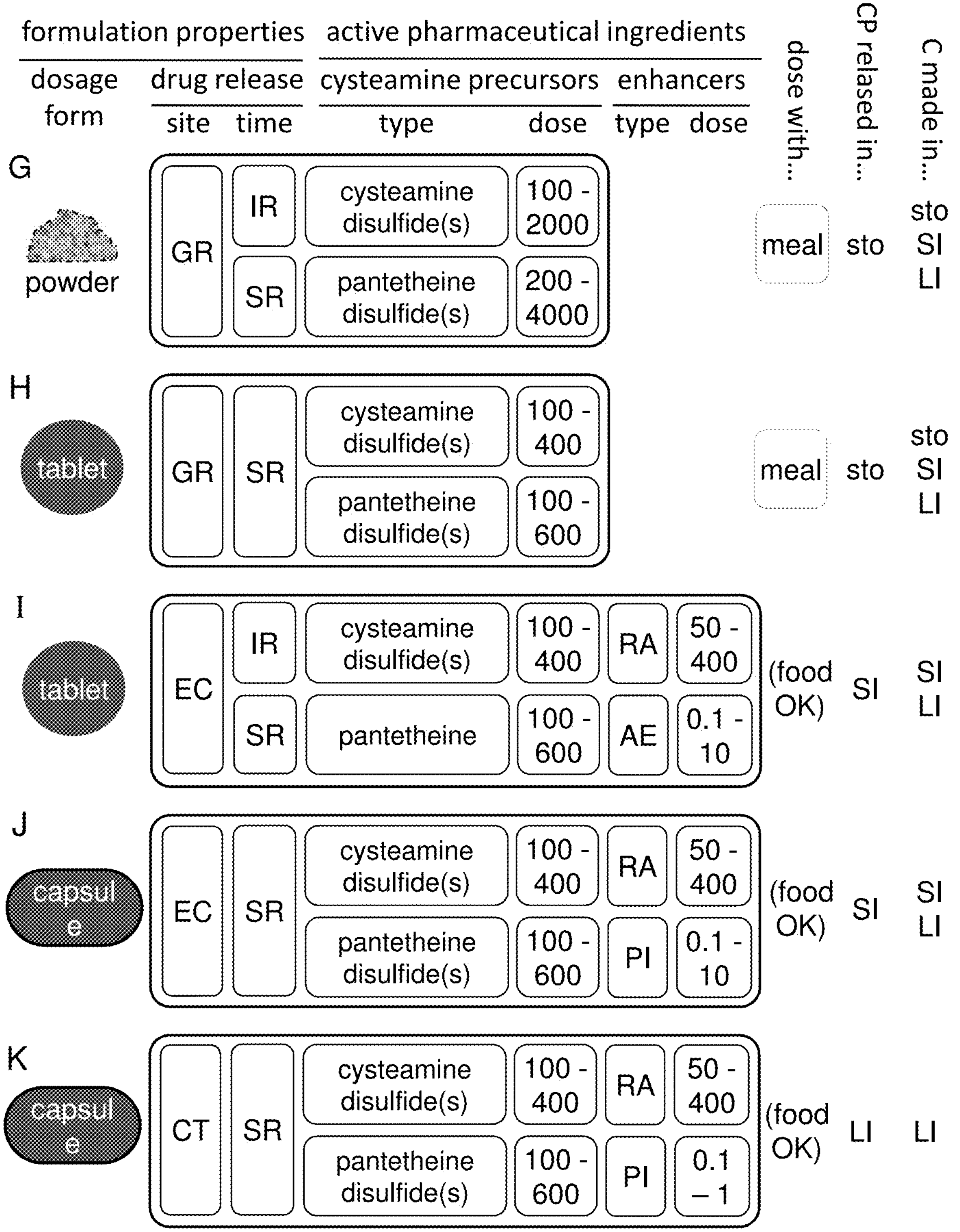
FIG. 15 is an illustration of exemplary pharmaceutical compositions with (i) one or two drug release profiles—for example composition G includes immediate and sustained release components; (ii) at least two types of cysteamine precursor(s) and up to two enhancers. Recommendations for administration with or without food are provided, as are site(s) of drug release and of in vivo conversion of cysteamine precursors to cysteamine. The exemplary compositions, and many others not shown, can be combined in various ratios.
Figure 16:
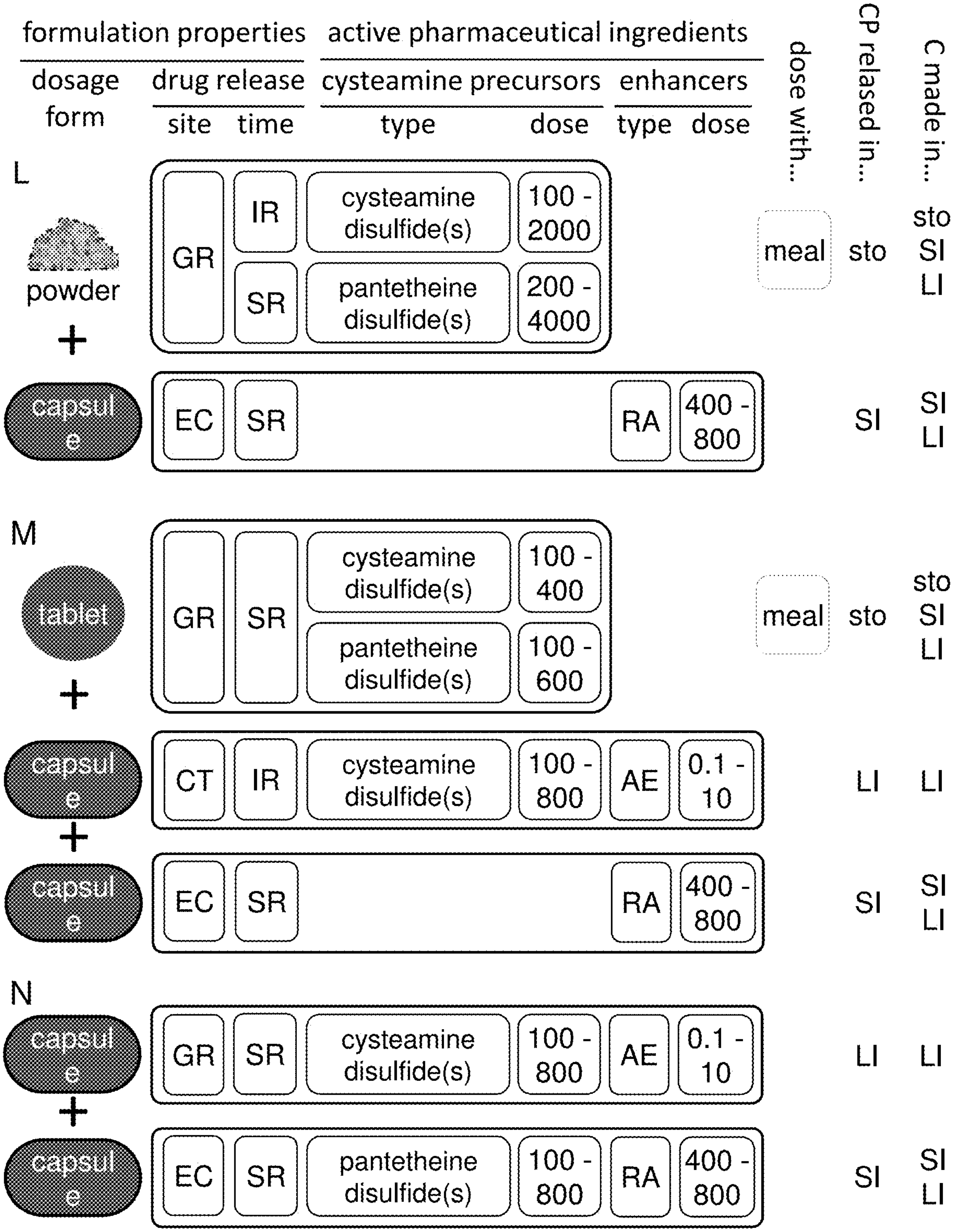
FIG. 16 is an illustration of exemplary multi-dose regimens, in which two or more compositions are administered together, or in sequence over a short time interval. Salient properties of the exemplary compositions are shown as in FIGS. 14 and 15. Included are examples of compositions which provide enhancers of cysteamine precursor degradation (e.g. reducing agents) but no cysteamine precursors. The separate formulation of enhancers allows them to be co-administered with cysteamine precursor-containing compositions in various ratios to optimize in vivo cysteamine generation or uptake. Separate formulation of enhancers further allows control of site and timing of enhancer release to optimize in vivo cysteamine generation or uptake.

FIGS. 14, 15 and 16 provide examples of pharmaceutical compositions of the invention, intended to illustrate aspects such as active ingredients (cysteamine precursors, enhancers of cysteamine precursor conversion to cysteamine and enhancers of cysteamine intestinal absorption), dose ranges (for all active components combined), formulation types (including mixed formulations), combinations of compositions and methods of administration (e.g. with food or with a meal). Active ingredients include cysteamine precursors as well as enhancers of in vivo cysteamine generation and enhancers of intestinal absorption of cysteamine.

Formulations for Oral Administration

The pharmaceutical compositions contemplated by the invention include those formulated for oral administration ("oral dosage forms"). Oral dosage forms can be, for example, in the form of tablets, capsules, a liquid solution or suspension, a powder, or liquid or solid crystals or granules, which contain the active ingredient(s) in a mixture with non-toxic pharmaceutically acceptable excipients. If formulated as a liquid, powder, crystals or granules the dose may be packaged in a manner that clearly demarcates a unit dose. For example a powder or granules or microparticles may be packaged in a sachet. A liquid may be packaged in a glass or plastic container.

Excipients are selected to provide acceptable organoleptic properties, to control drug release properties, to facilitate efficient manufacturing and to ensure long term stability of pharmaceutical compositions, among other considerations known to those skilled in the arts of pharmacology, pharmaceutics and drug manufacturing. The excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, preservatives, buffering agents, stabilizing agents and the like. Many of these excipients are sold by multiple excipient manufacturers in a variety of chemical forms, and/or can be used at different concentrations, and/or in different combinations with other excipients, with ensuing differences in performance characteristics. Specific excipients may accomplish more than one purpose in a formulation.

Formulations for oral administration may also be presented as chewable tablets, as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

One category of useful formulations mainly controls the rate of drug release (e.g. immediate and sustained release formulations), albeit with significant implications for where drug is released. A second category of useful formulations mainly controls the anatomical site of drug release (e.g. gastroretentive formulations for drug release in the stomach, colon-targeted formulations for the large intestine) albeit with implications for the timing of release. Enteric coated formulations have important elements of both: they are designed to remain intact in the acidic stomach environment, and often to dissolve in the more alkaline small intestine, which is a kind of anatomical targeting, yet they are often refer erred to as delayed release formulations, highlighting the time control element. However, colon targeted formulations may also have an enteric coating to prevent dissolution in the stomach, highlighting the complex relationship between anatomical targeting and control of the rate of drug release. Further, there is extensive overlap between the excipients used in time-based and anatomically- or physiologically-targeted formulations. These types of formulation can be combined in various ways to create a plurality of compositions with different drug release profiles, in both time and space. Such compositions can in turn be combined in different amounts and ratios to individualize therapeutic regiments to accommodate biochemical and physiologic variation among patients, as well as variation in disease type, extent and activity.

Gastroretentive Formulations

Gastroretentive formulations may be employed for release of a cysteamine precursor, or a salt thereof, from a composition of the invention in the stomach and to control the release of the active component(s) of the composition in the stomach over an extended period of time. In other words, since the point of a gastroretentive formulation is prolonged gastric residence, the accompanying excipients should provide for sustained release of active ingredients over the entire period of time that the gastroretentive dosage form is expected to remain in the stomach, and optionally longer, including the time of transit through the small intestine and into the colon. The gastroretention of active components of the invention may be achieved by various mechanisms, such as mucoadhesion, flotation, sedimentation, swelling and expansion, and/or by the simultaneous administration of pharmacological agents which delay gastric emptying. Excipients used in gastroretentive formulations, as well as the size and shape of pharmaceutical compositions, vary according to the mechanism of gastroretention.

Mucoadhesive/Bioadhesive Gastroretentive Formulations

Mucoadhesion relates to adhesion of a polymer utilized in the formulation to the gastrointestinal mucus layer until it is removed spontaneously from the surface as a result of ongoing mucus production. Bioadhesion, sometimes used interchangeably with mucoadhesion, also encompasses adhesion of a polymer or other component of a pharmaceutical composition to molecules on the surface of gastrointestinal epithelial cells. The purpose of mucoadhesion and bioadhesion is to increase the time that a pharmaceutical composition is in close proximity to gastrointestinal epithelial cells, including the cell types capable of cysteamine precursor cleavage (i.e. cells that express pantetheinase on their surface), and cysteamine uptake and transport into the circulation (e.g. cells expressing organic cation transporters). Mucoadhesive polymers can be used in formulating large dosage forms such as tablets or capsules and small dosage forms such as microparticles or microspheres. Various physiological factors such as peristalsis, mucin type, mucin turnover rate, gastrointestinal pH, fast/fed state and type of foods in the fed state affect the degree and persistence of mucoadhesion. The mechanism of mucoadhesion is thought to be through the formation of electrostatic and hydrogen bonds at the polymer-mucus boundary. Generally, mucoadhesion is achieved with polymers having affinity for gastrointestinal mucous and selected from synthetic or natural bioadhesive materials such as polyacrylic acids, methacrylic acids and derivatives of both, polybrene, polylysine, polycarbophils, carbomers, alginates, chitosan, cholestyramine, gums, lectins, polyethylene oxides, sucralfate, tragacanth, dextrins (e.g. hydroxypropyl beta-cyclodextrin), polyethylene glycol (PEG), gliadin, cellulose and cellulose derivatives such as hydroxypropyl methylcellulose (HPMC), or mixtures thereof. For example cross-linked acrylic and methacrylic acid copolymers available under the Trade Names CARBOPOL (e.g. Carbopol 974P and 971P) and POLYCARBOPHIL have been used in mucoadhesive formulations. (Hombach J. and A. Bernkop-Schnürch. Handbook of Experimental Pharmacology 197:251 (2010)). Other bioadhesive cationic polymers include acidic gelatin, polygalactosamine, poly-aminoacids such as polylysine, polyornithine, polyquaternary compounds, prolamine, polyimine, diethylaminoethyldextran (DEAE), DEAE-imine, polyvinylpyridine, polythiodiethylaminomethylethylene (PTDAE), polyhistidine, DEAE-methacrylate, DEAE-acrylamide, poly-p-aminostyrene, polyoxethane, Eudragit RL, Eudragit RS, GAFQUAT, polyamidoamines, cationic starches, DEAE-dextran, DEAE-cellulose and copolymethacrylates, including copolymers of HPMA, N-(2-hydroxypropyl)-methacrylamide (e.g. see U.S. Pat. No. 6,207,197).

Mucoadhesion is most effective when applied to small particles (e.g. microparticles). Mucoadhesive formulations may be combined with one or more other gastroretentive formulation methods described below, including floating formulations, expanding/swelling formulations, or any type of sustained release formulation.

Floating Gastroretentive Formulations

Flotation as a gastric retention mechanism is effective in formulations of the active component (e.g. cysteamine precursor) having a bulk density lower than that of gastric fluid and/or chyme (partially digested food in the stomach) so as to remain buoyant in the stomach. Generally a density of less than 1 gram per cubic centimeter is desirable, more preferably a density of less than 0.9 grams per cubic centimeter. Buoyancy can be achieved by (i) using low density materials, including lipids, (ii) pre-forming a gas bubble or bubbles in the center of a composition, or (iii) using effervescent excipients to generate gas bubbles in vivo. Pharmaceutical compositions of the latter type must be designed so that gas generated by the effervescent excipients remains in the composition and thereby contributes to its buoyancy. For example, the effervescent excipients can be embedded in a matrix of polymers to trap the bubbles in the composition. The latter type of buoyant formulations generally utilize matrices prepared with swellable polymers or polysaccharides and effervescent couples, e.g., sodium bicarbonate and citric or tartaric acid or matrices containing chambers of entrapped air or liquids that generate gas upon contact with liquid gastric contents at body temperature. Floating gastroretentive formulations have been reviewed extensively (e.g. Kotreka, U.K. Critical Reviews in Therapeutic Drug Carrier Systems, 28:47 (2011)).

Floating pharmaceutical compositions designed for gastric retention have been known in the art for some time. For example, U.S. Pat. Nos. 4,126,672, 4,140,755 and 4,167,558, each of which is incorporated herein by reference, describe a "hydrodynamically balanced" drug delivery system (HBS) in tablet form having a density less than that of gastric fluid (i.e. less than 1 gram per cubic centimeter). Consequently the composition floats on the stomach fluid or chyme, thereby avoiding ejection through the pylorus during muscular contractions of the stomach. Drug is continuously released from a cellulose-derived hydrocolloid such as methylcellulose, hydroxyalkylcelluloses (e.g. hydroxypropylcellulose, hydroxypropylmethylcellulose, hydroxyethylcellulose) or sodium carboxymethyl-cellulose, which, upon contact with gastric fluid, forms a water-impermeable barrier on the surface of the composition that gradually erodes, slowly releasing drug. A two-layered floating tablet, with an outer layer formulated for immediate release and an inner layer formulated for sustained release, is also disclosed in U.S. Pat. No. 4,140,755, incorporated herein by reference.

A similar hydrodynamically balanced floating formulation for sustained delivery of L-dopa and a decarboxylase inhibitor has also been described (see U.S. Pat. No. 4,424,235). Hydrocolloids, such as acacia, gum tragacanth, locust bean gum, guar gum, karaya gum, agar, pectin, carrageen, soluble and insoluble alginates, carboxypolymethylene, gelatin, casein, zein and bentonite can be useful in the preparation of floating formulations of the invention. The floating formulation can include up to about 60% of a fatty material or mixture of fatty materials selected from beeswax, cetyl alcohol, stearyl alcohol, glyceryl monostearate, hydrogenated castor oil and hydrogenated cottonseed oil (fats and oils have a lower density than gastric fluid). The floating formulations can promote sustained release of the cysteamine precursor and provide elevated plasma cysteamine levels for a longer period of time. The prolonged elevated plasma cysteamine levels permit less frequent dosing.

The floating compositions of the present invention may contain gas generating agents. Methods for formulating floating compositions using gas generating compounds are known in the art. For example, floating minicapsules containing sodium bicarbonate are described in U.S. Pat. No. 4,106,120. Similar floating granules based on gas generation are described in U.S. Pat. No. 4,844,905. Floating capsules have been described in U.S. Pat. No. 5,198,229.

Floating compositions may optionally contain an acid source and a gas-generating carbonate or bicarbonate agent, which together act as an effervescent couple, producing carbon dioxide gas which provides buoyancy to the formulation. Effervescent couples consisting of a soluble organic acid and an alkali metal carbonate salt form carbon dioxide when the mixture comes into contact with water or when the alkaline component comes into contact with an acidic liquid (e.g. gastric juice). Typical examples of acids used include citric acid, tartaric acid, malic acid, fumaric acid or adipic acid. Typical examples of gas generating alkalis used include sodium bicarbonate, sodium carbonate, sodium glycine carbonate, sodium sesquicarbonate, potassium carbonate, potassium bicarbonate, calcium carbonate, calcium bicarbonate, ammonium bicarbonate, sodium bisulfite, sodium metabisulfite, and the like. The gas generating agent interacts with an acid source triggered by contact with water, or with the hydrochloric acid in gastric juice, to generate carbon dioxide or sulfur dioxide that gets entrapped in the matrix of the composition and improves its floating characteristics. In one embodiment the gas generating agent is sodium bicarbonate and the acid source is citric acid.

The kinetics of flotation are important because if the composition is not lighter than gastric fluid and/or chyme soon after reaching the stomach there is a chance it will be rapidly expelled via the pylorus. Some compositions have a lower density than gastric fluid and chyme upon ingestion, such as compositions that contain pre-formed gas bubbles, or that contain low density materials such as lipids. For those floating compositions that must attain a density below that of gastric fluid and/or chyme after reaching the stomach (i.e. effervescent formulations) a density lower than 1 gram per cubic centimeter is preferably reached within 30 minutes, more preferably within 15 minutes, and most preferably within ten minutes after contact with gastric fluid. The duration of floating is also important and should be matched to the duration of drug release. That is, if the composition is designed to release drug over 6 hours it should also be able to float for six hours. Preferably a floating composition maintains a density less than 1 for at least 5 hours, more preferably 7.5 hours, still more preferably 10 hours or longer.

A large dose of cysteamine precursor (e.g. 2-10 grams) may be necessary to effectively treat some cysteamine-sensitive diseases, and/or to achieve adequate blood levels in large adult subjects. Since the amount of any active agent that can be contained in standard dosage forms (e.g. tablets, capsules) is limited by the ability of patients to swallow large compositions, and further since the administration of multiple tablets or capsules can be inconvenient or unpleasant (or impossible for patients with dysphagia), alternative dosage forms that do not constrain the amount of active agent in a unit dosage form are useful. Powders, granules and liquids are examples of non-size limited dosage forms, which can nevertheless be delivered in unit dosage amounts by suitable packaging, e.g. in a sachet or vial. In some embodiments of the present invention a floating gastroretentive composition of the invention is administered in liquid form. In a further embodiment the liquid composition includes alginate. In other embodiments active pharmaceutical ingredients are delivered in the form of a powder or granules that can be sprinkled on food.

One type of liquid gastroretentive floating drug delivery system utilizes alginate as an excipient. Alginic acid is a linear block polysaccharide copolymer made of beta-D-mannuronic acid and alpha-L-guluronic acid residues connected by 1,4 glycosidic linkages. It is used for a wide variety of purposes in pharmaceutical compositions, including as a sustained release polymer (see Murata et al., Eur J Pharm Biopharm 50:221 (2000)). Gaviscon is the brand name of a floating liquid alginate formulation that contains an antacid. It has been used to treat gastroesophageal reflux for decades, so the safety of chronic alginate ingestion is well established. Floating formulations of alginate with small molecule drugs have been described (see Katayama et al., Biol Pharm Bull. 22:55 (1999); and: Itoh et al., Drug Dev Ind Pharm. 36:449 (2010)). Floating formulations that form a layer on the surface of the stomach contents are sometimes referred to as raft-forming formulations. Raft-forming floating/gelling sustained release compositions have been described by Prajapati et al., J Control Release 168:151 (2013); and by Nagarwal et al., Curr Drug Deliv. 5:282 (2008).

U.S. Pat. No. 4,717,713, herein incorporated by reference, discloses liquid (drinkable) formulations that, upon contact with gastric contents, form a semi-solid gel-like matrix in the stomach, thereby effecting controlled release of a drug from the gelatinous matrix. Gel-forming vehicles are disclosed, including xanthan gum, sodium alginate, complex coacervate pairs such as gelatin or other polymers and carrageenan, and thermal gelling methylcellulose, all or a subset of which can be combined in various ratios to influence the dissolution and/or diffusion rate of suspended pharmaceutically active agent(s). Other excipients used include carbonate compounds such as calcium carbonate, effective as both a promoter of gelling and as a gas-generating agent to float the gel. Xyloglucans and gellan gums may also be used as gelling agents, or in combinations of gelling agents.

Liquid (drinkable) floating formulations may include microparticles, which may be provided as a liquid suspension (either a concentrate or ready for use) or as a powder which can be added to a liquid (e.g. water, juice or other beverage). Floating gastroretentive compositions may also be delivered in the form of powders to be sprinkled over, or otherwise mixed with, food.

Floating gastroretentive formulations may include mucoadhesive polymers or other mucoadhesive ingredients (see U.S. Pat. Nos. 6,207,197 and 8,778,396, incorporated herein by reference), and may utilize polymers such as polyethylene oxide, polyvinyl alcohol, sodium alginate, ethylcellulose, poly(lactic) co-glycolic acids (PLGA), polylactic acids, polymethacrylates, polycaprolactones, polyesters, polyacrylic acids and polyamides.

Swelling and Expanding Gastroretentive Compositions

Swelling and expansion is a gastric retention mechanism wherein, upon contact with gastric fluid the composition swells to an extent that prevents its exit from the stomach through the pylorus. As a result, the composition is retained in the stomach for a prolonged period of time, for example until the surface of the composition is eroded to reduce its diameter to less than the diameter of the pylorus, or until food is substantially emptied from the stomach, at which time strong muscular contractions (sometimes called the "housekeeper wave") sweep across the stomach, clearing its contents. The composition is excluded from passing through the pyloric sphincter as it exceeds a diameter of approximately 14-16 mm in the swollen or expanded state. Preferably the composition exceeds a diameter of 16-18 mm. Swelling may be combined with floating, which keeps the formulation away from the pylorus, particularly in the fed state.

The concept of a formulation which swells upon contact with gastric fluid and consequently is retained in the stomach is known since the 1960s. U.S. Pat. No. 3,574,820 discloses tablets which swell in contact with gastric fluid to such a size that they cannot pass the pylorus and therefore are retained in the stomach. Similarly, U.S. Pat. No. 5,007,790 describes tablets or capsules composed of hydrophilic, water-swellable, cross-linked polymers that quickly swell to promote gastric retention, while allowing slow dissolution of drug molecules mixed with the polymers.

U.S. Patent Publication No. 20030104053, incorporated herein by reference, discloses unit dosage form tablets for the delivery of pharmaceuticals wherein the active component is dispersed in a solid unitary matrix that is formed of a combination of poly (ethylene oxide) and hydroxypropyl methylcellulose. This combination is said to offer unique benefits in terms of release rate control and reproducibility while allowing both swelling of the tablet to effect gastric retention and gradual disintegration of the tablet to clear the tablet from the gastrointestinal tract after release of the drug has occurred. U.S. Pat. No. 6,340,475, also assigned to DepoMed, herein incorporated by reference, highlights unit oral dosage forms of active components developed by incorporating them into polymeric matrices comprised of hydrophilic polymers that swell upon imbibing water to a size that is large enough to promote retention of the dosage form in the stomach during the fed mode. The polymeric matrix is formed of a polymer selected from the group consisting of poly (ethylene oxide), cellulose, crosslinked polyacrylic acids, xanthan gum and alkyl-substituted celluloses like hydroxymethyl-cellulose, hydroxyethyl-cellulose, hydroxypropyl-cellulose, hydroxypropylmethyl-cellulose, carboxymethyl-cellulose and microcrystalline cellulose.

Further, swelling gastroretentive systems based on gums have also been developed by DepoMed researchers. U.S. Pat. No. 6,635,280, incorporated herein by reference, discloses controlled release oral dosage forms for highly water soluble drugs comprising one or more polymers forming a solid polymeric matrix which swells upon imbibition of water to a size that is large enough to promote retention of the dosage form in the stomach during the fed mode. A polymeric matrix may be formed of a polymer selected from the following: poly(ethylene oxide), cellulose, alkyl-substituted celluloses, crosslinked polyacrylic acids, and xanthan gum. U.S. Pat. No. 6,488,962, incorporated herein by reference, discloses optimal tablet shapes that prevent passage through the pylorus while remaining convenient to swallow. The tablets are made using water swellable polymers including cellulose polymers and their derivatives, polysaccharides and their derivatives, polyalkylene oxides, polyethylene glycols, chitosan, poly(vinyl alcohol), xanthan gum, maleic anhydride copolymers, poly(vinyl pyrrolidone), starch and starch-based polymers, maltodextrins, poly (2-ethyl-2-oxazoline), poly(ethyleneimine), polyurethane hydrogels, crosslinked polyacrylic acids and their derivatives, as well as copolymers of the above listed polymers, including block copolymers and graft polymers.

U.S. Pat. No. 6,723,340, incorporated herein by reference, discloses optimal polymer mixtures for making swelling gastroretentive compositions. The mixtures provide optimal control of swelling and drug release parameters as well as control of dissolution/erosion parameters, so as to ensure passage of the composition into the small intestine upon substantially complete drug release. Preferred polymer mixtures include combinations of poly(ethylene oxide) and hydroxypropyl methylcellulose. Preferred molecular weight ranges and viscosity ranges are provided for the polymer mixtures.

The methods described in the foregoing patent publications have been used to formulate four U.S. FDA approved swelling gastroretentive formulations described in multiple publications (e.g. reviewed in: Berner et al., Expert Opin Drug Deliv. 3:541 (2006)).

U.S. Patent Publication No. 20080220060, incorporated herein by reference, discloses gastroretentive formulations comprising an active substance granulated with a mixture of a weak gelling agent, a strong gelling agent and a gas generating agent. Herein the strong gelling agent is selected from the group consisting of methyl cellulose, hydroxypropyl methyl cellulose, hydroxypropyl cellulose with the exclusion of low-substituted hydroxypropyl cellulose, hydroxyethyl cellulose, ethyl cellulose, sodium carboxymethyl cellulose, xanthan gum, guar gum, carrageenan gum, locust bean gum, sodium alginate, agar-agar, gelatin, modified starches, co-polymers of carboxyvinyl polymers, co-polymer of acrylates, co-polymers of oxyethylene and oxypropylene and mixtures thereof. The patent also describes manufacturing methods. U.S. Pat. No. 7,674,480 discloses swelling gastroretentive formulation methods that provide for very rapid swelling using mixtures including a superdisintegrant, tannic acid and one or more hydrogels. U.S. Patent Publication No. 20040219186, incorporated herein by reference, provides expandable gastric retention device comprising a gel formed from a polysaccharide, based on xanthan gum or locust bean gum or a combination thereof. U.S. Patent Publication No. 20060177497, incorporated herein by reference, discloses gellan gum based oral controlled release dosage forms as a platform technology for gastric retention. The dosage form further comprises hydrophilic polymers such as guar gum, hydroxypropyl methylcellulose, carboxymethyl cellulose sodium salt, xanthan gum.

U.S. Pat. No. 6,660,300 discloses a biphasic swelling gastroretentive formulation technology, suitable for delivering water soluble drugs, in which swelling and drug release are accomplished by separate compartments of a composition: an inner solid particulate phase contains the drug and one or more hydrophilic polymers, one or more hydrophobic polymers and/or one or more hydrophobic materials such as waxes, fatty alcohols and/or fatty acid esters. An outer solid continuous phase (in which granules of the drug-containing inner phase are embedded) is formed using one or more hydrophobic polymers and/or one or more hydrophobic materials such as waxes, fatty alcohols and/or fatty acid esters. Tablets and capsules are disclosed.

Other excipients useful In a swelling or expandable matrix formulation include (i) a water-swellable polymer matrix and (ii) hydrophilic polymers selected from the following: polyalkylene oxides, particularly poly(ethylene oxide), polyethylene glycol and poly(ethylene oxide)-poly (propylene oxide) copolymers; cellulosic polymers; acrylic acid and methacrylic acid polymers, copolymers and esters thereof, preferably formed from acrylic acid, methacrylic acid, methyl acrylate, ethyl acrylate, methyl methacrylate, ethyl methacrylate, and copolymers thereof, with each other or with additional acrylate species such as aminoethyl acrylate; maleic anhydride copolymers; polymaleic acid; poly(acrylamides) such as polyacrylamide per se, poly (methacrylamide), poly(dimethylacrylamide), and poly(N-isopropyl-acrylamide); poly(olefinic alcohol)s such as poly (vinyl alcohol), poly(N-vinyl lactams) such as poly(vinyl pyrrolidone), poly(N-vinyl caprolactam), and copolymers thereof polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxyethylated propylene glycol, and mono- and di-polyoxyethylated trimethylene glycol; polyoxyethylated sorbitol and polyoxyethylated glucose; polyoxazolines, including poly(methyloxazoline) and poly(ethyloxazoline); polyvinylamines; polyvinylacetates, including polyvinylacetate per se as well as ethylene-vinyl acetate copolymers, polyvinyl acetate phthalate, and the like, polyimines, such as polyethyleneimine; starch and starch-based polymers; polyurethane hydrogels; chitosan; polysaccharide gums; zein; and shellac, ammoniated shellac, shellac-acetyl alcohol, and shellac n-butyl stearate. The gastroretentive formulation may also include any combination of a floating formulation, mucoadhesive formulation, expandable matrix formulation, modified shape formulation and/or a magnetic formulation.

In some embodiments the pharmaceutical composition of the present invention is a gastroretentive composition which is retained in the stomach as a result of swelling to a size that inhibits passage through the pylorus. In further embodiments the gastroretentive composition is retained in the stomach by both swelling and floating mechanisms.

Unfolding, Shape-Changing Gastroretentive Formulations

Pharmaceutical compositions that unfold, decompress or otherwise change size and/or shape upon contact with liquid gastric contents have also been described and are suitable delivery vehicles for the compounds and formulations of the invention. Such compositions employ a similar principal to swelling/expanding gastroretentive formulations in that they change shape in the stomach to a size and/or geometry that does not easily permit passage through the pylorus. Methods and materials for making unfolding, uncoiling or other shape-changing gastroretentive compositions are known in the art. For example U.S. Pat. No. 3,844,285 describes a variety of such devices intended for veterinary use in ruminants, however the basic principles also apply to human gastroretentive formulations. U.S. Pat. No. 4,207,890 describes a controlled release drug delivery system consisting of a "collapsed, expandable, imperforate polymer envelope containing within it an effective expanding amount of an expanding agent, agent" which swells and unfolds on contact with gastric juice, and is consequently retained in the stomach in the expanded state. The composition is administered inside a capsule in collapsed form. Unfolding and shape changing gastroretentive compositions have been reviewed (e.g. Klausner et al., Journal of Controlled Release 90:143 (2003)).

An exemplary unfolding gastroretentive technology called the "Accordion Pill" is being developed by Intec Pharma (Jerusalem, Israel). Multi-layer planar structures of various shapes (in which at least one layer contains a drug) are folded into an accordion or staircase-like shape and packaged inside a capsule, as described in: Kagan, L. Journal of Controlled Release 113:208 (2006). Additional features of the Accordion Pill and related technologies are disclosed in U.S. Pat. No. 6,685,962, herein incorporated by reference, including pharmaceutical excipients preferably used in its construction. The capsule dissolves upon contact with stomach contents, releasing a folded composition which rapidly unfolds and is thereafter retained in the stomach for up to 12 hours when administered with a regular meal.

Other gastroretentive technologies include superporous hydrogels and Ion exchange resin systems. Superporous hydrogels swell rapidly (within a minute of contacting liquid) due to rapid water uptake via numerous interconnected pores. Compositions may swell up to 100 times or more their original size, yet retain sufficient mechanical strength to withstand the forces of gastric contraction due to co-formulation with hydrophilic polymers such as croscarmellose sodium (e.g. brand name: Ac-Di-Sol). Ion exchange resin beads can be loaded with negatively charged drugs and made to float using gas generating agents (e.g. bicarbonate, which reacts with chloride ion in the gastric fluid to generate carbon dioxide gas). The beads are encapsulated in a semipermeable membrane which traps the gas, resulting in long-term flotation of the beads.

Gastroretentive formulations may also include any combination of a mucoadhesive, floating, raft-forming, swelling, unfolding/shape changing, superporous hydrogel or ion exchange resin formulation. Such combinations are known to those skilled in art. For example U.S. Pat. No. 8,778,396 ("Multi-unit gastroretentive pharmaceutical dosage form comprising microparticles"), herein incorporated by reference in its entirety, describes a combined mucoadhesive floating gastroretentive formulation consisting of microparticles.

The compositions of the present invention may include, but are not limited to, hydrophilic polymers having swelling and/or mucoadhesive properties to further promote gastroretention. Hydrophilic polymers having swelling and/or mucoadhesive properties suitable for incorporation in the compositions of present invention include, but are not limited to, polyalkylene oxides; cellulosic polymers; acrylic acid and methacrylic acid polymers, and esters thereof, maleic anhydride polymers; polymaleic acid; poly(acrylamides); poly(olefinic alcohol)s; poly(N-vinyl lactams); polyols; polyoxyethylated saccharides; polyoxazolines; polyvinylamines; polyvinylacetates; polyimines; starch and starch-based polymers; polyurethane hydrogels; chitosan; polysaccharide gums; zein; shellac-based polymers; polyethylene oxide, hydroxypropyl cellulose, hydroxypropyl methyl cellulose, hydroxyethyl cellulose, sodium carboxy methylcellulose, calcium carboxymethyl cellulose, methyl cellulose, polyacrylic acid, maltodextrin, pregelatinized starch and polyvinyl alcohol, copolymers and mixtures thereof.

Release of active ingredients from a composition may be achieved through use of suitable retardants that include excipients well known in the pharmaceutical art for their release retarding properties. Examples of such release retardants include, but are not limited to, polymeric release retardants, non-polymeric release retardants or any combinations thereof.

Polymeric release retardants employed for the purpose of the present invention include, but are not limited to, cellulose derivatives; polyhydric alcohols; saccharides, gums and derivatives thereof; vinyl derivatives, polymers, copolymers or mixtures thereof; maleic acid copolymers; polyalkylene oxides or copolymers thereof; acrylic acid polymers and acrylic acid derivatives; or any combinations thereof. Cellulose derivatives include, but are not limited to, ethyl cellulose, methylcellulose, hydroxypropylmethylcellulose (HPMC), hydroxypropyl cellulose (HPC), hydroxyethyl cellulose, hydroxymethyl cellulose, hydroxyethyl methyl cellulose, carboxymethyl cellulose (CMC), or combinations thereof. Polyhydric alcohols include, but are not limited to, polyethylene glycol (PEG) or polypropylene glycol; or any combinations thereof. Saccharides, gums and their derivatives include, but are not limited to, dextrin, polydextran, dextran, pectin and pectin derivatives, alginic acid, sodium alginate, starch, hydroxypropyl starch, guar gum, locust bean gum, xanthan gum, karaya gum, tragacanth, carrageenan, acacia gum, arabic gum, fenugreek fibers or gellan gum or the like; or any combinations thereof. Vinyl derivatives, polymers, copolymers or mixtures thereof include, but are not limited to, polyvinyl acetate, polyvinyl alcohol, mixtures of polyvinyl acetate (8 parts w/w) and polyvinylpyrrolidone (2 parts w/w) (Kollidon SR), copolymers of vinyl pyrrolidone, vinyl acetate copolymers, polyvinylpyrrolidone (PVP); or combinations thereof. Polyalkylene oxides or copolymers thereof include, but are not limited to, polyethylene oxide, polypropylene oxide, poly (oxyethylene)-poly (oxypropylene) block copolymers (poloxamers) or combinations thereof. Maleic acid copolymers include, but are not limited to, vinylacetate maleic acid anhydride copolymer, butyl acrylate styrene maleic acid anhydride copolymer or the like or any combinations thereof. Acrylic acid polymers and acrylic acid derivatives include, but are not limited to, carbomers, methacrylic acids, polymethacrylic acids, polyacrylates, polymethacrylates or the like or combinations thereof. Polymethacrylates, include, but are not limited to, a) copolymer formed from monomers selected from methacrylic acid, methacrylic acid esters, acrylic acid and acrylic acid esters c) copolymer formed from monomers selected from ethyl acrylate, methyl methacrylate and trimethylammonioethyl methacrylate chloride, or the like or any combinations thereof. Non-polymeric release retardants employed for the purpose of the present invention include, but are not limited to, fats, oils, waxes, fatty acids, fatty acid esters, long chain monohydric alcohols and their esters or combinations thereof. In an embodiment, non-polymeric release retardants employed in the present invention, include, but are not limited to, Cutina (hydrogenated castor oil), Hydrobase (hydrogenated soybean oil), Castorwax (hydrogenated castor oil), Croduret (hydrogenated castor oil), Carbowax, Compritol (glyceryl behenate), Sterotex (hydrogenated cottonseed oil), Lubritab (hydrogenated cottonseed oil), Apifil (wax yellow), Akofine (hydrogenated cottonseed oil), Softtisan (hydrogenated palm oil), Hydrocote (hydrogenated soybean oil), Corona (lanolin), Gelucire (macrogolglycerides lauriques), Precirol (glyceryl palmitostearate), Emulcire (cetyl alcohol). Plurol diisostearique (polyglyceryl diisostearate), and Geleol (glyceryl stearate), and mixtures thereof.

The gastroretentive compositions of the present invention may be in a form such as, but not limited to, a monolithic or multi-layered dosage form or in-lay system. In one embodiment of the present invention the gastroretentive compositions are in the form of a bilayered or trilayered solid dosage form. In an illustrative embodiment, a solid pharmaceutical composition in the form of an expanding bilayered system for oral administration is adapted to deliver an active pharmaceutical component from a first layer immediately upon reaching the gastrointestinal tract, and to deliver a further pharmaceutical agent which may be same or different from a second layer, in a modified manner over a specific time period. The second layer may be formulated to expand in the composition, thereby prolonging retention of the composition in the stomach.

In a further illustrative embodiment a solid pharmaceutical composition for oral administration contains two layers: one comprising an active component along with a suitable release retardant and the other layer comprising swellable agent in combination with other excipients. In another embodiment of the present invention, a solid pharmaceutical composition for oral administration contains an in-lay system which is a specialized dosage form comprising a first tablet containing active component(s) which is placed inside a second tablet comprising excipients that ensure gastric retention. In this system the active component containing tablet is small and is covered on all sides except at least one side with a blend of excipient comprising swellable polymers or a flotation system, or both, that ensures gastric retention.

In yet another embodiment of the present invention, the dosage form may be optionally coated. Surface coatings may be employed for organoleptic purposes (particularly with thiols or disulfides that have an odor, or an unpleasant taste), for drug labeling purposes (e.g. a color coding system for dosage forms), for aesthetic purposes, for dimensionally stabilizing the compressed dosage form, or for retarding drug release. The surface coating may be any conventional coating which is suitable for enteral use. The coating may be carried out using any conventional technique employing conventional ingredients. A surface coating can for example be obtained using a quick-dissolving film using conventional polymers such as, but not limited to, hydroxypropyl methyl cellulose, hydroxypropyl cellulose, carboxymethyl cellulose, polyvinyl alcohol, poly methacrylates or the like. Coating excipients and methods for using them are well known in the art. See for example: McGinity, James W. and Linda A. Felton, Aqueous Polymeric Coatings for Pharmaceutical Dosage Forms, Third Edition, Informa Healthcare, 2008.

Further, in another embodiment of the present invention, the compositions are in the form of multiparticulates including, but not limited to, pellets, microspheres, microcapsules, microbeads, microparticles or nanoparticles having prolonged transit in the intestine to effectively deliver active agents that require longer retention times in the intestinal tract. Multiparticulate systems may be (i) bioadhesive or mucoadhesive, thereby delaying gastrointestinal transit, or (ii) may float on top of the gastric contents, optionally forming a gel-like layer, or (iii) may be coated with a pH sensitive outer layer or layers that dissolve in the mildly acidic environment of the small intestinem, or in the neutral to slightly basic environment of the ileum (typically the gut segment with the highest pH), or (iv) may be formed using a drug containing polymer that is not digestible by human enzymes but is digestible by enzymes produced by enteric bacteria, leading to drug release in the distal ileum and colon. In an embodiment, the compositions of the present invention, in the form of multiparticulates, are gastroretentive. Such multiparticulate systems may be prepared by methods including, but not limited to, pelletization, granulation, spray drying, spray congealing and the like.

A suitable polymeric release controlling agent may be employed in the compositions of the present invention. In one embodiment, the polymeric release controlling agent is pH independent or pH dependent or any combination thereof. In another embodiment, the polymeric release controlling agent employed in the compositions of the present invention may be swelling or non-swelling. In a further embodiment, polymeric release controlling agents that may be employed in the compositions of the present invention include, but are not limited to, cellulose derivatives, saccharides or polysaccharides, poly(oxyethylene)-poly(oxypropylene) block copolymers (poloxamers), vinyl derivatives or polymers or copolymers thereof, polyalkylene oxides and derivatives thereof, maleic copolymers, acrylic acid derivatives or the like or any combinations thereof.

Controlled release compositions for oral use may be constructed to release the active drug by controlling the dissolution and/or the diffusion of the active drug substance. Any of a number of strategies can be pursued in order to obtain controlled release and thereby optimize the plasma concentration vs time profile. In one example, controlled release is obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner. Examples include single or multiple unit tablet or capsule compositions, oil solutions, liquids, suspensions, emulsions, microcapsules, microspheres, nanoparticles, powders and granules. In certain embodiments, compositions include biodegradable, pH, and/or temperature-sensitive polymer coatings.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

Alternatively, certain cysteamine precursors or enhancers of in vivo cysteamine generation or absorption may be formulated and administered as medical foods. Medical foods are regulated by the US FDA as foods, not drugs. Methods for formulating medical foods are known in the art. See, for example, U.S. Patent Publication No. 20100261791, for descriptions of methods for preparing and administering active compounds in foods or beverages. Nutracia, a medical food company based in The Netherlands, has over 250 patent applications and patents describing methods for combining pharmacologically active agents with foods or drinks.

Coatings

The pharmaceutical compositions formulated for oral delivery, such as tablets or capsules of the present invention can be coated or otherwise compounded to provide a dosage form affording the advantage of delayed or extended release. The coating may be adapted to release the active drug substance in a predetermined pattern (e.g., in order to achieve a controlled release formulation) or it may be adapted not to release the active drug substance until after passage of the stomach, e.g., by use of an enteric coating (e.g., polymers that are pH-sensitive ("pH controlled release"), polymers with a slow or pH-dependent rate of swelling, dissolution or erosion ("time-controlled release"), polymers that are degraded by enzymes ("enzyme-controlled release" or "biodegradable release") and polymers that form firm layers that are destroyed by an increase in pressure ("pressure-controlled release")). Exemplary enteric coatings that can be used in the pharmaceutical compositions described herein include sugar coatings, film coatings (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or coatings based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose. Furthermore, a time delay material such as, for example, glyceryl monostearate or glyceryl distearate, may be employed.

For example, the tablet or capsule can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release.

When an enteric coating is used, desirably, a substantial amount of the drug is released in the lower gastrointestinal tract. Alternatively, leaky enteric coatings may be used to provide a release profile intermediate between immediate release and delayed release formulations. For example U.S. patent application 20080020041 A1 discloses pharmaceutical formulations coated with an enteric material that releases at least a portion of an active ingredient upon contacting gastric fluid, with the remainder released upon contacting intestinal fluid.

In addition to coatings that effect delayed or extended release, the solid tablet compositions may include a coating adapted to protect the composition from unwanted chemical changes (e.g., chemical degradation prior to the release of the active drug substance). The coating may be applied on the solid dosage form in a similar manner as that described in Encyclopedia of Pharmaceutical Technology, vols. 5 and 6, Eds. Swarbrick and Boyland, 2000.

For controlled release formulations, the active component of the composition may be targeted for release in the small intestine. The formulation may contain an enteric coating such that the composition is resistant to the low pH environment found in the stomach, but sensitive to the higher pH environment of the small intestine. To control the release of the active component in the small intestine, a multiparticulate formulation may be employed to prevent simultaneous release of the active component. A multiparticulate composition may include a plurality of individual enteric coated cores that include a hydrophobic phase containing a cysteamine precursor, or a salt thereof, dispersed in a microcrystalline cellulose-based gel and a hydrophilic phase containing a hydrogel. The microcrystalline cellulose (MCC) functions as a release controlling polymer for the cysteamine precursor, or a salt thereof, preventing dose dumping and stabilizing the cysteamine precursor, or a salt thereof, while the cores are being dissolved or eroded in the intestine. Two or more multiparticulate compositions that differ with respect to excipients in the core or the coating layer may be combined in one pharmaceutical composition (e.g. a capsule, powder or liquid) so as to release active ingredients (e.g. cysteamine precursors) over a longer time period. Alternatively the same effect can be achieved by using different concentrations of excipients in two or more batches of microparticles and then combining the microparticles from different batches in a chosen ratio (e.g. 1:1) so as to effect a targeted drug release profile.

The composition may include a plurality of individual enteric coated cores containing about 15% w/w to about 70% w/w cysteamine precursor, or a salt thereof, about 25% w/w to about 75% w/w microcrystalline cellulose, and about 2% w/w to about 15% w/w methylcellulose, wherein the % w/w is the % w/w of the enteric coated cores.

In some cases, including a continuous proteinaceous subcoating layer covering the individual cores and separating the individual cores from their respective enteric coatings may be advantageous because the proteinaceous subcoating layer further enhances the stability of the cysteamine precursor, or a salt thereof. The continuous proteinaceous subcoating is adapted to prevent the cysteamine precursor, or a salt thereof, from mixing with the enteric coating. Some preferred proteinaceous subcoatings have the following attributes: the subcoating may comprise a gelatin film adhered to the core and/or the subcoating may comprise a dried proteinaceous gel.

In a particular embodiment, the enteric coated cores release no more than about 20% of the cysteamine precursor, or a salt thereof, within about two hours of being placed in a 0.1 N HCl solution and, subsequently, no less than about 85% of the cysteamine precursor, or a salt thereof, within about eight hours of being placed in a substantially neutral pH environment.

Preferably, the enteric coated cores are spheroidal and not more than 3 mm in diameter.

To prevent adherence of separately administered compositions in the stomach, compositions of the invention may be coated with an anti-adhering agent. Anti-adherents may also be used to prevent microparticles from sticking to each other. For example, compositions may be coated with a thin outermost layer of microcrystalline cellulose powder. Alternatively, adherence can be prevented by coating with a polymer that is insoluble in gastric juice but permeable and swellable. For example a 30% polyacrylate dispersion (e.g. Eudragit NE30D, Evonik Industries) has been shown to prevent adherence of floating minitablets in the stomach (see Rouge et al., European Journal of Pharmaceutics and Biopharmaceutics 43:165 (1997)).

Commercial forms of the listed excipients used in enteric coatings include, for example, various brands of polymethacrylates (a chemically heterogeneous group of compounds that includes amino methacrylate copolymer, ammonio methacrylate copolymer, ethyl acrylate copolymer dispersion, methyl methacrylate copolymer dispersion, methacrylic acid copolymer and methacrylic acid copolymer dispersion) which are sold as product lines by companies including, without limitation, Ashland, BASF Fine Chemicals (Kollicoat product line), ColorCon (Acryl-EZE product line), Eastman Chemical (Eastacryl product line) and Evonik Industries (Eudragit product line).

Formulations for Ileal and Colonic Drug Release

In some embodiments, ileum and/or colon-targeted formulations can be used to deliver cysteamine precursors to the distal ileum and colon. (The term "colon targeted" is used herein to refer to both ileum-targeted and colon-targeted formulations; any composition that starts to release drug in the ileum is likely to also release drug in the colon, and some drug released in the ileum is likely to reach the colon.) Drug delivery advantages of colon-targeted compositions include prolonged contact with the large intestinal epithelium and the presence of colonic bacteria that can be exploited for site specific delivery.

From a pharmacokinetic perspective colonic absorption of cysteamine is desirable because, due to its extremely short half life, cysteamine must be continuously produced in the gastrointestinal tract (and absorbed) to maintain blood levels in the therapeutic range. An ingested pharmaceutical composition (if not a gastroretentive composition) may arrive in the colon three to five hours after ingestion (on average, in most subjects) if ingested in the fasted condition, or six to 10 hours (on average, in most subjects) after ingestion with food. The only way to sustain blood cysteamine levels in the therapeutic range after the dosage form reaches the colon is to ensure cysteamine is generated and absorbed in the colon. Some cysteamine precursors released in the small intestine may pass into the colon intact and be degraded to cysteamine in the colon. However, to provide robust cysteamine generation in the colon cysteamine precursors should be formulated for release in the colon (or ileum), where they can be degraded to cysteamine and absorbed. Colon-targeted compositions are not intended to be used alone as therapy for cysteamine-sensitive diseases, but rather to complement formulations directed to other areas of the gastrointestinal tract.

Two approaches to colon-targeted delivery have been developed extensively and are described below.

The first approach involves exploitation of enzymes produced in the colon by enteric bacteria. Enteric bacteria can digest a variety of polymers that are indigestible by human enzymes present in saliva, gastric juice, intestinal fluid or pancreatic juice. Pharmaceutical compositions containing such polymers cannot be digested—and therefore active ingredients admixed with the polymers cannot escape—until they encounter enzymes produced by enteric bacteria in the distal ileum (where the density of bacteria starts to increase) or the colon (where there may be 1,000,000,000,000 bacteria per milliliter of colon contents).

A cysteamine precursor and/or other active ingredient (e.g. an enhancer of in vivo cysteamine generation or absorption) can be mixed with a polymer that retards drug release and is only digestible (in the human gastrointestinal tract) by enzymes produced by enteric bacteria. Polymers used for colon-targeted drug delivery based on selective degradation by enteric bacteria include dextran hydrogels (Hovgaard, L., and H. Brondsted, J. Controlled Rel. 36:159 (1995)), crosslinked chondroitin (Rubinstein et al., Pharm. Res. 9:276 (1992)), and hydrogels containing azoaromatic moieties (Brondsted, H. and J. Kopoecek, Pharm Res. 9:1540 (1992); and Yeh et al., J. Controlled Rel. 36:109 (1995)).

Covalent linkage of a drug with a carrier to form a precursor that is stable in the stomach and small intestine and releases the drug in the large intestine upon enzymatic cleavage by the intestinal microflora; examples of these precursors include azo-conjugates, cyclodextrin-conjugates, glycoside-conjugates, glucuronate conjugates, dextran-conjugates, polypeptide and polymeric conjugates. The basic principle is that the covalent bond linking drug to carrier must be indigestible by human enzymes but digestible by enteric bacterial enzymes.

The second approach involves exploitation of high pH in the ileum relative to other parts of the gastrointestinal tract. In healthy subjects the pH in the gastrointestinal tract increases from the duodenum (approximately pH 5.5 to 6.6 from the proximal to the distal duodenum) to the terminal ileum (approximately pH 7-7.5), then decreases in the cecum (around pH 6.4), and then increases again from the right to the left side of the colon with a final value of about pH 7.

Compositions may be coated with a pH-sensitive polymer that dissolves only at neutral to mildly alkaline pH (e.g. above pH 6.5, above pH 6.8 or above pH 7). Beneath the pH sensitive coating is a sustained release formulation from which drug is slowly released by diffusion, erosion or a combination. This approach is described in U.S. Pat. No. 5,900,252, incorporated herein by reference.

The enteric bacterial and pH based colon targeting methods can be combined. See, for example: Naeem et al., Colloids Surf B Biointerfaces S0927 (2014). The study describes coated nanoparticles formed using bacteria-digestible polymers. Another technology that combines pH and bacterial enzyme digestion to deliver drug-containing liquid-filled capsules to the colon is described in U.S. Patent Publication No. 20070243253, which discloses formulations that utilize polymers including starch, amylose, amylopectin, chitosan, chondroitin sulfate, cyclodextrin, dextran, pullulan, carrageenan, scleroglucan, chitin, curdulan and levan, together with pH sensitive coatings that dissolve above about pH 5 or higher.

Other approaches to colon-targeted drug delivery employ: (i) time release systems where once a multicoated formulation passes the stomach the outer coat starts to dissolve and, based on the thickness and composition of the coatings, drug is released after a lag time of 3-5 hrs, which is about the transit time of the small intestine; (ii) redox-sensitive polymers where a combination of azo- and disulfide polymers, provide drug release in response to the low redox potential of the colon; (iii) bioadhesive polymers which selectively adhere to the colonic mucous, slowing transit of the dosage form to allow drug release the drug; and/or (iv) osmotic controlled drug delivery where drug is released through a semi-permeable membrane due to osmotic pressure.

The book "Oral Colon-Specific Drug Delivery" by David R. Friend (CRC Press, 1992) provides and overview of older colon-targeting methods (many of which are still useful), such as dextran-based delivery systems, glycoside/glycosidase-based delivery, azo-bond prodrugs, hydroxypropyl methacrylamide copolymers and other matrices for colon delivery. Colon-targeted drug delivery has been reviewed more recently by, for example: Bansal et al., Polim Med. 44:109 (2014). Recent approaches include use of novel polymers digestible only by enzymes produced by enteric bacteria, including natural polymers found in a variety of plants, as well as microbeads, nanoparticles and other microparticles.

Methods of Treatment

The present invention relates to novel compositions and methods useful for treating cysteamine sensitive diseases and disorders. Treatment entails oral administration of cysteamine precursors, convertible to cysteamine in the gastrointestinal tract. An important class of cysteamine precursors are mixed disulfides which, upon reduction in vivo, provide two thiols. Both thiols may be convertible to cysteamine in vivo, or just one. Cysteamine precursors in which both thiols are convertible to cysteamine are a preferred class of therapeutic agents for diseases including cystinosis, cystic fibrosis, malaria, and viral and bacterial infections. Non-limiting examples of such mixed disulfides include cysteamine-pantetheine and cysteamine-4-phosphopantetheine.

For some other diseases a second thiol, not convertible into cysteamine, may be selected to complement or augment the therapeutic effects of cysteamine. In certain embodiments mixed disulfide cysteamine precursors for therapy of neurogenerative and neuropsychiatric diseases include a second thiol from the following group: N-acetylcysteine, cysteine methyl ester, cysteine ethyl ester, gamma glutamylcysteine, gamma glutamylcysteine ethyl ester, homocysteine, cysteine and dihydrolipoic acid.

Combinations of mixed disulfide cysteamine precursors provide further flexibility in addressing the pathophysiology of specific diseases, or in tailoring treatment regimens to account for inter-patient variation in disease status, disease activity, drug metabolism or drug sensitivity. For example a mixed disulfide in which both thiols are convertible to cysteamine in vivo may be co-administered with a mixed disulfide in which just one thiol is convertible to cysteamine in vivo. The ratio of the two types of mixed disulfide may vary from about 1:1 to about 1:10.

Cysteamine precursors may be co-administered with agents that enhance the biochemical processes required for (i) in vivo conversion of the precursor to cysteamine and (ii) subsequent absorption of cysteamine by enterocytes. Such enhancers may be selected and dosed to augment or complement the therapeutic effects of a cysteamine precursor in a particular disease, or to individualize a therapeutic regimen for a specific patient. For example, disulfide cysteamine precursors may be co-administered with reducing agents that enhance disulfide bond reduction. The reducing agent may be a physiological compound such as the thiols glutathione, cysteine, homocysteine, gamma-glutamylcysteine, or it may be an analog of one of those compounds such as N-acetylcysteine, cysteine methyl ester, cysteine ethyl ester or gamma glutamylcysteine ethyl ester, or it may be a dithiol such as dihydrolipoic acid, or a non-thiol reducing agent such as vitamin C (ascorbic acid).

Cysteamine and other thiols released from the mixed disulfides of the invention may provide therapeutic effects via any of several mechanisms.

Cysteamine has pleiotropic chemical and pharmacological effects in the body, including (i) antioxidant, (ii) reducing agent and participant in thiol-disulfide exchanges, (iii) enzyme inhibitor and (iv) copper chelator. Cysteamine also modulates plasma levels of certain disease-associated chemicals and proteins. For example, cysteamine: (v) lowers triglycerides and low density lipoprotein-associated cholesterol, high levels of which have been associated with heart disease and atherosclerosis, and (vi) lowers total adiponectin as well as the relative abundance of adiponectin multimers, high levels of which are associated with metabolic syndrome and other diseases. Cysteamine also has (v) anti-parasitic, (vi) anti-bacterial and (vii) anti-viral effects, as well as (viii) antifibrotic effects, all via uncertain mechanisms.

(i) Cysteamine can act directly as an antioxidant, neutralizing reactive oxygen species (ROS) by providing a reducing group.

(ii) Cysteamine can increase the level of other physiologic antioxidants, including glutathione (GSH), the major antioxidant in the body, and cysteine, an important antioxidant in serum and in the gastrointestinal tract. The antioxidant and GSH-restoring properties of cysteamine are relevant to a broad range of diseases in which high levels of oxidized lipids, proteins or small molecules, often accompanied by low levels of GSH, contribute to pathogenesis. Diseases in which abnormal oxidation products are contributing factors include neurodegenerative diseases, cystic fibrosis and impaired immune function associated with HIV infection (see Herzenberg et al., Proc Natl Acad Sci USA. 94:1967 (1997); and Bhaskar et al., J Biol Chem. 290:1020 (2015)). GSH, a tripeptide, is degraded to its constituent amino acids by proteases in the gut. Therefore oral GSH is not an efficient way to deliver GSH to the body. Cysteamine therapy is an effective way to boost GSH levels.

(iii) Cysteamine can chemically reduce, or participate in thiol-disulfide exchange reactions with glutathione containing disulfide and cysteine containing disulfides (including cystine), thereby producing free glutathione and cysteine, which in turn can reduce other oxidized compounds or neutralize reactive oxygen species. Free cysteine (e.g. generated from cysteamine-cystine exchange) can also be utilized in glutathione synthesis. In addition to promoting thiol-disulfide exchanges with free cysteines and cysteines, cysteamine can also interact with cystine and cysteinyl residues in proteins, including a variety of redox-sensing proteins that control cellular anti-oxidant defense mechanisms. Cysteamine also inhibits pathological cystine accumulation in cystinosis via a thiol-disulfide exchange reaction with lysosomal cystine to form cysteine and cysteine-cysteamine mixed disulfide, both of which can exit lysosomes in the absence of a functional cystinosin gene. (Cysteine-cysteamine disulfide is transported by a lysine/heptahelical protein transporter encoded by the PQLC2 gene.)

(iv) Cysteamine inhibits tissue transglutaminase (also called transglutaminase 2, or TG2), a cytoplasmic enzyme implicated in the pathogenesis of Huntington's disease. Cystamine, the disulfide of two cysteamines is also a TG2 inhibitor, and has been tested more extensively than cysteamine in Huntington's disease models. However in the strongly reducing environment of the cytoplasm virtually all cystamine is reduced to cysteamine. Therefore cysteamine, is likely the active form of cystamine (see: Jeitner et al., Biochem Pharmacol. 69:961 (2005)). Cystamine improves motor function and extends life-span in several mouse models of Huntington's disease. These beneficial effects may be mediated by Brain-Derived Neurotrophic factor (BDNF), which increases upon cystamine treatment. Cystamine also inhibits the cytoplasmic enzyme caspase-3, again likely through cysteamine creation. The abnormal, pathogenic product of the Huntington's disease gene, huntingtin, induces activation of caspase-3 and consequent release of cytochrome c from mitochondria in cultured cells, ultimately leading to apoptosis. At high concentrations (e.g. 25 millimolar) cysteamine also inhibits matrix metalloproteinases (MMPs), a group of zinc-dependent endopeptidases with physiologic roles in angiogenesis, wound healing, and tissue remodeling. MMPs are overexpressed in some cancers and contribute to invasion and metastasis by degrading extracellular matrix. Cysteamine inhibits migration and invasion by pancreatic cancer cells in vitro and growth of pancreatic cancer xenografts in vivo (Fujisawa et al., PLoS One. 7:e34437 (2012)).

(v) Cysteamine, like some other thiols, is a strong copper chelator, which can be a cause of major side-effects in some cystinosis patients, who already have low copper and ceruloplasmin levels as a consequence of their disease-associated renal insufficiency. However, copper chelation may be therapeutically beneficial in neurodegenerative diseases, for example Alzheimer's disease.

(vi) Cysteamine reduces levels of oxidized proteins and inhibits myofibroblast proliferation via TGF-beta independent mechanisms in two mouse models of chronic kidney disease. Myofibroblasts produce extracellular matrix, including collagen, and abnormal myofibroblast proliferation is associated with scarring, contraction and loss of organ function in a variety of chronic fibrotic diseases, including diseases of the kidney (e.g. Alport's disease, focal segmental glomerulosclerosis), lung (e.g. cystic fibrosis, pulmonary fibrosis, chronic obstructive pulmonary disease) and liver (e.g. non-alcoholic fatty acid liver disease, non-alcoholic steatohepatitis and alcoholic steatohepatitis).

(vii) Cysteamine inhibits proliferation of the parasite that causes malaria, *Plasmodium alciparum*, both in vitro and in mouse models of malaria, without adversely modulating host inflammatory responses. Administration of the cysteamine precursor pantethine prevents the cerebral syndrome in mice infected with the *Plasmodium berghei* ANKA strain. Cysteamine also potentiates the therapeutically important artemisinin family of anti-malarials. In some embodiments artemisinin-cysteamine precursor combinations are used to treat malaria, including emerging artemisinin-resistant *Plasmodium* strains as well as cerebral malaria. Preferred cysteamine precursors for therapy of malaria are those from which two cysteamines can be generated; that is, disulfide cysteamine precursors in which both of the thiols generated upon reduction are convertible into cysteamine. Exemplary disulfide cysteamine precursors include those formed by joining cysteamine and pantetheine or cysteamine and 4-phosphopantetheine. Preferred enhancers of disulfide bond reduction to be co-administered with disulfide cysteamine precursors include the thiols pantetheine, 4-phosphopantetheine, dephospho-coenzyme A and coenzyme A, each of which is itself a cysteamine precursor.

(viii) Cysteamine promotes multimerization of adiponectin, a signaling molecule produced by adipocytes. Low levels of adiponectin have been associated with insulin resistance and inflammation and may contribute to the pathogenesis of both type I and type II diabetes. High molecular weight adiponectin may help mediate insulin signaling. Pediatric patients with nonalcoholic fatty liver disease (NAFLD) treated with cysteamine for 24 weeks had increased levels of high molecular weigh adiponectin multimers. Cysteamine may be therapeutically useful in conditions associated with low adiponectin levels, including insulin-resistant metabolic diseases such as diabetes. In addition to total adiponectin, the distribution of adiponectin multimers can independently explain variability in metabolic traits among individuals and populations.

(ix) Cysteamine has pleiotropic anti-viral effects. For example, it may inhibit HIV replication by interfering with the production of infectious viral particles, by blocking proviral DNA formation or by forming mixed disulfides with cysteine residues of proteins, thereby modifying the disulfide bridge architecture of the cell membrane and limiting adsorption of the virus. Cysteamine can also inhibit growth of influenza virus types A, B and C, including avian influenza virus subtypes such as H5N1, H1N2, H2N2, H3N2, H3N8, H5N1, H5N2, H5N3, H5N8, H5N9, H7N1, H7N2, H7N3, H7N4, H7N7, H9N2, and H10N7. Cysteamine may also inhibit proliferation of Spanish, Asian and Hong Kong infuenza virus strains, as well as swine, equine and canine infuenza viruses. U.S. Pat. No. 8,415,398 discloses anti-viral uses of cysteamine.

In specific diseases cysteamine may act via one of the above mechanisms of action, via multiple mechanisms, or via one or more mechanisms that have not yet been identified.

Diseases and disorders for which there is evidence of cysteamine efficacy include cystinosis; neurodegenerative disease; neurodevelopmental disorders, e.g. Rett syndrome; mitochondrial disorders, e.g., Leigh syndrome, MELAS, MERFF, Friedreich's ataxia and conditions associated with mutations in the POLG gene, as well as some forms of autism; fibrotic diseases of the kidney (e.g., Alport's disease, focal segmental glomerulosclerosis (FSGS)), of the liver (e.g. non-alcoholic steatohepatitis (NASH) and alcoholic steatohepatitis (ASH)), and of the lung (pulmonary fibrosis, chronic obstructive pulmonary disease (COPD), cystic fibrosis (CF)); parasitic infection (e.g., malaria and cerebral malaria); sickle cell anemia; cancer; stroke; bacterial infection, including biofilm-forming bacteria such as *Pseudomonas aeruginosa*; viral infection, including influenza virus and human immunodeficiency virus infection (AIDS); metabolic diseases including metabolic syndrome X and non-alcoholic fatty liver disease (NAFLD); metal poisoning, including copper and poisoning; and protection against radiation toxicity.

Other thiols disulfide bonded to cysteamine or to a compound degradable to cysteamine, can provide complementary therapeutic efficacy. For example the disulfide formed by reacting cysteamine with L-cysteine, or with an L-cysteine derivative such as L-cysteine methyl ester, L-cysteine ethyl ester, N-acetylcysteine, N-acetylcysteine ethyl ester or N-acetylcysteine amide may have complementary efficacy in the treatment of neurogenerative disease, or in the chelation and excretion of toxic metals.

The compositions of the invention will provide improved treatment for these diseases by allowing better control of cysteamine blood levels (i.e. maintaining cysteamine in the therapeutic range for prolonged periods) and, in the case of mixed disulfides, optionally by providing a second therapeutic thiol moiety, thereby improving efficacy and patient convenience while reducing side effects and patient non-compliance with therapy.

Neurodegenerative Diseases

Neurodegenerative diseases include Huntington's disease (HD), Parkinson's disease (PD), Alzheimer's disease (AD) and neurodegeneration with brain iron accumulation (NBIA), also referred to as Hallervorden-Spatz syndrome. These diseases, which are caused to varying degrees by known gene mutations, are characterized by progressive loss of structure or function of neurons, including neuronal death. HD is entirely attributable to expansion of a CAG triplet in exon 1 of the HTT gene, while NBIA is associated with mutations in about 10 genes, the most common being PANK2 (30-50% of cases). A smaller fraction of PD and AD cases are genetic in origin. Neurodegenerative diseases are also associated with a variety of protein misfolding abnormalities (e.g., aggregation of alpha-synuclein, hyperphosphorylation and aggregation of tau protein, and aggregation of beta amyloid protein), as well as misregulation of protein degradation pathways (e.g., the ubiquitin-proteasome pathway and autophagy-lysosome pathways), membrane damage, mitochondrial dysfunction, defects in axonal transport, or misregulation of programmed cell death pathways (e.g., apoptosis and autophagy).

Huntington's disease (HD) cells have very low levels of the enzyme cystathionine gamma-lyase (CSE), an important generator of cysteine from cystathionine. The defect occurs at the transcriptional level and may be an important mediator of neurodegeneration. Administration of cysteine to HD tissues and to an animal model of HD reverses oxidative stress and other abnormalities. There is also evidence for cysteine efficacy in other neurodegenerative diseases, including neurodegeneration with iron accumulation, Parkinson's disease, Alzheimer's disease, and neurodevelopmental disorders, e.g., Rett syndrome and other MECP-2 associated disorders. However, orally administered cysteine has low bioavailability and in large doses may be toxic.

Cysteamine crosses the blood brain barrier, can promote formation of cysteine in vivo (e.g. by thiol-disulfide exchange with cystine), and can provide a source of sulfur for cysteine biosynthesis. Cysteamine has exhibited beneficial effects in three different mouse models of HD. Four studies have shown beneficial effects in the R6/2 mouse model. The R6/2 HD mouse model contains a transgene expressing exon 1 of a mutant human HTT allele with a very long CAG triplet repeat. Beneficial affects of cysteamine include amelioration of weight loss and motor abnormalities, and prolongation of survival. One study has shown benefit in the R6/1 mouse model, which also contains an exon-1 transgene with a smaller expanded CAG repeat and a milder phenotype. Cysteamine has also been shown to be beneficial in the YAC128 mouse model of HD, which contains a full-length HTT gene with an expanded CAG repeat. The mechanism of action of cysteamine is uncertain.

In February 2014, Raptor Pharmaceutical Corp. announced results from a planned 18 month interim analysis of an ongoing 3-year Phase 2/3 clinical trial of RP103 (delayed-release cysteamine bitartrate) in Huntington's disease. A total of 96 patients with HD were randomized to treatment with RP103 or placebo. RP103 treated patients were dosed at 1200 mg cysteamine/day, approximately half the dose used for cystinosis. Eighty nine patients completed the initial 18 month phase. Analysis of all 96 patients enrolled in the trial showed a positive trend toward slower worsening of Total Motor Score (TMS) in patients treated with RP103, the primary endpoint of the study. TMS progression was 32% slower in patients treated with RP103 vs. those treated with placebo after 18 months treatment (4.51 vs. 6.68 respectively, p=0.19). In 66 patients not taking concurrent tetrabenazine, RP103 treatment resulted in a statistically significant delay in disease progression as measured by TMS when compared to the placebo group (2.84 points vs. 6.78 respectively, p=0.03).

For the treatment of neurodegenerative diseases or psychiatric diseases described herein, the cysteamine precursor is desirably selected from the following group of mixed disulfides: cysteamine+pantetheine, cysteamine+cysteine, cysteamine+N-acetylcysteine, cysteamine+N-acetylcysteine amide, cysteamine+N-acetylcysteine ethyl ester, cysteamine+3-mercaptopyruvate, cysteamine+γ-glutamylcysteine ethyl ester, pantetheine+cysteine, pantetheine+N-acetylcysteine, cysteamine+N-acetylcysteine amide, pantetheine+N-acetylcysteine ethyl ester, pantetheine+3-mercaptopyruvate, pantetheine+γ-glutamylcysteine ethyl ester, 2 cysteamines+dihydrolipoic acid, 2 pantetheines+dihydrolipoic acid, cysteamine+pantetheine+dihydrolipoic acid, cysteamine+AD4+dihydrolipoic acid, and cysteamine+N-acetylcysteine ethyl ester+dihydrolipoic acid. The treatment regimen optionally includes an enhancer described herein, such as a reducing agent, a pantetheinase inducer, or a PPAR agonist.

Liver Diseases

Non-alcoholic fatty liver disease (NAFLD) is the most common chronic liver disease in the United States and Europe and its incidence is increasing rapidly in the Asia-Pacific region. Estimates of NAFLD prevalence in the United States range from 23% to 33.6%. It has been estimated that up to 80% of patients with metabolic syndrome (approximately 47 million people in the United States) may also have NAFLD. In some patients NAFLD progresses to non-alcoholic steatohepatitis (NASH), a potentially lethal disease, and an increasing cause of liver failure, with an estimated prevalence of 2% to 5.7% in the U.S.

There is no FDA-approved treatment for NAFLD, NASH or alcoholic steatohepatitis (ASH). Clinical trials of a variety of agents including the anti-oxidant vitamin E, the hypoglycemic agent metformin and the PPAR gamma agonists pioglitazone and rosiglitazone have yielded disappointing results. Phase 2 clinical trials of the semi-synthetic bile acid derivative obeticholic acid, a farnesoid X receptor agonist, have been promising. Other experimental therapies targeting insulin resistance and are being tested.

In 2011, Dohil et al. (Aliment Pharmacol. Ther. 33:1036 (2011)) conducted a small, open-label 24 week pilot trial of enteric-coated cysteamine in 11 children with NAFLD. Cysteamine reduced serum levels of the liver enzymes ALT and AST (indices of hepatocyte damage) in 7 of 11 patients, an effect which persisted for six months after therapy ended. However, there was no effect on body mass index (BMI). This open-label Phase 2a clinical trial involved children with a biopsy-confirmed diagnosis of moderate to severe NAFLD and baseline ALT and AST levels at least twice the upper limit of normal. These patients received enteric-coated cysteamine twice daily for six months, followed by a six-month post-treatment monitoring period. Among all patients there was a mean 54% reduction in ALT (p=0.004), meeting the pre-defined primary endpoint of at least 50% ALT reduction from baseline. In addition, patients saw improvements in secondary endpoints including AST (41% avg reduction, p=0.02), cytokeratin 18 (45% avg reduction, p=0.026), and adiponectin (35% avg reduction, p=0.023). Serum transaminases were measured following drug withdrawal and the reductions in ALT and AST persisted during the 6 month post-treatment phase. Following this proof of concept study by Dohil et al., Raptor Pharmaceutical Corp. initiated a clinical trial in cooperation with the National Institute of Diabetes and Digestive and Kidney Diseases (NIDDK). The trial, called Cysteamine Bitartrate Delayed-Release for the Treatment of Non-alcoholic Fatty Liver Disease in Children (CyNCh), has enrolled 160 pediatric participants at ten U.S. centers in the NIDDK-sponsored NASH Clinical Research Network.

CyNCh is a multicenter, double-masked, randomized, placebo-controlled, phase IIb clinical trial of treatment with either delayed-release cysteamine (RP103) capsules (300 mg orally twice daily for patients<65 kg, 375 mg orally twice daily for patients>65-80 kg or 450 mg orally twice daily for patients>80 kg) or placebo for children with histologically-confirmed NAFLD. Cysteamine doses almost 3 times lower than those used to treat cystinosis were possible because first-pass metabolism of cysteamine in the liver removes about 40% of the cysteamine absorbed by the intestine, which is a hurdle for systemic therapy of cysteamine-sensitive diseases but an advantage in the treatment of liver diseases.

Other liver diseases that could benefit from cysteamine therapy include alcoholic steatohepatitis, and acute on chronic liver failure.

For the treatment of liver diseases described herein, the cysteamine precursor is desirably selected from the following group of mixed disulfides: cysteamine+pantetheine, cysteamine+cysteine, cysteamine+N-acetylcysteine, cysteamine+N-acetylcysteine ethyl ester, cysteamine+glutathione, cysteamine+glutathione-monoethyl ester, cysteamine+glutathione-diethyl ester, cysteamine+gamma-glutamyl-cysteine, cysteamine+γ-glutamylcysteine ethyl ester, cysteamine+cysteinylglycine, cysteamine+dihydrolipoic acid, pantetheine+cysteine, pantetheine+N-acetylcysteine, pantetheine+N-acetylcysteine ethyl ester, pantetheine+glutathione, pantetheine+glutathione-monoethyl ester, pantetheine+glutathione-diethyl ester, pantetheine+gamma-glutamyl-cysteine, pantetheine+γ-glutamylcysteine ethyl ester, pantetheine+cysteinylglycine, pantetheine+dihydrolipoic acid, 2 cysteamines+dihydrolipoic acid, 2 pantetheines+dihydrolipoic acid, 2 N-acetylcysteines+dihydrolipoic acid, NAC+cysteamine+dihydrolipoic acid, cysteamine+pantetheine+dihydrolipoic acid, N-acetylcysteamine+pantetheine+dihydrolipoic acid, and cysteamine+cysteine+dihydrolipoic acid. The treatment regimen optionally includes an enhancer described herein, such as a reducing agent, a pantetheinase inducer, or a PPAR agonist.

Malaria

In vitro and in vivo evidence for the effectiveness of cysteamine in malaria, both as a sole treatment and as a potentiator of artemisinin, have been described above. Cysteamine treatment could benefit patients with malaria and cerebral malaria.

Resistance to artemisinin is characterized by significantly delayed clearance of parasites following artemisinin treatment. Artemisinin derivatives have half-lives of the order of an hour, and therefore require at least daily dosing over several days. For example, the WHO-approved adult dose of co-artemether (artemether-lumefantrine) is 4 tablets at 0, 8, 24, 36, 48 and 60 hours (six doses). Due to its similar short half-life, cysteamine could be dosed followed the same schedule if using an immediate release formulation of a cysteamine precursor, or could be dosed every 12 hours for 3 days, at doses similar to the doses used for the treatment of patients with cystinosis, i.e. 2.5 g/day in adults.

Cystinosis

Cystinosis is a rare, autosomal recessive inherited lysosomal storage disease. It is the most frequent and potentially treatable cause of the inherited renal Fanconi syndrome. Untreated, kidney function rapidly deteriorates by the end of the first decade of life leading to end-stage renal disease which requires kidney transplantation. Two major milestones in cystinosis management, cystine-depleting therapy with cysteamine and renal allograft transplantation, have had a considerable impact on the prognosis for cystinosis patients. However, compliance with cysteamine therapy has been a major problem due to significant side effects and a strict 6-hourly dosing regimen when using the immediate release formulation of cysteamine bitartrate (Cystagon®). Recently, a new twice-daily delayed-release enteric-coated formula of cysteamine bitartrate (Procysbi®) has been approved by the FDA in the US and by the EMA in Europe, for treatment of cystinosis, and has been shown to be a safe and effective alternative to Cystagon®. The recommended maintenance dose of cysteamine (every 6 hours for the immediate-release formulation, Cystagon®, or twice per day for the delayed-release formulation, Procysbi®) is 1.3 grams per square meter of body surface area per day. The dose can be increased up to 1.95 grams/m2/day if the white blood cell cystine level remains higher than 1 nanomolar ½ cystine per milligram of WBC protein.

For the treatment of cystinosis diseases described herein, the cysteamine precursor is desirably selected from the following group of mixed disulfides: cysteamine+pantetheine, cysteamine+N-acetylcysteamine, cysteamine+allyl mercaptan, cysteamine+cysteine, cysteamine+3-mercaptopyruvate, N-acetylcysteamine+pantetheine, N-acetylcysteamine+N-acetylcysteamine, N-acetylcysteamine+allyl mercaptan, N-acetylcysteamine+cysteine, and N-acetylcysteamine+3-mercaptopyruvate. The treatment regimen optionally includes an enhancer described herein, such as a reducing agent, a pantetheinase inducer, or a PPAR agonist.

Inherited Mitochondrial Diseases

Cysteamine directly scavenges ROS including superoxide free radicles, aldehydes (toxic products of lipid peroxidation) and hydrogen peroxide. Cysteamine also contributes to the formation of other reducing thiols by disulfide bond reduction and by participating in thiol-disulfide exchange reactions, including reactions with cystine that yield cysteine and cysteine-cysteamine mixed disulfide. This reaction increases of the cellular cysteine pool. Cysteine is the rate limiting substrate in glutathione (GSH) biosynthesis. Glutathione is a tripeptide composed of the amino acids cysteine, glutamate and glycine.

Low GSH levels compromise mitochondrial function, which may aggravate inherited mitochondrial diseases. Salmi et al. (Scandinavian Journal of Clinical and Laboratory Investigation, 2012) studied a cohort of children with biochemically and/or genetically confirmed mitochondrial diseases and found altered plasma thiol levels and redox state, indicating an increase in oxidative stress and depletion of antioxidant supplies. The ability of cysteamine to increase cellular thiol levels, including cysteine, could potentially address the relative thiol deficiency in patients with mitochondrial diseases. The ability of cysteamine to directly scavenge ROS may counter the increased oxidative stress and improve the compromised mitochondria function in these diseases.

In 2014, Raptor Pharmaceuticals initiated an open label, dose-escalating phase 2 trial with its delayed-release cysteamine, RP103, administered up to 1.3 g/m2/day in two divided doses, every 12 hours, for up to 6 months in patients with in Leigh syndrome and other inherited mitochondrial diseases.

Exemplary inherited mitochondrial diseases include, but are not limited to, Friedreich's Ataxia, Leber's hereditary optic neuropathy, myoclonic epilepsy and ragged-red fibers, Mitochondrial encephalomyopathy, lactic acidosis, and stroke-like syndrome (MELAS), Kearn-Sayre syndrome, subacute necrotizing encephalopathy (Leigh's Syndrome), and mitochondrial cardiomyopathies and other syndromes due to multiple mitochondrial DNA deletions. Additional mitochondrial diseases include neurogenic muscle weakness, ataxia and retinitis pigmentosa (NARP), progressive external opthalmoplegia (PEO), and Complex I disease, Complex II disease, Complex III disease, Complex IV disease and Complex V disease, which relates to dysfunction of the OXPHOS complexes. And also, mutations in the POLG gene as well as some forms of autism.

For the treatment of mitochondrial diseases described herein, the cysteamine precursor is desirably selected from the following group of mixed disulfides: cysteamine+pantetheine, cysteamine+N-acetylcysteamine, cysteamine+3-mercaptopyruvate, cysteamine+dihydrolipoic acid, 2 cysteamines+dihydrolipoic acid, 2 pantetheines+dihydrolipoic acid, cysteamine+pantetheine+dihydrolipoic acid, cysteamine+N-acetylcysteamine+dihydrolipoic acid, and cysteamine+pantetheine+dihydrolipoic acid. The treatment regimen optionally includes an enhancer described herein, such as a reducing agent, a pantetheinase inducer, or a PPAR agonist.

Cystic Fibrosis and Other Chronic Respiratory Conditions

Cystic fibrosis (CF) is caused by loss-of-function mutations in the CFTR gene, which encodes a cAMP-regulated chloride channel expressed in a variety of epithelial cells. Defective CFTR function leads to major clinical manifestations including chronic lung inflammation with increased susceptibility to respiratory tract bacterial infections, pancreatic dysfunction and male infertility. A three base deletion mutation, AF508, accounts for about 70-90% of CF in Northern Europe and North America. AF508-CFTR can retain partial chloride channel activity if rescued at the plasma membrane by corrector molecules, but in this case AF508-CFTR is rapidly recycled from the plasma membrane and diverted to lysosomal degradation. Thus stabilizing AF508-CFTR at the plasma membrane remains a challenging task. Loss of functional CFTR induces reactive oxygen species (ROS)- and transglutaminase 2-mediated crosslinking of BECN1 and sequestration of phosphatidylinositol 3-kinase (PtdIns3K) class III within intracellular aggresomes, leading to lung inflammation. Cystamine can restore BECN1 function and autophagy, reduce SQSTM1 accumulation and blunt inflammation in human cells and in the airways of mouse models homozygous for the AF508-CFTR mutation. Moreover, administration of cystamine can rescue intracellular trafficking and stabilize a fully functional AF508-CFTR at the plasma membrane of epithelial cells, thus complementing the beneficial effects of CFTR corrector molecules. The effects of cystamine in rescuing autophagy and controlling inflammation extend well after drug washout, but are abrogated by CFTR depletion during withdrawal. Cysteamine (Lynovex® from Novabiotics®) demonstrated at least comparable mucolytic activity to currently available mucolytic agents. Cysteamine was bactericidal against *Pseudomonas aeruginosa* and other CF pathogens. Cysteamine activity was not sensitive to high ionic concentrations characteristic of the CF lung. Cysteamine prevented the formation of, and disrupted established *P. aeruginosa* biofilms. Cysteamine was synergistic with conventional CF antibiotics; reversing the antibiotic resistance of CF bacterial pathogens. An oral (gel capsule) form of Lynovex® has completed Phase IIa trials. Novabiotics is developing Lynovex for cystic fibrosis and also for COPD and other chronic respiratory conditions as a single treatment with both mucolytic and anti-microbial effects.

For the treatment of lung diseases described herein, the cysteamine precursor is desirably selected from the following group of mixed disulfides: cysteamine+pantetheine, cysteamine+N-acetylcysteamine, cysteamine+allyl mercaptan, cysteamine+cysteine, cysteamine+3-mercaptopyruvate, N-acetylcysteamine+pantetheine, N-acetylcysteamine+N-acetylcysteamine, N-acetylcysteamine+allyl mercaptan, N-acetylcysteamine+cysteine, and N-acetylcysteamine+3-mercaptopyruvate. The treatment regimen optionally includes an enhancer described herein, such as a reducing agent, a pantetheinase inducer, or a PPAR agonist.

Kidney Diseases

Cysteamine was effective in two mouse models of kidney fibrosis: ureteral stenosis and renal ischemia/reperfusion injury (Okamura et al., J. Am. Soc. Nephrol. 25:43 (2014)). These results suggest previously unrecognized antifibrotic actions of cysteamine via TGF-β-independent mechanisms, including oxidative stress reduction and attenuation of the myofibroblast response to kidney injury.

Fibrosis is also one of the main manifestations of genetic forms of glomerular disease, including focal segmental glomerulosclerosis, Alport's syndrome and thin base membrane disease.

For the treatment of kidney diseases described herein, the cysteamine precursor is desirably selected from the following group of mixed disulfides: cysteamine+pantetheine, cysteamine+N-acetylcysteamine, cysteamine+allyl mercaptan, cysteamine+cysteine, cysteamine+3-mercaptopyruvate, N-acetylcysteamine+pantetheine, N-acetylcysteamine+N-acetylcysteamine, N-acetylcysteamine+allyl mercaptan, N-acetylcysteamine+cysteine, and N-acetylcysteamine+3-mercaptopyruvate. The treatment regimen optionally includes an enhancer described herein, such as a reducing agent, a pantetheinase inducer, or a PPAR agonist.

Example 10 describes a rat pharmacokinetic study of a cysteamine precursor in which kidney levels of cysteamine following administration of a cysteamine precursor were far higher 10.5 hours after dose administration than have been reported after administration of cysteamine bitartrate (Dohil et al. Clin. Pharmacol. Drug Dev. 4:170 (2012)).

Hereditary Diseases Caused by Arginine to Cysteine Mutation

Certain hereditary disease can be treated using the methods and compositions of the invention. For example, disease causing mutations include DNA sequence changes that alter the codon for arginine to the codon for cysteine. A subset of such mutations occur in proteins which retain partial function, or which at a minimum are stable enough to be completely synthesized by ribosomes and transported to their normal destination (e.g. the plasma membrane, the mitochondria, the nucleus, etc.). Cysteamine can form a disulfide bond with the aberrant cysteine residue and, in doing so, mimic arginine to some extent, thereby restoring to some degree normal protein function (e.g. see Gahl et al. Am J Med Genet 20:409 (1985)). Thus any hereditary disease with an arginine to cysteamine change is a candidate for cysteamine precursor therapy. Such diseases include hemophilia A, due to arginine to cysteamine mutation in the factor VIII gene; pure autosomal dominant spastic paraplegia, due to arginine to cysteamine mutation in the CPT1C gene; spinocerebellar ataxia 35, due to arginine to cysteamine mutation in the TGM6 gene; and many other diseases.

The sustained levels of cysteamine possible with cysteamine precursors and enhancers better addresses the need for ongoing cysteaminylation of mutant proteins.

For the treatment of hereditary diseases caused by arginine to cysteine mutation described herein, the cysteamine precursor is desirably selected from the following group of mixed disulfides: cysteamine+pantetheine, cysteamine+N-acetylcysteamine, cysteamine+allyl mercaptan, cysteamine+cysteine, cysteamine+3-mercaptopyruvate, N-acetylcysteamine+pantetheine, N-acetylcysteamine+N-acetylcysteamine, N-acetylcysteamine+allyl mercaptan, N-acetylcysteamine+cysteine, and N-acetylcysteamine+3-mercaptopyruvate. The treatment regimen optionally includes an enhancer described herein, such as a reducing agent, a pantetheinase inducer, or a PPAR agonist.

Cardiovascular Diseases

Heart disease due to atherosclerosis associated with chronic hypercholesterolemia, and ischemic heart disease are treatable with cysteamine precursors.

For the treatment of cardiovascular diseases described herein, the cysteamine precursor is desirably selected from the following group of mixed disulfides: cysteamine+coenzyme A, N-acetylcysteamine+coenzyme A, pantetheine+coenzyme A, dephospho-coenzyme A+coenzyme A, coenzyme A+coenzyme A, cysteamine+pantetheine, cysteamine+N-acetylcysteamine, cysteamine+pantetheine, cysteamine+bucillamine, pantetheine+bucillamine, pantetheine+dihydrolipoic acid, coenzyme A+dihydrolipoic acid, 2 cysteamines+bucillamine, 2 cysteamines+dihydrolipoic acid, cysteamine+pantetheine+bucillamine, and cysteamine+pantetheine+dihydrolipoic acid. The treatment regimen optionally includes an enhancer described herein, such as a reducing agent, a pantetheinase inducer, or a PPAR agonist.

Neurodevelopmental Disorders

Neurodevelopmental disorders, including Rett syndrome and other MECP2 associated disorders are treatable with cysteamine precursors.

Other Diseases

Exposure of erythrocytes from sickle cell anemia patients to cysteamine led to a marked inhibition of sickling under hypoxic conditions, a decrease in mean corpuscular hemoglobin concentration, and a significant increase in oxygen affinity. The oxygen affinity of the cysteamine-treated erythrocytes was less dependent on their mean corpuscular hemoglobin concentration than that of untreated sickle cells.

Antineoplastic effects of cysteamine have been demonstrated in cancer cell lines and xenograft models (Fujisawa et al., e34437 (2012)). Notably, cysteamine prolonged survival of mice in a dose-dependent manner without toxicity. Matrix metalloproteinase activity was significantly decreased in animal xenografts and in cancer cell lines treated with cysteamine.

Long-term cysteamine therapy promotes adiponectin multimerization, suggesting that cysteamine may be therapeutic in conditions associated with insulin-resistance, oxidative stress, and depressed adiponectin levels as well as ischemic injury.

For the treatment of hematological diseases described herein, the cysteamine precursor is desirably selected from the following group of mixed disulfides: cysteamine+pantetheine, cysteamine+N-acetylcysteamine, cysteamine+N-acetylcysteine ethyl ester, cysteamine+N-acetylcysteine amide, N-acetylcysteamine+N-acetylcysteamine, and cysteamine+allyl mercaptan. The treatment regimen optionally includes an enhancer described herein, such as a reducing agent, a pantetheinase inducer, or a PPAR agonist.

For the treatment of infectious diseases described herein, the cysteamine precursor is desirably selected from the following group of mixed disulfides: cysteamine+pantetheine, cysteamine+N-acetylcysteamine, cysteamine+allyl mercaptan, cysteamine+cysteine, cysteamine+3-mercaptopyruvate, N-acetylcysteamine+pantetheine, N-acetylcysteamine+N-acetylcysteamine, N-acetylcysteamine+allyl mercaptan, N-acetylcysteamine+cysteine, and N-acetylcysteamine+3-mercaptopyruvate. The treatment regimen optionally includes an enhancer described herein, such as a reducing agent, a pantetheinase inducer, or a PPAR agonist.

Dosing Regimens

The present methods for modulating plasma cysteamine levels in the treatment of cysteamine sensitive disorders are carried out by administering one or more compositions containing one or more cysteamine precursors and optionally one or more enhancers of in vivo cysteamine generation and/or absorption for a time and in an amount sufficient to result in elevated plasma levels of cysteamine adequate to provide an effective treatment of a cysteamine sensitive disease or disorder. For example, while both gastroretentive and non-gastroretentive sustained release formulations can, by themselves, provide cysteamine precursor release over 3, 5, 8 or more hours, it may be desirable, in order to achieve more steady blood levels of cysteamine in the therapeutic concentration range for longer time periods, to co-administer either of those formulation types with one or more other compositions, such as an immediate release, delayed release or colon-targeted composition. Compostions that contain two types of formulation, referred to as mixed formulations, may also be administered.

The amount and frequency of administration of the compositions can vary depending on, for example, what is being administered (e.g. which cysteamine precursors, which enhancers, which types of formulation), the disease, the state of the patient, and the manner of administration. In therapeutic applications, compositions can be administered to a patient suffering from elevated WBC cystine levels (e.g., cystinosis) in an amount sufficient to decrease or least partially decrease the WBC cystine levels, preferably below recommended levels. The dosage is likely to depend on such variables as the type and extent of progression of the disease, the severity of the pain (e.g., acute, subacute, or chronic), the age, weight and general condition of the particular patient, the relative biological efficacy of the composition selected, inter-individual variation in cysteamine metabolism, formulation of the excipient, the route of administration, and the judgment of the attending clinician. Effective doses can be estimated from dose-response curves derived from in vitro or animal model test system. An effective dose is a dose that produces a desirable clinical outcome by, for example, in the case of cystinosis, decreasing WBC cystine levels, the case of NASH halting or reversing liver fibrosis, in the case of a neurodegenerative disease improving cognitive, motor or emotional function as measured by a clinically validated test.

The amount of a cysteamine precursor, or salt thereof per dose can vary. The upper end of the dose range for cysteamine bitartrate is 1.95 grams per square meter of body surface area per day (only counting the weight of the cysteamine), which amounts to about 3.7 grams/day of cysteamine base for an average adult. However, that amount of cysteamine is associated with significant side effects and in some cases discontinuation of therapy.

The molecular weight of cysteamine precursors varies widely, as does the fraction convertible to cysteamine in vivo. Several examples may serve to illustrate the variation. The molecular weight of cysteamine base is 77.15 g/mol. The molecular weight of the thiol pantetheine is 278.37 g/mol. Therefore a cysteamine-pantetheine disulfide has a molecular weight of approximately 353.52 (adjusting for two protons lost in the oxidation reaction) and is convertible in vivo to two cysteamines which together weigh 154.3. Thus about 43.6% of a cysteamine-pantetheine disulfide is convertible to cysteamine. Assuming 100% conversion of the cysteamine-pantetheine disulfide to cysteamine in vivo, and further assuming equivalent bioavailability, a maximum dose of cysteamine-pantetheine disulfide is in the range of 8.5 grams/day for a 70 kg adult, or about 0.12 grams/kg/day. The bioavailability of cysteamine precursors, when dosed to match the in vivo cysteamine generating and absorbing capacity of a patient, is expected to be moderately higher than that of cysteamine salts. In vivo conversion of cysteamine precursors to cysteamine is unlikely to be 100%, but very high rates of conversion can be achieved by calibration of dosing regimens to pharmacokinetic parameters, and by co-administration of appropriate enhancers of cysteamine precursor breakdown and absorption.

The disulfide pantethine has a molecular weight of 554.723 g/mol and, upon reduction and pantetheinase cleavage yields two molecules of cysteamine (i.e. 27.8% of pantethine will become cysteamine). Thus, making the same assumptions as above, a maximum dose of pantethine is in the range of 13 grams/day for a 70 kg adult, or about 0.19 grams/kg/day.

For a large cysteamine precursor like coenzyme A (MW 767.535 g/mol), that only yields one molecule of cysteamine, the fraction of a dose convertible to cysteamine is only about 10%, and consequently the maximum dose of coenzyme A could be up to 37 grams/day for a 70 kg adult, or about 0.5 grams/kg/day. For that reason coenzyme A is not preferred as a sole treatment for diseases that require high blood levels of cysteamine for good therapeutic effect, but may be combined with other cysteamine precursors that more efficiently deliver cysteamine.

The low end of the useful range of cysteamine precursor doses is not determined by side effects and tolerability limits, but entirely by efficacy, which may vary considerably from one disease to another. For example, because first pass metabolism by the liver (which clears about 40% of absorbed cysteamine from the blood) does not affect cysteamine delivery to the liver the range of effective doses for liver diseases is lower than for other diseases.

For example, a subject can receive from about 0.01 g/kg to about 0.5 g/kg of a cysteamine precursor. Generally, the cysteamine and pantetheine compound is administered in an amount such that the peak plasma concentration ranges from 1 μM-45 μM. Exemplary dosage amounts can fall between about 0.01 to about 0.2 g/kg; about 0.05 to about 0.2 g/kg; about 0.1 to about 0.2 g/kg; about 0.15 to about 0.2 g/kg; about 0.05 g/kg to about 0.25 g/kg; about 0.1 g/kg to about 0.25 g/kg; about 0.15 g/kg to about 0.25 g/kg; about 0.1 g/kg to about 0.50 g/kg; about 0.2 to about 0.5 g/kg; about 0.3 to about 0.5 g/kg; or about 0.35 to about 0.5 g/kg. Exemplary dosages can be about 0.005 g/kg, about 0.01 g/kg, about 0.015 g/kg, about 0.02 g/kg, about 0.03 g/kg, about 0.05 g/kg, about 0.1 g/kg, about 0.15 g/kg, about 0.2 g/kg or about 0.5 g/kg. Exemplary peak plasma concentrations can range from 5-20 μM, 5-15 μM, 5-10 μM, 10-20 μM, 10-15 μM, or 15-20 μM. The peak plasma concentrations may be maintained for 2-14 hours, 4-14 hours, 6-14 hours, 6-12 hours, or 6-10 hours.

The frequency of treatment may also vary. The subject can be treated one or more times per day (e.g., once, twice, or thrice) or every so-many hours (e.g., about every 8, 12, or 24 hours). Preferably, the pharmaceutical composition is administered 1 or 2 times per 24 hours. The time course of treatment may be of varying duration, e.g., for two, three, four, five, six, seven, eight, nine, ten, or more days, two weeks, 1 month, 2 months, 4 months, 6 months, 8 months, 10 months, more than one year or for life. For example, the treatment can be twice a day for three days, twice a day for seven days, twice a day for ten days. Treatment cycles can be repeated at intervals, for example weekly, bimonthly or monthly, which are separated by periods in which no treatment is given. The treatment can be a single treatment or can last as long as the life span of the subject (e.g., many years).

Combination Therapies

In vitro data suggests that cysteamine is likely to be metabolized by multiple CYP enzymes, including CYP1A2, CYP2B6, CYP2C8, CYP2C9, CYP2C19, CYP2D6, and CYP2E1, but not by CYP2A6 or CYP3A4. Cysteamine is not an inhibitor of CYP1A2, CYP2A6, CYP2B6, CYP2C8, CYP2C9, CYP2C19, CYP2D6, CYP2E1 and CYP3A4 in vitro. In vitro, cysteamine is a substrate of P-gp and OCT2, but not a substrate of BCRP, OATP1B1, OATP1B3, OAT1, OAT3 and OCT1. Cysteamine is not an inhibitor of OAT1, OAT3 and OCT2.

There is no known interaction of cysteamine with other compounds and therefore cysteamine precursors could be used with several other drugs used for the treatment of the multiple indications listed above. For example: The composition of the invention can be administered in combination with one or more anti-neurodegenerative drugs such as but not limited to the acetylcholinesterase inhibitors donepezil (Aricept®), rivastigmine (Exelon®), or galantamine (Razadyne®) to treat mild to moderate Alzheimer's disease; Memantine (Namenda®) to treat mild to severe Alzheimer's; levodopa combined with carbidopa (e.g. Parcopa®, Sinemet®) to treat Parkinson's disease; also dopamine agonists including pramipexole (Mirapex®), ropinirole (Requip®) and rotigotine (given as a patch, Neupro®), short-acting injectable dopamine agonists, e.g. apomorphine (Apokyn®) used for symptomatic relief, MAO-B inhibitors, including selegiline (Eldepryl®, Zelapar®) and rasagiline (Azilect®), catechol O-methyltransferase (COMT) inhibitors, entacapone (Comtan®), Anticholinergics (Cogentin®), amantadine, sedatives, antidepressants, and other drugs to manage Parkinson's disease and Alzheimer's disease symptoms including behavioral problems associated with those disorders; tetrabenazine (Xenazine®) and other, non-approved, anti-choreic treatments such as olanzapine, aripiprazole, risperidone or tiapride for Huntington's disease.

There is no FDA-approved treatment for mitochondrial diseases but pharmacologically active agents such as vitamins, micronutrients and coenzyme Q10 have been tested. A quinone, EPI-743, initially designed to interact with the electron transport chain, might work through increasing the level of glutathione and is in clinical trials for mitochondrial diseases.

No definite treatment exists for Alport's syndrome, however research indicates that angiotensin-converting enzyme (ACE) inhibitors can reduce proteinuria and the progression of renal disease.

Artemisinins are among the most important anti-malaria drugs due to their efficacy and the still small number of resistant strains. Artemisinins are not recommended as monotherapy to reduce the emergence of resistant strains, however this has already occurred in some areas. Chemically artemesinin is a sesquiterpene lactone containing an unusual peroxide bridge, believed to be important for its anti-malarial activity. Semisynthetic derivatives of artemisinin have been developed, including artesunate (water-soluble: for oral, rectal, intramuscular, or intravenous use), artemether (lipid-soluble: for oral, rectal or intramuscular use), dihydroartemisinin, artelinic acid and artemotil. Other analogs have also been synthesized (e.g. Posner et al., J. Med. Chem. 42:300 (1999)).

Drugs used to treat metabolic syndrome are tailored to target the specific components of the metabolic syndrome that are present in a patient. Cholesterol lowering agents, including statins and fibrates, are useful in some patients. Blood pressure medications of various classes can also be used. Drugs used to treat type 2 diabetes include metformin.

Cysteamine precursors may be combined with any of the above agents.

Biomarkers

The treatment methods of the invention can include following one or more biomarkers as a guide to selecting a dosing regimen or patient selection. Biomarkers can be measured as follows:

Plasma cysteamine pharmacokinetics, based on a 2-compartment model, to determine absorption and elimination half-lives, and the "flip-flop" pharmacokinetic profile characteristic of a drug with a rate of intra-intestinal production and absorption slower than the rate of elimination.

Cystinosis: pre-dose white blood cell (WBC) cystine level lower than 1 nmol ½ cystine/mg WBC protein, providing that the treatment is well tolerated. Patients can still benefit from treatment if pre-dose WBC cystine level is lower than 2 nmol ½ cystine/mg protein.

Mitochondrial diseases: Exemplary mitochondrial activity markers include, but are not limited to, free thiol levels, glutathione (GSH), reduced glutathione (GSSH), total glutathione, advanced oxidation protein products (AOPP), ferric reducing antioxidant power (FRAP), lactic acid, pyruvic acid, lactate/pyruvate ratios, phosphocreatine, NADH (NADH+H+) or NADPH(NADPH+H+), NAD or NADP levels, ATP, anaerobic threshold, reduced coenzyme Q, oxidized coenzyme Q; total coenzyme Q, oxidized cytochrome C, reduced cytochrome C, oxidized cytochrome C/reduced cytochrome C ratio, acetoacetate, β-hydroxy butyrate, acetoacetate/β-hydroxy butyrate ratio, 8-hydroxy-2'-deoxyguanosine (8-OHdG), levels of reactive oxygen species, levels of oxygen consumption (VO2), levels of carbon dioxide output (VCO2), and respiratory quotient (VCO2/VO2).

Neurodegenerative diseases: Cysteamine activity in neurodegenerative disorders could potentially be linked to activation of the NFkB pathway, necessary for synaptic plasticity in the CNS; to upregulation of survivin (BIRC5) and Bcl-2-like protein 12 (BCL2L12), both well characterized anti-apoptotic proteins; to increased expression of heat shock protein (HSP40, HSP90), mitigating pathologies involving protein misfolding, which would benefit neurodegenerative disorders involving protein oligomerization, including HD, AD and PD; to increased expression and secretion of BDNF, further supporting neuronal survival and growth; to inhibition of transglutaminase and caspase; or simply to increased free cysteine levels in the brain that might significantly impact HD.

Fibrotic diseases: It is contemplated that administration of the product increases the systemic level of cysteamine, blocking signaling through the TGF-β pathway, inhibiting myofibroblast activation and proliferation, inhibiting expression of a wide variety of matrix components and upregulating MMP-1 and MMP-3.

Parasitic infection: It is contemplated that administration of the product increases the systemic level of cysteamine that would have a synergistic effect with artemisinin and derivatives for the treatment of malaria and cerebral malaria.

For all indications, adverse events will be measured using appropriate criteria. Adverse events include skin rash, skin lesions, seizure, lethargy, somnolence, depression, encephalopathy, gastrointestinal ulceration and/or bleeding, nausea, vomiting, loss of appetite (anorexia), diarrhea, fever, and abdominal pain. The severity of AEs is categorized using the Common Terminology Criteria for Adverse Events (CTCAE), Version 3.0 [Cancer Therapy Evaluation Program, 2003] or otherwise as follows: MILD (Grade 1): experience is minor and does not cause significant discomfort to subject or change in activities of daily living (ADL); subject is aware of symptoms but symptoms are easily tolerated; MODERATE (Grade 2): experience is an inconvenience or concern to the subject and causes interference with ADL, but the subject is able to continue with ADL; SEVERE (Grade 3): experience significantly interferes with ADL and the subject is incapacitated and/or unable to continue with ADL; LIFE THREATENING (Grade 4): experience that, in the view of the Investigator, places the subject at immediate risk of death from the event as it occurred (i.e., it does not include an event that had it occurred in a more severe form, might have caused death). By the CTCAE criteria defined above, the Grade 5 category is death Kits Any of the pharmaceutical compositions described herein can be used together with a set of instructions, i.e., to form a kit. The kit may include instructions for use of the pharmaceutical compositions as a therapy as described herein. For example, the instructions may provide dosing and therapeutic regimes for use of the compounds of the invention for modulating cysteamine concentration in plasma in the treatment of cysteamine sensitive disorders.

The formulated agents can be packaged together as a kit. Non-limiting examples include kits that contain, e.g., two pills, a pill and a powder, a suppository and a pill, a tablet, etc. Additionally, the unit dose kit can contain instructions for preparation and administration of the compositions. The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

EXAMPLES

The following examples are put forth so as to provide those of ordinary skill in the art with a complete disclosure and description of how the methods and systems claimed herein are performed and evaluated, and are intended to be purely exemplary of the invention and are not intended to limit the scope of what the inventors regard as their invention.

Example 1. Efficient Synthesis of Mixed Disulfides

Versatile methods for efficient synthesis of mixed disulfides have been described by several research groups (see reviews by Witt et al. Langmuir 23:2318 (2007); Musiejuk et al. Org. Prep. and Proc. 47.2:95 (2015)), including methods specific to cysteine and cysteine analogs (e.g., Szymelfejnik et al. Synthesis 22:3528 (2007); Gormer et al. J. Org. Chem. 75.5:1811 (2010)). Recent improvements, have been reported, for example based on the use of 2,3-dichloro-5,6-dicyanobenzoquinone (DDQ) to facilitate thiol-disulfide exchange (Musiejuk et al. RSC Advances 5.40:31347 (2015)).

These methods allow for preferential synthesis of the mixed disulfide (vs. the two homodimeric disulfides) when combining two different thiols. In the present example the thiols cysteamine and pantetheine are coupled using the procedure described by Antoniow et al., Synthesis 3:363 (2007). Other pairs of thiols can also be selectively coupled using variants of this procedure.

The reagents for this procedure are: (i) bis(5,5-dimethyl-2-thiono-1,3,2-dioxaphosphorinanyl)disulfide (referred to as "dithiophosphoric acid reagent" for short), (ii) bromine, (iii) cysteamine, (iv) dichloromethane and (v) pantetheine. All reagents are pharmaceutical grade.

- Step 1. Make a 7 millimolar solution of dithiophosphoric acid reagent in dry (anhydrous) dichloromethane at −5° C. under a nitrogen atmosphere (e.g. add 27.6 grams of disulfide reagent to 1 liter of dichloromethane).
- Step 2. Add bromine to the above solution to a final concentration of 6 millimolar, at −5° C. under a nitrogen atmosphere.
- Step 3. Make an 11 millimolar solution of pantetheine in dry dichloromethane.
- Step 4. Thirty minutes after completing step 2 add a volume of the pantetheine solution (from step 3) that is 5 percent of the volume of the solution made in step 2 (e.g. add 50 mls. of pantetheine solution to 1 liter of the step 2 solution). Stir at room temperature for 30 minutes.
- Step 5. Wash the reaction product with deionized water (500 milliliters), then dry over anhydrous MgSO4, filter and evaporate under vacuum.
- Step 6. Purify the residue by column chromatography (SiO2; CH2Cl2-hexane, 1:1) to yield pure disulfide of disulfide reagent-pantetheine (DR-P).
- Step 7. To a 0.5 millimolar solution of DR-P suspended in dichloromethane add cysteamine (0.5 millimolar, in dry dichloromethane) and triethanolamine (2 millimolar) in a ratio of 6:4:2 (DR-P:cysteamine:triethanolamine) and stir at room temperature for 15 minutes.
- Step 8. To the step 7 reaction volume add (i) five volumes of dichloromethane (ii) five volumes of distilled water and (iii) five volumes of either: (a) a saturated aqueous solution of $NaHCO_3$ or (b) 1 M HCl.
- Step 9. Dry the organic layer from step 8 over anhydrous MgSO4, filter and evaporated under vacuum
- Step 10. Suspend the residue from step 9 and purify by column chromatography on a silica gel.

Details on the above protocol and references to numerous other protocols for selective disulfide synthesis can be found in Musiejuk, M. and D. Witt. Organic Preparations and Procedures International 47:95 (2015).

Example 2. Selective Synthesis of Mixed Disulfides Containing Cysteine or Cysteine Analogs Among the thiols useful for producing mixed disulfide cysteamine precursors are cysteine, cysteine ethyl ester, cysteine methyl ester, N-acetylcysteine, N-acetylcysteine ethyl ester, N-acetylcysteine amide and homocysteine, as well as cysteine containing compounds including cysteinylglycine, gamma glutamylcysteine, gamma glutamylcysteine ethyl ester, as well as glutathione (which is a tripeptide of glycine, L-cysteine, and L-glutamate, with L-glutamate having an isopeptide bond with the amino moiety of L-cysteine) and glutathione derivatives.

A useful protocol for coupling the foregoing and other cysteine derivatives or cysteine containing compounds to cysteamine, N-acetylcysteamine, pantetheine, 4-phosphopantetheine, dephospho-coenzyme A, coenzyme A or suitable analogs or derivatives of those compounds is described in Szymelfejnik et al., Synthesis 22:3528 (2007).

This method exploits the selective reactivity of 5,5-dimethyl-2-thioxo-1,3,2-dioxaphosphorinan-2-yldisulfanyl derivatives toward cysteine derivatives to produce almost exclusively unsymmetrical disulfides. For example, a variety of asymmetric disulfides were synthesized with N-acetylcysteine and cysteine ethyl ester in yields of 93% and 98% yield, respectively (Szymelfejnik et al. Synthesis 2007).

In the present example pantetheine is coupled to cysteine ethyl ester. (See Disulfide Table 1B in FIG. 18; disulfide cysteamine precursor "2+13" is pantetheine disulfide bonded to cysteine ethyl ester.) The first step of the procedure is synthesis of (5,5-Dimethyl-2-thioxo-1,3,2-dioxaphosphorinan-2-yl)disulfanyl bromide, which is then coupled to pantetheine in step 2. Starting in step 5 the pantetheine is disulfide bonded to cysteine ethyl ester, taking advantage of the excellent leaving group properties of the dithiophosphate anion.

Step 1. To a solution of 5,5-dimethyl-2-thioxo-1,3,2-dioxaphosphorinan-2-yl)disulfide (e.g. 2.76 grams; 7.0 millimoles) in anhydrous dichloromethane (100 mls) add, at −30° C. and under nitrogen gas, bromide (0.96 grams; 6.0 millimoles). Allow reaction to proceed for 15 minutes.

Step 2. Add to the above a solution of pantetheine (3.062 grams, 11 millimoles) in anhydrous dichloromethane (5 mls). Stir the mixture at room temperature for 30 minutes.

Step 3. Wash the mixture with distilled deionized water (50 mls), dry using anhydrous MgSO4, then filter, and evaporate under vacuum.

Step 4. Purify the residue by column chromatography (silica gel, using a 1:1 dichlormethane:hexane mixture) to yield (5,5-Dimethyl-2-thioxo-1,3,2-dioxaphosphorinan-2-yl)disulfanyl-pantetheine (referred to in subsequent steps as Disulfide 1).

Step 5. To a solution of Disulfide 1 (0.5 millimoles) in dichloromethane (6 mls), add a solution of cysteine ethyl ester hydrochloride (0.5 millimoles) and triethylamine (0.28 mls, 2.0 millimoles) in dichlormethane (4 mls). Stir for 15 min at room temperature.

Step 7. Dilute the mixture with dichloromethane (50 mls), then wash with either: (i) 1 M KHSO4 (25 mls) or (ii) 0.25 M NaOH (25 mls).

Step 8. Dry using anhydrous MgSO4, filter, and evaporate under vacuum.

Step 8. Purify the residue by column chromatography (silica gel, using a 25:1 mixture of dicholormethane:methanol, or recrystallize in chloroform.

This small scale synthesis can be adjusted to find optimal synthesis conditions (e.g. yielding greater than 90%, or greater than 95% mixed disulfide. Subsequently the reaction can be scaled up to produce pharmacological quantities of the disulfide. Other cysteine analogs can be coupled to cysteamine, N-acetylcysteamine, pantetheine, 4-phosphopantetheine, dephospho-coenzyme A, coenzyme A or suitable analogs or derivatives using variants of this procedure.

For additional details consult: Szymelfejnik et al., Synthesis 22:3528 (2007).

Example 5. Co-Formulation of Compound 1 and Compound 3

Seven hundred (700) parts by weight compound 1 (pantetheine-cysteamine dihydrochloride), two hundred (200) parts by weight compound 3 (n-acetylcysteamine-n-acetylcysteamine dihydrochloride), six hundred and forty (640) parts by weight distilled water, and 2,000 parts by weight food grade microcrystalline cellulose are thoroughly blended at room temperature. The resulting powdery mixture is used for filling standard, two-piece hard gelatin capsules with 800 mg per capsule.

Example 6. Co-Formulation of Compound 2 and Compound 3 and Cystamine

Six hundred and fifty (650) parts by weight compound 2 (pantetheine-n-acetylcysteamine dihydrochloride), six hundred and fifty (650) parts by weight compound 3 (n-acetylcysteamine-n-acetylcysteamine dihydrochloride), two hundred (200) parts by weight cystamine, and one thousand and ninety (1090) parts by weight distilled water and two thousand (2000) parts by weight food-grade microcrystalline cellulose are thoroughly blended at room temperature. The resulting powdery mixture is used to fill paper sachets, with 3,000 milligrams per sachet.

Example 7. Gastroretentive Formulation of Compound 3

An exemplary gastroretentive formulation of the invention is Acuform® (Depomed), a polymer-based technology designed to optimize drug delivery. Acuform allows for targeted, controlled delivery of a pharmaceutical composition of compound 3 to the upper gastrointestinal (GI) tract through use of unique swelling polymers that allow a tablet of the composition to be retained in the stomach for approximately five to ten hours. During this time, the tablet's active component, compound 3, is steadily delivered to the upper GI tract at the desired rate and time. This gradual, sustained release allows for more of the drug to be absorbed in the upper GI tract, offering the potential for greater treatment efficacy and increased treatment tolerability with the convenience of once- or twice-daily dosing.

Example 8. Therapy of Nephropathic Cystinosis

Dose formulations and treatment regimens for three patients with cystinosis are described, to illustrate both demographic variability in the patient population and how inter-individual biochemical variation in drug absorption, metabolism and response can be overcome by exploiting the drug and dosage form flexibility provided by the invention. These examples illustrate the principles of cysteamine precursor selection, dosage form selection and dose regimen individualization.

Patient 1: an 18 month baby newly diagnosed with cystinosis after presentation with failure to thrive and excessive urination due to renal Fanconi syndrome. Solid medication is not acceptable in this patient. A solid medication, of the sort currently available, could in principle be crushed and mixed with food, however the actual dose would then depend on a variety of poorly controlled variables including (i) the amount of drug-food mixture ingested, (ii) the homogeneity of the mixture, if not all consumed (iii) possible drug-food interactions and (iv) conditions used to store and prepare the food (e.g. heating), particularly if unconsumed drug-food mixture is saved for a future meal to avoid wasting money on unconsumed drug. A further complication is that 6 hour dosing intervals (as required with Cystagon®, the instant release formulation of cysteamine) do not conform to the baby's mealtimes or the parents sleep schedules.

A preferable dosage form would be completely consumed, even when it is not the babies meal time; would contain a homogeneous concentration of drug; and would be sufficiently dilute that small amounts of non-consumed or regurgitated drug would only have a small effect on the total dose ingested. Further, compliance with prescribed therapy would be improved (in this case compliance by the baby's parents) if the dosing interval could be extended to 12 hours rather than 6 hours.

The dosage form selected for this 14 kg baby is compound 3, formulated as delayed release microparticles in a sweetened drinkable syrup at a concentration of 50 mg per milliliter of syrup.

Disease control is monitored via periodic measurement of white blood cell cystine levels. The therapeutic target, as for all cystinosis patients, is to suppress white blood cell (WBC) cystine to less than 1 nanomole of ½ cystine per mg of WBC protein. If the first cystine measurement, typically performed at 4 to 6 weeks after initiation of therapy, reveals inadequate cystine suppression the dose may be increased to 1000 mg/day in two divided doses. If this higher dose is still not effective in controlling WBC cystine levels the dose can be further increased in increments of 150 mg/day. (Since high doses of the cysteamine-pantetheine disulfide do not generate the high Cmax associated with cysteamine bitartrate formulations there is considerable scope to increase the dose further, if necessary.) If adequate suppression of WBC cystine is not achieved at 1,500 mg/day the dose can be increased further, while monitoring for side effects, or a second formulation of cysteamine-pantetheine can be added to provide increased plasma cysteamine levels late in the 12 hour dosing period. For example a sustained-release liquid microparticle formulation designed to provide cysteamine mainly during the 6-12 hour interval following ingestion can be mixed with the original syrup in a ratio determined empirically by measuring plasma cysteamine levels or preferably WBC cystine levels.

The liquid formulation is compatible with rapid administration at any time, including with meals or between meals (whether breast milk, formula milk or baby food). The 9-10 ml dose volume is a trivial amount for an 18 month to consume, but sufficient that failure to consume a small amount (e.g. due to leakage from the mouth or a burp) will not affect the total dose much. The sweetener enhances the appeal of the medication.

The microparticles are in the size range 50-500 micrometers, and preferably between 100-400 micrometers, hence able to remain suspended in liquid for a prolonged period, particularly in the presence of a suspending agent (e.g. 3% low molecular weight carboxymethylcellulose and 0.25% TWEEN 20). Batches of separately produced particles within that size range are mixed in the final product to broaden the duration of drug release (e.g. separate batches of 75, 150 and 450 micrometer particles are mixed in a 1:2:1 ratio). Particle sizes may be determined using sieve analysis through a sieve shaker having USP standard wire mesh sieves conforming to ASTM specifications.

The particles consist of an inner core of drug admixed homogeneously with one or more matrix excipients using a wet kneading process, and surrounded by at least three coatings. The core excipient is microcrystalline cellulose, starch, polyvinylpyrrolidone, polyvinylpyrrolidone-vinyl acetate copolymer, or any other excipient compatible with the wet kneading process. The drug loading (fraction of drug in the final product, by mass) is between 50-90 percent.

The first coating helps fix the size of the particles and serves as a diffusion membrane, enabling regulated drug release; it consists of a three part mixture of (i) a cellulose derivative (e.g. hydroxypropyl cellulose phthalate, ethylcellulose, carboxylmethyl cellulose acetate, carboxylmethylcellulose acetate butyrate), or copolymers of esters of methacrylic and acrylic acid, or methyl methacrylates, (ii) a lipid excipient (e.g. hydrogenated cotton soy oil or castor oil), and (iii) a suitable plasticizing agent (e.g. diethyl phthalate or mono glycerol acetate).

The second, third, and any additional coatings alternate between hydrophilic and lipophilic layers with an outermost hydrophilic layer. The outer hydrophilic layer provides an enteric coating formed from a pH sensitive excipient that is resistant to dissolution at acidic pH but susceptible to dissolution at neutral or near-neutral pH (e.g. pH over 6), such as dimethylaminoethyl methacrylates, methacrylic acid, and methacrylic acid esters in varying ratios, sometimes referred to collectively as poly(meth)acrylates or methacrylic acid/ethyl acrylate copolymers, optionally blended with hydroxypropylmethyl cellulose. Commercial versions of enteric coatings made with these excipients are marketed under the brand names Acryl-EZE, Acryl-EZE MP (Colorcon, Inc.), Eastacryl 30D (Eastman Chemical Co.), various Eudragit products such as Eudragit L 100 (Evonik Industries); Kollicoat MAE 30 D and Kollicoat MAE 30 DP (BASF Chemicals).

Lipophilic coating(s) may include fatty acids, carnauba wax, beeswax and the like.

The particles can be manufactured in separate batches with different numbers of coatings, different coating thicknesses or different coating compositions in the different batches, to achieve an extended drug release profile lasting at least six hours and preferably eight or more hours.

The medication can be provided as an aqueous suspension of the microparticles with sweetening agents and suspending agents, or it may be provided as a dry mixture designed for reconstitution at the time of use. In either event the liquid formulation has rheological properties that facilitate prolonged suspension of the microparticles.

Controlled release microparticles formulated for liquid delivery are disclosed in U.S. Pat. No. 5,405,619, which encompasses many of the elements described above, while providing additional useful excipients and details about formulation and manufacturing methods.

Patient 2: A ten year old, 35 kg boy with cystinosis is treated with Cystagon® for seven years. His current dose is 700 mg four times per day (2.8 grams per day), which is unusually high for a 35 kg patient. The dose amounts to six pills (four 150 mg and two 50 mg tablets) every six hours, or 24 pills per day. The young patient hates being woken at midnight and at 6 AM to take his medication, hates swallowing the pills, which are huge (size 0), hates the body odor and bad breath Cystagon® often causes (his friends notice it and tease him). He has developed a variety of strategies for skipping doses or, when that is not possible, lessening cysteamine side effects. He has learned, for example, that he can avoid some side effects by ingesting his medication with or shortly after a large meal, less cysteamine being absorbed with food, especially proteins or fat. He is able to accomplish this at school whenever the school nurse doesn't remain to watch him swallow all his pills before starting lunch, which he can generally arrange by taking a long time to swallow each pill. As a result of these avoidance measures his WBC cystine level is typically over 2.5 nanomoles ½ cystine/mg of protein. To address the inadequate metabolic control his doctor has increased the boy's cysteamine dose to its present high level, which would be supra-therapeutic if it is actually ingested as prescribed. As a result of this excessive dose the boy is more likely to experience side effects on those occasions when he actually ingests a full dose on an empty stomach, as prescribed.

A preferable dosage form for this patient would be one that eliminates the high peak cysteamine blood levels that follow drug ingestion, which are the proximate cause of most of the side effects he experiences; would eliminate the need for midnight and 6 AM awakenings, which are disruptive for the patient and his parents; would reduce the burden of swallowing six pills every six hours; would eliminate the need for dosing at school, with all the associated drama; and, by encouraging better compliance, would allow the high dose to be reduced while achieving better disease control.

The dosage forms initially selected for this patient are compound 1 administered at a high dose (e.g., 50 to 150 mg/kg) and formulated for immediate release (IR) followed by ascorbic acid administered 3+ hours after the administration of compound 1. Both compound 1 and the ascorbic acid can be provided as microparticles in a powdered form packaged in color coded sachets of various sizes which can be opened and combined with food, or a beverage, in the required amount. The powders can be mixed with milk and sugary cereal (the patient's preferred breakfast), and with most other meals, including fat and protein-rich meals.

The dosing regimen is able to provide elevated plasma cysteamine levels across an 8 hour dosing interval. The ratio of the two powders and timing of administration can easily be adjusted to optimize the cysteamine time-concentration profile in individual patients.

This powdered formulation of compound 1 can utilize an ion exchange resin core with a variety of optional coatings to provide immediate, delayed or sustained release. The resulting powder can be added to food directly, or after suspension in water or other liquids.

The immediate release powder consists of drug admixed with an uncoated ion exchange resin such as sodium polystyrene sulfonate (e.g. Amberlite® IRP 69 brand of resin, sold by Rohm and Haas).

The synthetic steps are:

Step 1. Dissolve cysteamine-pantetheine disulfide in distilled water.

Step 2. Add Amberlite® IRP 69 gradually to the Step 1 solution and stir for one hour, during which drug resin complexes are formed.

Step 3. Remove water by filtration, and the rinse the drug-resin mixture twice with distilled water to remove any displace salt ions.

Step 4. Dry the drug-resin mixture until the moisture content is 3%-7%, then pass through a CO-MIL device (Quadro Engineering Corp.) fitted with a standard 40 mesh screen, which restricts passage of granules with a particulate size over about 410 micrometers (i.e., the granules passing through the mesh are smaller than about 410 micrometers).

Patient 3. A 22 year old cystinosis patient, post kidney transplant, and suffering from diabetes, hypothyroidism and swallowing abnormalities is treated with over a dozen medications, many administered several times per day. Her cystinosis is treated with Procysbi®, 2,400 mg/day in two divided doses, (8 size-0 150 mg capsules per dose). However she frequently experienced severe stomach pain after Procysbi® ingestion, as well as nausea and vomiting, and these gastrointestinal side effects often preventer her from taking her other medications on schedule, or caused other medications to be vomited. This is particularly a concern with respect to her immunosuppressive regimen, without which she is at risk of losing her transplanted kidney.

Control of WBC cystine is barely adequate, ranging from 1 to 1.45 nanomoles of ½ cystine per mg of protein on different visits. In an effort to discover the cause of the gastrointestinal side effects her doctor measures her plasma cysteamine level one hour after ingestion and finds it is 78 micromolar. That high level could certainly account for her gastrointestinal symptoms, but her doctor is disinclined to reduce her Procysbi® dose in view of the marginal cystine control.

A preferable dosage form for this patient would eliminate, or at least lessen the gastrointestinal side effects, which are likely caused by high peak cysteamine blood levels, while also reducing the number of pills, which, together with the patient's other medications, represent a significant physical and psychological burden.

The dosage form selected for this patient is a combination of compound 1 administered at a high dose (e.g., 50 to 150 mg/kg) administered concurrently with a low dose of cystamine (e.g., 10 to 40 mg/kg).

Example 9. Therapy of Non-Alcoholic Steatohepatitis (NASH)

An overweight 50 year old male non-drinker with impaired glucose tolerance, gastroesophageal reflux disease (GERD) and a body mass index (BMI) of 36 is noted to have elevated liver enzymes on routine examination; both aspartate transaminase (AST) and alanine transaminase (ALT) are over four times the upper limit of the normal range. The finding of significantly elevated liver enzymes is suggestive of liver cell damage, and led to a diagnostic workup for liver disease. Tests for liver cancer and viral hepatitis are negative, and other potential infectious and toxicological causes of elevated liver enzymes are excluded, precipitating a liver biopsy. The biopsy reveals steatosis, hepatocyte ballooning, inflammation and significant fibrosis. These findings, in the context of the clinical picture, led to a diagnosis of non-alcoholic steatohepatitis (NASH).

The patient is instructed to change his diet and to start a program of moderate exercise. Six months of diet and lifestyle counseling failed to bring about weight loss, improvement in glucose tolerance or reduction in ALT or AST levels, prompting initiation of pharmacotherapy. The patient is treated with compound 2, formulated as an in situ gelling liquid. The target dose is 20 mg cysteamine free base per kg of body weight and the starting dose is one quarter of that amount, gradually increased over four to six weeks to the target dose, while adjusting for any side effects (i.e. slower dose ramping or a lower final dose in the event of significant side effects).

The reducing agents vitamin C and vitamin E are administered in capsule form, formulated for delayed release in the proximal small intestine, two to four hours after each dose of compound 2, at the patients convenience (e.g. before lunch and before going to bed), to enhance disulfide bond reduction in the gastrointestinal tract (and hence maximize conversion of cysteamine-N-acetylcysteine to its two component thiols), and as complementary therapeutic agents. The daily dose of vitamin C is 2 grams and the daily dose of vitamin E is 800 international units of alpha tocopherol, RRR stereoisomer, which amounts to 533.3 milligrams per day (1 IU of tocopherol is defined as ⅔ milligrams of RRR-alpha-tocopherol). Half those amounts are administered twice per day. A regimen of vitamin C and vitamin E has previously been shown effective in reducing liver fibrosis scores in NASH patients (see Harrison et al., Am J Gastroenterol. 98:2485 (2003)).

To ingest this substantial quantity of drug in a tablet or capsule form would entail swallowing over a dozen large pills per day (not including other medications), an ordeal for the patient. The liquid formulation, provided as a sweetened drink with excipients that masked any unpleasant taste of the drug, is designed to be swallowed with meals, making drug ingestion easy and thereby improving compliance. (In fact substantially greater quantities of cysteamine precursors can easily be administered via liquid formulations.) A second benefit of the liquid gelling formulation is that it is lighter than food, so it floats, in gel form, on top of the chyme and provides a layer of protection against reflux of acidic stomach contents into the esophagus. (Liquid gelling formulations, such as Gaviscon® Algicon® and Gastron®, were first developed for therapy of gastroesophageal reflux.)

Example 10. Pharmacokinetic Study of Compound 2 (N-Acetylcysteamine-(R)-Pantetheine Disulfide)

N-acetylcysteamine-(R)-pantetheine disulfide (the disulfide make by combining thiols 6 and 2 in FIG. 17, and hence referred to as compound 2) was synthesized as illustrated in FIG. 25. Compound 2 was then administered orally to male Sprague-Dawley rats at three dose levels to evaluate its pharmacokinetic (PK) parameters, particularly with respect to the time course of cysteamine production.

The doses, expressed in milligrams of cysteamine base per kilogram of body weight, were calculated and are expressed herein as follows: one molecule of compound 2, upon disulfide bond reduction, deacetylation of N-acetylcysteamine (to yield cysteamine) and cleavage of pantetheine by pantetheinase (to generate one cysteamine and one pantothenic acid), yields two molecules of cysteamine. Therefore one mole of compound 2, weighing 395.54 grams, yields two moles of cysteamine, each weighing 77.15 grams/mole×2=154.3 grams. Thus on a mass basis 154.3/395.54=38.5% of compound 2 is convertible to cysteamine after degradation. Conversely, to calculate a dose of compound 2 in terms of cysteamine base, the dose of cysteamine base is multiplied×2.5974. For example, to calculate a 30 mg/kg cysteamine base-equivalent dose of compound 2 multiply 30 mg/kg×2.5974=77.92 mg/kg. Thus in the discussion below, and in the accompanying figures, a "30 mg/kg" dose of compound 2 means 77.92 mg/kg was administered, a "60 mg/kg" dose of compound 2 means 155.84 mg/kg was administered and a "120 mg/kg" dose of compound 2 means 311.68 mg/kg was administered. The purpose of this nomenclature, which is widely used in the literature concerning cysteamine salts, is to facilitate comparison of doses of different cysteamine precursors and cysteamine salts.

Compound 2 was administered via gavage to three groups of rats (3 rats per group) at doses selected to deliver approximately 30 mg/kg (group 1), 60 mg/kg (group 2) and 120 mg/kg (group 3) of cysteamine base. All doses were dissolved in 3 milliliters of saline before administration to fasted rats (however, the 120 mg/kg dose did not completely dissolve in saline, so those rats actually received a lower dose than planned; see discussion of tissue analysis below).

The compound 2 doses were prepared for 250 gram rats, but the actual masses of the rats at the time of drug administration varied from 267-300 grams, so the actual doses, normalized to body weight, ranged from 26.1-27.1 mg/kg in group 1, 51.7-56.2 mg/kg in group 2 and 108.3-109.5 mg/kg in group 3. Nonetheless, for convenience those doses are referred to as 30, 60 and 120 mg/kg.

A control group of rats (group 5) was administered cysteamine hydrochloride in 3 milliliters of saline via gavage at a dose selected to deliver 30 mg/kg of cysteamine base. (The mass of cysteamine HCl is 113.6 Daltons, 77.15 Daltons of which, or 67.91%, is cysteamine base; conversely, to calculate a dose of cysteamine HCl from a dose of cysteamine base multiply the latter×1.47. For example, to calculate the cysteamine HCl dose that will deliver 30 mg/kg cysteamine base multiply 30×1.47=44.2 mg/kg.) The cysteamine hydrochloride doses were prepared for 250 gram rats, but the actual masses of the rats at the time of drug administration varied from 281-285 grams, so the actual dose levels, normalized to body weight, ranged from 26.3-26.7 mg/kg in group 5.

Blood samples were obtained from rats immediately before dosing and 5, 10, 20, 30, 45, 60, 90, 120, 180, 240, 300 and 600 minutes after dosing via carotid artery catheters surgically implanted before the PK study. Plasma was obtained from blood by centrifugation and snap frozen. Several days later plasma samples were thawed on ice and each plasma sample was aliquoted to two paired tubes (20 μL per tube), one of which was processed for measurement of thiols (after quantitative disulfide bond reduction), while the other was processed for analysis of disulfides.

To quantitatively reduce disulfide bonds the plasma in the first tube was treated with 5 mM tris(2-carboxyethyl)phosphine (TCEP), a selective and potent disulfide bond reducing agent, using a protocol reported by Dohil et al. (2012). Briefly, 2.2 ul of freshly prepared 50 mM TCEP stock solution was added to 20 ul of plasma and the sample incubated at 37 degrees C. for 45 minutes. The volume of plasma in the paired (non-reduced) sample was adjusted by adding 2.2 ul of deionized water.

After the TCEP reduction step all plasma samples were deproteinized by adding 3.5 volumes of ice cold acetonitrile (ACN)/1% formic acid (FA) solution containing internal standards (77 μL of ACN/1% FA solution was added to 22.2 μL of plasma). The internal standards were deuterated (d4) cysteamine (Toronto Research Chemicals), deuterated (d8) valine and deuterated (d8) phenylalanine (both obtained from Cambridge Isotope Laboratories; Andover, MA), each at a final concentration of 0.2 ug/ml in the ACN/1% FA solution.

The denatured protein was pelleted by centrifugation at 14,000 rpm for 10 minutes at 4 degrees C. in an Eppendorf microcentrifuge. The supernatant (25 ul) was removed to a new tube, mixed with 75 ul of ACN/0.1% FA solution and injected directly into a 150×2 mm Atlantis hydrophilic interaction liquid chromatography (HILIC) column (Waters; Milford, MA). Metabolites were analyzed using a Nexera X2 U-HPLC (Shimadzu) and a Q-Exactive hybrid quadrupole Orbitrap mass spectrometer (Thermo Fisher Scientific). The column was eluted isocratically at a flow rate of 360 μl/min with 5% mobile phase A (10 mM ammonium formate and 0.1% formic acid in water) for 1 min followed by a linear gradient to 40% mobile phase B (acetonitrile with 0.1% formic acid) over 7 minutes. The electrospray ionization voltage was 3.5 kV and data were acquired using full scan analysis over m/z 70-800 at 70,000 resolution and a 3 Hz data acquisition rate. Mass spectrometry in the positive ion mode was found to produce better signals from the analytes of interest. The ionization source voltage was ~3.0 kV and the source temperature was 325° C. MS data were processed using Tracefinder (version 3.2, Thermo Fisher Scientific).

Standard curves were generated for cysteamine, N-acetylcysteamine and pantetheine (all from Sigma-Aldrich) by serial dilution in plasma (100, 75, 50, 25, 15, 10, 5, 3, 1 and 0.5 uM), and then used to interpolate plasma concentrations of those substances from LC-MS ion counts.

In addition to the plasma samples, gastrointestinal contents (stomach contents, proximal small intestinal contents, distal small intestinal contents and cecum/colon contents), liver, kidney and spleen were obtained from rats at the end of the study (10.5 hours after dosing) and snap frozen. Tissue levels of cysteamine, N-acetyl cysteamine and pantothenic acid were measured in the gastrointestinal contents and in liver and kidney tissue. The protocol for tissue analysis entailed (i) smashing frozen tissue fragments over dry ice to obtain small pieces; (ii) weighing several frozen tissue pieces (~25-150 ug) into a tared 1.5 ml microcentrifuge tube with two metal ball bearings and immediately storing on dry ice; (iii) homogenizing tissue fragments cryogenically using a Retsch Cryomill at 250 hertz for 5 minutes; (iv) dividing the samples into two tubes and incubating 20 ul of suspended homogenized tissue powder with 2.2 ul of 50 mM TCEP (5 mM final concentration) for 45 minutes at 37 degrees C., or adding 2.2 ul of deionized water, (v) adding an equal volume (w:v) of acetonitrile:methanol (1:1) to both samples (TCEP, no TCEP), and pelleting precipitated protein by centrifugation for 10 minutes at 14,000 rpm in an Eppendorf microcentrifuge at 4 degrees C.; (vi) transferring 25 ul of supernatant to a new tube containing 75 ul of ACN/0.1% FA; (vii) injecting samples on the LC-MS apparatus described above, using the same column and run conditions as for plasma samples.

Results: In the compound 2 dosed rats cysteamine was produced and absorbed over a significantly longer period of time than in cysteamine HCl dosed rats. The peak cysteamine plasma concentration (Cmax) in the cysteamine HCl-dosed rats occurred 15 minutes after gavage. Thereafter the cysteamine concentration declined to less than half maximal by 90 minutes (FIG. 30A). In contrast, peak cysteamine concentration in the compound 2 dosed rats (120 mg/kg; group 3) occurred at 180 minutes (FIG. 30B). Further, while the shape of the plasma concentration-time curve in cysteamine hydrochloride-dosed rats is a high, sharp peak, in the compound 2-dosed rats the plasma concentration-time curve more nearly approximates a plateau (compare FIGS. 30A and 30B). The peak plasma cysteamine concentration in the cysteamine HCl dosed rats (over 200 uM) is higher than is observed in human subjects, and would be associated with severe toxicity in humans. When administered to Sprague-Dawley rats at a lower dose (20 mg/kg cysteamine base equivalent) cysteamine bitartrate produced a Cmax of 81.9 uM, occurring between 5-22.5 minutes after administration, and cysteamine levels returned to baseline by 2 hours (Dohil et al. 2012).

(Analysis of gastrointestinal contents from the 120 mg/kg rats revealed that a substantial amount of undissolved drug remained stuck in the stomachs of rats 8 and 9 ten hours after dosing, indicating that these rats did not receive the full dose. Thus the curve in FIG. 30B is an underestimate of the cysteamine exposure that would have been achieved with a full dose.)

Comparison of the 30 mg/kg, 60 mg/kg and 120 mg/kg compound 2 doses (FIG. 31A) reveals a progressive increase in Cmax and an equally important progressive delay in Tmax, the time at which Cmax occurs: the peak plasma concentration in the 30 mg/kg group occurred initially at 30 minutes, and then that level was reached again at 90 minutes with a very small drop in between. Tmax in the 60 mg/kg group occurred at 90 minutes, and in the 120 mg/kg group at 180 minutes. At all three doses there appears to be a bi-phasic character to the cysteamine concentration time curve, with an initial rise peaking at around 30 minutes, followed by a second (and in the 60 and 120 mg/kg dose groups, higher) peak at 1.5-3 hours.

Upon disulfide bond reduction in the gastrointestinal tract compound 2 yields two thiol moieties: N-acetylcysteamine and pantetheine. Cysteamine is subsequently produced by two independent processes: deacetylation of the former and pantetheinase cleavage of the latter. The time course of those two processes can be monitored by observing gut and plasma levels of N-acetylcysteamine and pantothenic acid, which is created (along with cysteamine) when pantetheine is cleaved. (Pantothenic acid has a longer half life than cysteamine in man, and it appears in rat.) FIG. 31B shows that (i) N-acetylcysteamine is absorbed into the blood (not previously known) with substantially similar kinetics as cysteamine, suggesting similar transport mechanisms. Further, there must be ongoing conversion of N-acetylcysteamine to cysteamine both in the gastrointestinal tract (where both N-acetylcysteamine and cysteamine are present) and in the blood to account for the high cysteamine levels. Pantothenic acid is also present in the gut contents and in plasma. Pantothenic acid levels increase rapidly in the first hour, indicating production of cysteamine by pantetheinase cleavage of pantetheine, then drop slightly at 90 minutes, then resumes a slow very gradual climb to 240 minutes (FIG. 31B), indicating both early and late contributions from pantetheine cleavage to cysteamine plasma levels.

Tissue levels of cysteamine at 10.5 hours were, remarkably, over 50 uM in both liver and kidney samples from all three rats in the 120 mg/kg group (rats 7, 8 and 9, comprising dosage group 3; FIG. 32). Plasma cysteamine levels in these three rats at 10 hours were 1.1, 0 and 1.5 uM. The much higher tissue levels may reflect (i) lower levels of pantetheinase in tissues compared to blood (or more specifically, lower pantetheinase levels in certain specific cell types, since pantetheinase is expressed in some kidney cells); and/or (ii) more deacetylase in tissues compared to plasma, resulting in more efficient conversion of N-acetylcysteamine to cysteamine in tissues than in blood. For comparison, when Sprague-Dawley rats were dosed with cysteamine bitartrate (20 mg/kg) the tissue half life of cysteamine was estimated at 25-29 min and it was inferred that over 95% of cysteamine would be eliminated by 150 minutes (Dohil et al. 2012). Since most of the therapeutic effects of cysteamine occur in tissues, not blood (kidney is the first organ to fail in patients with cystinosis), the presence of cysteamine in kidney and liver ten hours after dosing is highly significant therapeutically.

Example 11. Pharmacokinetics of Cysteamine after Administration of Different Disulfides to Rats Methods The pharmacokinetics of cysteamine in blood plasma were analyzed after administration of either cysteamine hydrochloride (30 mg/kg), cystamine dihydrochloride (30 mg/kg), pantethine (30 mg/kg) or pantetheine-cysteamine disulfide (aka TTI-0102; compound 1) (100 mg/kg) to rats.

The doses are expressed in terms of the milligrams of cysteamine base deliverable by each compound, per kilogram of body weight. They were calculated as follows: one molecule of TTI-0102, upon disulfide bond reduction, yields one molecule of cysteamine and one molecule of pantetheine. Subsequent cleavage of pantetheine by intestinal pantetheinase yields one cysteamine and one pantothenic acid. Thus one molecule of TTI-0102 yields two molecules of cysteamine. Therefore one mole of TTI-0102 (formula weight: 353.52 grams) yields two moles of cysteamine (formula weight: 77.15 grams/mole), so 77.15×2=154.3 grams of cysteamine are delivered per 353.52 grams of TTI-0102. Thus on a mass basis 154.3/353.52=43.65% of TTI-0102 is convertible to cysteamine after degradation. Conversely, to calculate a dose of TTI-0102 in terms of cysteamine base, divide the mass of TTI-0102 by the mass of delivered cysteamine base: 353.52/154.3=2.291. Therefore, to calculate a 30 mg/kg cysteamine-equivalent dose of TTI-0102 multiply 30 mg/kg×2.291=68.73 mg/kg. Thus in the discussion below, and in the accompanying figures, a "30 mg/kg" dose of TTI-0102 means 68.73 mg/kg was administered, a "60 mg/kg" dose of TTI-0102 means 137.46 mg/kg was administered and a "100 mg/kg" dose of TTI-0602 (aka compound 2) means 229.1 mg/kg was administered. The purpose of this nomenclature, which is standard in the cysteamine pharmacology literature, is to facilitate comparison of doses of different cysteamine precursors and cysteamine salts. (Similar calculations were performed for the other three molecules. The mass of cysteamine HCl is 113.6 Daltons, 77.15 Daltons of which, or 67.91%, is cysteamine base; conversely, to calculate a dose of cysteamine HCl from a dose of cysteamine base multiply the latter×1.47. For example, to calculate the cysteamine HCl dose that will deliver 30 mg/kg cysteamine base multiply 30×1.47=44.2 mg/kg.) Each of the four compounds was administered via gavage to three male Sprague-Dawley rats weighing approximately 300 grams. All doses were dissolved in 2.5 milliliters of saline.

Blood samples were obtained from rats immediately after dosing (within one minute) and 10, 20, 30, 45, 60, 90, 120, 180, 240, 300 and 360 minutes after dosing via carotid artery catheters surgically implanted before the PK study. Plasma was obtained from blood by centrifugation, snap frozen and stored at −80 degrees Celcius. Several days later plasma samples were thawed on ice and each aliquoted to two paired tubes (20 μL per tube), one of which was processed for measurement of thiols (after quantitative disulfide bond reduction), while the other was processed for analysis of disulfides.

To quantitatively reduce disulfide bonds the plasma in the first tube was treated with 5 mM tris(2-carboxyethyl)phosphine (TCEP), a potent and selective disulfide bond reducing agent, using a protocol reported by Dohil et al. (2012). Briefly, 2.2 ul of freshly prepared 50 mM TCEP stock solution was added to 20 ul of plasma and the sample incubated at 37 degrees C. for 45 minutes. The volume of plasma in the paired (non-reduced) sample was adjusted by adding 2.2 ul of deionized water.

After the TCEP reduction step all plasma samples were deproteinized by adding 3.5 volumes of ice cold acetonitrile (ACN)/1% formic acid (FA) solution containing internal standards (77 μL of ACN/1% FA solution was added to 22.2 μL of plasma). The internal standards were deuterated (d4) cysteamine (Toronto Research Chemicals), deuterated (d8) valine and deuterated (d8) phenylalanine (both obtained from Cambridge Isotope Laboratories; Andover, MA), each at a final concentration of 0.2 ug/ml in the ACN/1% FA solution.

The denatured protein was pelleted by centrifugation at 14,000 rpm for 10 minutes at 4 degrees C. in a microcentrifuge. The supernatant (25 ul) was removed to a new tube, mixed with 75 ul of ACN/0.1% FA solution and injected directly into a 150×2 mm Atlantis hydrophilic interaction liquid chromatography (HILIC) column (Waters; Milford, MA). Metabolites were analyzed using a Nexera X2 U-HPLC (Shimadzu) and a Q-Exactive hybrid quadrupole Orbitrap mass spectrometer (Thermo Fisher Scientific). The column was eluted isocratically at a flow rate of 360 μl/min with 5% mobile phase A (10 mM ammonium formate and 0.1% formic acid in water) for 1 min followed by a linear gradient to 40% mobile phase B (acetonitrile with 0.1% formic acid) over 7 minutes. The electrospray ionization voltage was 3.5 kV and data were acquired using full scan analysis over m/z 70-800 at 70,000 resolution and a 3 Hz data acquisition rate. Mass spectrometry in the positive ion mode was found to produce better signals from the analytes of interest. The ionization source voltage was ~3.0 kV and the source temperature was 325° C. MS data were processed using Tracefinder (version 3.2, Thermo Fisher Scientific).

Standard curves were generated for cysteamine and pantetheine (from Sigma-Aldrich) by serial dilution in plasma (100, 75, 50, 25, 15, 10, 5, 3, 1 and 0.5 uM) or in relevant tissue matrix. The slope of the best fit line through the standards was used to calculate plasma concentrations of those substances from LC-MS ion counts.

In addition to the plasma samples, gastrointestinal contents (stomach contents, proximal small intestinal contents, distal small intestinal contents and cecum/colon contents) were obtained from rats at the end of the study (6 hours after dosing) and snap frozen. Tissue levels of cysteamine and pantetheine were measured in the gastrointestinal contents. The protocol for tissue analysis entailed (i) smashing frozen tissue fragments over dry ice to obtain small pieces; (ii) weighing several frozen tissue pieces (~25-150 ug) into a tared 1.5 ml microcentrifuge tube with two metal ball bearings and immediately storing on dry ice; (iii) homogenizing tissue fragments cryogenically using a Retsch Cryomill at 250 hertz for 5 minutes; (iv) thawing each sample on ice, adding two volumes of water (w:v., i.e. 2 microliters of water were added for each milligram of homogenized tissue) to make an approximately 1:3 dilution; (v) removing 20 ul of the resuspended tissue powder to a new tube, adding 2.2 ul of 50 mM TCEP (5 mM final concentration) and incubating for 45 minutes at 37 degrees C. (TCEP treated samples), or adding 2.2 ul of deionized water in place of TCEP (no TCEP samples); (vi) adding 3.5 volumes of acetonitrile:0.1% formic acid, vortex mixing for 15 seconds, and then pelleting precipitated protein by centrifugation for 10 minutes at 14,000 rpm in a microcentrifuge at 4 degrees C.; (vii) transferring 25 ul of supernatant to a new tube containing 75 ul of ACN/0.1% FA; (vii) injecting samples on the LC-MS apparatus described above, using the same column and run conditions as for plasma samples.

Results and Discussion:

In rats dosed with cysteamine HCl (30 mg/kg) there is a rapid spike in plasma cysteamine levels; the pharmacokinetic parameters indicate that half of the dose is absorbed in one minute and the peak observed concentration (~50 uM) occurs at the first measured time point, 10 minutes after gavage. Cysteamine levels decline to low micromolar levels by 4 hours (FIG. 1). High cysteamine levels are associated with halitosis, body odor, nausea, vomiting, anorexia and stomach pain.

In rats dosed with cystamine HCl (30 mg/kg) the plasma cysteamine peak occurs later (between 30-60 minutes) and is broader (greater AUC than cysteamine HCl). Cysteamine levels then descend to baseline values by about 4 hours (FIG. 1). Thus, surprisingly, cystamine delivered to the stomach in saline (i.e. an instant release dosage form) provides a superior exposure to cysteamine when compared to cysteamine itself, however the high peak levels and rapid elimination are similar to cysteamine hydrochloride dosed rats.

Unexpectedly, in rats dosed with pantethine (30 mg/kg) the plasma cysteamine levels never exceed 2.5 micromolar. Thus pantethine, in the absence of agents to enhance disulfide bond reduction and/or pantetheinase expression, is a poor cysteamine delivery agent in rats. (Human gastrointestinal physiology differs from rat physiology in several potentially significant ways, including pH and glutathione volume and concentration.)

In rats dosed with TTI-0102 (100 mg/kg) plasma cysteamine levels don't peak until 90 minutes, then remain elevated above 10 uM until after 4 hours, and above 5 uM for the entire six hour period evaluated. Further, the AUC (499 minute*ug/L) is greater than cysteamine HCl AUC (365), while the Cmax is lower (34.4 uM vs. ~55.3 uM, respectively) (FIG. 2). Thus TTI-0102 (100 mg/kg) provides greater exposure to cysteamine than cysteamine hydrochloride, cystamine dihydrochloride or pantethine, provides plasma levels above 5 and 10 micromolar over a longer time, and has a lower Cmax then the former two, all of which are desirable pharmacological properties.

In general rodent metabolism of cysteamine is more rapid (e.g. shorter half life) than in humans, so the rat pharmacokinetic parameters should not be interpreted as directly translatable to the human setting. Nonetheless the dose.

Example 12. Pharmacokinetics of Cysteamine in Rat Plasma after Administration of Pantetheine-Cysteamine Mixed Disulfide (TTI-0102) at 30, 60 or 100 mg/kg When rats are dosed with TTI-0102 at 30 mg/kg, 60 mg/kg or 100 mg/kg (FIG. 2) the AUC progressively increases with dose (175, 252, 499 minute*ug/L, respectively), as expected. Unexpectedly, however, (i) Cmax remains nearly constant (29.4, 34.4, 34.4 uM, across the three doses), and (ii) the duration of plasma cysteamine exposure progressively increases with dose. In particular, the differences in AUC, absorption half life and mean residence time (MRT) between the 60 and 100 mg/kg TTI-0102 doses are remarkable. Thus high levels of compound 1 (e.g., 50-150 mg/kg provide a nearly ideal pharmacokinetic pattern, keeping plasma cysteamine below levels that cause side effects, but above levels required for efficacy, particularly when sustained over long periods.

Example 13. Gastrointestinal Metabolism of Cysteamine and Pantetheine-Cysteamine Mixed Disulfide (TTI-0102) in Rats Analysis of gastrointestinal contents from the cystamine hydrochloride (30 mg/kg) dosed rats, and the 30, 60, and 100 mg/kg rats revealed several unexpected differences between the three compound 1 dose levels (FIG. 3). In rats dosed with 100 mg/kg compound 1 high levels of pantetheine are present at all levels of the gastrointestinal tract (stomach, proximal and distal small intestine, colon) at six hours after dosing. In the proximal and distal small intestine (SI) samples were processed with and without the disulfide bond reducing agent TCEP. Comparison of the "no TCEP" samples to the TCEP samples reveals that about half the pantetheine is in the form of the thiol, where the other (approximately) half is apparently disulfide bound to another thiol. The fact that there are high concentrations of free pantetheine in the small intestine (613 uM in the proximal SI, 219 uM in the distal SI) indicates that pantetheinase cleavage was a limiting factor in converting pantetheine to cysteamine (and pantothenic acid). Therefore co-administration of a pantetheinase inducing agent with compound 1, or at some interval (e.g. 2-4 hours) following administration of compound 1 (100 mg/kg) would be expected to improve conversion of pantetheine to cysteamine, and boost cysteamine plasma levels starting several hours after dose administration, when they start to decline. Natural products that regulate expression of the pantetheinase genes (VNN1 and VNN2) are known in the art and include, for example sulphoraphane, S-allyl cysteine, diallyl trisulfide, oxidized fat, omega-3 fatty acids and oleylethanolamide. Drugs that induce expression of pantetheinase include PPAR alpha agonists, PPAR gamma agonists. In general, drugs or natural products that induce Nrf2 expression are useful. (Nrf2 is a transcription factor that activates pantetheinase expression.)

Analysis of cysteamine levels in the proximal and distal SI of compound 1 (100 mg/kg) rats reveals moderate free cysteamine concentrations of 129 and 34 uM, respectively (no TCEP samples). After TCEP reduction those levels increase to 430 and 899 uM, respectively. A similar patter is observed with pantetheine. Thus a substantial fraction of the cysteamine in the small intestine is disulfide bound (whether in the form of unreduced compound 1, or disulfide bonded to another thiol via thiol-disulfide exchange), with the fraction increasing significantly from the proximal SI to the distal SI. This may be explained by the presence of higher concentrations of bile-derived glutathione in the proximal SI. (Bile is the main source of glutathione in the gastrointestinal tract, thought enterocytes also secrete glutathione and cysteine.) Thus there is insufficient reducing power in the gastrointestinal tract to reduce (or keep reduced) all of the compound 1. This limits the conversion of compound 1 to cysteamine (either via disulfide bond reduction or reduction followed by pantetheinase cleavage). Administration of a physiological reducing agent with, or after compound 1 (100 mg/kg) may increase the efficiency of conversion of compound 1 to cysteamine. A variety of physiological thiols can be used, including, for example, glutathione, glutathione diethyl ester, gamma glutamylcysteine, dihydrolipoic acid, N-acetylcysteine, homocysteine, pantetheine, 4-phosphopantetheine, dephospho-coenzyme A, coenzyme A, vitamin E or ascorbic acid. Any of these agents can be administered with or after compound 1, or co-formulated with compound 1. Useful formulations may include delayed release or sustained release formulations that provide the reducing agent at the time (e.g. 2 hours after compound 1 release starts) and place (e.g. distal small intestine) where extra disulfide bond reducing power is most needed.

Analysis of colon contents (TCEP reduced) reveals high concentrations of both cysteamine and pantetheine, confirming incomplete conversion of the compound 1 precursor to cysteamine, and therefore scope for further improving the shape of the drug concentration-time curve by increasing cysteamine production and absorption during 4-12 hour interval after dosing. For example, administration of high doses of compound 1 (e.g. 100 mg/kg or higher) with a high calorie meal will prolong release of compound 1 from the stomach and extend the period during which it is reduced, pantetheine cleaved and absorbed as cysteamine. A gastroretentive formulation of compound 1 is another way to accomplish the purpose of prolonged release from the stomach.

Example 14. Synthesis of Mixed Disulfides—Acylation of Cystamine

A wide variety of methods for synthesizing mixed disulfides have been described (see reviews by Witt et al. Langmuir 23:2318 (2007); Musiejuk et al. Org. Prep. and Proc. 47.2:95 (2015)). However, notwithstanding extensive investigation of the chemistry of disulfide bond formation (e.g., Singh et al. Sulfur-Containing Functional Groups (1993)), efficient methods for joining a specific pair of thiols have to be determined empirically. Further, in developing synthetic methods for drug substance considerations such as impurity profile (both the identity and amount of impurities), scalability (using inexpensive processes and equipment), solid state (e.g. amorphous or crystalline, which may have different solubility of stability characteristics) and salt form (which can also affect dissolution, stability and palatability) have to be considered.

The following examples are put forth to provide those of ordinary skill in the art with a detailed description of how the methods and systems claimed herein are performed and evaluated, and are intended to be purely exemplary of the invention and are not intended to limit the scope of what the inventors regard as their invention. Indeed, possible improvements are also discussed.

The example below describes a synthesis of TTI-0102 and salts thereof. This method may be adapted to synthesis of other asymmetric disulfides.

Reagents and Methods.

The seven reagents for hemi-acylation of cystamine by pantothenate are listed below:

| | Reagent | Chemical Abstracts Service (CAS) # | Equivalents |
|---|---|---|---|
| 1. | cystamine dihydrochloride | 56-17-7 | 2-4 |
| 2. | hemicalcium pantothenate | 137-08-6 | 1 |
| 3. | N,N'-dicyclohexylcarbodiimide (DCC) | 538-75-0 | 3-5 |
| 4. | 1-Hydroxybenzotriazole hydrate ($HOBt\ H_2O$) | 123333-53-9 | 1-3 |
| 5. | Solvents: methanol, dimethylformamide, water | | |

The reaction scheme is illustrated in FIG. 36, panel A. Reagents 1, 2 and 3 were dissolved in a mixture of DMF (80 mL) and $H_2O$ (160 mL). Subsequently the mixture was cooled to 0° C. and reagent 4 dissolved in 80 mL of DMF was added dropwise. The reaction was stirred 1 hour at 0° C. and then stirred at room temperature overnight. The crude reaction material was then loaded on a silica gel column and TTI-0102 separated from un-acylated cystamine, double-acylated cystamine (pantethine), and other undesired side products (see details in Example 5). TTI-0102 elutes before cystamine, which is the major contaminant.

Alternatively either TTI-0102 or contaminating substances can be selectively crystallized and the crystals separated from dissolved substances. See example 17 for discussion of salt forms and precipitation of TTI-0102.

Results.

TTI-0102 yield from the acylation reaction is 95% to 97%. After chromatographic purification, the proton NMR spectrum is free of detectable contaminating peaks (FIG. 37).

Observations.

The acylation reaction has the following advantages: (i) small number of steps, (ii) readily obtainable raw materials, (iii) high yield (97%) and (iv) scalable. In large scale synthesis the chromatographic purification can be omitted, or used as a "polishing" step, by selective crystallization of TTI-0102 (see example 17).

Example 15. Synthesis of Mixed Disulfides—Thiol Disulfide Exchange of Cysteamine and Pantethine The example below describes a synthesis of TTI-0102 and salts thereof. This method may be adapted to synthesis of other asymmetric disulfides.

Reagents and Methods.

The reagents for cysteamine-pantethine disulfide exchange are listed below:

| | Reagent | CAS No. | Amount | Equivalents | Concentration |
|---|---|---|---|---|---|
| 1. | (D)-Pantethine | 16816-67-4 | 1 g | 1 | 1.8 mM |
| 2. | cysteamine (free base) | 60-23-1 | 0.42 g | 3 | 5.4 mM |
| 3. | Solvents: acetic acid (AcOH), methanol (MeOH), and water | | | | |

The reaction scheme is illustrated in FIG. 36, panel B. First, reagents 1 and 2 were dissolved in 20 mL MeOH and stirred overnight at room temperature. Reaction times as short as one hour may be used.

Chromatography Purification.

The reaction mixture was divided into 2 gram portions (based on expected 50% of product), evaporated under vacuum, and resuspend in 10 mL of DCM:MeOH:AcOH (ratio 10:3:0.1) (e.g., 10 mL per 2 grams expected product). A silica gel column (Sigma Aldrich Silica Gel Cat #60737, CAS No. 112926-00-8) was prepared using 30 cubic cm (15 g dry gel) per 1 gram of expected product. After loading the resuspended reaction material, the column was washed with 300 mL of a solvent mixture of DCM:MeOH:AcOH (ratio 10:3:0.1), subsequently washed with solvent mixture of DCM:MeOH:AcOH (10:4:0.1) (300 ml), and again washed with solvent mixture of DCM:MeOH:AcOH (10:5:0.1). Column fractions were collected and assayed for product content by thin layer chromatography (TLC) on silica gel using TLC-PET plates (Merck Item no. 99577) resolved in solvent mixture DCM:MeOH (3:1). Product was detected on TLC at $R_f$ of %. Fractions containing pure product were collected, concentrated, and dried under vacuum. The $^1H$ NMR (500 MHz) was performed on representative sample.

Results.

TTI-0102 yield from the cysteamine-pantethine reaction is 50% to 55%. After chromatographic purification the proton NMR spectrum is free of detectable contaminating peaks Observations.

The thiol-disulfide exchange reaction has the following advantages: (i) few steps and mild conditions ("one pot" reaction), (ii) readily obtainable, inexpensive raw materials, (iii) moderate yield, and (iv) scalable. The thiol-disulfide exchange reaction may be compatible with a continuous process.

Example 16. Synthesis of Mixed Disulfides—Thiol Disulfide Exchange of Pantetheine and Cystamine The example below describes a synthesis of TTI-0102 and salts thereof. This method may be adapted to synthesis of other asymmetric disulfides.

Reagents and Methods.

The reagents for hemi-acylation of cystamine by pantothenate are listed below:

| | Reagent | Equivalents | amount |
|---|---|---|---|
| 1. | (D)-Pantetheine | 3 eq | 2.6 g, 9.3 mmol |
| 2. | cysteamine hydrochloride | 1 eq | 700 mg, 3.1 mmol |
| 3. | MeONa | 1.3 eq | prepared by adding 162 mg 60% NaH to 5 ml MeOH |

Methods.

As in the cysteamine-pantethine version of this reaction (Example 15) the solvent is methanol. Pantetheine can be purchased, or produced from pantethine by disulfide bond reduction. Reagent 1 was dissolved in 10 ml of MeOH. Subsequently reagent 2 solution was added and stirred for 15 minutes at room temperature. The reagent 3 was separately dissolved in 10 ml of MeOH, and added to reaction mixture. The whole mixture was stirred overnight at room temperature.

Example 17. TTI-0102 Salt Forms—Physical Characteristics and Precipitation

TTI-0102 was prepared as in Example 14. The crude product was obtained by evaporation of water and DMF. The residue was suspended in ethyl acetate/water; precipitated dicyclohexylurea (DCU) was filtered off. The solution was evaporated and suspended in methanol. The precipitate (unreacted pantothenic acid) was filtered off. The filtrate was concentrated and then dissolved in a small volume of methanol. After addition of dichloromethane the cystamine hydrochloride precipitated and was filtered off. After evaporation of solvent, the residue was crystallized from methanol:acetone (1:10) to provide TTI-1 hydrochloride.

The tartrate salt was formed and crystallized from a MeOH:DCM mixture. The solid form was filtered off (precipitate) and filtrate was evaporated.

Observations.

TTI-0102 free base, when dried, is a clear to slightly yellow glassy solid. This observation led to the investigation of salt forms of TTI-0102. The acetate salt of TTI-0102 is more stable than the free base, and can be lyophilized to a solid form (a white, bubble-filled solid) which can be crushed to produce a powder. The tartrate salt of TTI-0102 can also be lyophilized to a solid form, and has the additional advantage of being more prone to precipitation than the acetate salt, as described above.

The acid addition salt of compound 1 can have any of the following formulas:

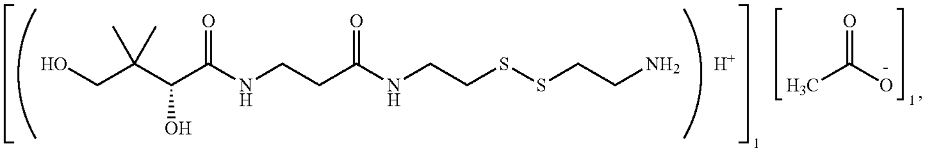

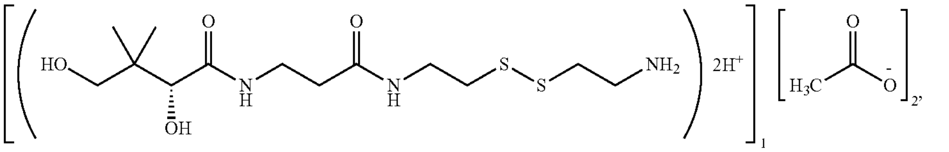

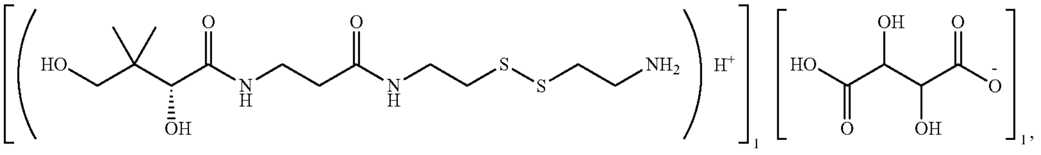

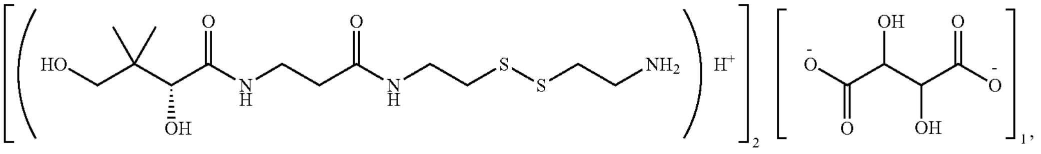

or

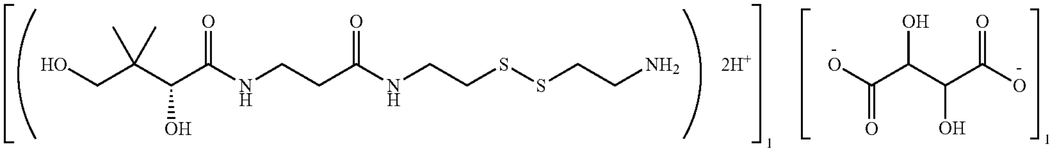

The form of the acid addition salt of compound 1 can be controlled by changing the molar ratio of the acid (e.g., carboxylic acid such as acetic acid or tartaric acid) to compound 1 in the solution in which the acid addition salt is formed, and/or by adjusting the pH of the solution from which the salt is isolated. Acid addition salts of compound 1 can display advantageous properties, such as stability with regard to degradation of the disulfide.

OTHER EMBODIMENTS

While the invention has been described in connection with specific embodiments thereof, it will be understood that it is capable of further modification and that this patent application is intended to cover any variations, uses or adaptations following, in general, the principles of the invention and including such departures from the present disclosure as come within the ordinary skill of the art to which the invention pertains, and as may be applied to the essential features hereinbefore set forth, within the spirit of the invention.

What is claimed is:

1. A method for treating a cysteamine sensitive disorder in a subject comprising orally administering to the subject a reducing agent and a dose of from 50 to 150 milligrams per kilogram of body weight (mg/kg) of compound 1:

(1)

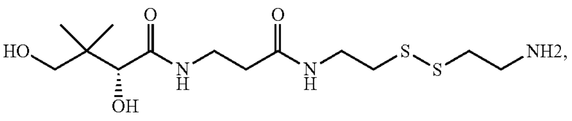

or a pharmaceutically acceptable salt thereof, one or more times daily.

2. The method of claim 1, wherein the reducing agent is administered to the subject between 2 hours and 8 hours after the administering of the dose.

3. The method of claim 1, wherein the reducing agent is selected from glutathione, glutathione diethyl ester, gamma glutamylcysteine, dihydrolipoic acid, N-acetylcysteine, homocysteine, pantetheine, 4-phosphopantetheine, dephospho-coenzyme A, coenzyme A, vitamin E, and ascorbic acid.

4. The method of claim 1, wherein the compound 1, or a pharmaceutically acceptable salt thereof, is formulated for immediate release.

5. The method of claim 1, wherein the compound 1, or a pharmaceutically acceptable salt thereof, is formulated as a powder and the dosage form is a sachet.

6. The method of claim 1, wherein the cysteamine sensitive disorder is selected from cystinosis; neurodegenerative disease; neurodevelopmental disease; neuropsychiatric disease; mitochondrial disease; fibrotic diseases of the kidney, of the liver, or of the lung; parasitic infection; sickle cell anemia; cancer; ischemic disease including ischemic heart disease or stroke; chronic obstructive pulmonary disease (COPD); cystic fibrosis (CF); bacterial infection; viral infection; non-alcoholic steatohepatitis (NASH); alcoholic steatohepatitis; and non-alcoholic fatty liver disease (NAFLD).

7. The method of claim 1, wherein the compound 1, or the pharmaceutically acceptable salt thereof, is administered to the subject once, twice, or three times daily.

8. The method of claim 1, wherein the dose comprises from 60 to 100 mg/kg of compound 1, or the pharmaceutically acceptable salt thereof.

9. The method of claim 1, wherein the dose comprises from 2,000 to 10,000 mg of the compound 1, or the pharmaceutically acceptable salt thereof.

10. The method of claim 1, wherein the compound 1, or the pharmaceutically acceptable salt thereof, is formulated as a tablet, a capsule, a liquid solution, or a suspension.

11. The method of claim 6, wherein:

(a) the cysteamine sensitive disorder is a neurodegenerative disease selected from the group comprising Huntington's disease, neurodegenerative disorders with brain iron accumulation, Parkinson's disease, and Alzheimer's disease;

(b) the cysteamine sensitive disorder is a neurodevelopmental disease selected from Rett syndrome and other disorders associated with MECP2 mutation;

(c) the cysteamine sensitive disorder is a mitochondrial disease selected from Leigh syndrome, Mitochondrial Encephalomyopathy, Lactic Acidosis, and Stroke-like episodes (MELAS), Myoclonic Epilepsy with Ragged Red Fibers (MERFF), and Friedreich's ataxia;

(d) the cysteamine sensitive disorder is a fibrotic disease selected from Alport's disease, focal segmental glomerulosclerosis (FSGS), alcoholic steatohepatitis (ASH), and pulmonary fibrosis; or (e) the cysteamine sensitive disorder is a bacterial infection or viral infection.

12. A method for treating a cysteamine sensitive disorder in a subject comprising orally administering to the subject a reducing agent and a dose of from 2,000 to 10,000 mg of compound 1 or a pharmaceutically acceptable salt thereof once daily (1)

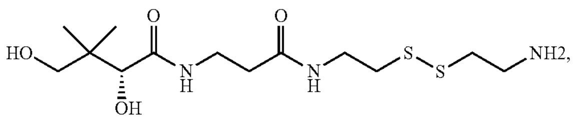

13. The method of claim 12, wherein the compound 1, or a pharmaceutically acceptable salt thereof, is formulated for immediate release.

14. The method of claim 12, wherein the compound 1, or a pharmaceutically acceptable salt thereof, is formulated as a powder and the dosage form is a sachet.

15. The method of claim 12, wherein the compound 1, or the pharmaceutically acceptable salt thereof, is formulated as a tablet, a capsule, a liquid solution, or a suspension.

16. The method of claim 12, wherein the cysteamine sensitive disorder is selected from cystinosis; neurodegenerative disease; neurodevelopmental disease; neuropsychiatric disease; mitochondrial disease; fibrotic diseases of the kidney, of the liver, or of the lung; parasitic infection; sickle cell anemia; cancer; ischemic disease including ischemic heart disease or stroke; chronic obstructive pulmonary disease (COPD); cystic fibrosis (CF); bacterial infection; viral infection; non-alcoholic steatohepatitis (NASH); alcoholic steatohepatitis; and non-alcoholic fatty liver disease (NAFLD).

17. The method of claim 16, wherein:

(a) the cysteamine sensitive disorder is a neurodegenerative disease selected from Huntington's disease, neurodegenerative disorders with brain iron accumulation, Parkinson's disease, and Alzheimer's disease;

(b) the cysteamine sensitive disorder is a neurodevelopmental disease selected from Rett syndrome and other disorders associated with MECP2 mutation;

(c) the cysteamine sensitive disorder is a mitochondrial disease selected from Leigh syndrome, MELAS, MERFF, and Friedreich's ataxia;

(d) the cysteamine sensitive disorder is a fibrotic disease selected from Alport's disease, focal segmental glomerulosclerosis (FSGS), alcoholic steatohepatitis (ASH), and pulmonary fibrosis; or (e) the cysteamine sensitive disorder is a bacterial infection or viral infection.

18. The method of claim 1, wherein the reducing agent is co-formulated with the dose of compound 1 or the pharmaceutically acceptable salt thereof.

19. The method of claim 12, wherein the reducing agent is selected from glutathione, glutathione diethyl ester, gamma glutamylcysteine, dihydrolipoic acid, N-acetylcysteine, homocysteine, pantetheine, 4-phosphopantetheine, dephospho-coenzyme A, coenzyme A, vitamin E, and ascorbic acid.

20. The method of claim 12, wherein the reducing agent is co-formulated with the dose of compound 1 or the pharmaceutically acceptable salt thereof.

* * * * *